US008034949B2

(12) United States Patent
Moritani et al.

(10) Patent No.: US 8,034,949 B2

(45) Date of Patent: Oct. 11, 2011

(54) PYRROLIDINE COMPOUND AND A PROCESS FOR PREPARING THE SAME

(75) Inventors: Yasunori Moritani, Osaka (JP); Shigeru Furukubu, Osaka (JP); Yasunori Tsuboi, Osaka (JP); Chieko Okagaki, Osaka (JP); Akira Oku, Osaka (JP); Naomitsu Hirano, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 223 days.

(21) Appl. No.: 11/579,950

(22) PCT Filed: May 27, 2005

(86) PCT No.: PCT/JP2005/010197

§ 371 (c)(1),
(2), (4) Date: Nov. 9, 2006

(87) PCT Pub. No.: WO2005/070919

PCT Pub. Date: Aug. 4, 2005

(65) Prior Publication Data

US 2007/0167440 A1 Jul. 19, 2007

(30) Foreign Application Priority Data

May 28, 2004 (JP) ................................. 2004-160059
Jan. 14, 2005 (JP) ................................. 2005-007833

(51) Int. Cl.
*C07D 213/72* (2006.01)
*C07D 207/00* (2006.01)
*A61K 31/44* (2006.01)

(52) U.S. Cl. ......................... 546/304; 514/349; 548/544

(58) Field of Classification Search .................. 548/544; 514/424
See application file for complete search history.

(56) References Cited

U.S. PATENT DOCUMENTS 5,624,941 A 4/1997 Barth et al.
6,509,367 B1 1/2003 Martin et al.
7,507,760 B2 * 3/2009 Pajouhesh et al. ............ 514/426

FOREIGN PATENT DOCUMENTS

| | | | |
|---|---|---|---|
| EP | 0 481 756 A | 4/1992 |
| EP | 1 179 341 A | 2/2002 |
| WO | WO 99/25686 A1 | 5/1999 |
| WO | WO-01/64632 A1 | 9/2001 |
| WO | WO-01/70700 A1 | 9/2001 |
| WO | WO-03/007887 A2 | 1/2003 |
| WO | WO-03/020314 A1 | 3/2003 |
| WO | WO-03/026647 A1 | 4/2003 |
| WO | WO-03/026648 A1 | 4/2003 |
| WO | WO-03/027069 A1 | 4/2003 |
| WO | WO-03/027076 A2 | 4/2003 |
| WO | WO-03/027114 A1 | 4/2003 |
| WO | WO-03/040107 A1 | 5/2003 |
| WO | WO-03/051850 A1 | 6/2003 |
| WO | WO-03/051851 A1 | 6/2003 |
| WO | WO 03/063781 A2 | 8/2003 |
| WO | WO-03/082190 A2 | 10/2003 |
| WO | WO-03/082191 A2 | 10/2003 |
| WO | WO-03/082833 A1 | 10/2003 |
| WO | WO-03/084930 A1 | 10/2003 |
| WO | WO-03/084943 A2 | 10/2003 |
| WO | WO-03/087027 A1 | 10/2003 |
| WO | WO 2005/070919 A1 | 8/2005 |

OTHER PUBLICATIONS

Hcaplus 125:86486.*
Twitchell, W. et al. J. Neurophysiol. 1997, vol. 78: pp. 43-50.* Valli et al., "Synthesis and metabotropic glutamate receptor antagonist activity of N1-substituted analogs of 2R,4R-4-aminopyrrolidine-2,4-dicarboxylic acid", Bioorg. & Med. Chem. Lett., vol. 8, 1998, pp. 1985-1990, XP002340489.
Bell et al., "3-Aminopyrrolidinone Farnesyltransferase Inhibitors: Design of Macrocyclic Compounds with Improved Pharmacokinetics and Excellent Cell Potency", J. Med. Chem., vol. 45, 2002, pp. 2388-2409, XP002340490.
Valli et al., Bioorganic & Medicinal Chemistry Letters, vol. 8, pp. 1985-1990, XP 002340489 (1998).
Bell et al., J. Med. Chem., vol. 45, pp. 2388-2409, XP 002340490 (2002).
Matsuda et al., Nature, vol. 346, pp. 561-564 (Aug. 9, 1990).
Munro et al., Nature, vol. 365, pp. 61-65 (Sep. 2, 1993).

* cited by examiner

*Primary Examiner* — Janet Andres
*Assistant Examiner* — Heidi Reese
(74) *Attorney, Agent, or Firm* — Birch, Stewart, Kolasch & Birch, LLP

(57) ABSTRACT

The present invention relates to a novel pyrrolidine compound, which has a potent antagonistic activity against central cannabinoid (CB1) receptor, having the formula [I]: wherein each of $R^1$ and $R^2$ is (A) optionally substituted aryl (or heteroaryl) group, or (B) both of the groups combine to form a group of the formula: one of $R^3$ and $R^4$ is hydrogen and another is hydrogen, hydroxyl, hydroxyalkyl, etc., or both of $R^3$ and $R^4$ combine to form oxo group, $R^5$ is hydrogen or alkyl, Y is single bond, oxygen atom or a group of the formula: —N($R^7$)—, $R^6$ is optionally substituted hydrocarbon group or optionally substituted cyclic group, $R^7$ is alkyl or alkyloxycarbonylalkyl, provided that $R^6$ is not 4-amino-5-chloro-2-methoxyphenyl group when Y is single bond and one of the $R^3$ and $R^4$ is hydrogen and another is hydroxymethyl, or a pharmaceutically acceptable salt thereof.

[I]

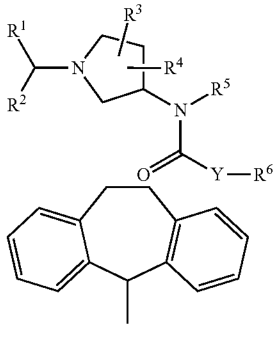

7 Claims, No Drawings

PYRROLIDINE COMPOUND AND A PROCESS FOR PREPARING THE SAME

TECHNICAL FIELD

The present invention relates to a novel pyrrolidine compound or a pharmaceutically acceptable salt thereof having a potent antagonistic activity against central cannabinoid (CB1) receptor and being useful as a medicament.

BACKGROUND ART

It is well known that, by intake of marijuana, various psychiatric or neurological reactions such as confusion of temporal or space sense, euphoria, alteration of memories, analgesia, hallucination and the like would be produced. The compounds generally referred to as "cannabinoid" including ⊿9-tetrahydrocannabinol (⊿9-THC) are responsible for many of such reactions. The effect of cannabinoid is considered to be produced by an interaction between the compound and its endogenous specific/high-affinity receptors. Two subtypes of cannabinoid receptors (CB1 and CB2) have been identified and cloned. The CB1 receptor is distributed in central nervous system (CNS) regions including brain (Nature, Vol. 346, 1990, pp 561-564) while the CB2 receptor is distributed in immune system including spleen (Nature, Vol. 365, 1993, pp 61-65).

Substances having affinity to such cannabinoid receptors (agonists, antagonists or inverse agonists) may produce various pharmacological effects like marijuana. In particular, substances having affinity to central CB1 receptor may be useful for treatment of a CNS disease such as a psychotic disorder, a neurological disorder and the like.

Examples of the known substances having affinity to CB1 receptor include a 4,5-dihydro-1H-pyrazole compound (WO01/70700, WO03/026648, WO03/026647), a 1H-imidazole compound (WO03/027076, WO03/007887, WO03/063781, WO03/040107), a pyrazine compound (WO03/051850, WO03/051851), a 1H-pyrazole compound (U.S. Pat. No. 5,624,941, U.S. Pat. No. 6,509,367), a pyridine compound (WO03/084930, WO03/084943, WO03/082191), an azethidine compound (WO01/64632, WO03/020314), an arylamide compound (WO03/087027, WO03/082190), a 1,5,6,7-tetrahydropyrrolo[3,2-c]pyridine compound (WO03/027114), a pyrrole compound (WO03/027069) and a 1,2,4-triazole compound (WO03/082833). Meanwhile, JP1993-17434 discloses that specific pyrrolidine compounds such as 4-amino-5-chloro-N-[1-(diphenylmethyl)-5-(hydroxymethyl)-3-pyrrolidinyl]-2-methoxy-benzamide increased gastric motility in mice, but there are no suggestion on whether or not the pyrrolidine compound has an antagonistic activity against CB1 receptor.

DISCLOSURE OF INVENTION

The present invention provides a novel pyrrolidine compound or a pharmaceutically acceptable salt thereof having a potent antagonistic activity against central cannabinoid (CB1) receptor and being useful as a medicament and a process for preparing the same.

The present invention relates to a compound of the formula [I]:

[I]

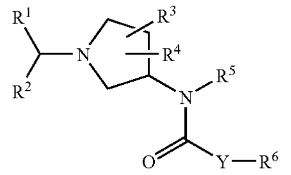

wherein each of $R^1$ and $R^2$ is (A) independently an aryl (or heteroaryl) group optionally substituted by the same or different one to three group(s) selected from (1) a halogen atom, (2) cyano group, (3) an alkyl group optionally substituted by one to three groups selected from a halogen atom and an alkyloxy group, (4) an alkyloxy group optionally substituted by one to three groups selected from a halogen atom, a cycloalkyl group, an alkyloxy group, a mono- or di-alkylamino group, a pyrrolidinyl group and a morpholino group, (5) an amino group optionally substituted by a group selected from an alkyl group, an alkyloxyalkyl group, a cycloalkyl group and a mono- or di-alkylamino-alkyl group, (6) a carbamoyloxy group optionally substituted by one to two alkyl groups, (7) an alkylsulfonyl group, (8) a cycloalkyloxy group, (9) a carbamoyl group optionally substituted by an alkyl group(s), (10) a nitro group, (11) an alkylthio group, (12) an aminosulfonyl group optionally substituted by an alkyl group(s), (13)) an alkylsulfinyl group, (14) an alkyleneoxy group and (15) an alkylenedioxy group, or (B) both of the groups combine each other together with an adjacent CH group to form a group of the formula:

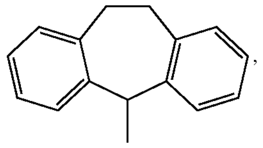

one of $R^3$ and $R^4$ is a hydrogen atom and another is a hydrogen atom, a hydroxyl group, a hydroxyalkyl group, a dialkylaminoalkyl group, an alkyloxy group, an alkyloxyalkyl group, an alkyloxyalkyloxy group, a carboxyl group, an alkyloxycarbonyl group, a saturated or unsaturated, 4- to 10-membered, nitrogen- or oxygen-containing heterocyclic group, a carbamoyl group or a mono- or dialkylcarbamoyl group (the alkyl moiety of said group being optionally substituted by a group selected from a halogen atom, a hydroxyl group, a mono- or di-alkylamino group and a saturated or unsaturated, 4- to 10-membered, nitrogen- or oxygen-containing heterocyclic group) or both of $R^3$ and $R^4$ combine each other to form an oxo group, $R^5$ is a hydrogen atom or an alkyl group, Y is a single bond, an oxygen atom or a group of the formula: —N($R^7$)—, $R^6$ is (1) a straight or branched chain hydrocarbon group optionally having a substituent(s) and optionally containing one or more double or triple bond in the molecule or (2) a cyclic group optionally having a substituent(s) and optionally containing one or more heteroatoms selected from a sulfur atom, an oxygen atom and a nitrogen atom, $R^7$ is an alkyl group or an alkyloxycarbonylalkyl group, provided that $R^6$ is not 4-amino-5-chloro-2-methoxyphenyl group when Y is a single bond and one of the $R^3$ and $R^4$ is hydrogen atom and another is hydroxymethyl group, or a pharmaceutically acceptable salt thereof.

In the compounds [I] of the present invention, examples of the aryl (or heteroaryl) group in $R^1$ and $R^2$ include a 5- or 6-membered aryl group (or 5- to 10 membered heteroaryl group having one or more heteroatom(s) selected from sulfur atom, oxygen atom and nitrogen atom) such as a phenyl group, a thienyl group, a pyridyl group, a pyrazinyl group, a benzofuranyl group, a benzimidazolyl group, a quinolyl group, a thiazolyl group, a pyrimidinyl group, a benzothiazolyl group and the like. Said aryl (or heteroaryl) group may be substituted by the same or different one to three groups selected from (1) a halogen atom, (2) a cyano group, (3) an alkyl group optionally substituted by one to three groups selected from a halogen atom, a cycloalkyl group and an alkyloxy group, (4) an alkyloxy group optionally substituted by one to three groups selected from a halogen atom, an alkyloxy group and a mono- or di-alkylamino group, (5) an amino group optionally substituted by an alkyl group, an alkyloxyalkyl group, a cycloalkyl group and a mono- or dialkylamino-alkyl group, (6) a carbamoyloxy group optionally substituted by one to two alkyl groups, (7) an alkylsulfonyl group, (8) a cycloalkyloxy group, (9) a carbamoyl group optionally substituted by an alkyl group(s), (10) a nitro group, (11) an alkylthio group, (12) an aminosulfonyl group optionally substituted by an alkyl group(s), (13) an alkylsulfinyl group, (14) an alkyleneoxy group and (15) an alkylenedioxy group.

Examples of the saturated or unsaturated, 4- to 10-membered, nitrogen- or oxygen-containing heterocyclic group in $R^3$ and $R^4$ include a heterocyclic group such as a pyrrolidinyl group, a morpholinyl group, a pyridyl group and the like. Among them, preferred examples of such group include a saturated or unsaturated, 5- to 6-membered, nitrogen-containing heterocyclic group.

In case that the $R^6$ is a straight or branched chain hydrocarbon group optionally having a substituent(s), examples of such group include a straight or branched chain $C_{1-12}$-hydrocarbon group optionally having a substituent(s). More concretely, the hydrocarbon group may be (1) a straight or branched chain $C_{1-12}$-alkyl group optionally having a substituent(s), (2) a straight or branched chain $C_{2-12}$-alkenyl group optionally having a substituent(s) or (3) a straight or branched chain $C_{2-12}$-alkynyl group optionally having a substituent(s).

In case that the $R^6$ is a straight or branched chain hydrocarbon group having a substituent(s), such hydrocarbon groups include a hydrocarbon group having the same or different one to three substituents selected from the group consisting of: (1) a cycloalkyl group optionally fused to a benzene ring, (2) an amino group optionally substituted by the same or different one or two groups selected from an alkyl group, an alkyloxycarbonyl group, an alkylcarbonyl group, an arylalkyloxycarbonyl group, an alkylsulfonyl group, a morpholinocarbonyl group, a mono- or dialkyl-carbamoyl group, a mono- or di-alkylaminosulfonyl group, a halogenoalkylcarbonyl group and an alkyloxycarbonylcarbamoyl group, (3) an aryl (or biaryl) group optionally substituted by the same or different one to three groups selected from a halogen atom, a hydroxyl group, an alkyl group, an alkyloxy group, a trihalogenoalkyl group, a trihalogenoalkyloxy group, an alkyloxyalkyloxy group, a morpholinoalkyloxy group, an alkyloxycarbonyl group, a mono- or di-alkylamino group and an alkyloxycarbonylamino group, (4) a saturated or unsaturated, 3- to 14-membered, sulfur-, nitrogen- or oxygen-containing heterocyclic group optionally substituted by the same or different one to three groups selected from a halogen atom, an oxo group, an alkyl group, an alkyloxycarbonyl group, an arylalkyloxycarbonyl group, a trihalogenoalkyl group, an alkylthio group and an aryl group, (5) a hydroxyl group, (6) an alkyloxy group optionally substituted by the same or different one to three groups selected from an alkyloxy group and aryl group, (7) an alkenyoxy group, (8) an aryloxy group optionally fused to a cycloalkyl ring and optionally substituted by the same or different one to three groups selected from a halogen atom, an alkyl group and a trihalogenoalkyloxy group, (9) a group of the formula: —$SR_a$ in which $R_a$ is an aryl group, an arylalkyl group or a saturated or unsaturated, 4- to 10-membered, nitrogen- or oxygen-containing heterocyclic group, (10) an alkyloxycarbonyl group, (11) an arylalkyloxycarbonyl group, (12) a cycloalkylcarbonyl group, (13) an arylcarbonyl group optionally substituted by the same or different one to three groups selected from a halogen atom and a trihalogenoalkyl group, (14) an arylsulfonyl group, and (15) a halogen atom.

In case that the substituent(s) in the straight or branched chain hydrocarbon group ($R^6$) is a saturated or unsaturated, 3- to 14-membered, sulfur-, oxygen- or nitrogen-containing heterocyclic group or a group containing said heterocyclic group, such heterocyclic group may be selected from a group of the formula:

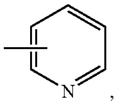 , 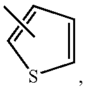 , 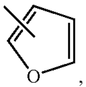 , 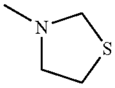 ,

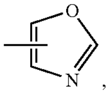 , 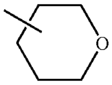 , 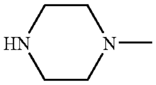 ,

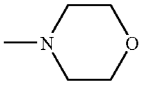 , 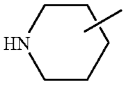 , 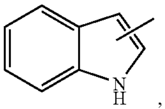 ,

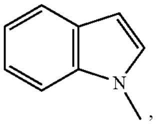 , 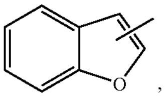 , 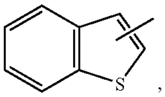 ,

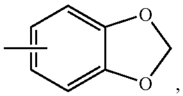 , 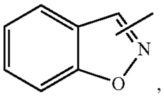 ,

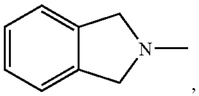 , 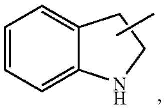 ,

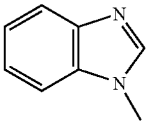 , 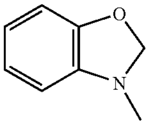 ,

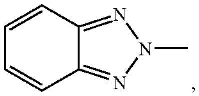 , 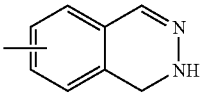 ,

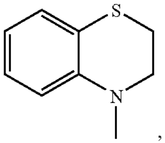 , 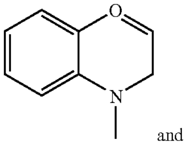 and

-continued

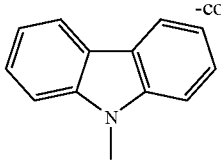

and said heterocyclic group may be further hydrogenated.

In case that $R^6$ is an optionally substituted cyclic group, examples of such cyclic group include a group selected from (1) an optionally substituted, 6- to 14-membered, mono-, bi- or tri-cyclic aryl group, (2) an optionally substituted mono-cyclo-, bicyclo- or tri-cyclo-$C_{3-10}$ alkyl group (said cycloalkyl group being optionally fused to a benzene ring), and (3) a saturated or unsaturated, 3- to 14-membered, sulfur-, nitrogen- or oxygen-containing heterocyclic group optionally having a substituent and optionally forming a spiro-ring with a cycloalkyl ring.

In case that the cyclic group represented by $R^6$ is an aryl group, such aryl group may be a phenyl group, a naphthyl group, a fluorenyl group and the like.

In case that the cyclic group represented by $R^6$ is a mono-cyclo-, bicyclo- or tricyclo-alkyl group such monocyclo-, bicyclo- or tricyclo-alkyl group may be a cyclopropyl group, a cyclobutyl group, a cyclopentyl group, a cyclohexyl group, a tricyclo[2.2.1.0]heptyl group and the like.

In case that the cyclic group represented by $R^6$ is a heterocyclic group, such heterocyclic group may be (1) a heteromonocyclic group selected from a pyrrolyl group, an imidazolyl group, a pyrazolyl group, a pyrrolidinyl group, a pyrrolinyl group, a 3H-pyrrolinyl group, an imidazolidinyl group, an imidazolinyl group, a pyrrazolidinyl group, a pyrrazolinyl group, a thiazolidinyl group, a piperidyl group, a piperazinyl group, an azethidinyl group, an isothiazolyl group, an isoxazolyl group, a pyridyl group, a pyrazinyl group, a pyrimidinyl group, a pyridazinyl group, a thienyl group, a thiazolyl group, a furyl group, a pyranyl group and a morpholinyl group, (2) a heterobicyclic group selected from a 1H-indazolyl group, an indolizinyl group, an indolyl group, a 3H-indolyl group, an isoindolyl group, an indolinyl group, an isoindolinyl group, a purinyl group, a quinolyl group, a tetrahydroquinolyl group, an isoquinolyl group, a tetrahydroisoquinolyl group, a phthalazinyl group, a naphthyridinyl group, a quinoxalinyl group, a quinazolinyl group, a cinnolinyl group, a pteridinyl group, a pyrazolopyrimidinyl group, a chromanyl group, an isochromanyl group, a chromenyl group, a benzotriazolyl group, a 2H-benzotriazolyl group, a benzofuranyl group, an isobenzofuranyl group, a dihydrobenzofuranyl group, a phthalimido group, a benzothienyl group, a benzoxazolyl group, a benzoisoxazolyl group, a benzoxazinyl group, a benzimidazolyl group, a furopyridyl group and a group of the formula:

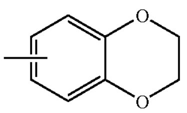

or

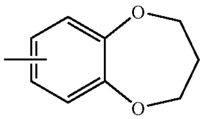

, (3) a heterotricyclic group selected from a furonaphthyl group, a dihydrofuronaphthyl group, a carbazolyl group, a β-carbolinyl group and a group of the formula:

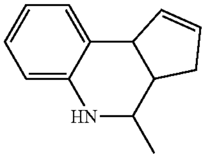

or (4) an oxaspirodecyl group.

Among the heterocyclic group mentioned above, a preferred example of the heterocyclic group may be a group of the formula:

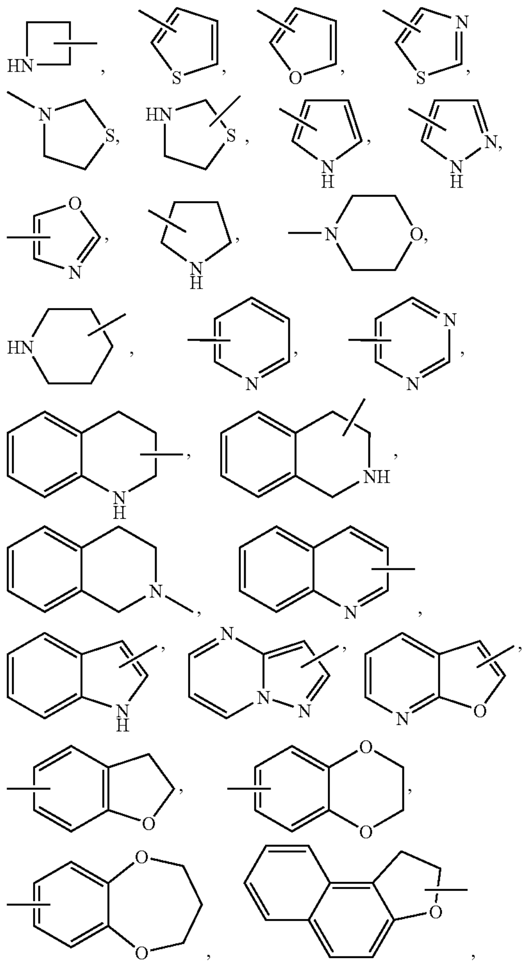

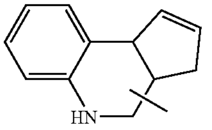

or

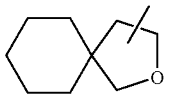

, and said heterocyclic group may be further hydrogenated.

In case that $R^6$ is a substituted cyclic group, examples of such cyclic group include those substituted by the same or different one to four groups selected from the group consisting of (1) a halogen atom, (2) an oxo group, (3) a nitro group, (4) a cyano group, (5) an alkyl group optionally substituted by the same or different one to three groups selected from a halogen atom, an arylcarbonyl group, a mono-, di- or tri-halogeno-arylcarbonyl group, an aryl group, a hydroxyl group, a saturated or unsaturated, 4- to 10-membered, nitrogen- or oxygen-containing heterocyclic group optionally substituted by an oxo group, an alkyloxy group and an imino group, (6) an aminoalkyl group (the amino moiety of said group being optionally substituted by the same or different one to two groups selected from an alkyloxycarbonyl group, an arylcarbonyl group, an aryl-alkyloxy-carbonyl group, an alkyl group an alkyloxyalkyl group and a cycloalkyl group), (7) a cycloalkyl group, (8) an alkenyl group optionally substituted by an alkyloxy-carbonyl group, (9) an amino group optionally substituted by one to two groups selected from an alkyl group, an alkyloxycarbonyl group, an arylalkyloxycarbonyl group, an alkyloxyalkyl group and a halogenoalkylcarbonyl group, (10) an aryl group optionally substituted by the same or different one to three groups selected from a halogen atom and a saturated or unsaturated, 4- to 10-membered, nitrogen- or oxygen-containing heterocyclic group, (11) a saturated or unsaturated, 4- to 10-membered, nitrogen- or oxygen-containing heterocyclic group optionally substituted by the same or different one to three groups selected from a halogen atom, an oxo group and a saturated or unsaturated, 4- to 10-membered, nitrogen- or oxygen-containing heterocyclic group, (12) an alkyloxy group optionally substituted by the same or different one to three groups selected from a halogen atom, an alkyloxy group, an aryl group, a saturated or unsaturated, 4- to 10-membered, nitrogen- or oxygen-containing heterocyclic group and a mono- or di-alkylamino group, (13) a cycloalkyloxy group, (14) a cycloalkenyloxy group, (15) an aryloxy group, (16) an arylcarbonyl group optionally substituted by the same or different one to three halogen atom(s), (17) an alkylcarbonyl group, (18) an alkyloxycarbonyl group, (19) an arylalkyloxycarbonyl group, (20) a group of the formula: —$SO_2R_b$ in which $R_b$ is an alkyl group, an aryl group optionally substituted by one to three halogen atoms, an amino group optionally substituted by one to two alkyl groups or a saturated or unsaturated, 4- to 10-membered, nitrogen- or oxygen-containing heterocyclic group optionally substituted by the same or different one to three alkyl groups, (21) an alkynyl group optionally substituted by a group selected from a mono- or di-alkylamino group and a saturated or unsaturated, 4- to 10-membered, nitrogen- or oxygen-containing heterocyclic group, (22) an alkylthio group (the alkyl moiety of said group being optionally substituted by a group selected from a hydroxyl group and an alkyloxy group), (23) a carbamoyl group (the amino moiety of said group being optionally substituted by an alkyl group) and (24) a carbamoyloxy group optionally substituted by one or two alkyl groups.

In case that the substituent(s) in the straight or branched chain hydrocarbon group represented by $R^6$ in the present compound [I] is an aryl group or an aryl-containing group, such aryl group may be a 6- to 14-membered, monocyclic-, bicyclic- or tricyclic-aryl group such as a phenyl group, a naphthyl group, a fluorenyl group and the like. Among them, preferred example may be a phenyl group. Besides, examples of the biaryl group include a biphenyl group.

In case that the substituent(s) in the straight or branched chain hydrocarbon group represented by $R^6$ is a group containing a saturated or unsaturated, 4- to 10-membered, nitrogen- or oxygen-containing heterocyclic group, such 4- to 10-membered heterocyclic group may be a furyl group, a pyrrolidinyl group, a piperidinyl group, a morpholinyl group, a pyridyl group, a piperazinyl group, benzimidazolyl group and the like.

More specific examples of the compound [I] in the present invention include, for example, a compound in which:

(A) $R^1$ and $R^2$ are (a) the same or different and a phenyl group optionally substituted by one to three groups selected from a halogen atom, a $C_{1-6}$ alkyloxy group and a cyano group, or (b) both of the groups combine together with an adjacent CH group to form a group of the formula:

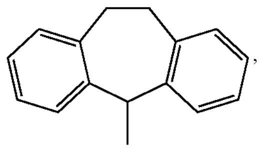

one of $R^3$ and $R^4$ is a hydrogen atom and another is a hydrogen atom or a hydroxyl group, $R^5$ is a hydrogen atom or a $C_{1-6}$ alkyl group, Y is a single bond or —O—, and $R^6$ is a straight or branched chain $C_{1-10}$ alkyl group optionally substituted by one to three groups selected from the group consisting of the following (i) to (xvii):

(i) a $C_{3-8}$ cycloalkyl group; (ii) a benzo-$C_{3-8}$ cycloalkyl group; (iii) an amino group (said group being optionally substituted by one or two groups selected from a $C_{1-6}$ alkyl group, a $C_{1-6}$ alkyloxy-carbonyl-carbamoyl group, a $C_{1-6}$ alkyloxy-carbonyl group, a $C_{1-6}$ alkyl-carbonyl group, a trihalogeno-$C_{1-6}$ alkyl-carbonyl group, a phenyl-$C_{1-6}$ alkyloxy-carbonyl group, a $C_{1-6}$ alkylsulfonyl group, a morpholino-carbonyl group, a carbamoyl group substituted by one or two $C_{1-6}$ alkyl groups and an aminosulfonyl group substituted by one or two $C_{1-6}$ alkyl groups); (iv) an aryl group selected from a phenyl group, a naphthyl group and a fluorenyl group (said aryl group being optionally substituted by one to three groups selected from a halogen atom, a hydroxyl group, a $C_{1-6}$ alkyl group, a $C_{1-6}$ alkyloxy group, a trihalogeno-$C_{1-6}$ alkyl group, a trihalogeno-$C_{1-6}$ alkyloxy group, a di($C_{1-6}$ alkyl)amino group and a $C_{1-6}$ alkyloxy-carbonylamino group); (v) a biphenyl group optionally substituted by a halogen atom(s); (vi) a saturated or unsaturated, 5- to 14-membered sulfur-, nitrogen- or oxygen-containing heterocyclic group (said heterocyclic group being optionally substituted by one to two groups selected from a halogen atom, an oxo group, a $C_{1-6}$ alkyl group, a $C_{1-6}$ alkyloxy-carbonyl group, a phenyl-$C_{1-6}$ alkyloxy-carbonyl group, a trihalogeno-$C_{1-6}$ alkyl group, a $C_{1-6}$ alkylthio group and a phenyl group); (vii) a hydroxyl group; (viii) a $C_{1-6}$ alkyloxy group (alkyl moiety of said group being optionally substituted by one to two groups selected from a $C_{1-6}$ alkyloxy group and a phenyl group); (ix) a $C_{2-6}$ alkenyloxy group; (x) an aryloxy group selected from a phenoxy group and a naphthyloxy group (aryl moiety of said group being optionally substituted by one to two groups selected from a halogen atom, a $C_{1-6}$ alkyl group and a trihalogeno-$C_{1-6}$ alkyloxy group, and being optionally fused to a $C_{3-8}$ cycloalkyl ring); (xi) a phenylthio group; (xii) a pyridylthio group; (xiii) a $C_{1-6}$ alkyloxy-carbonyl group (alkyl moiety of said group being optionally substituted by a phenyl group); (xiv) a $C_{3-8}$ cycloalkyl-carbonyl group; (xv) a benzoyl group; (xvi) a benzenesulfonyl group; and (xvii) a halogen atom; or (B) $R^1$ and $R^2$ are the same or different and a phenyl group optionally substituted by one to three halogen atoms, both $R^3$ and $R^4$ are a hydrogen atom, $R^5$ is a hydrogen atom, Y is a single bond and $R^6$ is a straight or branched chain $C_{2-6}$ alkenyl (or $C_{2-6}$ alkynyl) group optionally substituted by one or two groups selected from the group consisting of the following (i) to (iii):

(i) a phenyl group optionally-substituted by one to three groups selected from a halogen atom, a $C_{1-6}$ alkyl group, a trihalogeno-$C_{1-6}$ alkyl group, a $C_{1-6}$ alkyloxy group, a $C_{1-6}$ alkyloxy-carbonyl group, a $C_{1-6}$ alkyloxy-$C_{1-6}$ alkyloxy group and a morpholino-$C_{1-6}$ alkyloxy group; (ii) a saturated or unsaturated 5- to 10-membered nitrogen- or oxygen-containing heterocyclic group optionally substituted by a halogen atom(s); and (iii) a phenyl-$C_{1-6}$ alkylthio group; or (C) $R^1$ and $R^2$ are the same or different and (a) a phenyl group optionally substituted by one to three groups selected from a group consisting of the following (i) to (xvi):

(i) a halogen atom; (ii) a cyano group; (iii) a nitro group; (iv) a $C_{1-6}$ alkyl group optionally substituted by one to three halogen atoms; (v) a $C_{1-6}$ alkyloxy-$C_{1-6}$ alkyl group; (vi) a $C_{1-6}$ alkyloxy group optionally substituted by one to three groups selected from a halogen atom, a di($C_{1-6}$ alkyl)amino group, a pyrrolidinyl group and a morpholino group; (vii) a $C_{1-6}$ alkyloxy-$C_{1-6}$ alkyloxy group; (viii) an amino group optionally substituted by one or two groups selected from a $C_{1-6}$ alkyl group, a $C_{1-6}$ alkyloxy-$C_{1-6}$ alkyl group, a $C_{3-8}$ cycloalkyl group and a di($C_{1-6}$ alkyl)amino-$C_{1-6}$ alkyl group; (ix) a di($C_{1-6}$ alkyl)carbamoyl group; (x) a $C_{1-6}$ alkylthio group; (xi) a $C_{1-3}$ alkyleneoxy group; (xii) a $C_{1-3}$ alkylenedioxy group; (xiii) a di($C_{1-6}$ alkyl)aminosulfonyl group; (xiv) a $C_{1-6}$ alkylsulfonyl group; (xv) a di($C_{1-6}$ alkyl)carbamoyloxy group and (xvi) a $C_{1-6}$ alkylsulfinyl group or (b) a sulfur-, oxygen- or nitrogen-containing 5- to 10 membered monocyclic or bicyclic heteroaryl group optionally substituted by one to three groups selected from a halogen atom, a cyano group, a $C_{1-6}$ alkyl group optionally substituted by one to three groups selected from a halogen atom and a $C_{1-6}$ alkyloxy group, a di($C_{1-6}$ alkyl) amino group, a $C_{3-8}$ cycloalkyloxy group, and a $C_{1-6}$ alkyloxy group optionally substituted by one to three groups selected from a halogen atom, a $C_{1-6}$ alkyloxy group and a $C_{3-8}$ cycloalkyl group, one of $R^3$ and $R^4$ is (a) a hydrogen atom and another is a hydrogen atom, a hydroxyl group, a carboxyl group, a hydroxy-$C_{1-6}$ alkyl group, a $C_{1-6}$ alkyloxy group, a $C_{1-6}$ alkyloxy-$C_{1-6}$ alkyl group, a $C_{1-6}$ alkyloxy-carbonyl group, a di($C_{1-6}$ alkyl)amino-$C_{1-6}$ alkyl group, a carbamoyl group (said group being optionally substituted by one or two groups selected from a di($C_{1-6}$ alkyl)amino-$C_{1-6}$ alkyl group, a morpholino-$C_{1-6}$ alkyl group, a hydroxy-$C_{1-6}$ alkyl group, a $C_{1-6}$ alkyl group, a halogeno-$C_{1-6}$ alkyl group and a pyridyl-$C_{1-6}$ alkyl group), a morpholino group or a pyrrolidinyl group or (b) $R^3$ and $R^4$ combine each other to form an oxo group, $R^5$ is a hydrogen atom or a $C_{1-6}$ alkyl group, Y is a single bond and $R^6$ is a 6- to 11-membered mono-, bi- or tri-cyclic aryl group optionally substituted by one to three groups selected from the group consisting of the following (i) to (xxv):

(i) a halogen atom; (ii) an oxo group; (iii) a nitro group; (iv) a cyano group; (v) a $C_{1-6}$ alkyl group (said group being optionally substituted by one to three groups selected from a halogen atom, a hydroxyl group, a $C_{1-6}$ alkyloxy group, a phenyl group, a morpholino group, a pyrrolidinyl group, an oxopyrrolidinyl group and a benzimidazolyl group); (vi) an amino-$C_{1-6}$ alkyl group (amino moiety of said group being optionally substituted by one or two groups selected from a $C_{1-6}$ alkyl group, a $C_{1-6}$ alkyloxy-$C_{1-6}$ alkyl group, a $C_{3-8}$ cycloalkyl group, a $C_{1-6}$ alkyloxy-carbonyl group and a phenyl-$C_{1-6}$ alkyloxycarbonyl group); (vii) a $C_{3-8}$ cycloalkyl group; (viii) a $C_{1-6}$ alkyloxy-carbonyl-$C_{2-6}$ alkenyl group; (ix) an amino group (said group being optionally substituted by one or two groups selected from a $C_{1-6}$ alkyl group, a $C_{1-6}$ alkyloxy-$C_{1-6}$ alkyl group, a trihalogeno-$C_{1-6}$ alkyl-carbonyl group, a $C_{1-6}$ alkyloxy-carbonyl group and a phenyl-$C_{1-6}$ alkyloxycarbonyl group); (x) a phenyl group; (xi) a heterocyclic group selected from a pyrazolyl group, a pyrrolyl group, a piperidyl group and a morpholino group (said heterocyclic group being optionally substituted by one to three groups selected from a halogen atom, an oxo group and a pyrimidinyl group); (xii) a $C_{1-8}$ alkyloxy group (said group being optionally substituted by one to three groups selected from a halogen atom, a $C_{1-6}$ alkyloxy group, a phenyl group, a morpholino group and an amino group substituted by one or two $C_{1-6}$ alkyl groups), (xiii) a $C_{3-8}$ cycloalkyloxy group; (xiv) a $C_{3-8}$ cycloalkenyloxy group; (xv) a phenoxy group; (xvi) a benzoyl group; (xvii) a $C_{1-6}$ alkyl-carbonyl group; (xviii) a $C_{1-6}$ alkyloxy-carbonyl group; (xix) an aminosulfonyl group optionally substituted by one or two $C_{1-6}$ alkyl groups; (xx) a piperazinylsulfonyl group optionally substituted by one to three $C_{1-6}$ alkyl groups; (xxi) a $C_{2-6}$ alkynyl group optionally substituted by one or two groups selected from an amino group substituted by one or two $C_{1-6}$ alkyl groups and a pyrrolidinyl group; (xxii) a $C_{1-6}$ alkylthio group optionally substituted by a hydroxyl group; (xxiii) a $C_{1-6}$ alkyloxy-$C_{1-6}$ alkylthio group; (xxiv) a carbamoyl group optionally substituted by one or two $C_{1-6}$ alkyl groups; and (xxv) a di($C_{1-6}$ alkyl)carbamoyloxy group; or (D) $R^1$ and $R^2$ are the same or different and a phenyl group optionally substituted by one to three halogen atoms, one of $R^3$ and $R^4$ is a hydrogen atom, another is a hydrogen atom or a $C_{1-6}$ alkyloxy group, $R^5$ is a hydrogen atom, Y is a single bond and $R^6$ is a $C_{3-10}$ mono- bi- or tri-cycloalkyl group (said cycloalkyl group being optionally fused to a benzene ring) optionally substituted by one to four groups selected from the group consisting of the following (i) to (vi):

(i) an oxo group; (ii) a $C_{1-6}$ alkyl group optionally substituted by a halogenobenzoyl group; (iii) an amino-a $C_{1-6}$ alkyl group (amino moiety of said group being optionally substituted by a $C_{1-6}$ alkyloxy-carbonyl group; (iv) an amino group optionally substituted by a $C_{1-6}$ alkyloxy-carbonyl group; (v) a phenyl group optionally substituted by one to three halogen atoms; and (vi) a benzoyl group optionally substituted by one to three halogen atoms; or (E) $R^1$ and $R^2$ are the same or different and (a) a phenyl group optionally substituted by one to three groups selected from a halogen atom, a cyano group, a $C_{1-6}$ alkyloxy group, a trifluoro-$C_{1-6}$ alkyl group, an amino group substituted by one or two groups selected from a $C_{1-6}$ alkyl group and a di($C_{1-6}$ alkyl)carbamoyloxy group and a $C_{1-6}$ alkyloxy-$C_{1-6}$ alkyl group or (b) a sulfur-, oxygen- or nitrogen-containing 5- to 10-membered heteroaryl group optionally substituted by one to three groups selected from a $C_{1-6}$ alkyloxy group, a di($C_{1-6}$ alkyl)amino group, a $C_{3-8}$ cycloalkyloxy group, a $C_{3-8}$ cycloalkyl-$C_{1-6}$ alkyloxy group and a trihalogeno-$C_{1-6}$ alkyloxy group, one of $R^3$ and $R^4$ is a hydrogen atom, another is a hydrogen atom or a $C_{1-6}$ alkyloxy group, $R^5$ is a hydrogen atom, Y is a single bond and $R^6$ is a saturated or unsaturated 3- to 14-membered, monocyclic- bicyclic- or tricyclic-heterocyclic group (said heterocyclic group optionally constituting a spiro-ring with a $C_{3-8}$ cycloalkyl group) optionally substituted by one to three groups selected from the group consisting of the following (i) to (xiv):

(i) an oxo group; (ii) a halogen atom; (iii) a cyano group; (iv) a $C_{1-6}$ alkyl group (said group being optionally substituted by one to three groups selected from a halogen atom, a $C_{1-6}$ alkyloxy group, an imino group, a phenyl group and a pyrrolidinyl group); (v) an amino-$C_{1-6}$ alkyl group (amino moiety of said group being optionally substituted by one or two $C_{1-6}$ alkyl groups); (vi) an amino group optionally substituted by one or two $C_{1-6}$ alkyl groups; (vii) a phenyl group optionally substituted by one to three halogen atoms;

(viii) a heterocyclic group selected from a furyl group, a pyridyl group and a pyrimidinyl group; (ix) a $C_{1-6}$ alkyloxy group optionally substituted by one to three groups selected from halogen atoms and a phenyl group; (x) a $C_{1-6}$ alkyl-carbonyl group; (xi) a $C_{1-6}$ alkyloxy-carbonyl group; (xii) a $C_{1-6}$ alkylsulfonyl group; (xiii) an aminosulfonyl group; (xiv) a benzenesulfonyl group optionally substituted by one to three halogen atoms; and (xv) a morpholinosulfonyl group; or (F) $R^1$ and $R^2$ are the same or different and a phenyl group optionally substituted by one to three halogen atoms, both $R^3$ and $R^4$ are a hydrogen atom, $R^5$ is a hydrogen atom, Y is a group of the formula: —$NR^7$—, $R^6$ is a $C_{1-6}$ alkyl group optionally substituted by a phenyl groups or a phenyl group optionally substituted by one to three halogen atoms and $R^7$ is a $C_{1-6}$ alkyl group or a $C_{1-6}$ alkyloxy-carbonyl-$C_{1-6}$ alkyl group.

In case that the cyclic group represented by $R^6$ in the compound [I] of the present invention is a substituted aryl group, preferred examples of such aryl group may be an aryl group substituted by the same or different one to three groups selected from an oxo group, a cyano group, a nitro group, a halogen atom, a $C_{1-6}$ alkyl group, a trifluoro-$C_{1-6}$ alkyl group, a diphenyl-$C_{1-6}$ alkyl group, a di($C_{1-6}$ alkyl)amino-$C_{1-6}$ alkyl group, a phenyl-$C_{1-6}$ alkyl group, a pyrrolidinyl-$C_{1-6}$ alkyl group, a benzimidazolyl-$C_{1-6}$ alkyl group, a $C_{1-9}$ alkyloxy group, a di- or tri-fluoro-$C_{1-6}$ alkyloxy group, a phenoxy group, a phenyl-$C_{1-6}$ alkyloxy group, a $C_{1-6}$ alkyloxy-$C_{1-6}$ alkyloxy group, an aminosulfonyl group, a di($C_{1-6}$ alkyl)aminosulfonyl group, a di($C_{1-6}$ alkyl)amino group, a $C_{1-6}$ alkyloxy-carbonylamino group, a $C_{1-6}$ alkyloxy-carbonyl group, a phenyl-$C_{1-6}$ alkyloxycarbonyl-amino group, a $C_{1-6}$ alkyloxy-carbonyl-$C_{2-6}$ alkenyl group, a $C_{1-6}$ alkyl-carbonyl group, a $C_{1-6}$ alkylthio group, a-di($C_{1-6}$ alkyl)carbamoyloxy group, a benzoyl group, a phenyl group, a $C_{3-8}$ cycloalkyl group, a $C_{3-8}$ cycloalkenyloxy group, a $C_{3-8}$ cycloalkyloxy group, a pyrrolyl group, an oxopyrrolidinyl group, a piperidyl group, a $C_{1-6}$ alkyl-piperazinyl-sulfonyl group, a pyrimidinyl-pyrazolyl group, a $C_{1-6}$ alkyloxy-carbonylamino-$C_{1-6}$ alkyl group, a phenyl-$C_{1-6}$ alkyloxy-carbonylamino-$C_{1-6}$ alkyl group, a di($C_{1-6}$ alkyl)amino-$C_{2-6}$ alkynyl group, a N—($C_{1-6}$ alkyloxy-$C_{1-6}$ alkyl)-N—($C_{1-6}$ alkyl)amino-$C_{1-6}$ alkyl group, a N—($C_{3-8}$ cycloalkyl)-N—($C_{1-6}$ alkyl)amino-$C_{1-6}$ alkyl group, a N-(trifluoro-$C_{1-6}$ alkyl-carbonyl)-N—($C_{1-6}$ alkyl)amino group, a pyrrolidinyl-$C_{2-6}$ alkynyl group, a $C_{1-6}$ alkyloxy-$C_{1-6}$ alkyl group, a hydroxy-$C_{1-6}$ alkyl group, a morpholino-$C_{1-6}$ alkyl group, a di($C_{1-6}$ alkyl)amino-$C_{1-6}$ alkyloxy group, a morpholino-$C_{1-6}$ alkyloxy group, a $C_{1-6}$ alkylthio group, a $C_{1-6}$ alkyloxy-$C_{1-6}$ alkylthio group, a hydroxy-$C_{1-6}$ alkylthio group, a di($C_{1-6}$ alkyl)carbamoyl group and a di($C_{1-6}$ alkyl)carbamoyloxy group.

In case that the $R^6$ is a substituted cycloalkyl group, preferred examples of such cycloalkyl group may be a mono-, bi- or tri-cycloalkyl group (said cycloalkyl group being optionally fused to a benzene ring) substituted by the same or different one to four groups selected from an oxo group, a $C_{1-6}$ alkyl group, a $C_{1-6}$ alkyloxy-carbonylamino-$C_{1-6}$ alkyl group, a halogenobenzoyl-$C_{1-6}$ alkyl group, a $C_{1-6}$ alkyloxy-carbonylamino group, a halogenobenzoyl group, a phenyl group and a halogenophenyl group.

In case that the $R^6$ is a substituted heterocyclic group, preferred examples of such heterocyclic group may be a heterocyclic group substituted by the same or different one to three groups selected from an oxo group, a chlorine atom, a bromine atom, a cyano group, a $C_{1-6}$ alkyl group, a $C_{1-6}$ alkyloxy group, a diphenyl-$C_{1-6}$ alkyl group, $C_{1-6}$ alkyl-carbonyl group, a trifluoro-$C_{1-6}$ alkyl group, a trifluoro-$C_{1-6}$ alkyloxy group, a $C_{1-6}$ alkyloxycarbonyl group, a di($C_{1-6}$ alkyl)amino-$C_{1-6}$ alkyl group, a di($C_{1-6}$ alkyl)amino group, a phenyl group, a chlorophenyl group, a pyrrolidinyl-$C_{1-6}$ alkyl group, a pyridyl group, a pyrimidinyl group, a furyl group, a $C_{1-6}$ alkyl-sulfonyl group, an aminosulfonyl group, a morpholinosulfonyl group, a benzenesulfonyl group, a $C_{1-6}$ alkyloxy-imino-$C_{1-6}$ alkyl group, a chlorobenzenesulfonyl group, a benzyl group and a benzyloxy group.

Among the above-mentioned compounds [I] of the present invention, examples of the preferred compound may be those in which $R^1$ is a group of the formula:

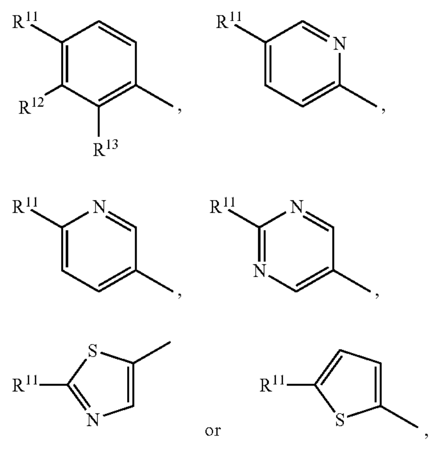

or $R^2$ is a group of the formula:

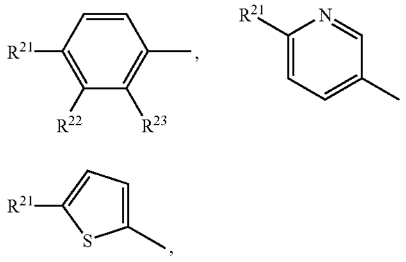

or each of $R^{11}$ and $R^{21}$ is independently a hydrogen atom, a cyano group, a halogen atom, a $C_{1-6}$ alkyloxy group optionally substituted by one to three groups selected from a halogen atom and a $C_{1-6}$ alkyloxy group, a $C_{1-6}$ alkyl group optionally substituted by one to three groups selected from a halogen atom and a $C_{1-6}$ alkyloxy group, a di($C_{1-6}$ alkyl) carbamoyloxy group, a $C_{3-8}$ cycloalkyloxy group, a $C_{3-8}$ cycloalkyl-$C_{1-6}$ alkyloxy group, a $C_{1-6}$ alkylthio group, a di($C_{1-6}$ alkyl)amino-$C_{1-6}$ alkyloxy group or a group of the formula: $(R^{14})(R^{15})N$—, each of $R^{12}$ and $R^{22}$ is independently a hydrogen atom, a halogen atom or a morpholino-$C_{1-6}$ alkyloxy group, each of $R^{13}$ and $R^{23}$ is independently a hydrogen atom or a halogen atom, $R^{14}$ and $R^{15}$ are the same or different and a hydrogen atom, a $C_{1-6}$ alkyl group, a $C_{1-6}$ alkyloxy-$C_{1-6}$ alkyl group, a $C_{3-8}$ cycloalkyl group or a di($C_{1-6}$ alkyl)amino-$C_{1-6}$ alkyl group and Y is single bond.

Among them, examples of the more preferred compound may be those in which one of $R^3$ and $R^4$ in the formula [I] is a hydrogen atom, and the other is a hydrogen atom, a hydroxyl group, a $C_{1-6}$ alkyloxy group or morpholino group.

Among the compounds mentioned above, examples of the further preferred compounds include a compound of the formula [I-A]:

[I-A]

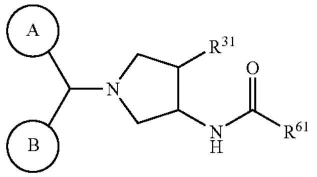

wherein Ring A is a group of the formula:

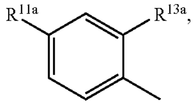
,
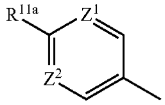
or
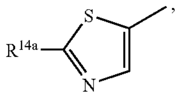
,

Ring B is a group of the formula:

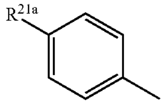
or
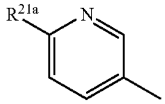

one of $Z^1$ and $Z^2$ is a group of the formula: =NH— and another is a group of the formula: =CH— or =N—, $R^{11a}$ and $R^{21a}$ are the same or different and (1) a hydrogen atom, (2) a halogen atom, (3) a cyano group, (4) a $C_{1-6}$ alkyloxy group optionally substituted by one to three groups selected from a halogen atom and a $C_{1-6}$ alkyloxy group, (5) a mono- or trifluoro-$C_{1-6}$ alkyl group, (6) a di($C_{1-6}$ alkyl)carbamoyloxy group, (7) a $C_{1-6}$ alkylthio group, (8) an amino group substituted by a $C_{1-6}$ alkyl group and a $C_{1-6}$ alkyloxy-$C_{1-6}$ alkyl group, (9) a $C_{3-8}$ cycloalkyloxy group, (10) a $C_{3-8}$ cycloalkyl-$C_{1-6}$ alkyloxy group or (11) a $C_{1-6}$ alkyloxy-$C_{1-6}$ alkyl group, $R^{13a}$ is a hydrogen atom or a halogen atom, $R^{14a}$ is a $C_{1-6}$ alkyloxy group, $R^{31}$ is a hydrogen atom, a hydroxyl group, a $C_{1-6}$ alkyloxy group or morpholino group, $R^{61}$ is (1) a phenyl group substituted by one or two group(s) selected from a halogen atom, a trifluoro-$C_{1-6}$ alkyl group, a $C_{1-6}$ alkyloxy group, a trifluoro-$C_{1-6}$ alkyloxy group, a di($C_{1-6}$ alkyl)carbamoyloxy group, a $C_{1-6}$ alkylthio group and a cyano group, (2) a pyridyl group substituted by one or two groups selected from a halogen atom and a cyano group or (3) a thienyl group substituted by a halogen atom or a trifluoro-$C_{1-6}$ alkyl group, or a pharmaceutically acceptable salt thereof.

Among the compounds [I] of the present invention, the most preferred one may be a compound selected from the group consisting of:

1-[bis-(4-chlorophenyl)methyl]-3-[[4-(trifluoromethoxy)benzoyl]amino]pyrrolidine;

1-[bis-(4-chlorophenyl)methyl]-3-[(4-chlorobenzoyl)amino]pyrrolidine;

1-[bis-(4-ethoxyphenyl)methyl]-3-[[4-(trifluoromethoxy)benzoyl]amino]pyrrolidine;

1-[bis-(4-isopropoxyphenyl)methyl]-3-[[4-(trifluoromethoxy)benzoyl]amino]pyrrolidine;

1-[bis-(4-chlorophenyl)methyl]-3-hydroxy-4-[[4-(trifluoromethoxy)benzoyl]amino]-pyrrolidine;

1-[(4-chlorophenyl)[4-[N-methyl-N-(2-methoxyethyl)amino]phenyl]methyl]-3-[[4-(trifluoromethoxy)benzoyl]amino]pyrrolidine;

1-[bis-(4-chlorophenyl)methyl]-3-methoxy-4-[[4-(trifluoromethoxy)benzoyl]amino]-pyrrolidine;

1-[bis-(4-chlorophenyl)methyl]-3-methoxy-4-[(4-chlorobenzoyl)amino]pyrrolidine;

1-[bis-(4-chlorophenyl)methyl]-3-ethoxy-4-[[4-(trifluoromethoxy)benzoyl]amino]-pyrrolidine;

1-[bis-(4-chlorophenyl)methyl]-3-ethoxy-4-[(4-chlorobenzoyl)amino]pyrrolidine;

1-[bis-(4-cyanophenyl)methyl]-3-[[4-(trifluoromethoxy)benzoyl]amino]pyrrolidine;

1-[(2-chlorophenyl)(4-chlorophenyl)methyl]-3-[[4-(trifluoromethoxy)benzoyl]amino]-pyrrolidine;

1-[bis-(4-chlorophenyl)methyl]-3-[(4-cyanobenzoyl)amino]pyrrolidine;

1-[(4-chlorophenyl)(4-cyanophenyl)methyl]-3-[[4-(trifluoromethoxy)benzoyl]amino]-pyrrolidine;

(3S,4S)-1-[bis-(4-chlorophenyl)methyl]-3-morpholino-4-[[4-(trifluoromethoxy)benzoyl]-amino]pyrrolidine;

(3S,4S)-1-[bis-(4-chlorophenyl)methyl]-3-hydroxy-4-[(2-fluoro-4-cyanobenzoyl)amino]-pyrrolidine;

(3R)-1-[(4-chlorophenyl)(4-cyanophenyl)methyl]-3-[[4-(trifluoromethyl)benzoyl]amino]-pyrrolidine;

(3S,4S)-1-[bis-(4-chlorophenyl)methyl]-3-ethoxy-4-[(4-chlorobenzoyl)amino]pyrrolidine;

(3S,4S)-1-[bis-(4-chlorophenyl)methyl]-3-methoxy-4-[(4-cyanobenzoyl)amino]-pyrrolidine;

(3S,4S)-1-[bis-(4-chlorophenyl)methyl]-3-ethoxy-4-[(4-cyanobenzoyl)amino]pyrrolidine;

(3S,4S)-1-[bis-(4-chlorophenyl)methyl]-3-ethoxy-4-[(2-fluoro-4-cyanobenzoyl)amino]-pyrrolidine;

(3S,4S)-1-[bis-(4-chlorophenyl)methyl]-3-morpholino-4-[(4-chlorobenzoyl)amino]-pyrrolidine;

(3R)-1-[(4-isopropyloxyphenyl)(4-cyanophenyl)methyl]-3-[[4-(trifluoromethoxy)-benzoyl]amino]pyrrolidine;

(3S,4S)-1-[(4-chlorophenyl)(4-cyanophenyl)methyl]-3-methoxy-4-[[4-(trifluoro-methoxy)benzoyl]amino]pyrrolidine;

(3S,4S)-1-[(4-chlorophenyl)(4-cyanophenyl)methyl]-3-methoxy-4-[[4-(trifluoromethyl)-benzoyl]amino]pyrrolidine;

(3S,4S)-1-[(4-chlorophenyl)(4-cyanophenyl)methyl]-3-ethoxy-4-[(4-cyanobenzoyl)-amino]pyrrolidine;

(3S,4S)-1-[(4-chlorophenyl)(4-cyanophenyl)methyl]-3-ethoxy-4-[[4-(trifluoromethoxy)-benzoyl]amino]pyrrolidine;

(3S,4S)-1-[(4-chlorophenyl)(4-cyanophenyl)methyl]-3-ethoxy-4-[[4-(trifluoromethyl)-benzoyl]amino]pyrrolidine;

(3S,4S)-1-[(4-chlorophenyl)(4-cyanophenyl)methyl]-3-ethoxy-4-[[3-fluoro-4-(trifluoro-methyl)benzolyl]amino]pyrrolidine;

(3S,4S)-1-[(4-chlorophenyl)(4-cyanophenyl)methyl]-3-ethoxy-4-[(2-fluoro-4-cyano-benzoyl)amino]pyrrolidine;

(3S,4S)-1-[(4-chlorophenyl)(4-cyanophenyl)methyl]-3-methoxy-4-[(2-fluoro-4-cyano-benzoyl)amino]pyrrolidine;

(3R)-1-[(4-cyanophenyl)[4-(trifluoromethyl)phenyl]methyl]-3-[[4-(trifluoromethoxy)-benzoyl]amino]pyrrolidine:

(3R)-1-[[(S)-4-cyanophenyl](4-chlorophenyl)methyl]-3-[[4-(trifluoromethoxy)benzoyl]-amino]pyrrolidine:

(3R)-1-[[(S)-4-cyanophenyl](4-chlorophenyl)methyl]-3-[[4-(trifluoromethyl)benzoyl]-amino]pyrrolidine;

(3R)-1-[(4-cyanophenyl)(6-methoxypyridin-3-yl)methyl]-3-[[4-(trifluoromethoxy)-benzoyl]amino]pyrrolidine;

(3R)-1-[(4-cyanophenyl)(6-methoxypyridin-3-yl)methyl]-3-[[4-(trifluoromethyl)benzoyl]amino]pyrrolidine;

(3R)-1-[(4-cyanophenyl)(4-isopropyloxyphenyl)methyl]-3-[[4-(trifluoromethyl)benzoyl]-amino]pyrrolidine;

(3R)-1-[(4-cyanophenyl)(4-isopropyloxyphenyl)methyl]-3-[(4-cyanobenzoyl)amino]-pyrrolidine;

(3R)-1-[(4-cyanophenyl)[2-fluoro-4-(trifluoromethyl)phenyl)]methyl]-3-[(4-cyano-benzoyl)amino]pyrrolidine;

(3R)-1-[(4-cyanophenyl)(4-isopropyloxyphenyl)methyl]-3-[(4-chlorobenzoyl)amino]-pyrrolidine;

(3R)-1-[(4-cyanophenyl)(4-ethoxyphenyl)methyl]-3-[(4-cyanobenzoyl)amino]pyrrolidine;

(3R)-1-[(4-cyanophenyl)(4-ethoxyphenyl)methyl]-3-[[4-(trifluoromethoxy)benzoyl]-amino]pyrrolidine;

(3R)-1-[(4-cyanophenyl)(4-ethoxyphenyl)methyl]-3-[[4-(trifluoromethyl)benzoyl]amino]-pyrrolidine;

(3R)-1-[(4-cyanophenyl)(4-ethoxyphenyl)methyl]-3-[(4-chlorobenzoyl)amino]-pyrrolidine;

(3R)-1-[(4-cyanophenyl)(6-isopropyloxypyridin-3-yl)methyl]-3-[(4-cyanobenzoyl)amino]pyrrolidine;

(3R)-1-[(4-cyanophenyl)(6-isopropyloxypyridin-3-yl)methyl]-3-[[4-(trifluoromethoxy)-benzoyl]amino]pyrrolidine;

(3R)-1-[(4-cyanophenyl)(6-isopropyloxypyridin-3-yl)methyl]-3-[[4-(trifluoromethyl)-benzoyl]amino]pyrrolidine;

(3R)-1-[(4-cyanophenyl)(6-isopropyloxypyridin-3-yl)methyl]-3-[(4-chlorobenzoyl)-amino]pyrrolidine;

(3R)-1-[(4-cyanophenyl)[4-(trifluoromethoxy)phenyl]methyl]-3-[(4-cyanobenzoyl)-amino]pyrrolidine;

(3R)-1-[(4-cyanophenyl)[4-(trifluoromethoxy)phenyl]methyl]-3-[(4-chlorobenzoyl)-amino]pyrrolidine;

(3R)-1-[(4-chlorophenyl)[4-(trifluoromethoxy)phenyl]methyl]-3-[(4-cyanobenzoyl)-amino]pyrrolidine;

(3R)-1-[(4-cyanophenyl)[4-(trifluoromethoxy)phenyl]methyl]-3-[[4-(trifluoromethyl)-benzoyl]amino]pyrrolidine;

(3R)-1-[(4-cyanophenyl)(4-chloro-2-fluorophenyl)]methyl]-3-[[4-(trifluoromethyl)-benzoyl]amino]pyrrolidine;

(3R)-1-[(4-cyanophenyl)(4-chlorophenyl)methyl]-3-[[5-(trifluoromethyl)-2-thenoyl]-amino]pyrrolidine;

(3R)-1-[(4-cyanophenyl)(4-methylthiophenyl)methyl]-3-[(4-cyanobenzoyl)amino]-pyrrolidine;

(3R)-1-[(S)-(4-cyanophenyl)[4-(trifluoromethyl)phenyl]methyl]-3-[(4-cyanobenzoyl)-amino]pyrrolidine;

(3R)-1-[(4-cyanophenyl)[4-(trifluoromethyl)phenyl]methyl]-3-[(2-fluoro-4-cyano-benzoyl)amino]pyrrolidine;

(3R)-1-[(4-cyanophenyl)(6-isopropyloxypyridin-3-yl)methyl]-3-[(2-fluoro-4-cyano-benzoyl)amino]pyrrolidine;

(3R)-1-[(4-cyanophenyl)(4-ethoxyphenyl)methyl]-3-[(2-fluoro-4-cyanobenzoyl)amino]-pyrrolidine;

(3R)-1-[(4-cyanophenyl)(4-isopropyloxyphenyl)methyl]-3-[(2-fluoro-4-cyanobenzoyl)-amino]pyrrolidine;

(3R)-1-[(4-cyanophenyl)(6-ethoxypyridin-3-yl)methyl]-3-[(2-fluoro-4-cyanobenzoyl)-amino]pyrrolidine;

(3R)-1-[(4-cyanophenyl)[6-(2,2-difluoroethoxy)-pyridin-3-yl]methyl]-3-[(2-fluoro-4-cyanobenzoyl)amino]pyrrolidine;

(3R)-1-[(4-cyanophenyl)(6-ethoxypyridin-3-yl)methyl]-3-[(4-cyanobenzoyl)amino]-pyrrolidine;

(3R)-1-[(4-cyanophenyl)[6-(2,2-difluoroethoxy)pyridin-3-yl]methyl]-3-[(4-cyanobenzoyl)amino]pyrrolidine;

(3R)-1-[(4-cyanophenyl)[6-(2-methoxyethoxy)-pyridin-3-yl]methyl]-3-[(4-cyanobenzoyl)amino]pyrrolidine;

(3R)-1-[(4-cyanophenyl)(2-isopropyloxypyrimidin-5-yl)methyl]-3-[(4-cyanobenzoyl)-amino]pyrrolidine;

(3R)-1-[(4-cyanophenyl)(4-fluoromethylphenyl)methyl]-3-[(4-cyanobenzoyl)amino]-pyrrolidine;

(3R)-1-[(4-cyanophenyl)(4-fluoromethylphenyl)methyl]-3-[(4-cyano-2-fluorobenzoyl)-amino]pyrrolidine;

(3R)-1-[(4-chlorophenyl)(2-isopropyloxypyrimidin-5-yl)methyl]-3-[(4-cyanobenzoyl)-amino]pyrrolidine;

(3R)-1-[(4-chlorophenyl)(2-isopropyloxypyrimidin-5-yl)methyl]-3-[(4-cyano-2-fluoro-benzoyl)amino]pyrrolidine;

(3R)-1-[(2-isopropyloxypyrimidin-5-yl)[4-(trifluoromethyl)phenyl]methyl]-3-[(4-cyano-benzoyl)amino]pyrrolidine;

(3R)-1-[(2-isopropyloxypyrimidin-5-yl)[4-(trifluoromethyl)phenyl]methyl]-3-[(4-cyano-2-fluorobenzoyl)amino]pyrrolidine;

(3R)-1-[(4-cyanophenyl)(2-isopropyloxypyrimidin-5-yl)methyl]-3-[(4-cyano-2-fluoro-benzoyl)amino]pyrrolidine;

(3R)-1-[(6-isopropyloxymethylpyridin-3-yl)[4-(trifluoromethyl)phenyl]methyl]-3-[(4-cyanobenzoyl)amino]pyrrolidine;

(3R)-1-[(4-cyanophenyl)(2-ethoxythiazol-5-yl)methyl]-3-[(4-cyanobenzoyl)amino]-pyrrolidine;

(3R)-1-[(4-cyanophenyl)(2-isopropyloxythiazol-5-yl)methyl]-3-[(6-cyanonicotinoyl)-amino]pyrrolidine;

(3R)-1-[(4-chlorophenyl)(6-methoxymethylpyridin-3-yl)methyl]-3-[(4-cyanobenzoyl)-amino]pyrrolidine;

(3R)-1-[(6-methoxymethylpyridin-3-yl)[4-(trifluoromethyl)phenyl]methyl]-3-[(4-cyano-benzoyl)amino]pyrrolidine;

(3R)-1-[(4-cyanophenyl)(6-methoxymethylpyridin-3-yl)methyl]-3-[(4-cyanobenzoyl)-amino]pyrrolidine;

(3R)-1-[(4-cyanophenyl)[6-(2-fluoroethoxy)pyridin-3-yl]methyl]-3-[(4-cyanobenzoyl)-amino]pyrrolidine;

(3R)-1-[(4-cyanophenyl)(4-fluoromethylphenyl)methyl]-3-[(4-ethoxybenzoyl)amino]-pyrrolidine;

(3R)-1-[(4-cyanophenyl)[4-(trifluoromethyl)phenyl]methyl]-3-[(4-methylthiobenzoyl)-amino]pyrrolidine;

(3R)-1-[(4-cyanophenyl)[4-(trifluoromethyl)phenyl]methyl]-3-[(5-bromo-2-thenoyl)-amino]pyrrolidine;

(3R)-1-[(4-cyanophenyl)(2-isopropyloxythiazol-5-yl)methyl]-3-[(4-cyano-2-fluoro-benzoyl)amino]pyrrolidine;

(3R)-1-[(4-cyanophenyl)(2-isopropyloxythiazol-5-yl)methyl]-3-[(4-cyanobenzoyl)-amino]pyrrolidine;

(3R)-1-[(4-methoxyphenyl)(6-isopropyloxypyridin-3-yl)methyl]-3-[(4-cyanobenzoyl)-amino]pyrrolidine;

(3R)-1-[(4-methoxyphenyl)(6-isopropyloxypyridin-3-yl)methyl]-3-[(4-cyano-2-fluoro-benzoyl)amino]pyrrolidine;

(3R)-1-[(4-methoxyphenyl)(6-isopropyloxypyridin-3-yl)methyl]-3-[[(6-cyanopyridin-3-yl)carbonyl]amino]pyrrolidine;

(3R)-1-[(4-ethoxyphenyl)(6-isopropyloxypyridin-3-yl)methyl]-3-[(4-cyanobenzoyl)-amino]pyrrolidine;

(3R)-1-[(4-ethoxyphenyl)(6-isopropyloxypyridin-3-yl)methyl]-3-[(4-cyano-2-fluoro-benzoyl)amino]pyrrolidine;

(3R)-1-[(4-ethoxyphenyl)(6-isopropyloxypyridin-3-yl)methyl]-3-[[(6-cyanopyridin-3-yl)-carbonyl]amino]pyrrolidine;

(3R)-1-[(4-isopropyloxyphenyl)(6-isopropyloxypyridin-3-yl)methyl]-3-[(4-cyano-benzoyl)amino]pyrrolidine;

(3R)-1-[(4-isopropyloxyphenyl)(6-isopropyloxypyridin-3-yl)methyl]-3-[(4-cyano-2-fluorobenzoyl)amino]pyrrolidine;

(3R)-1-[(4-isopropyloxyphenyl)(6-isopropyloxypyridin-3-yl)methyl]-3-[[(6-cyano-pyridin-3-yl)carbonyl]amino]pyrrolidine;

(3R)-1-[(4-cyanophenyl)[2-(2,2,2-trifluoroethoxy)pyrimidin-5-yl]methyl]-3-[(4-cyano-benzoyl)amino]pyrrolidine;

(3R)-1-[(4-cyanophenyl)[2-(2,2,2-trifluoroethoxy)pyrimidin-5-yl]methyl]-3-[(4-cyano-2-fluorobenzoyl)amino]pyrrolidine;

(3R)-1-[(4-cyanophenyl)[2-(2,2,2-trifluoroethoxy)pyrimidin-5-yl]methyl]-3-[[(6-cyano-pyridin-3-yl)carbonyl]amino]pyrrolidine;

(3R)-1-[(4-cyanophenyl)(2-ethoxypyrimidin-5-yl)methyl]-3-[(4-cyanobenzoyl)amino]-pyrrolidine;

(3R)-1-[(4-cyanophenyl)(2-ethoxypyrimidin-5-yl)methyl]-3-[(4-cyano-2-fluorobenzoyl)-amino]pyrrolidine;

(3R)-1-[(4-cyanophenyl)[6-(1-fluoromethyl-2-fluoroethoxy)pyridin-3-yl]methyl]-3-[(4-cyanobenzoyl)amino]pyrrolidine;

(3R)-1-[(4-cyanophenyl)(6-isopropyloxypyridin-3-yl)methyl]-3-[(4-dimethylamino-carbonyloxybenzoyl)amino]pyrrolidine;

(3R)-1-[(4-cyanophenyl)[4-(trifluoromethyl)phenyl]methyl]-3-[(4-dimethylamino-carbonyloxybenzoyl)amino]pyrrolidine;

(3R)-1-[bis-(6-isopropyloxypyridin-3-yl)methyl]-3-[(4-cyanobenzoyl)amino]pyrrolidine;

(3R)-1[(4-cyanophenyl)(2-ethoxythiazol-5-yl)methyl]-3-[(4-cyano-2-fluorobenzoyl)-amino]pyrrolidine;

(3R)-1-[(4-cyanophenyl)(2-ethoxythiazol-5-yl)methyl]-3-[[(6-cyanopyridin-3-yl)-carbonyl]amino]pyrrolidine;

(3R)-1-[bis-(6-isopropyloxypyridin-3-yl)methyl]-3-[(4-cyano-2-fluorobenzoyl)amino]-pyrrolidine;

(3R)-1-[bis-(6-isopropyloxypyridin-3-yl)methyl]-3-[[(6-cyanopyridin-3-yl)carbonyl]-amino]pyrrolidine;

(3R)-1-[(4-cyanophenyl)(4-dimethylaminocarbonyloxyphenyl)methyl]-3-[(4-cyano-benzoyl)amino]pyrrolidine;

(3R)-1-[(4-cyanophenyl)(4-dimethylaminocarboliyloxyphenyl)methyl]-3-[(4-cyano-2-fluorobenzoyl)amino]pyrrolidine;

(3R)-1-[(4-cyanophenyl)(4-dimethylaminocarbonyloxyphenyl)methyl]-3-[[(6-cyano-pyridin-3-yl)carbonyl]amino]pyrrolidine;

(3R)-1-[(4-cyanophenyl)(2-dimethylaminopyrimidin-5-yl)methyl]-3-[(4-cyanobenzoyl)-amino]pyrrolidine;

(3R)-1-[(4-cyanophenyl)(2-dimethylaminopyrimidin-5-yl)methyl]-3-[(4-cyano-2-fluoro-benzoyl)amino]pyrrolidine;

(3R)-1-[(4-cyanophenyl)(2-dimethylaminopyrimidin-5-yl)methyl]-3-[[(6-cyanopyridin-3-yl)carbonyl]amino]pyrrolidine;

(3R)-1-[(4-cyanophenyl)(2-diethylaminopyrimidin-5-yl)methyl]-3-[(4-cyanobenzoyl)-amino]pyrrolidine;

(3R)-1-[(4-cyanophenyl)(2-diethylaminopyrimidin-5-yl)methyl]-3-[(4-cyano-2-fluoro-benzoyl)amino]pyrrolidine;

(3R)-1-[(4-cyanophenyl)(2-diethylaminopyrimidin-5-yl)methyl]-3-[[(6-cyanopyridin-3-yl)carbonyl]amino]pyrrolidine;

(3R)-1-[(4-cyanophenyl)[4-[N-(2-methoxyethyl)-N-methylaminophenyl]]methyl]-3-[[(6-cyanopyridin-3-yl)carbonyl]amino]pyrrolidine;

(3R)-1-[(4-cyanophenyl)[4-(N-isopropyl-N-methylamino)phenyl]methyl]-3-[(4-cyano-benzoyl)amino]pyrrolidine;

(3R)-1-[(4-cyanophenyl)[4-(N-ethyl-N-methylamino)phenyl]methyl]-3-[(4-cyano-benzoyl)amino]pyrrolidine;

(3R)-1-[(4-cyanophenyl)[4-[N-(2-methoxyethyl)-N-methylaminophenyl]]methyl]-3-[(4-cyano-2-fluorobenzoyl)amino]pyrrolidine;

(3R)-1-[(4-cyanophenyl)[4-(N-isopropyl-N-methylamino)phenyl]methyl]-3-[(4-cyano-2-fluorobenzoyl)amino]pyrrolidine;

(3R)-1-[(4-cyanophenyl)[4-(N-ethyl-N-methylamino)phenyl]methyl]-3-[(4-cyano-2-fluorobenzoyl)amino]pyrrolidine;

(3R)-1-[(4-cyanophenyl)[4-(N-methyl-N-n-propylamino)phenyl]methyl]-3-[(4-cyano-benzoyl)amino]pyrrolidine;

(3R)-1-[(4-cyanophenyl)[4-(N-methyl-N-n-propylamino)phenyl]methyl]-3-[(4-cyano-2-fluorobenzoyl)amino]pyrrolidine;

(3R)-1-[(4-cyanophenyl)[4-[N-(2-methoxyethyl)-N-methylaminophenyl]]methyl]-3-[[(6-cyanopyridin-3-yl)carbonyl]amino]pyrrolidine;

(3R)-1-[(4-cyanophenyl)[4-(N-isopropyl-N-methylamino)phenyl]methyl]-3-[[(6-cyano-pyridin-3-yl)carbonyl]amino]pyrrolidine;

(3R)-1-[(4-cyanophenyl)[4-(N-ethyl-N-methylamino)phenyl]methyl]-3-[[(6-cyano-pyridin-3-yl)carbonyl]amino]pyrrolidine;

(3R)-1-[(4-cyanophenyl)[4-(N-methyl-N-n-propylamino)phenyl]methyl]-3-[[(6-cyano-pyridin-3-yl)carbonyl]amino]pyrrolidine;

(3R)-1-[(4-cyanophenyl)(6-cyclobutyloxypyridin-3-yl)methyl]-3-[(4-cyanobenzoyl)-amino]pyrrolidine;

(3R)-1-[(4-cyanophenyl)(6-cyclobutyloxypyridin-3-yl)methyl]-3-[(4-cyano-2-fluoro-benzoyl)amino]pyrrolidine;

(3R)-1-[(4-cyanophenyl)(6-cyclobutyloxypyridin-3-yl)methyl]-3-[[(6-cyanopyridin-3-yl)-carbonyl]amino]pyrrolidine;

(3R)-1-[(4-cyanophenyl)(6-cyclopentyloxypyridin-3-yl)methyl]-3-[(4-cyanobenzoyl)-amino]pyrrolidine;

(3R)-1-[(4-cyanophenyl)(6-cyclopentyloxypyridin-3-yl)methyl]-3-[(4-cyano-2-fluoro-benzoyl)amino]pyrrolidine;

(3R)-1-[(4-cyanophenyl)(6-cyclopentyloxypyridin-3-yl)methyl]-3-[[(6-cyanopyridin-3-yl)carbonyl]amino]pyrrolidine;

(3R)-1-[(4-cyanophenyl)(6-cyclopropylmethoxypyridin-3-yl)methyl]-3-[(4-cyano-benzoyl)amino]pyrrolidine;

(3R)-1-[(4-cyanophenyl)(6-cyclopropylmethoxypyridin-3-yl)methyl]-3-[(4-cyano-2-fluorobenzoyl)amino]pyrrolidine;

(3R)-1-[(4-cyanophenyl)(6-cyclopropylmethoxypyridin-3-yl)methyl]-3-[[(6-cyano-pyridin-3-yl)carbonyl]amino]pyrrolidine;

(3R)-1-[(4-cyanophenyl)[6-(3-pentyloxy)pyridin-3-yl]methyl]-3-[(4-cyanobenzoyl)-amino]pyrrolidine;

(3R)-1-[(4-cyanophenyl)[6-(3-pentyloxy)pyridin-3-yl]methyl]-3-[(4-cyano-2-fluoro-benzoyl)amino]pyrrolidine;

(3R)-1-[(4-cyanophenyl)[6-(3-pentyloxy)pyridin-3-yl]methyl]-3-[[(6-cyanopyridin-3-yl)-carbonyl]amino]pyrrolidine;

(3R)-1-[(4-cyanophenyl)[6-(2,2,2-trifluoroethoxy)pyridin-3-yl]methyl]-3-[(4-cyano-benzoyl)amino]pyrrolidine;

(3R)-1-[(4-cyanophenyl)[6-(2,2,2-trifluoroethoxy)pyridin-3-yl]methyl]-3-[(4-cyano-2-fluorobenzoyl)amino]pyrrolidine; and (3R)-1-[(4-cyanophenyl)[6-(2,2,2-trifluoroethoxy)pyridin-3-yl]methyl]-3-[[(6-cyano-pyridin-3-yl)carbonyl]amino]pyrrolidine; or a pharmaceutically acceptable salt thereof.

When the compound [I] of the present invention has an asymmetric carbon atom(s) in its molecule, it may exist in the form of a stereoisomer thereof (diastereoisomers, optical isomers) owing to said asymmetric carbon atom(s) thereof, and the present invention also includes one of the stereoisomers and a mixture thereof.

A compound [I] of the present invention shows a potent antagonistic activity against CB1 receptor and may be useful as: (i) an agent for prevention and/or treatment of a CB1 receptor-mediated diseases such as psychosis including schizophrenia, anxiety disorders, stress, depression, epilepsy, neurodegenerative disorders, spinocerebellar disorders, cognitive disorders, craniocerebral trauma, panic attack, peripheral neuropathy, glaucoma, migraine, Parkinson's disease, Alzheimer's disease, Huntington's disease, Raynaud's syndrome, tremor, obsessive-compulsive disorders, amnesia, geriatric dementia, thymic disorders, Tourette's syndrome, tardive dyskinesia, bipolar disorders, cancer, drug-induced dyskinesia, dystonia, septic shock, hemorrhagic shock, hypotension, insomnia, immunological diseases including inflammations, multiple screlosis, emesis, diarrhea, asthma, appetite disorders such as bulimarexia and the like, obesity, non insulin-dependent diabetes mellitus (NIDDM), memory disorders, urinary disorders, cardiovascular disorders, infertility disorders, infections, demyelination-related diseases, neuroinflammation, viral encephalitis, cerebral vascular incidents, cirrhosis of the liver or intestinal transit disorders; (ii) an agent for withdrawal from a chronic treatment, alcohol dependence or drug abuse (e.g., an opioid, barbiturate, marijuana, cocaine, amphetamine, phencyclidine, a hallucinogenic agent, a benzodiazepine compound and the like); (iii) an agent for enhancing analgesic activity of analgesic or narcotic drugs and the like; or (iv) an agent for smoking cessation (withdrawal from smoking or nicotine dependence).

In addition, the compound [I] of the present invention shows a low toxicity and is safe as medicaments.

The compound [I] of the present invention can be clinically used either in the free form or in the form of a pharmaceutically acceptable salt thereof. The pharmaceutically acceptable salt of the compound [I] includes a salt with an inorganic acid such as hydrochloride, sulfate, phosphate or hydrobromide, or a salt with an organic acid such as acetate, fumarate, oxalate, citrate, methanesulfonate, benzenesulfonate, tosylate or maleate. Besides, when the compound [I] of the present invention has a carboxyl group(s) and the like in its molecule, examples of the pharmaceutically acceptable salt include, salts with a base such as alkaline metal (e.g., sodium salt, potassium salt) or alkaline earth metal (e.g., calcium salt).

The compound [I] or a pharmaceutically acceptable salt thereof includes either intramolecular salt or an additive thereof, and solvates or hydrates thereof.

The present compound [I] or a pharmaceutically acceptable salt thereof can be either orally or parenterally, and can be formulated into a conventional pharmaceutical preparation such as tablets, granules, capsules, powders, injections or inhalants.

The dose of the compound [I] of the present invention or a pharmaceutically acceptable salt thereof may vary in accordance with the administration routes, and the ages, weights and conditions of the patients. For example, when administered in an injection preparation, it is usually in the range of about 0.0001 to 1.0 mg/kg/day, preferably in the range of about 0.001 to 0.1 mg/kg/day. When administered in an oral preparation, it is usually in the range of about 0.001 to 100 mg/kg/day, preferably in the range of 0.01 to 10 mg/kg/day.

The compound [I] of the present invention can be prepared by the following methods but should not be construed to be limited thereto.

(Method A)

According to the present invention, a compound [I] can be prepared by reacting a compound of the formula [II]:

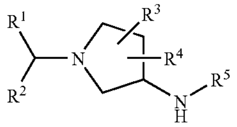

[II]

wherein the symbols are the same as defined above with a compound of the formula [III]:

$$R^6—Y—COOR^0 \quad [III]$$

wherein $R^0$ is a hydrogen atom, an alkyl group or a benzyl group and other symbols are the same as defined above or a salt thereof.

When $R^0$ is a hydrogen atom, the above-mentioned reaction can be carried out in a solvent in the presence of a condensing agent, and in the presence or absence of an activating agent and a base. Examples of the solvent include any solvent which does not disturb the reaction, such as methylene chloride, chloroform, dimethylformaide, dimethylacetamide, tetrahydrofuran, dioxane, toluene, benzene, 1,2-dichloroethane, 1-methyl-pyrrolidinone, 1,2-dimethoxyethane and the like.

The condensing agent may be, for example, dicyclohexylcarbodiimide (DCC), 1-ethyl-3-(3-dimethylaminopropyl) carbodiimide hydrochloride (WSC HCl), diphenyl-phosphoryl azide (DPPA), carbonyldiimidazole (CDI), diethylcyanophosphonate (DEPC), diisopropylcarbodiimide (DIPCI), benzotriazol-1-yloxytrispyrrolidinophosphonium hexafluorophosphate (PyBOP), carbonylditriazole, N-cyclohexylcarbodiimide-N'-propyloxymethylpolystyrene (PS-carbodiimide), N-ethoxycarbonyl-2-ethoxy-1,2-dihydro quinoline (EEDQ), 2-(7-azabenzotriazol-1-yl)-1,1,3,3-tetramethyluronium hexafluoro-phosphate (HATU), 2-(1H-benzotriazol-1-yl-1,1,3,3-tetramethyluronium hexafluorophosphate (HBTU), bromotrispyrrolidinophosphonium hexafluorophosphate (PyBroP), 2-(1H-benzotriazol-1-yl)-1,1,3,3-tetramethyluronium tetrafluoroborate (TBTU), chloro-1,1,3,3-tetramethyluronium hexachloroantimonate (ACTU) and the like.

Examples of the activating agent include 1-hydroxybenzotriazole (HOBt), 1-hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 1-hydroxybenzotriazole-6-sulfonamidomethylpolystyrene (PS-HOBt) and the like.

The base includes, for example, pyridine, triethylamine, diisopropylethylamine, 4-methylmorpholine, 1,8-diazabicyclo[5,4,0]-7-undecene (DBU) and the like.

In the above-mentioned process, the compound [II] can be used in an amount of 0.33 to 1.5 moles, preferably 0.5 to 1.0 moles per one mole of the compound [III]. The condensing agent can be used in an amount of 1.0 to 3.0 moles, preferably 1.0 to 1.2 moles per one mole of the compound [II] or [III]. The base can be used in an amount of 1.0 to 3.0 moles, preferably 1.0 to 1.2 moles per one mole of the compound [II] or [III]. The activating agent can be used in an amount of 0.1 to 2.0 moles, preferably 0.2 to 1.0 moles per one mole of the compound [II] or [III]. The reaction can be carried out at 0 to 150° C., preferably 20 to 80° C.

When $R^0$ in the compound [III] is hydrogen atom, the reaction process A can be carried out by converting the compound [III] to a reactive derivative at the carboxyl group and the like (e.g., an acid halide, a mixed acid anhydride) and reacting the reactive derivative with the compound [II] in the presence of the base in or without the solvent.

When $R^0$ in the compound [III] is a lower alkyl group or a benzyl group, the reaction process A can be also carried out by converting the compound [III] to a corresponding carboxylic acid compound by a conventional manner such as hydrolysis, acidolysis using hydrochloric acid, formic acid, trifluoroacetic acid and the like or hydrogenation and then reacting the carboxylic acid compound with the compound [II] by the above-mentioned manner.

(Method B)

According to the present invention, a compound [I] can be prepared by reacting a compound of the formula [IV]:

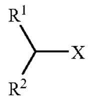

[IV]

wherein X is a reactive residue and other symbols are the same as defined above with a compound of the formula [V]:

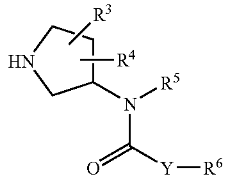

[V]

wherein the symbols are the same as defined above.

The above-mentioned reaction can be carried out in a solvent in the presence of a base and in the presence or absence of an additive. Examples of the solvent include any solvent which does not disturb the reaction, such as tetrahydrofuran, dimethylformaide, dimethylacetamide, dimethylsulfoxide, ethanol, isopropyl alcohol, acetonitrile, 1,4-dioxane, 1,3-dimethyl-2-imidazolidinone and the like. The base includes potassium carbonate, sodium carbonate, triethylamine, diisopropylethylamine, pyridine, sodium hydroxide, potassium hydroxide and the like. The additive includes sodium iodide, copper(I) iodide, copper(II) iodide, copper powder, potassium iodide, a tetraalkylammonium halide (e.g., tetrabutylammonium chloride, tetraethyl-ammonium chloride) and the like.

The reactive residue represented by X may be a halogen atom such as fluorine atom, chlorine atom, bromine atom or iodine atom, trifluoromethanesulfonyloxy group, p-toluenesulfonyloxy group, methanesulfonyloxy group, hydroxyl group and the like.

When X is hydroxyl group, Mitsunobu reagents such as triphenylphosphinediethylazodicarboxylate, triphenylphosphinediisopropyl azodicarboxylate and the like can be used in the present reaction.

In the above-mentioned process, the compound [IV] can be used in an amount of 0.33 to 3.0 moles, preferably 0.66 to 1.5 moles per one mole of the compound [V]. The base can be used in an amount of 1.0 to 3.0 moles, preferably 1.0 to 1.2 moles per one mole of the compound [IV] or [V]. The additive can be used in an amount of 0.1 to 2.0 moles, preferably 0.2 to 1.0 moles per one mole of the compound [IV] or [V]. The reaction can be carried out at 50 to 150° C., preferably 80 to 120° C.

(Method C)

Among the compounds [I] of the present invention, a compound of the formula [I-a]:

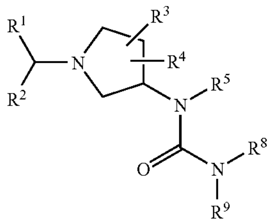

[I-a]

wherein each of $R^8$ and $R^9$ is independently a group selected from an alkyl group, an arylalkyl group, an alkyloxycarbonylalkyl group and an aryl group optionally substituted by a halogen atom, or both of the groups combine each other together with an adjacent nitrogen atom to form a heterocyclic group (said heterocyclic group being optionally fused to a benzene ring and optionally substituted by a halogenoaryl group), and other symbols are the same as defined above can be also prepared by reacting a compound [II] with a compound of the formula [VI]:

$(R^8)(R^9)NH$ [VI]

wherein the symbols are the same as defined above in the presence of a compound of the formula [VII]:

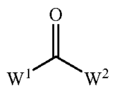

[VII]

wherein $W^1$ and $W^2$ are the same or different and a removing group.

In the compound [VII], examples of $W^1$ and $W^2$ include an imidazolyl group, a halogen atom or a phenoxy group. Concrete examples of such compound include 1,1'-carbonyldiimidazole, phosgene, triphosgene and the like.

Examples of the solvent include any solvent which does not disturb the reaction, such as acetonitrile, dichloromethane, tetrahydrofuran and the like.

In the above-mentioned process, the compound [II] can be used in an amount of 0.33 to 2.0 moles, preferably 0.66 to 1.0 moles per one mole of the compound [VI]. The compound [VII] can be used in an amount of 1.0 to 3.0 moles, preferably 1.0 to 1.2 moles per one mole of the compound [II] or [VI]. The reaction can be carried out at 0 to 150° C., preferably 20 to 80° C.

Moreover, the compound [I-a] can be prepared by: a) reacting the compound [II] with the compound [VII] to obtain a compound of the formula [VIII]:

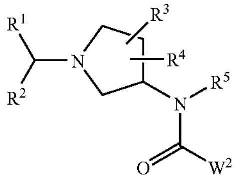

[VIII]

wherein the symbols are the same as defined above and, if necessary, after converting the product to its reactive derivative, reacting the product with the compound [VI], or b) reacting the compound [VI] with the compound [VII] to obtain a compound of the formula [IX]:

[IX]

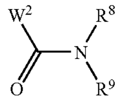

wherein the symbols are the same as defined above and, if required, after converting the product to its reactive derivative, reacting the product with the compound [II].

Examples of the reactive derivative of the compound [VIII] or [IX] include those in which $W^2$ is converted to a group of the formula:

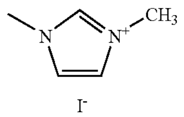

and such reactive derivative can be obtained by reacting the compound [IX] in which a group corresponding to $W^2$ is an imidazolyl group with methyl iodide.

The reaction of the compound [II] or the compound [IV] with the compound [VII] can be carried out at 0 to 150° C., preferably at 20 to 80° C. The compound [VII] can be used in an amount of 1.0 to 3.0 moles, preferably 1.0 to 1.2 moles per one mole of the compound [II] or [VI]. The compound [VII] can be used in an amount of 1.0 to 3.0 moles, preferably 1.0 to 1.2 moles per one mole of the compound [II] or [VI]. Examples of the solvent include any solvent which does not disturb the reaction, such as acetonitrile, dichloromethane, tetrahydrofuran and the like.

The reaction to convert the compound [VIII] or [IX] to its reactive derivative can be carried out by treating such compound with methyl iodide at 0 to 150° C., preferably at 40 to 80° C. The compound [VII] can be used in an amount of 1.0 to 3.0 moles, preferably 1.0 to 1.2 moles per one mole of the compound [VIII] or [IX]. Examples of the solvent include any solvent which does not disturb the reaction, such as acetonitrile, dichloromethane, tetrahydrofuran and the like.

The reaction of the compound [VIII] (or its reactive derivative) with the compound [VI] or the reaction of the compound [IX] (or its reactive derivative) with the compound [II] can be conducted in the presence of a base at 0 to 150° C., preferably at 20 to 80° C. Such reactive derivative can be used in an amount of 0.33 to 3.0 moles, preferably 0.66 to 1.5 moles per one mole of the compound [VI] or [II]. Examples of the base include triethylamine and the like. Examples of the solvent include any solvent which does not disturb the reaction, such as acetonitrile, dichloromethane, tetrahydrofuran and the like.

The objective compound [I] of the present invention can be also prepared by intramolecularly converting the substituent(s) in $R^1$, $R^2$ and/or $R^6$, or the group $R^3$ and/or $R^4$ of the compound [I] as obtained above to the other desired substituent(s) or the other groups within the scope the present invention. The intramolecular conversion processes can be selected according to the kinds of the objective substituents or groups, and may be carried out, for example, in the following methods (a) to (k).

Method (a): A compound [I] in which the substituent(s) in $R^1$ and/or $R^2$ is cyano group can be obtained by reacting a corresponding compound [I] in which the substituent(s) in $R^1$ and/or $R^2$ is a halogen atom with zinc cyanide in the presence of a catalyst and an additive. Examples of said catalyst include a palladium catalyst such as palladium(II) acetate, tris(dibenzylideneacetone)dipalladium(0), trans-dichloro-bis-(tricyclohexylphosphine)palladium(II), tetrakis(triphenylphosphine)palladium(0) and the like. Examples of the additive include a phosphine compound such as 1,1'-bis-(diphenylphosphino)ferrocene, racemic 2,2'-bis(diphenylphosphino)-1,1'-binaphthyl, 2-(di-tert-butylphosphino)biphenyl, 2-(dicyclohexylphosphino)biphenyl, 2-dicyclohexyl-phosphino-2'-(N,N'-dimethylamino)biphenyl, tri-tert-butylphospine and the like.

Method (b): A compound [I] in which the substituent(s) in $R^1$ and/or $R^2$ is an alkylamino group or a cycloalkylamino group can be obtained by reacting a corresponding compound [I] in which the substituent(s) in $R^1$ and/or $R^2$ is a halogen atom with a mono- or di-alkylamine or a cycloalkylamine in the presence of a catalyst, an additive and a base. Examples of the catalyst and the additive may be the palladium compounds and the phosphine compounds exemplified in Method (a), respectively. Examples of the base include potassium carbonate, cesium carbonate and the like.

Method (c): A compound [I] in which $R^3$ and $R^4$ combine each other to form an oxo group can be obtained by oxidizing a corresponding compound [I] in which one of the $R^3$ and $R^4$ is a hydrogen atom and another is a hydroxyl group. The oxidation can be carried out in a solvent in the presence of an oxidizing agent such as activated dimethylsulfoxide and the like. Dimethylsulfoxide can be activated by oxalyl chloride, dicyclohexylcarbodiimide, trifluoroacetic anhydride, acetic anhydride, chlorine, sulfur trioxide-pyridine complex and the like.

Method (d): A compound [I] in which the $R^3$ or $R^4$ is an alkyloxy group can be obtained by reacting a corresponding compound [I] in which $R^3$ or $R^4$ is a hydroxyl group with an alkyl halide in an appropriate solvent.

Method (e): Among the compound [I] of the present invention, a compound of the formula [I-b]:

[I-b]

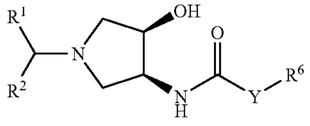

wherein the symbols are the same as defined above can be obtained by treating a corresponding compound of the formula [I-c]:

[I-c]

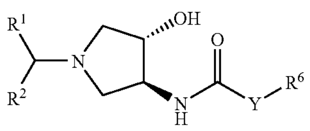

wherein the symbols are the same as defined above with methanesulfonylchloride, heating to obtain a compound of the formula [X]:

[X]

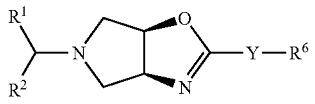

wherein the symbols are the same as defined above and then hydrolyzing the product [X].

Method (f): A compound [I] in which the $R^3$ or $R^4$ is a hydroxyalkyl group can be obtained by reducing a corresponding compound [I] in which $R^3$ or $R^4$ is an alkyloxycarbonylalkyl group. The reduction can be carried out in the presence of a reducing agent such as lithium borohydride and the like.

Method (g): A compound [I] in which the $R^6$ is an alkylamino-substituted heterocyclic group (e.g., an alkylaminopyridyl group) can be obtained by reacting a corresponding compound [I] in which $R^6$ is a halogen-substituted heterocyclic group with an alkylamine in an appropriate solvent in the presence of a base (e.g., potassium carbonate, cesium carbonate).

Method (h): A compound [I] in which the $R^6$ is an alkyloxy-substituted heterocyclic group (e.g., an alkyloxypyridyl group) can be obtained by reacting a corresponding compound [I] in which $R^6$ is a halogen-substituted heterocyclic group with an alkanol in a solvent in the presence of a base (e.g., potassium carbonate, cesium carbonate).

Method (i): A compound [I] in which a substituent(s) in $R^6$ is a group containing an amino group substituted by an acyl group (e.g., an alkyloxycarbonyl group, an alkylcarbonyl group, an arylalkyloxycarbonyl group, an alkylsulfonyl group, a amorpholinocarbonyl group, a mono- or dialkylcarbamoyl group a mono- or dialkylaminosulfonyl group or a halogenoalkylcarbonyl group) can be obtained by reacting a corresponding compound [I] in which the substituent in $R^6$ is a group containing an amino group with an acylating agent containing the desired substituent in the same manner as described in Method A.

Method (j): A compound [I] in which the $R^3$ or $R^4$ is a nitrogen-containing heterocyclic group (e.g., 1-pyrrolidinyl group), namely a group of the formula:

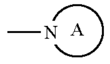

wherein the Ring A is a 4- to 10-membered heterocyclic group can be obtained by converting a corresponding compound [I] in which $R^3$ or $R^4$ is a hydroxyl group to its reactive derivative (e.g., a corresponding compound having a methanesulfonyloxy group) and then reacting the reactive derivative with a cyclic amine compound of the formula:

wherein the symbol is the same as defined above in the presence of a base.

Method (k): A compound [I] in which the $R^3$ or $R^4$ is a mono- or di-alkyl-carbamoyl group can be obtained by reacting a corresponding compound [I] in which $R^3$ or $R^4$ is a carboxyl group with a mono- or dialkyl-amine compound in the same manner as described in Method A.

Method (l): A compound [I] in which the substituent(s) in $R^1$ and/or $R^2$ is an alkylsulfinyl (or alkylsulfonyl) group can be obtained by oxidizing the corresponding compound in which the substituent(s) in $R^1$ and/or $R^2$ is an alkylthio group. The oxidation can be carried out in a solvent (e.g., methylene chloride) in the presence of an oxidizing agent (e.g., m-chloroperbenzoic acid).

If necessary, the compounds [I] of the present invention obtained in the aforementioned Processes A to C or Methods (a) to (k) can be converted to a pharmaceutically acceptable salt thereof by a conventional manner.

A compound [II] as a synthetic intermediate for preparing the compound [I] of the present invention can be obtained by reacting a compound [IV] with a compound of the formula [XI]:

[XI]

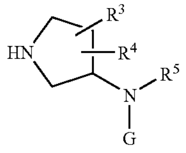

wherein G is an amino-protecting group and the other symbols are the same as defined above and then removing the amino-protecting group from the product.

The reaction of the compound [IV] with the compound [XI] can be carried out in the same manner as described in the aforementioned Method B. Examples of the amino-protecting group include an arylalkyloxycarbonyl group such as bezyloxycarbonyl group, an alkyloxycarbonyl group such as ethyloxycarbonyl group or tert-butoxycarbonyl group and the like.

A compound [V] mentioned above can be obtained by reacting a compound of the formula [XII]:

[XII]

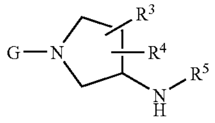

wherein the symbols are the same as defined above with a compound [III] and then removing the amino-protecting group from the product. The reaction of the compound [XII] with the compound [III] can be carried out in the same manner as described in the aforementioned Method A.

Among the above-mentioned compound [IV], a compound [IV] in which the reactive residue (X) is a hydroxyl group (compound [IV-a]) can be obtained by (1) reacting an aldehyde compound [VIII] with a Grignard reagent (or an organic lithium compound) [XIV], or (2) reducing a ketone compound [XV] as shown in the following reaction scheme wherein M is a halogenated magnesium or lithium and the other symbols are the same as defined above.

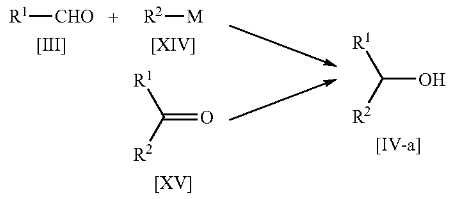

[III] [XIV] [XV] [IV-a]

The reaction of the compound [XIII] with the Grignard reagent (or the organic lithium compound) [XIV] can be carried out in the presence or absence of a solvent. Examples of the solvent include any solvent which does not disturb the reaction, such as tetrahydrofuran, diethylether, 1,4-dimethoxyethane and the like.

The reduction of the compound [XV] can be carried out in the presence of a conventional reducing agent such as sodium borohydride, lithium borohydride, lithium aluminum hydride, sodium bis(2-methoxyethoxy)aluminum hydride and the like. The hydroxyl group (X) in a reaction product (compound [IV-a]) of such process can be converted, in a conventional manner, to other reactive residue (e.g., a halogen atom such as fluorine atom, chlorine atom, bromine atom or iodine atom, trifluoromethanesulfonyloxy group, p-toluenesulfonyloxy group, methanesulfonyloxy group, hydroxyl group and the like).

In conducting the above mentioned processes, when the starting materials or intermediate compounds have a functional group(s), if necessary, the protection of the functional groups and the following deprotection thereof may be carried out in accordance with a conventional manner.

Throughout the present description and claims, the "halogen atom" means fluorine, chlorine, bromine or iodine atom. The "alkyl group" means a straight or branched chain alkyl group having 1 to 12 carbon atoms, preferably 1 to 6 carbon atoms. The "alkenyl group" means a straight or branched chain alkenyl group having 2 to 12 carbon atoms, preferably 2 to 6 carbon atoms. The "alkynyl group" means a straight or branched chain alkynyl group having 2 to 12 carbon atoms, preferably 2 to 6 carbon atoms. The "cycloalkyl group" means a cycloalkyl group having 3 to 10 carbon atoms, preferably 3 to 8 carbon atoms. The "cycloalkenyl group" means a cycloalkenyl group having 3 to 10 carbon atoms, preferably 3 to 10 carbon atoms. The "alkyleneoxy group" means a straight or branched chain alkyleneoxy group having 1 to 6 carbon atoms, preferably 1 to 3 carbon atoms. The "alkylenedioxy group" means a straight or branched chain alkylenedioxy group having 1 to 6 carbon atoms, preferably 1 to 3 carbon atoms.

BEST MODE FOR CARRYING OUT THE INVENTION

The compounds of the present invention are illustrated in more detail by the following Examples but should not be construed to be limited thereto.

Example 1

To a solution of (3R)-1-[bis-(4-chlorophenyl)methyl]-3-aminopyrrolidine (2.05 g, compound obtained in Reference Example 11) and triethylamine (1.35 mL) in methylene chloride (30 mL) was added dropwise 4-(trifluoromethoxy)benzoyl chloride (1.21 mL) under ice-cooling and the mixture was stirred at room temperature for 1 hour. To the reaction mixture was added water and the mixture is extracted with chloroform (×2). The organic layer was filtered through a NH-silica gel (10 g of Chromatorex NH-silica gel; Fuji Silicia Chem.) and the filtrate was evaporated in vacuo. The crude product was triturated in ethyl acetate/hexane to obtain (3R)-1-[bis-(4-chlorophenyl)methyl]-3-[[4-(trifluoromethoxy)benzoyl]amino]pyrrolidine (2.70 g; yield: 83%) as crystals.

MS(APCI) m/z; 508/510 $[M+H]^+$

Example 2

(1) A compound obtained in Reference Example 8 (2.01 g) was treated in the same manner as described in Reference Examples 11-(2) and 6-(2) to give (3,4-trans)-1-[bis-(4-chlorophenyl)methyl]-3-hydroxy-4-aminopyrrolidine dihydrochloride (2.13 g; yield: 51%). MS(APCI) m/z; 337/339 $[M+H]^+$ (2) To a solution of the compound obtained in the above step (1) (1.50 g) and sodium hydrogencarbonate (1.55 g) in ethyl acetate (50 mL) and water (50 mL) was added dropwise 4-(trifluoromethoxy)benzoyl chloride (635 μL) under ice-cooling and the mixture was stirred at the same temperature for 1 hour. The organic layer was separated and filtered through a NH-silica gel bead (5 g of Chromatorex NH-silica gel) and the filtrate was evaporated in vacuo. The crude product was triturated in ethyl acetate/hexane to obtain (3,4-trans)-1-[bis-(4-chlorophenyl)methyl]-3-hydroxy-4-[[4-(trifluoromethoxy)benzoyl]amino]pyrrolidine (1.61 g; yield: 84%) as crystals.

MS(APCI) m/z; 525/527 $[M+H]^+$

Example 3

To a solution of the compound obtained in Reference Example 11 (26.9 mg) and 6-methylnicotinic acid (20.5 mg) in chloroform (1 mL) was added successively a 0.5M 1-hydroxybenzotriazole/dimethylformamide (0.4 mL) and 0.5M 1-ethyl-3-[3-(dimethyl-amino)propyl]carbodiimide hydrochloride/chloroform (0.4 mL) and the mixture was stirred at room temperature overnight. To the reaction mixture was added an aqueous saturated sodium hydrogencarbonate solution (1 mL), water (2 mL) and chloroform (2 mL) and the mixture was stirred for 15 minutes. A chloroform layer in the mixture was separated and evaporated in vacuo. The crude product was purified by HPLC (XTerra Prep MS C18 column; solvent: 10 mM ammonium carbonate/methanol=80:20→5:95), dissolved in tert-butylalcohol (1.5 mL) and lyophilized to give (3R)-1-[bis-(4-chlorophenyl)methyl]-3-[(6-methylnicotinoyl)amino]pyrrolidine (40.7 mg; yield: 92%) as a powder. MS(ESI) m/z; 440/442 $[M+H]^+$

Example 4

To a solution of 6-methylnicotinic acid (35 mg) in ethanol (1 mL) was added 2N sodium hydroxide solution (0.14 mL) and the mixture was stirred at 60° C. for 2 hours. After cooling to room temperature, to the reaction mixture was added 5N HCl (0.06 mL) and the mixture was evaporated in vacuo to give 6-methyloxynicotinic acid. The product was treated in the same manner as described in Example 3 to give (3R)-1-[bis-(4-chlorophenyl)methyl]-3-[(6-methoxynicotinoyl)amino]pyrrolidine (28.0 mg; yield: 61%) as a powder.

MS(ESI) m/z; 456/458 $[M+H]^+$

Example 5

(1) The corresponding materials were treated in the same manner as described in Reference Examples 2 and 4-(3) to give bis-(4-ethoxyphenyl)methyl chloride.

(2) The compound obtained in the above step (1) (545 mg) was treated in the same manner as described in Reference Example 11 to give (3R)-1-[bis-(4-ethoxyphenyl)methyl]-3-(tert-butoxycarbonylamino)pyrrolidine (671 mg; yield: 76%).

MS(APCI) m/z; 441 $[M+H]^+$ (3) To a solution of the compound obtained in the above step (2) (52 mg) in 1.5M 2,6-lutidine/methylene chloride (1 mL) was added 1.0M trimethylsilyl trifluoromethanesulfonate/methylene chloride (1 mL) and the mixture was stirred at room temperature for 25 hours. To the reaction mixture was added methanol (500 μL) and the mixture was diluted with chloroform and washed with an aqueous saturated sodium hydrogencarbonate solution. The organic layer was filtered through a NH-silica gel bead and evaporated in vacuo. The residue was dissolved in methylene chloride (2 mL) and thereto was added triethylamine (28 μL) and 4-(trifluoromethoxy)benzoyl chloride (26 μL). The mixture was stirred at room temperature for 15 hours. To the reaction mixture was added water and the mixture was extracted with chloroform. The extract was evaporated in vacuo and the residue was purified by HPLC (XTerra Prep MS C18 column; Waters Inc.; Solvent: water/methanol=1:1→5:95) to give (3R)-1-[bis-(4-ethoxyphenyl)methyl]-3-[[4-(trifluoromethoxy)benzoyl]amino]pyrrolidine (27.2 mg, yield: 38%) as an amorphous powder.

MS(APCI) m/z; 529 $[M+H]^+$

Example 6

A mixture of [bis-(4-chlorophenyl)]chloromethane (compound obtained in Reference Example 11-(1), 342 mg), (3,4-trans)-3-(ethoxycarbonyl)-4-[[4-(trifluoro-methoxy)benzoyl]amino]pyrrolidine (375 mg, compound obtained in Reference Example 7) and diisopropylamine (0.44 mL) in dioxane was stirred at 85° C. overnight. The reaction mixture was evaporated to remove dioxane and the residue was purified by a column chromatography on silica gel (solvent; n-hexane/ethyl acetate=4:1) to give (3,4-trans)-1-[bis-(4-chlorophenyl)methyl]-3-(ethloxycarbonyl)-4-[[4-(trifluoromethoxy)-benzoyl]amino]pyrrolidine (249 mg, yield: 51%) as a powder.

MS(APCI) m/z; 581/583 $[M+H]^+$

Example 7

(1) 4-Methoxybenzaldehyde (243 μL) was treated in the same manner as described in Reference Example 5-(1) to give (4-chlorophenyl)(4-methoxyphenyl)methanol (279 mg, yield: 56%).

MS(APCI) m/z; 231/233 $[M+H-H_2O]^+$ (2) To a solution of the compound obtained in the above step (1) (220.6 mg) and triehylamine (250 μL) in methylene chloride (2 mL) was added methanesulfonyl chloride (82 μL) under ice-cooling and the mixture was stirred at the same temperature for 1 hour. To the reaction mixture was added (3R)-3-[[4-(trifluoromethoxy)benzoyl]amino]-pyrrolidine (364 mg, compound obtained in Reference Example 6) and acetonitrile (3 mL) and the mixture was stirred at 80° C. for 16 hours. To the reaction mixture was added water and the mixture was extracted with ethyl acetate. The extract was evaporated in vacuo and the resultant crude product was purified by a column chromatography on silica gel (solvent; hexane/ethyl acetate=4:1→2:1), dissolved in tert-butylalcohol (1.5 μL) and lyophilized to give (3R)-1-[(4-chlorophenyl)(4-methoxy-phenyl)methyl]-3-[[4-(trifluoromethoxy)benzoyl]amino]pyrrolidine (241.5 mg, yield: 54%) as a powder.

MS(ESI) m/z; 505/507 $[M+H]^+$

Example 8

A mixture of the compound obtained in Example 1 (60 mg), tris(dibenzylideneacetone)dipalladium (8.6 mg), 1,1'-bis(diphenylphosphino)ferrocene (10.4 mg), zinc cyanide (16.6 mg) and zinc powder (3.7 mg) in dimethylacetamide (0.5 mL) was stirred at 200° C. for 10 minutes by using Microwave Synthetic System (Discover; CEM Ltd.). The reaction mixture was diluted with ethyl acetate and thereto was added water. The organic layer was separated and evaporated in vacuo. The residue was purified by a column chromatography on silica gel (solvent; hexane/ethyl acetate=2:1→1:1), dissolved in tert-butylalcohol and lyophilized to give (3R)-1-[bis-(4-cyanophenyl)methyl]-3-[[4-(trifluoromethoxy)benzoyl]amino]pyrrolidine (32.1 mg, yield: 56%) as a powder.

MS(APCI) m/z; 491 $[M+H]^+$

Example 9

A mixture of the compound obtained in Example 1 (50 mg), tris(dibenzylideneacetone)dipalladium (0.9 mg), 2-(dicyclohexylphosphino)-2'-(N,N-dimethylamino)biphenyl (1.5 mg), cyclopentylamine (24 μL) and 1.0M lithium bis(trimethylsilyl)amide/tetrahydrofuran (0.35 mL) was stirred at 110° C. for 10 minutes by using Microwave Synthetic System (Discover; CEM Ltd.). The reaction mixture was diluted with ethyl acetate and thereto was added water. The organic layer was separated and evaporated in vacuo. The residue was purified by HPLC (XTerra Prep MS C18 column; Waters Inc., solvent; water/methanol=1:1→5:95), dissolved in tert-buthanol and lyophilized to give (3R)-1-[bis-[4-(cyclopentylamino)phenyl]methyl]-3-[[4-(trifluoromethoxy)benzoyl]amino]pyrrolidine (18.7 mg, yield: 32%) as a powder.

MS(ESI) m/z; 639 $[M+H+MeOH]^+$

Example 10

A mixture of the compound obtained in Example 1 (50 mg), tris(dibenzylideneacetone)dipalladium (0.9 mg), 2-(dicyclohexylphosphino)-2'-(N,N-dimethylamino)biphenyl (1.5 mg), n-butylmethylamine (29 μL) and 1.0M lithium bis(trimethylsilyl)amide/tetrahydrofuran (0.35 mL) was stirred at 110° C. for 10 minutes by using Microwave Synthetic System (Discover; CEM Ltd.). The reaction mixture was diluted with ethyl acetate and thereto was added water. The organic layer was separated and evaporated in vacuo. The residue was purified by HPLC (XTerra Prep MS C18 column; Waters Inc., solvent; water/methanol=1:1→5:95), dissolved in tert-buthanol and lyophilized to give (3R)-1-[[4-(n-butylmethylamino)phenyl](4-chlorophenyl)methyl]-3-[[4-(trifluoromethoxy)benzoyl]amino]pyrrolidine (12.6 mg, yield: 23%; compound a) and (3R)-1-[bis-[4-(n-butylmethylamino)phenyl]methyl]-3-[[4-(trifluoromethoxy)benzoyl]amino]pyrrolidine (18.0 mg, yield: 30%; compound b) as a powder, respectively.

Compound a: MS(ESI) m/z; 560/562 $[M+H]^+$

Compound b: MS(ESI) m/z; 643 $[M+H+MeOH]^+$

Example 11

To a solution of dimethylsulfoxide (54 μL) in methylene chloride (2 mL) was added trifluoroacetic anhydride (86 μL) under nitrogen gas atmosphere and under cooling in dry ice/ acetone bath and the mixture was stirred for 10 minutes. Thereto was added a suspension of the compound obtained in Example 2 (99 mg) in methylene chloride (4 mL) and the mixture was stirred at the same temperature for 1 hour. Thereto was added diisopropylethylamine (215 μL) and the mixture was stirred for 40 minutes. To the reaction mixture was added methanol (0.2 mL) and the mixture was stirred at room temperature for 3 hours. To the reaction mixture was added water and the mixture was extracted with chloroform. The extract was evaporated in vacuo and the residue was purified by a column chromatography on silica gel (solvent; hexane/ethyl acetate=9:1→2:1) to give 1-[bis-(4-chlorophenyl)methyl]-3-oxo-4-[[4-(trifluoromethoxy)benzoyl]-amino]pyrrolidine (41.5 mg; yield: 43%) as an amorphous powder.

MS(ESI) m/z; 523/525 $[M+H]^+$

Example 12

To a solution of (3S,4R)-1-[bis-(4-chlorophenyl)methyl]-3-hydroxy-4-[[4-(trifluoromethoxy)benzoyl]amino]pyrrolidine (75.6 mg, an optical isomer of the compound obtained in Example 2) in acetonitrile (8 mL)/dimethylformamide (2 mL) was added successively methyl iodide (233 μL) and silver oxide (216.8 mg) and the mixture was stirred at room temperature for 23 hours. The reaction mixture was filtered through Cerite, washed with acetonitrile and evaporated in vacuo. The crude product was purified by a column chromatography on silica gel (solvent; hexane/ethyl acetate=4:1→2:1) to give (3S,4R)-1-[bis-(4-chlorophenyl)methyl]-3-methoxy-4-[[4-(trifluoro-methoxy)benzoyl]amino]pyrrolidine (39.5 mg; yield: 51%) as an amorphous powder.

MS(ESI) m/z; 539/541 $[M+H]^+$

Example 13

(1) To a solution of the compound obtained in Example 2 (400 mg) and triethylamine (215 μL) in chloroform (8 mL) was added dropwise methanesulfonyl chloride (83 μL) under nitrogen gas atmosphere and ice-cooling and the mixture was stirred at 60° C. for 2 hours. After cooling to room temperature, to the reaction mixture was added water and the organic layer was separated and evaporated in vacuo. The crude product was purified by a flash column chromatography on NH-silica gel (Chromatorex NH-silica gel; Fuji Silicia Chem., solvent: hexane/ethyl acetate=2:1→0:1) to give 5-[bis-(4-chlorophenyl)methyl]-2-[4-(trifluoromethoxy)phenyl]-3a,6a-dihydro-3-pyrrolino[3,4-d]oxazole (361 mg, yield: 94%) as an amorphous powder.

MS(APCI) m/z; 507/509 $[M+H]^+$ (2) To a solution of the compound obtained in the above step (1) (360 mg) in methanol (2.5 mL) was added 6N HCl (1.5 mL) and the mixture was stirred at 65° C. for 30 minutes. After cooling to room temperature, the reaction mixture was diluted with tetrahydrofuran, treated with cation-exchange resin (ISOLUTE SCX; IST Ltd., solvent: methanol/tetrahydrofuran=1:1→1N ammonia/methanol) and evaporated in vacuo to give (3,4-cis)-1-[bis-(4-chlorophenyl)methyl]-3-hydroxy-4-[[4-(trifluoromethoxy)-benzoyl]amino]pyrrolidine (301 mg, yield: 81%) as an amorphous powder.

MS(APCI) m/z; 525/527 $[M+H]^+$

Example 14

To a solution of the compound obtained in Example 482 (100 mg) in tetrahydrofuran/ethanol was added lithium borohydride (13 mg) and the mixture was stirred at room temperature for 15 hours. The reaction mixture was evaporated in vacuo and to the residue was added a potassium hydrogensulfate solution. The mixture was extracted with ethyl acetate and the organic layer was evaporated in vacuo. The crude product was purified by a column chromatography on silica gel (solvent; ethyl acetate/hexane=1:1) to give (2S,4R)-1-[bis-(4-chlorophenyl)methyl]-2-hydroxy-methyl-4-[(4-chlorobenzoyl)amino]pyrrolidine (72 mg, yield: 73%) as a powder.

MS(APCI) m/z; 489/491 $[M+H]^+$

Example 15

To a solution of the compound obtained in Example 27 (32 mg) in N-methylpyrrolidone was added potassium carbonate (26 mg) and 1N dimethylamine/methanol (0.5 mL) and the mixture was stirred at 100° C. for 15 hours. To the reaction mixture was added water and the mixture was extracted with chloroform. The organic layer was evaporated in vacuo and the crude product was purified by a column chromatography on silica gel (solvent; ethyl acetate/hexane=1:1) to give (3R)-1-[bis-(4-chlorophenyl)methyl]-3-[[6-(dimethylamino)nicotinoyl]amino]pyrrolidine (8 mg, yield: 37%) as a powder.

MS(APCI) m/z; 469/471 $[M+H]^+$

Example 16

To a solution of (3R)-1-[bis-(4-chlorophenyl)methyl]-3-[(5-bromonicotinoyl)-amino]pyrrolidine (50 mg) in toluene was added copper iodide (7 mg), cesium carbonate (15 mg), sodium iodide (15 mg), phenanthroline (14 mg) and ethanol (0.1 mL) and the mixture was stirred at 100° C. for 15 hours. The reaction mixture was evaporated in vacuo and to the residue was added an aqueous saturated sodium hydrogencarbonate solution was added. The mixture was extracted with ethyl acetate and the organic layer was evaporated in vacuo. The residue was purified by a column chromatography on silica gel (solvent; ethyl acetate/hexane=1:1) to give (3R)-1-[bis-(4-chlorophenyl)methyl]-3-[(5-ethoxynicotinoyl)amino]pyrrolidine (12 mg, yield: 26%) as a powder.

MS(APCI) m/z; 470/472 $[M+H]^+$

Example 17

To the compound obtained in Example 46 (20 mg) was added 4N HCl/dioxane and the mixture was stirred at room temperature for 15 hours. The reaction mixture was evaporated in vacuo to give (3R)-1-[bis-(4-chlorophenyl)methyl]-3-[((2S)-2-amino-3-phenylpropionyl)amino]pyrrolidine. To the compound was added triethylamine (0.05 mL) and chloroform and then added dropwise 4-morpholincarbonyl chloride (0.03 mL) under ice-cooling. The mixture was stirred at room temperature for 15 hours. To the reaction mixture was added an aqueous saturated sodium hydrogencarbonate solution and the mixture was extracted. The organic layer was separated and evaporated and, the residue was purified by a column chromatography on silica gel (solvent; ethyl acetate/hexane=1:1) to give (3R)-1-[bis-(4-chlorophenyl)methyl]-3-[[(2S)-2-(morpholinocarbonylamino)-3-phenylpropionyl]amino]pyrrolidine (12 mg, yield: 58%) as a powder.

MS(ESI) m/z; 581 $[M+H]^+$

Example 18

(1) To a solution of the compound obtained in Example 13 (60 mg) and triethylamine (24 μL) in methylene chloride (1 mL) was added dropwise methanesulfonyl chloride (11 μL)

under ice-cooling and the mixture was stirred for 30 minutes. The reaction mixture was diluted with ethyl acetate. After adding water, the organic layer was separated and evaporated in vacuo. The crude product was purified by a flash column chromatography on NH-silica gel (Chromatorex NH-silica gel, solvent; hexane/ethyl acetate=4:1→0:1), dissolved in tert-butylalcohol (1.5 μL) and lyophilized to give (3,4-cis)-1-[bis-(4-chlorophenyl)methyl]-3-methanesulfonyloxy-4-[[4-(trifluoromethoxy)-benzoyl]amino]pyrrolidine (38.2 mg, yield: 56%) as a powder.

MS(APCI) m/z; 603/605 $[M+H]^+$ (2) To a solution of the compound obtained in the above step (1) (31.3 mg) in dimethylformamide (0.3 mL) was added pyrrolidine (45 μL) and the mixture was stirred at 150° C. for 10 minutes by using Microwave Synthetic System (Discover). The reaction mixture was diluted with ethyl acetate. After adding water, the organic layer was separated and evaporated in vacuo. The crude product was purified by HPLC (XTerra Prep MS C18 column, solvent; water/methanol=1:1→5:95), dissolved in tert-butylalcohol and lyophilized to give (3,4-trans)-1-[bis-(4-chlorophenyl)methyl]-3-(1-pyrrolidinyl)-4-[[4-(trifluoromethoxy)benzoyl]amino]pyrrolidine (13.2 mg, yield: 44%) as a powder.

MS(APCI) m/z; 578/580 $[M+H]^+$

Example 19

(1) To a solution of the compound obtained in Example 6 (248.8 mg) in methanol (3 mL) and tetrahydrofuran (3 mL) was added 1N sodium hydroxide solution (0.86 mL) under ice-cooling and the mixture was stirred at room temperature for 4 hours. The reaction mixture was evaporated in vacuo and the residue was acidified with an aqueous saturated citric acid solution (about pH 3). The mixture was extracted with ethyl acetate and the organic layer was washed with water and a saturated brine, dried over magnesium sulfate and evaporated in vacuo. The residue was triturated in diisopropylether and the resultant solid materials were collected by filtration to give (3,4-trans)-1-[bis-(4-chloro-phenyl)methyl]-3-carboxy-4-[[4-(trifluoromethoxy)benzoyl]amino]pyrrolidine (181.1 mg, yield: 76%) as a solid.

MS(APCI) m/z; 553/555 $[M+H]^+$ (2) To a solution of the compound obtained in the above step (1) (30.0 mg) in dimethylformamide (1.0 mL) was added 1-hydroxybenzotriazole (17 mg) and 1-ethyl-3-[3-(dimethylamino)propyl]carbodiimide hydrochloride (21 mg) and the mixture was stirred at room temperature for 30 minutes. To the reaction mixture was added N,N'-dimethylethylenediamine (0.011 mL) and the mixture was stirred at room temperature overnight. The reaction mixture was poured into water/ethyl acetate. The organic layer was washed successively with an aqueous saturated sodium hydrogencarbonate solution, water and a saturated brine, dried over magnesium sulfate and evaporated in vacuo. The residue was triturated and the resultant solid materials were collected by filtration to give (3,4-trans)-1-[bis-(4-chlorophenyl)methyl]-3-[2-(dimethylamino)ethylcarbamoyl]-4-[[4-(trifluoromethoxy)benzoyl]amino]pyrrolidine (25.1 mg, yield: 75%) as a powder.

MS(APCI) m/z; 623/625 $[M+H]^+$

Example 20

To a solution of N,N'-carbonyldiimidazole (16 mg) in tetrahydrofuran was added dropwise a solution of the compound obtained in Reference Example 11 (32 mg) in tetrahydrofuran under ice-cooling and the mixture was stirred for 30 minutes. To the mixture was added dropwise 1,2,3,4-tetrahydroisoquinoline (13 mg) and the mixture was stirred at room temperature for 15 hours. The reaction mixture was evaporated in vacuo and thereto was added an aqueous saturated sodium hydrogencarbonate solution. The mixture was extracted with chloroform and the extract was evaporated in vacuo. The crude product was purified by a column chromatography on silica gel (solvent; ethyl acetate/hexane) to give (3R)-1-[bis-(4-chlorophenyl)methyl]-3-[(2-1,2,3,4-tetrahydro isoquinolyl)carbonylamino]pyrrolidine (30 mg, yield: 62%) as a powder.

MS(APCI) m/z; 480/482 $[M+H]^+$

Example 21

A mixture of the compound obtained in Reference Example 11 (32.1 mg), 4-cyanobenzoic acid (29.4 mg), 1-hydroxyazabenzotriazole (20.4 mg), N-cyclohexyl-carbodiimide-N'-propyloxymethylpolystyrene (PS-carbodiimide, 275 mg) and dimethylformamide (2 mL) was stirred at room temperature overnight by using a parallel synthetizer (MiniBlock; Mettler Toledo). The reaction mixture was filtered and the resin was washed with dimethylformamide (1 mL×2). To the filtrate was added macroporous triethylammoniummethylpolystyrenecarbonate (265.2 mg) and tris(2-aminoethyl)aminomethyl polystyrene (82.9 mg) and the mixture was stirred at room temperature overnight. The reaction mixture was treated with a cation-exchange resin (ISOLUTE SCX; IST Ltd.) and washed with dimethylformamide. The objective product was eluted with 10% ammonia-methanol and purged by nitrogen gas to remove solvent. The residue was purified by a column chromatography on silica gel (ISOLUTE SI; IST Ltd., solvent; chloroform/hexane=20:1→chloroform→chloroform/ethyl acetate=10:1), evaporated in vacuo and lyophilized to give (3R)-1-[bis-(4-chlorophenyl)methyl]-3-[(4-cyanobenzoyl)amino]pyrrolidine (30.9 mg, yield: 69%) as a powder.

MS(APCI) m/z; 450/452 $[M+H]^+$

Example 22

(1) 4-Bromobenzaldehyde (4.0 g) was treated in the same manner as described in reference Example 5 to give chloro (4-chlorophenyl)(4-bromophenyl)methane (5.08 g, yield: 75%). MS(APCI) m/z; 279/281 $[M+H-HCl]^+$ (2) The compound obtained in the above step (1) (1.73 g) was treated in the same manner as described in Example 6 to give 1-[(4-bromophenyl)(4-chlorophenyl)methyl]-3-[[4-(trifluoromethoxy)benzoyl]amino]pyrrolidine (1.65 g, yield: 82%).

MS(APCI) m/z; 553/555 $[M+H]^+$ (3) A mixture of the compound obtained in the above step (2) (60 mg), tris(dibenzylideneacetone)dipalladium (4.0 mg), 1,1'-bis(diphenylphosphino)ferrocene (4.8 mg), zinc cyanide (7.6 mg), water (50 μL) and dimethylformamide (0.5 mL) was stirred at 200° C. for 10 minutes by using a microwave synthetic system (Discover; CEM). The reaction mixture was diluted with ethyl acetate. After adding water, the organic layer was separated and evaporated in vacuo. The crude product was purified by a column chromatography on silica gel (solvent; hexane/ethyl acetate=4:1→1:1), dissolved in tert-butylalcohol and lyophilized to give 1-[(4-chlorophenyl)(4-cyanophenyl)-methyl]-3-[[4-(trifluoromethoxy)benzoyl]amino]pyrrolidine (13.4 mg, yield: 25%) as a powder.

MS(APCI) m/z; 500/502 $[M+H]^+$

Examples 23 to 431

The corresponding materials were treated in the same manner as described in one of the aforementioned Examples 1 to 5 to give the compounds as shown in the following Table 1 (Nos. 1 to 68).

TABLE 1 (No. 1)

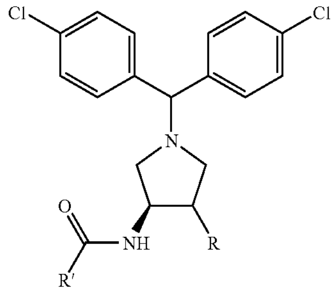

| Ex. Nos. | R | R' | Physicochemical properties etc. |
| --- | --- | --- | --- |
| 23 |  | 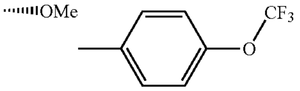 | powder MS(APCI)539/541[M + H]+ |
| 24 |  | 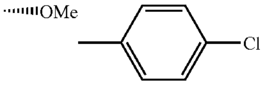 | powder MS(APCI)489/491[M + H]+ |
| 25 | 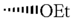 | 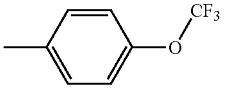 | powder MS(APCI)553/555[M + H]+ |
| 26 |  | 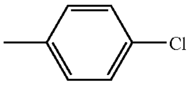 | powder MS(APCI)503/505[M + H]+ |

Me: methyl group,
Et: ethyl group

TABLE 1 (No. 2)

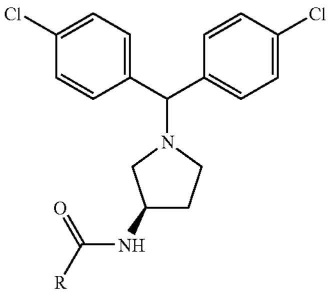

| Ex.Nos. | R | Physicochemical properties etc. |
| --- | --- | --- |
| 27 | 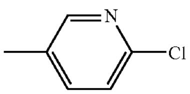 | powder MS(APCI)460/462[M + H]+ |

TABLE 1 (No. 2)-continued

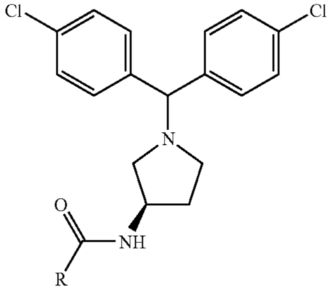

| Ex.Nos. | R | Physicochemical properties etc. |
| --- | --- | --- |
| 28 | 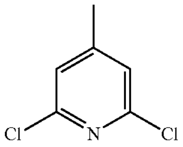 | powder MS(APCI)494/496[M + H]+ |

TABLE 1 (No. 2)-continued

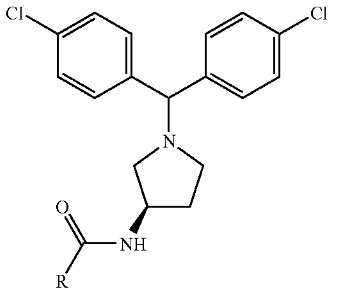

| Ex.Nos. | R | Physicochemical properties etc. |
|---|---|---|
| 29 | 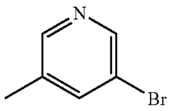 | powder MS(APCI)504/506[M + H]+ |
| 30 | 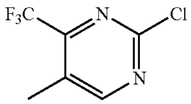 | powder MS(APCI)529/531[M + H]+ |

TABLE 1 (No. 2)-continued

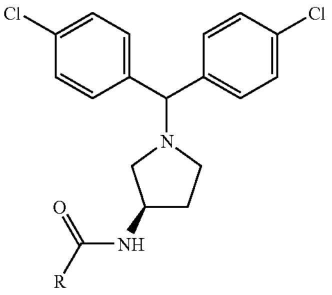

| Ex.Nos. | R | Physicochemical properties etc. |
|---|---|---|
| 31 | 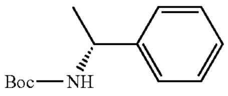 | oil MS(APCI)554/556[M + H]+ |
| 32 | 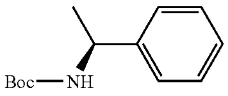 | powder MS(APCI)554/556[M + H]+ |

Boc: tert-butyloxycarbonyl group

TABLE 1 (No. 3)

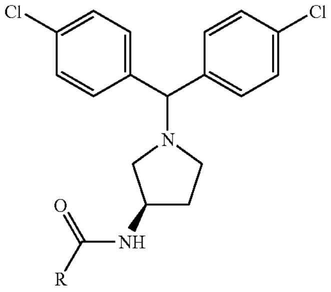

| Ex. Nos. | R | Physicochemical properties etc. |
|---|---|---|
| 33 | 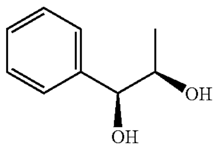 | powder MS(APCI)485/487[M + H]+ |
| 34 | 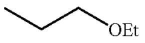 | solid MS(APCI)421/423[M + H]+ |
| 35 | 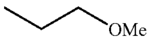 | solid MS(APCI)407/409[M + H]+ |
| 36 | 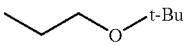 | solid MS(APCI)449/451[M + H]+ |
| 37 | 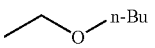 | solid MS(APCI)435/437[M + H]+ |
| 38 | 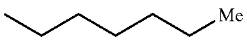 | solid MS(APCI)433/435[M + H]+ |
| 39 | 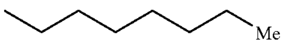 | solid MS(APCI)447/449[M + H]+ |
| 40 | 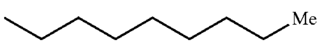 | solid MS(APCI)461/463[M + H]+ |

TABLE 1 (No. 3)-continued
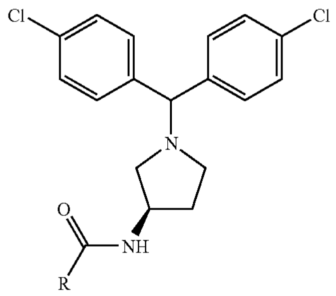
| Ex. Nos. | R | Physicochemical properties etc. |
|---|---|---|
| 41 | 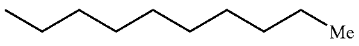 | solid<br>MS(APCI)475/477[M + H]+ |
Me: methyl group,
Et: ethyl group,
n-Bu: n-butyl group,
t-Bu: tert-butyl group
TABLE 1 (No. 4)
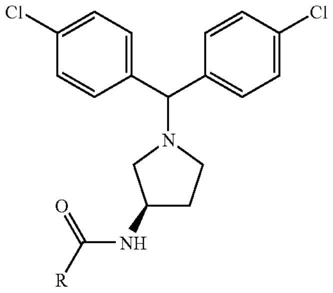
| Ex. Nos. | R | Physicochemical properties etc. |
|---|---|---|
| 42 | 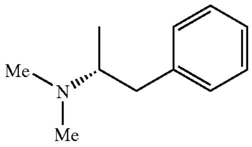 | solid<br>MS(APCI)496/498[M + H]+ |
| 43 | 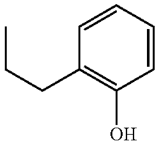 | solid<br>MS(APCI)469/471[M + H]+ |
| 44 | 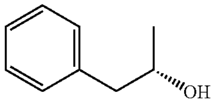 | powder<br>MS(APCI)469/471[M + H]+ |
| 45 | 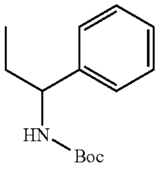 | powder<br>MS(APCI)568/570[M + H]+ |

TABLE 1 (No. 4)-continued

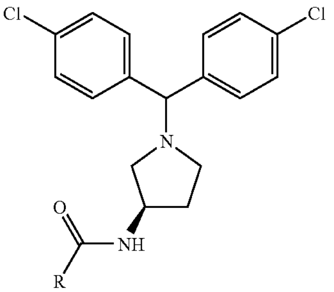

| Ex. Nos. | R | Physicochemical properties etc. |
|---|---|---|
| 46 | 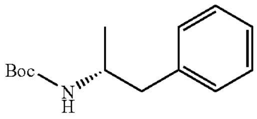 | powder<br>MS(APCI)568/570[M + H]+ |
| 47 | 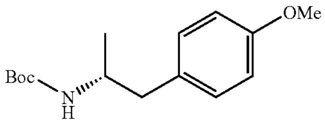 | powder<br>MS(APCI)598/600[M + H]+ |

Me: methyl group,
Boc: tert-butyloxycarbonyl group

TABLE 1 (No. 5)

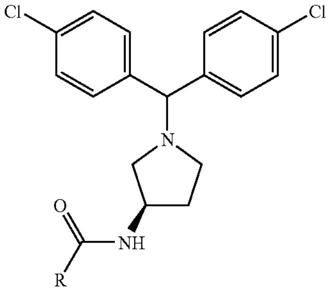

| Ex. Nos. | R | Physicochemical properties etc. |
|---|---|---|
| 48 | 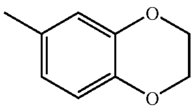 | powder<br>MS(APCI)483/485[M + H]+ |
| 49 | 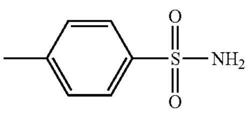 | powder<br>MS(APCI)5O4/5O6[M + H]+ |
| 50 | 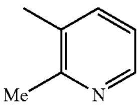 | powder<br>MS(APCI)440/442[M + H]+ |
| 51 | 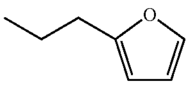 | powder<br>MS(APCI)443/445[M + H]+ |

TABLE 1 (No. 5)-continued

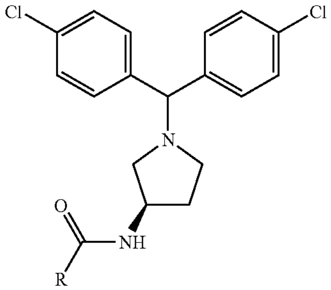

| Ex. Nos. | R | Physicochemical properties etc. |
|---|---|---|
| 52 | 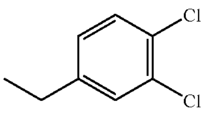 | powder<br>MS(APCI)507/509[M + H]+ |
| 53 | 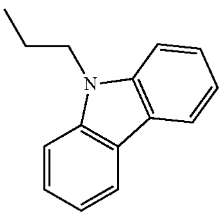 | powder<br>MS(APCI)542/544[M + H]+ |

Me: methyl group

TABLE 1 (no. 6)
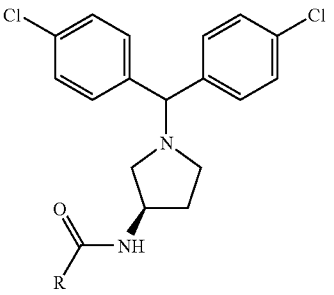
| Ex. Nos. | R | Physicochemical properties etc. |
|---|---|---|
| 54 | 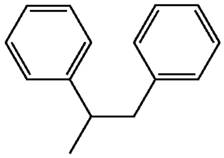 | powder MS(APCI)529/531[M + H]+ |
| 55 | 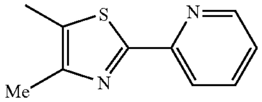 | powder MS(APCI)523/525[M + H]+ |
| 56 | 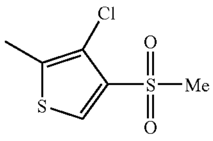 | powder MS(APCI)543/545[M + H]+ |
| 57 | 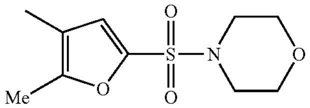 | powder MS(APCI)578/580[M + H]+ |
| 58 | 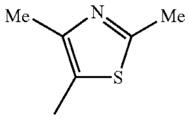 | powder MS(APCI)460/462[M + H]+ |
| 59 | 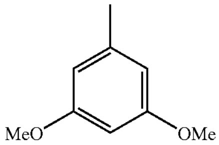 | powder MS(APCI)485/487[M + H]+ |
Me: methyl group TABLE 1 (No. 7)

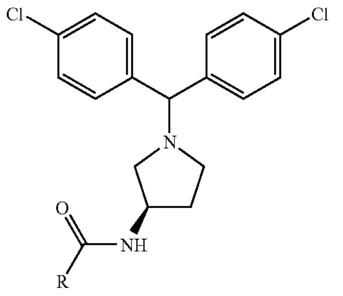

| Ex. Nos. | R | Physicochemical properties etc. |
|---|---|---|
| 60 | 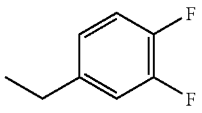 | powder MS(APCI)475/477[M + H]+ |
| 61 | 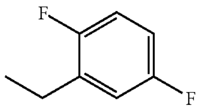 | powder MS(APCI)475/477[M + H]+ |
| 62 | 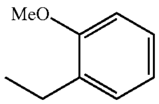 | powder MS(APCI)469/471[M + H]+ |

TABLE 1 (No. 7)-continued

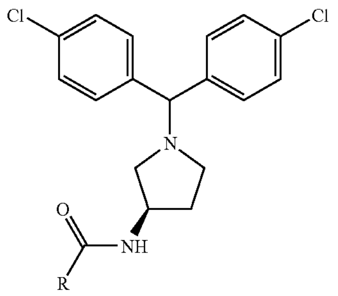

| Ex. Nos. | R | Physicochemical properties etc. |
|---|---|---|
| 63 | 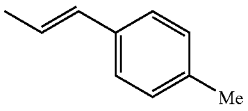 | powder MS(APCI)465/467[M + H]+ |
| 64 | 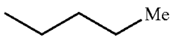 | powder MS(APCI)405/407[M + H]+ |
| 65 | 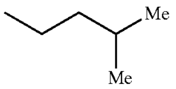 | powder MS(APCI)419/421[M + H]+ |
| 66 | 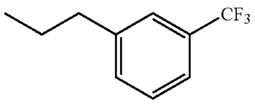 | powder MS(APCI)521/523[M + H]+ |

Me: methyl group

TABLE 1 (No. 8)

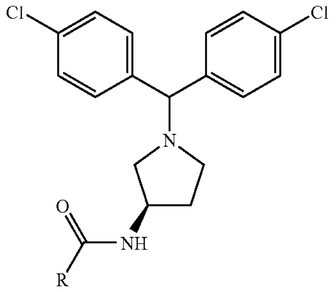

| Ex. Nos. | R | Physicochemical properties etc. |
|---|---|---|
| 67 | 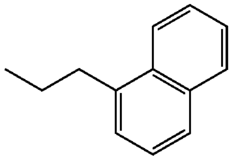 | powder MS(APCI)503/505[M + H]+ |
| 68 | 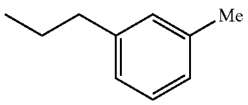 | powder MS(APCI)467/469[M + H]+ |
| 69 | 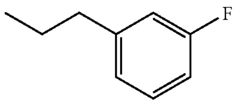 | powder MS(APCI)471/473[M + H]+ |

TABLE 1 (No. 8)-continued

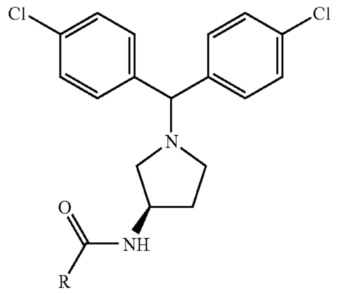

| Ex. Nos. | R | Physicochemical properties etc. |
|---|---|---|
| 70 | 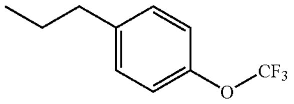 | powder<br>MS(APCI)537/539[M + H]+ |
| 71 | 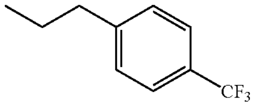 | powder<br>MS(APCI)521/523[M + H]+ |
| 72 | 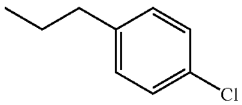 | powder<br>MS(APCI)487/489[M + H]+ |
| 73 | 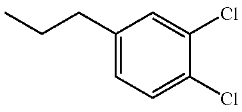 | powder<br>MS(APCI)521/523[M + H]+ |

Me: methyl group

TABLE 1 (No. 9)

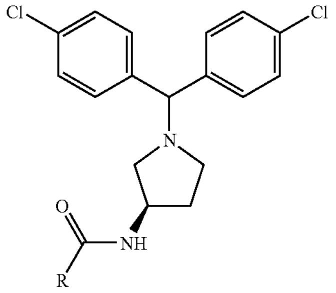

| Ex. Nos. | R | Physicochemical properties etc. |
|---|---|---|
| 74 | 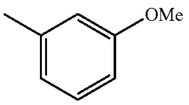 | powder<br>MS(APCI)455/457[M + H]+ |
| 75 | 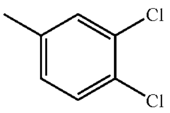 | powder<br>MS(APCI)493/495[M + H]+ |

TABLE 1 (No. 9)-continued

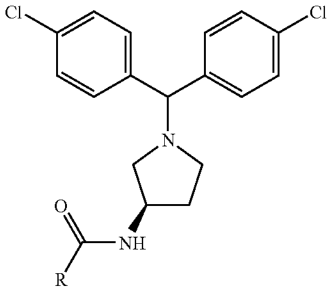

| Ex. Nos. | R | Physicochemical properties etc. |
|---|---|---|
| 76 | 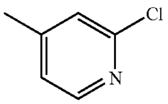 | powder<br>MS(APCI)460/462[M + H]+ |

Me: methyl group

TABLE 1 (No. 10)
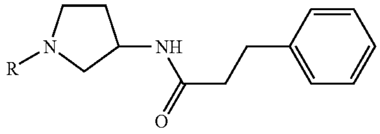
| Ex. Nos. | R | Physicochemical properties etc. |
|---|---|---|
| 77 | 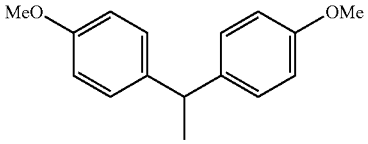 | powder<br>MS(APCI)445[M + H]+ |
| 78 | 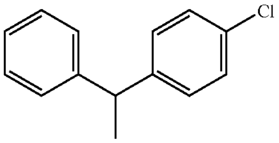 | powder<br>MS(APCI)419/421[M + H]+ |
| 79 | 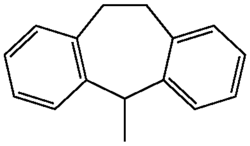 | powder<br>MS(APCI)411[M + H]+ |
| 80 | 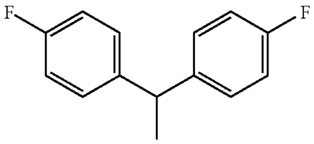 | powder<br>MS(APCI)421[M + H]+ |
Me: methyl group
TABLE 1 (No. 11)
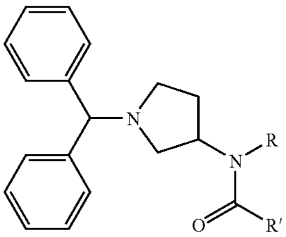
| Ex. Nos. | R | R' | Physicochemical properties etc. |
|---|---|---|---|
| 81 | H | 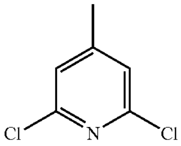 | powder<br>MS(SSI)426 |
TABLE 1 (No. 11)-continued
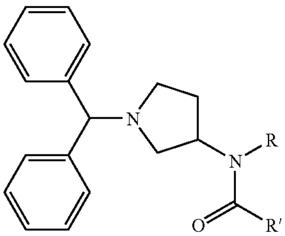
| Ex. Nos. | R | R' | Physicochemical properties etc. |
|---|---|---|---|
| 82 | Me | 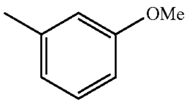 | powder<br>MS(SSI)400 |
Me: methyl group TABLE 1 (No. 12)
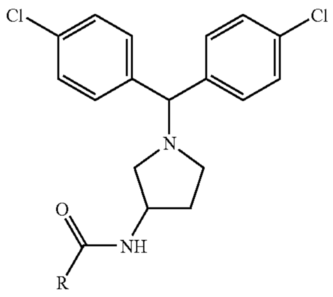
| Ex. Nos. | R | Physicochemical properties etc. |
|---|---|---|
| 83 | 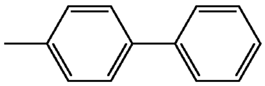 | powder MS(SSI)501 |
| 84 | 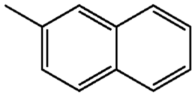 | powder MS(SSI)475 |
| 85 | 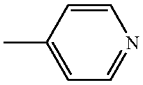 | powder MS(SSI)426 |
| 86 | 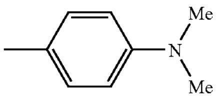 | powder MS(SSI)468 |
| 87 | 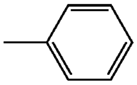 | powder MS(SSI)425 |
| 88 | 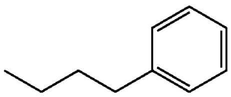 | powder MS(SSI)467 |
| 89 | 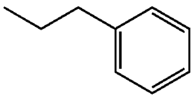 | powder MS(SSI)453 |
Me: methyl group
TABLE 1 (No. 13)
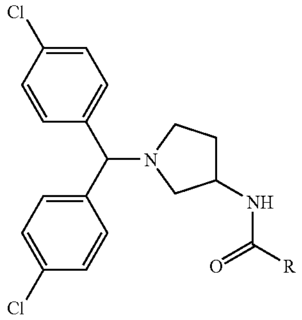
| Ex. Nos. | R | Physicochemical properties etc. |
|---|---|---|
| 90 | 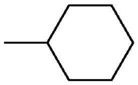 | powder MS(SSI)431 |
| 91 | 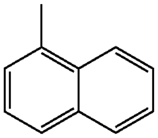 | powder MS(SSI)475 |
| 92 | 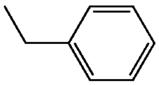 | powder MS(SSI)439 |
| 93 | 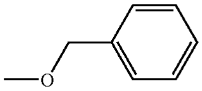 | powder MS(SSI)455 |
| 94 | 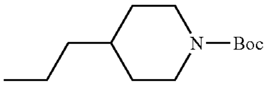 | powder MS(SSI)560 |
| 95 | 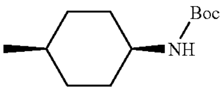 | powder MS(SSI)546 |
| 96 | 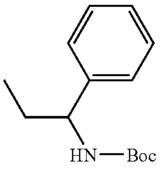 | powder MS(SSI)568 |
Boc: tert-butyloxycarbonyl group TABLE 1 (No. 14)

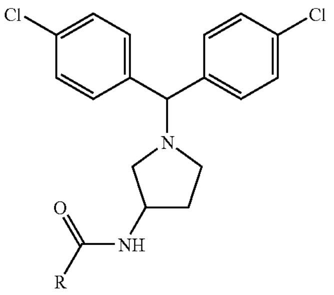

| Ex. Nos. | R | Physicochemical properties etc. |
|---|---|---|
| 97 | 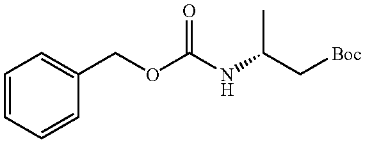 | powder MS(SSI)626 |
| 98 | 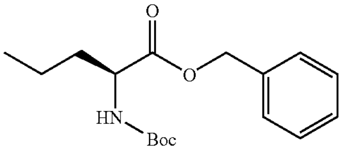 | powder MS(SSI)640 |
| 99 | 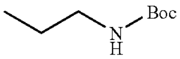 | powder MS(SSI)492 |
| 100 | 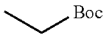 | powder MS(SSI)463 |
| 101 | 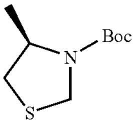 | powder MS(SSI)536 |
| 102 | 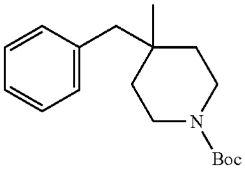 | powder MS(SSI)622 |

Boc: tert-butyloxycarbonyl group

TABLE 1 (No. 15)

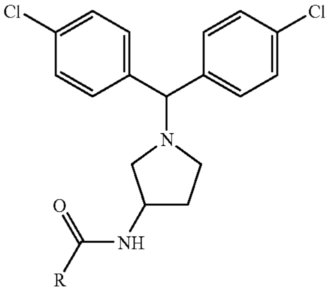

| Ex. Nos. | R | Physicochemical properties etc. |
|---|---|---|
| 103 | 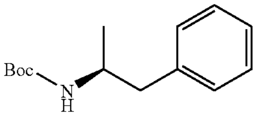 | powder MS(APCI) 568/570 [M + H]+ |
| 104 | 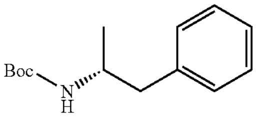 | powder MS(APCI) 568/570[M + H]+ |
| 105 | 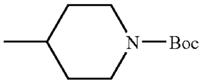 | powder MS(SSI)532 |
| 106 | 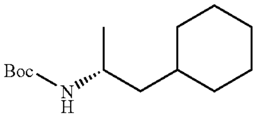 | powder MS(SSI)574 |
| 107 | 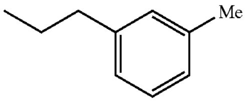 | powder MS(SSI)467 |
| 108 | 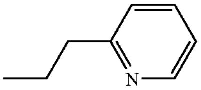 | powder MS(SSI)454 |
| 109 | 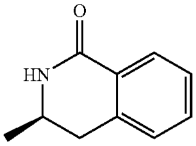 | powder MS(SSI)494 |

Me: methyl group,
Boc: tert-butyloxycarbonyl group

TABLE 1 (No. 16)
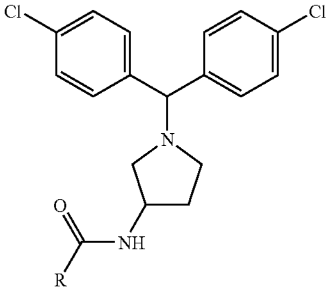
| Ex. Nos. | R | Physicochemical properties etc. |
|---|---|---|
| 110 | 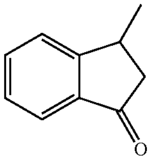 | powder MS(SSI)479 |
| 111 | 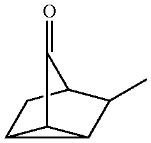 | powder MS(SSI)455 |
| 112 | 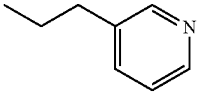 | powder MS(SSI)454 |
| 113 | 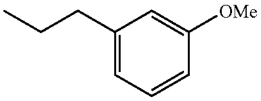 | powder MS(SSI)483 |
| 114 | 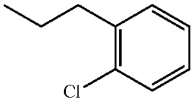 | powder MS(SSI)487 |
| 115 | 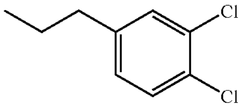 | powder MS(SSI)522 |
| 116 | 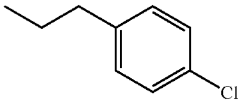 | powder MS(SSI)487 |
Me: methyl group
TABLE 1 (No. 17)
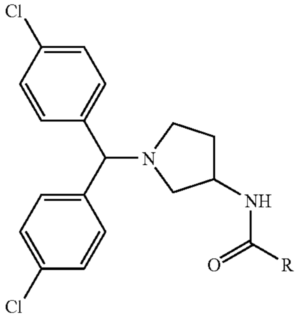
| Ex. Nos. | R | Physicochemical properties etc. |
|---|---|---|
| 117 | 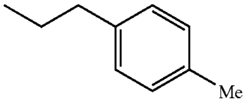 | powder MS(SSI)467 |
| 118 | 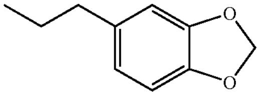 | powder MS(SSI)497 |
| 119 | 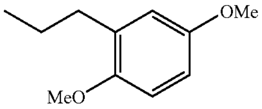 | powder MS(SSI)513 |
| 120 | 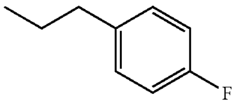 | powder MS(SSI)471 |
| 121 | 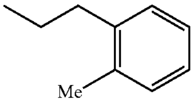 | powder MS(SSI)467 |
| 122 | 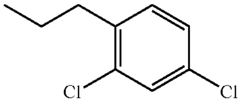 | powder MS(SSI)522 |
| 123 | 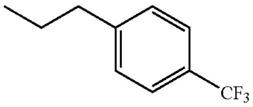 | powder MS(SSI)521 |
Me: methyl group TABLE 1 (No. 18)
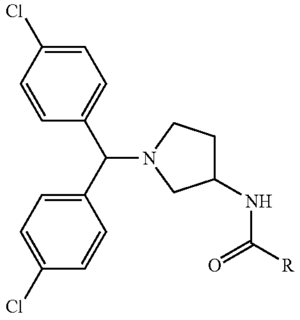
| Ex. Nos. | R | Physicochemical properties etc. |
|---|---|---|
| 124 | 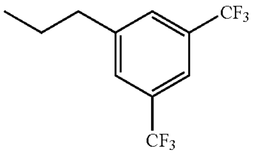 | powder MS(SSI)589 |
| 125 | 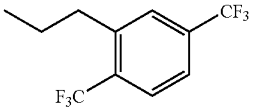 | powder MS(SSI)589 |
| 126 | 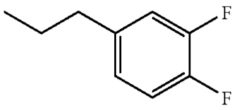 | powder MS(SSI)489 |
| 127 | 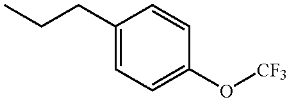 | powder MS(SSI)537 |
| 128 | 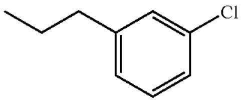 | powder MS(SSI)487 |
| 129 | 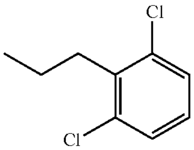 | powder MS(SSI)522 |
| 130 | 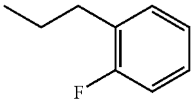 | powder MS(SSI)471 |
TABLE 1 (No. 19)
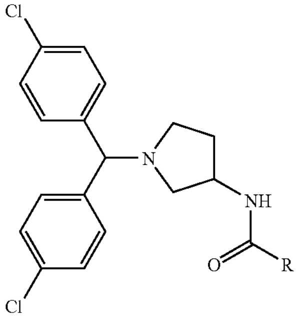
| Ex. Nos. | R | Physicochemical properties etc. |
|---|---|---|
| 131 | 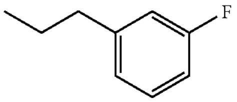 | powder MS(SSI)471 |
| 132 | 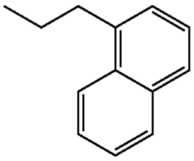 | powder MS(SSI)503 |
| 133 | 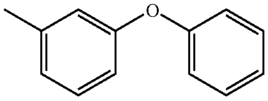 | powder MS(SSI)517 |
| 134 | 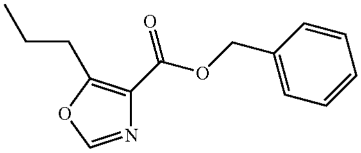 | powder MS(SSI)578 |
| 135 | 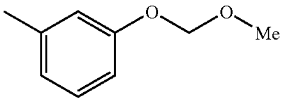 | powder MS(SSI)485 |
| 136 | 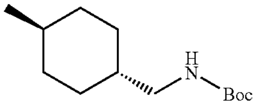 | powder MS(SSI)560 |
Me: methyl group,
Boc: tert-butyloxycarbonyl group TABLE 1 (No. 20)
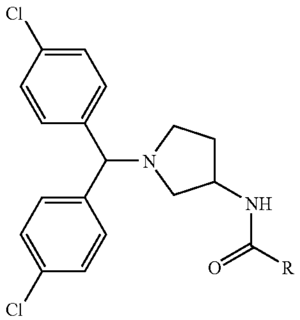
| Ex. Nos. | R | Physicochemical properties etc. |
|---|---|---|
| 137 | 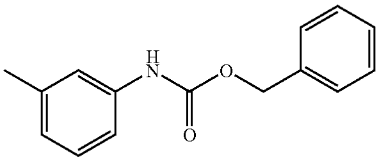 | powder MS(SSI)574 |
| 138 | 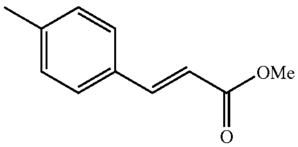 | powder MS(SSI)509 |
| 139 | 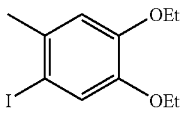 | powder MS(SSI)639 |
| 140 | 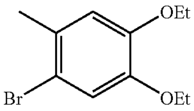 | powder MS(SSI)564 |
| 141 | 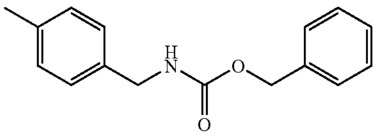 | powder MS(SSI)588 |
| 142 | 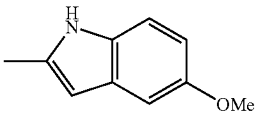 | powder MS(SSI)494 |
| 143 | 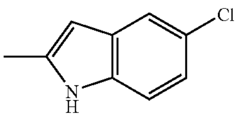 | powder MS(SSI)498 |
Me: methyl group,
Et: ethyl group
TABLE 1 (No. 21)
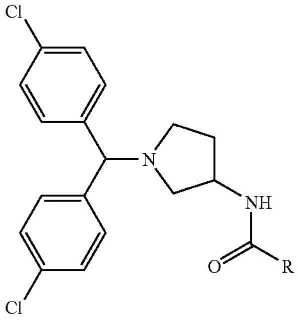
| Ex. Nos. | R | Physicochemical properties etc. |
|---|---|---|
| 144 | 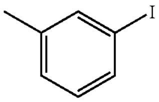 | powder MS(SSI)551 |
| 145 | 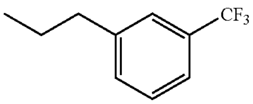 | powder MS(SSI)521 |
| 146 | 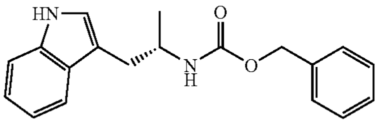 | powder MS(SSI)641 |
| 147 | 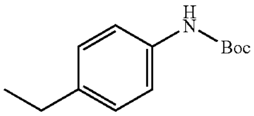 | powder MS(SSI)554 |
| 148 | 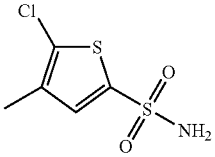 | powder MS(SSI)544 |
| 149 | 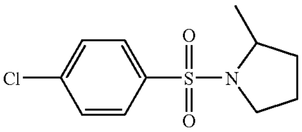 | powder MS(SSI)592 |
Boc: tert-butyloxycarbonyl group TABLE 1 (No. 22)
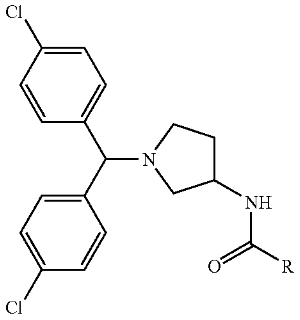
| Ex. Nos. | R | Physicochemical properties etc. |
|---|---|---|
| 150 | 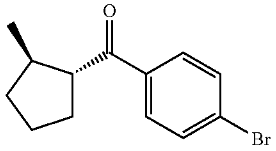 | powder MS(SSI)600 |
| 151 | 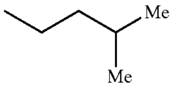 | powder MS(SSI)419 |
| 152 | 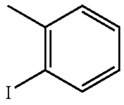 | powder MS(SSI)551 |
| 153 | n-Bu | powder MS(SSI)405 |
| 154 | 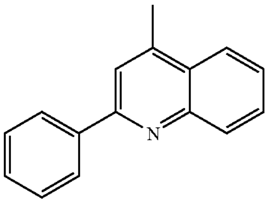 | powder MS(SSI)552 |
| 155 | 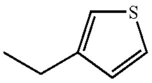 | powder MS(SSI)445 |
| 156 | 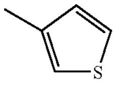 | powder MS(SSI)431 |
Me: methyl group,
n-Bu: n-butyl group
TABLE 1 (No. 23)
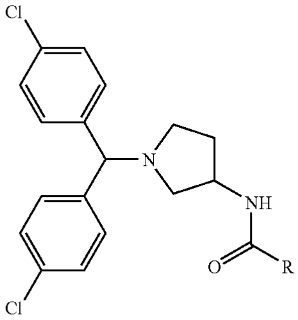
| Ex. Nos. | R | Physicochemical properties etc. |
|---|---|---|
| 157 | 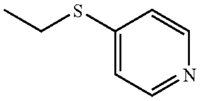 | powder MS(SSI)472 |
| 158 | 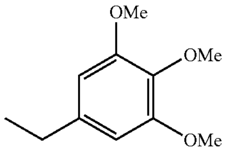 | powder MS(SSI)529 |
| 159 | 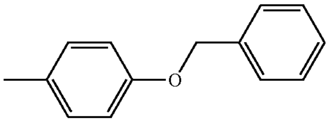 | powder MS(SSI)531 |
| 160 | 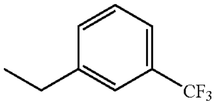 | powder MS(SSI)507 |
| 161 | 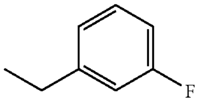 | powder MS(SSI)457 |
| 162 | 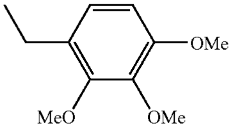 | powder MS(SSI)529 |
Me: methyl group TABLE 1 (No. 24)
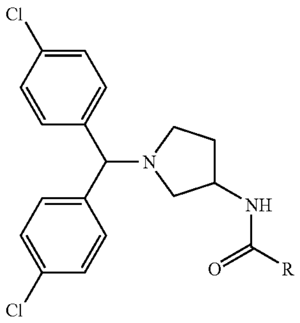
| Ex. Nos. | R | Physicochemical properties etc. |
|---|---|---|
| 163 | 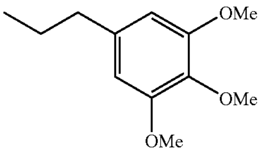 | powder MS(SSI)543 |
| 164 | 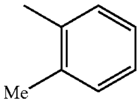 | powder MS(SSI)439 |
| 165 | 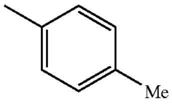 | powder MS(SSI)439 |
| 166 | 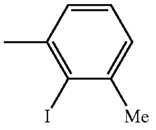 | powder MS(SSI)565 |
| 167 | 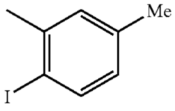 | powder MS(SSI)565 |
| 168 | 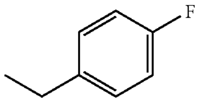 | powder MS(SSI)457 |
| 169 | 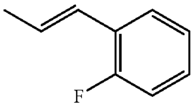 | powder MS(SSI)469 |
Me: methyl group
TABLE 1 (No. 25)
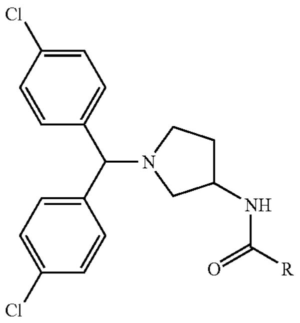
| Ex. Nos. | R | Physicochemical properties etc. |
|---|---|---|
| 170 | 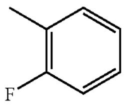 | powder MS(SSI)443 |
| 171 | 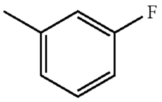 | powder MS(SSI)443 |
| 172 | 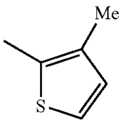 | powder MS(SSI)445 |
| 173 | 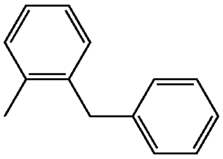 | powder MS(SSI)515 |
| 174 | 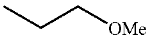 | powder MS(SSI)407 |
| 175 | 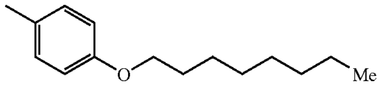 | powder MS(SSI)553 |
| 176 | 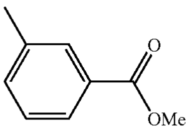 | powder MS(SSI)483 |
Me: methyl group TABLE 1 (No. 26)
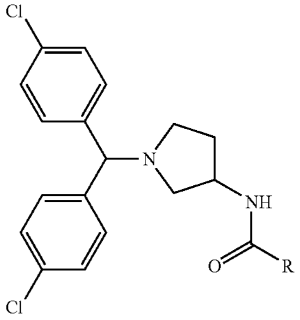
| Ex. Nos. | R | Physicochemical properties etc. |
|---|---|---|
| 177 | 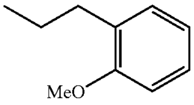 | powder MS(SSI)483 |
| 178 | 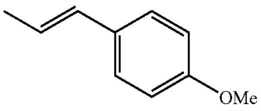 | powder MS(SSI)481 |
| 179 | 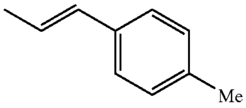 | powder MS(SSI)465 |
| 180 | 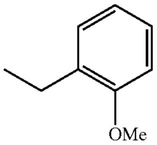 | powder MS(SSI)469 |
| 181 | 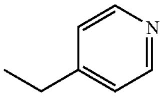 | powder MS(SSI)440 |
| 182 | 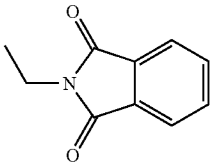 | powder MS(SSI)508 |
| 183 | 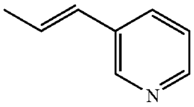 | powder MS(SSI)452 |
Me: methyl group
TABLE 1 (No. 27)
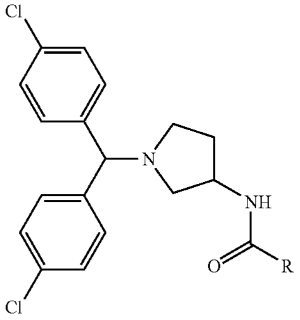
| Ex. Nos. | R | Physicochemical properties etc. |
|---|---|---|
| 184 | 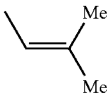 | powder MS(SSI)403 |
| 185 | 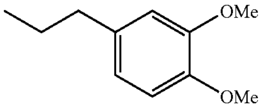 | powder MS(SSI)513 |
| 186 | 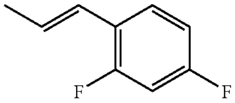 | powder MS(SSI)487 |
| 187 | 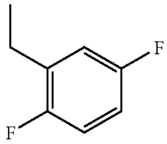 | powder MS(SSI)475 |
| 188 | 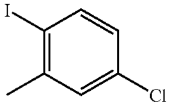 | powder MS(SSI)585 |
| 189 | 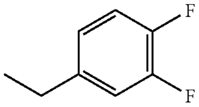 | powder MS(SSI)475 |
| 190 | 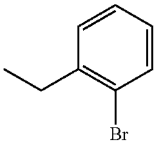 | powder MS(SSI)518 |
Me: methyl group TABLE 1 (No. 28)
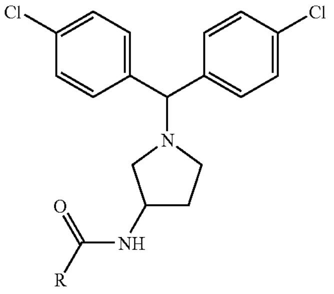
| Ex. Nos. | R | Physicochemical properties etc. |
|---|---|---|
| 191 | 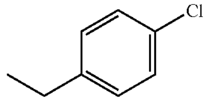 | powder MS(SSI)473 |
| 192 | 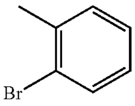 | powder MS(SSI)504 |
| 193 | 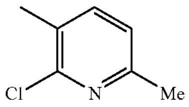 | powder MS(SSI)474 |
| 194 | 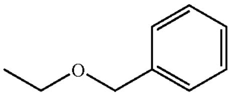 | powder MS(SSI)469 |
| 195 | 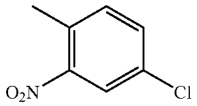 | powder MS(SSI)504 |
| 196 | 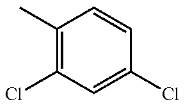 | powder MS(SSI)494 |
Me: methyl group
TABLE 1 (No. 29)
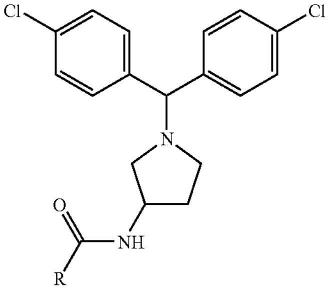
| Ex. Nos. | R | Physicochemical properties etc. |
|---|---|---|
| 197 | 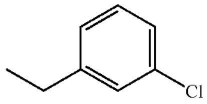 | powder MS(SSI)473 |
| 198 | 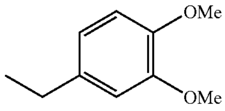 | powder MS(SSI)499 |
| 199 | 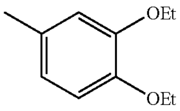 | powder MS(SSI)513 |
| 200 | 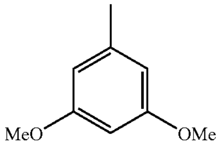 | powder MS(SSI)485 |
| 201 | 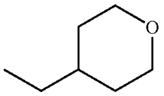 | powder MS(SSI)447 |
| 202 | 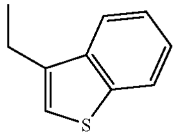 | powder MS(SSI)495 |
Me: methyl group,
Et: ethyl group TABLE 1 (No. 30)
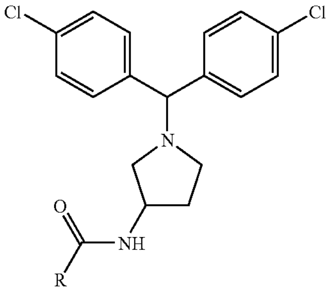
| Ex. Nos. | R | Physicochemical properties etc. |
|---|---|---|
| 203 | 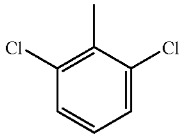 | powder MS(SSI)494 |
| 204 | 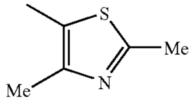 | powder MS(SSI)460 |
| 205 | 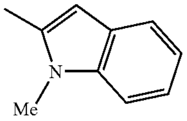 | powder MS(SSI)478 |
| 206 | 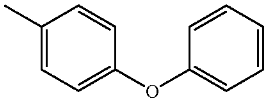 | powder MS(SSI)517 |
| 207 | 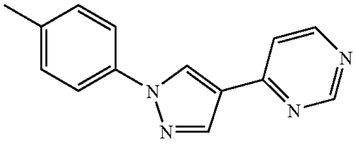 | powder MS(SSI)569 |
| 208 | 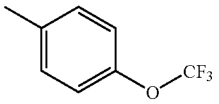 | powder MS(SSI)509 |
| 209 | 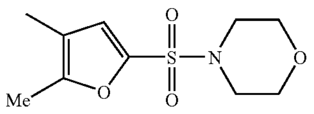 | powder MS(SSI)578 |
Me: methyl group
TABLE 1 (No. 31)
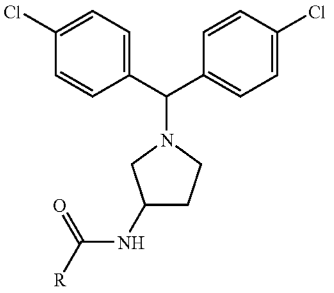
| Ex. Nos. | R | Physicochemical properties etc. |
|---|---|---|
| 210 | 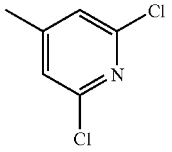 | powder MS(SSI)495 |
| 211 | 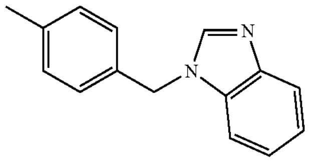 | powder MS(SSI)555 |
| 212 | 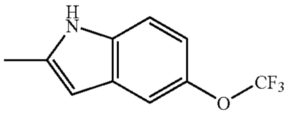 | powder MS(SSI)548 |
| 213 | 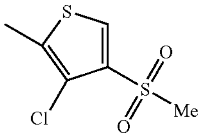 | powder MS(SSI)543 |
| 214 | 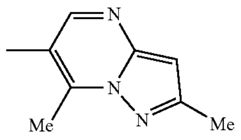 | powder MS(SSI)494 |
| 215 | 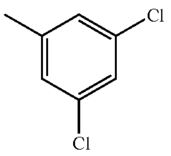 | powder MS(SSI)494 |
Me: methyl group TABLE 1 (No. 32)
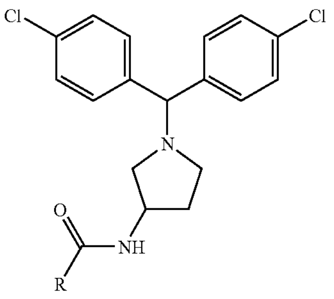
| Ex. Nos. | R | Physicochemical properties etc. |
| --- | --- | --- |
| 216 | 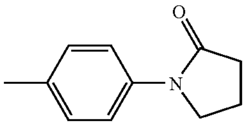 | powder MS(SSI)508 |
| 217 | 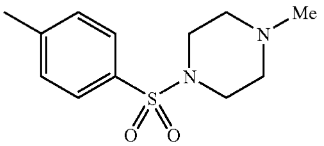 | powder MS(SSI)587 |
| 218 | 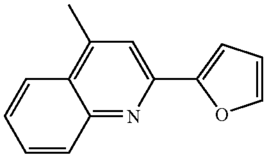 | powder MS(SSI)542 |
| 219 | 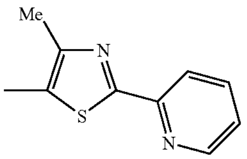 | powder MS(SSI)523 |
| 220 | 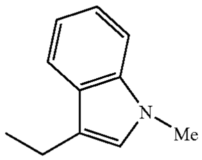 | powder MS(SSI)492 |
Me: methyl group
TABLE 1 (No. 33)
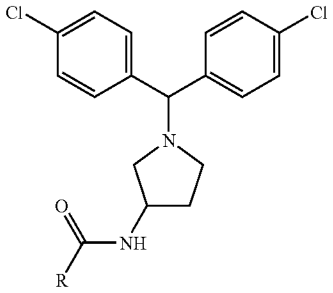
| Ex. Nos. | R | Physicochemical properties etc. |
| --- | --- | --- |
| 221 | 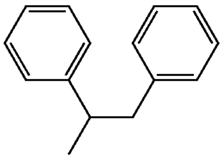 | powder MS(SSI)529 |
| 222 | 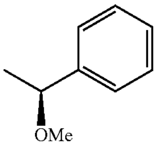 | powder MS(SSI)469 |
| 223 | 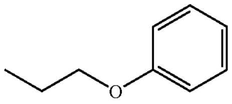 | powder MS(SSI)469 |
| 224 | 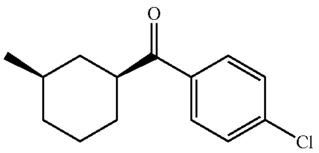 | powder MS(SSI)569 |
| 225 | 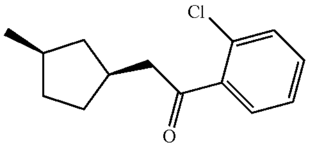 | powder MS(SSI)569 |
| 226 | 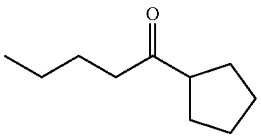 | powder MS(SSI)487 |
Me: methyl group TABLE 1 (No. 34)
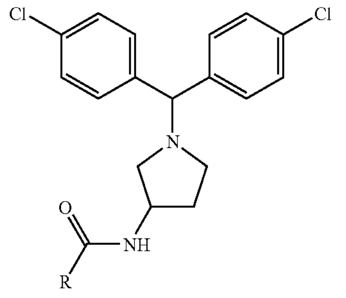
| Ex. Nos. | R | Physicochemical properties etc. |
| --- | --- | --- |
| 227 | 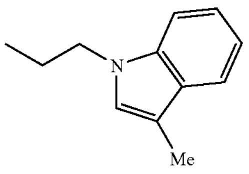 | powder MS(SSI)506 |
| 228 | 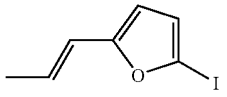 | powder MS(SSI)567 |
| 229 | 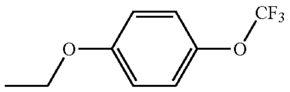 | powder MS(SSI)539 |
| 230 | 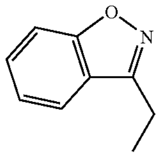 | powder MS(SSI)480 |
| 231 | 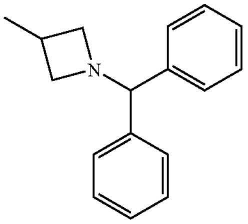 | powder MS(SSI)570 |
| 232 | 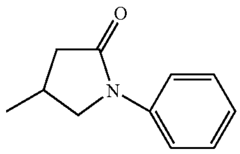 | powder MS(SSI)508 |
Me: methyl group
TABLE 1 (No. 35)
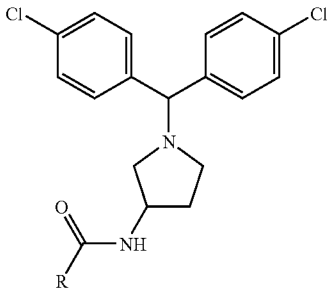
| Ex. Nos. | R | Physicochemical properties etc. |
| --- | --- | --- |
| 233 | 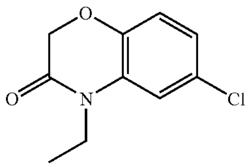 | powder MS(SSI)544 |
| 234 | 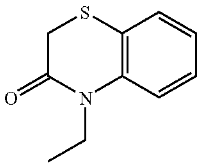 | powder MS(SSI)526 |
| 235 | 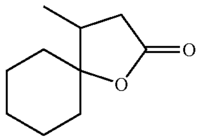 | powder MS(SSI)501 |
| 236 | 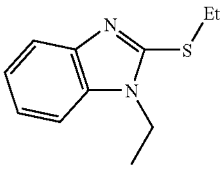 | powder MS(SSI)539 |
| 237 | 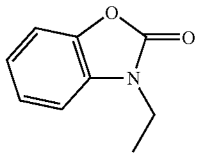 | powder MS(SSI)496 |
Et: ethyl group TABLE 1 (No. 36)
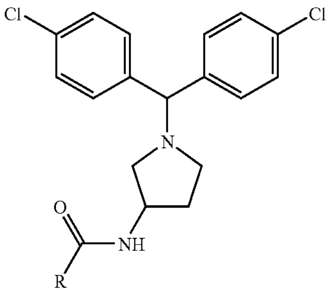
| Ex. Nos. | R | Physicochemical properties etc. |
|---|---|---|
| 238 | 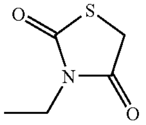 | powder MS(SSI)478 |
| 239 | 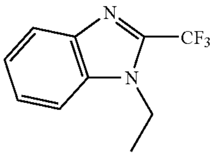 | powder MS(SSI)547 |
| 240 | 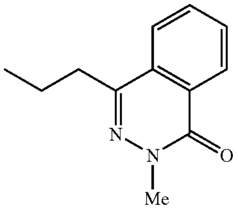 | powder MS(SSI)535 |
| 241 | 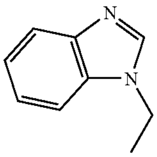 | powder MS(SSI)479 |
| 242 | 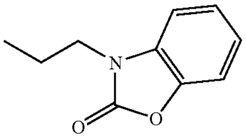 | powder MS(SSI)510 |
Me: methyl group
TABLE 1 (No. 37)
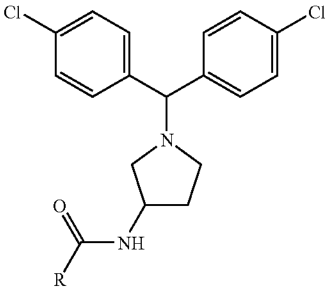
| Ex. Nos. | R | Physicochemical properties etc. |
|---|---|---|
| 243 | 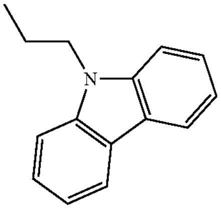 | powder MS(SSI)542 |
| 244 | 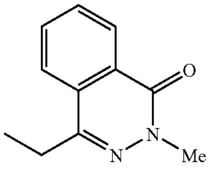 | powder MS(SSI)521 |
| 245 | 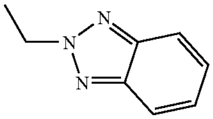 | powder MS(SSI)480 |
| 246 | 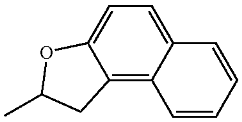 | powder MS(SSI)517 |
| 247 | 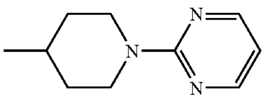 | powder MS(SSI)510 |
| 248 | 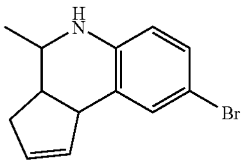 | powder MS(SSI)597 |
Me: methyl group TABLE 1 (No. 38)
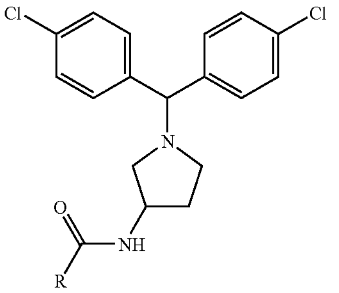
| Ex. Nos. | R | Physicochemical properties etc. |
|---|---|---|
| 249 | 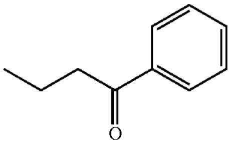 | powder MS(SSI)481 |
| 250 | 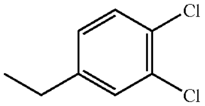 | powder MS(SSI)508 |
| 251 | 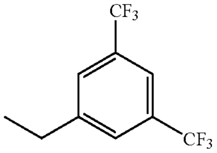 | powder MS(SSI)575 |
| 252 | 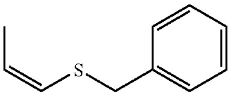 | powder MS(SSI)497 |
| 253 | 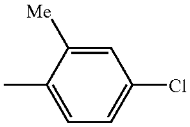 | powder MS(SSI)473 |
| 254 | 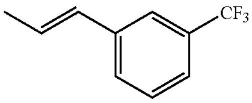 | powder MS(SSI)519 |
Me: methyl group
TABLE 1 (No. 39)
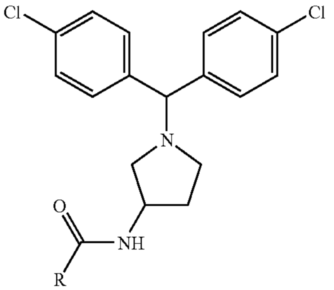
| Ex. Nos. | R | Physicochemical properties etc. |
|---|---|---|
| 255 | 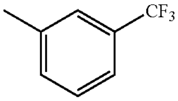 | powder MS(SSI)493 |
| 256 | 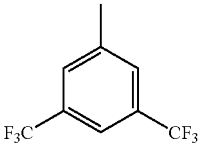 | powder MS(SSI)561 |
| 257 | 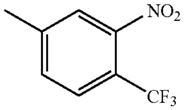 | powder MS(SSI)538 |
| 258 | 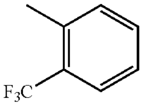 | powder MS(SSI)493 |
| 259 | 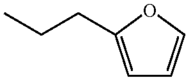 | powder MS(SSI)443 |
| 260 | 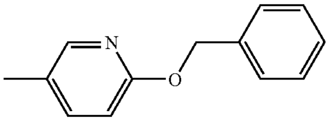 | powder MS(SSI)532 |
| 261 | 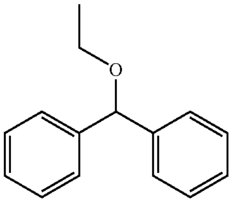 | powder MS(SSI)545 |

TABLE 1 (No. 40)
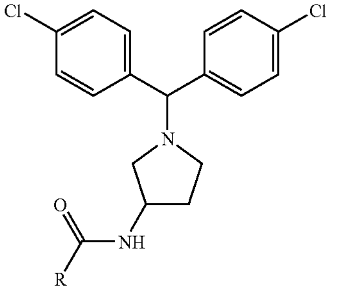
| Ex. Nos. | R | Physicochemical properties etc. |
|---|---|---|
| 262 | 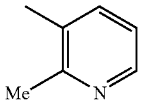 | powder MS(SSI)440 |
| 263 | 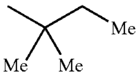 | powder MS(SSI)419 |
| 264 | 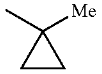 | powder MS(SSI)403 |
| 265 | 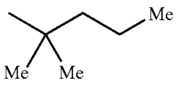 | powder MS(SSI)433 |
| 266 | 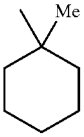 | powder MS(SSI)445 |
| 267 | 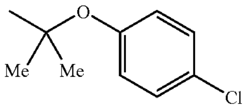 | powder MS(SSI)517 |
| 268 | 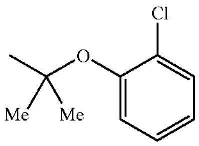 | powder MS(SSI)517 |
| 269 | 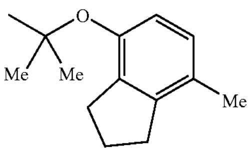 | powder MS(SSI)537 |
Me: methyl group
TABLE 1 (No. 41)
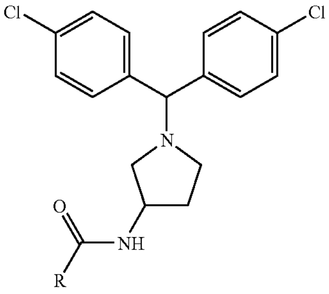
| Ex. Nos. | R | Physicochemical properties etc. |
|---|---|---|
| 270 | 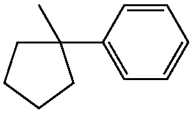 | powder MS(SSI)493 |
| 271 | 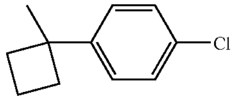 | powder MS(SSI)513 |
| 272 | 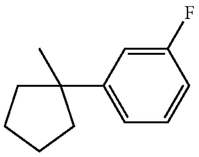 | powder MS(SSI)511 |
| 273 | 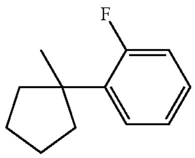 | powder MS(SSI)511 |
| 274 | 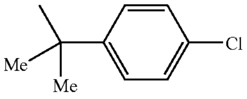 | powder MS(SSI)501 |
| 275 | 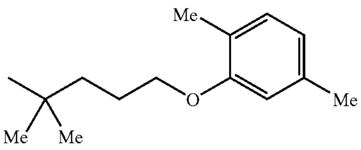 | powder MS(SSI)553 |
Me: methyl group TABLE 1 (No. 42)
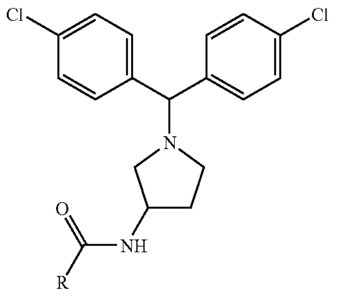
| Ex. Nos. | R | Physicochemical properties etc. |
|---|---|---|
| 276 | 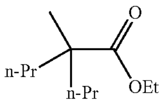 | powder MS(SSI)519 |
| 277 | 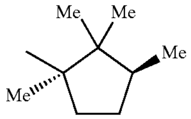 | powder MS(SSI)473 |
| 278 | 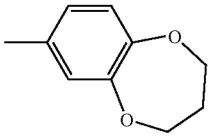 | powder MS(SSI)497 |
| 279 | 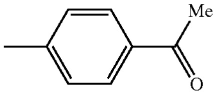 | powder MS(SSI)467 |
| 280 | 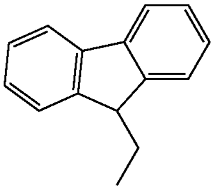 | powder MS(SSI)527 |
| 281 | 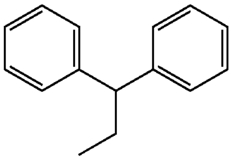 | powder MS(SSI)529 |
Me: methyl group,
Et: ethyl group,
n-Pr: n-propyl group
TABLE 1 (No. 43)
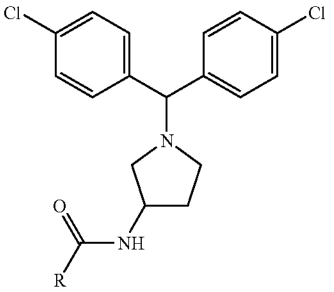
| Ex. Nos. | R | Physicochemical properties etc. |
|---|---|---|
| 282 | 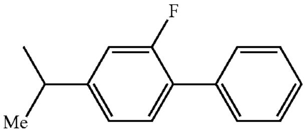 | powder MS(SSI)547 |
| 283 | 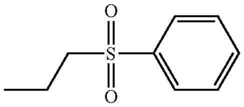 | powder MS(SSI)517 |
| 284 | 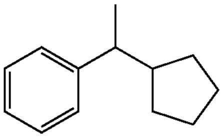 | powder MS(SSI)507 |
| 285 | 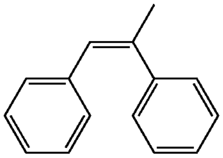 | powder MS(SSI)527 |
| 286 | 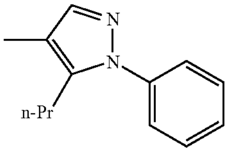 | powder MS(SSI)533 |
| 287 | 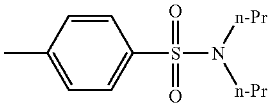 | powder MS(SSI)588 |
Me: methyl group,
n-Pr: n-propyl group TABLE 1 (No. 44)
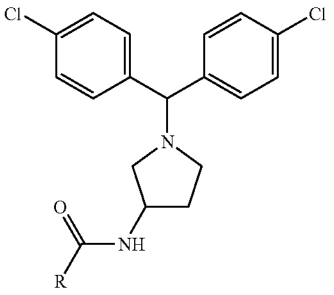
| Ex. Nos. | R | Physicochemical properties etc. |
|---|---|---|
| 288 | 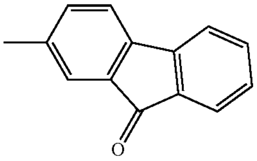 | powder MS(SSI)527 |
| 289 | 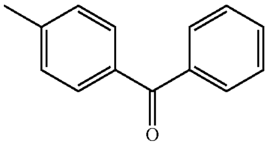 | powder MS(SSI)529 |
| 290 | 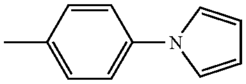 | powder MS(SSI)490 |
| 291 | 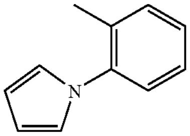 | powder MS(SSI)490 |
| 292 | 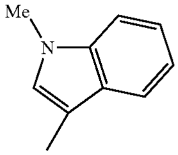 | powder MS(SSI)478 |
| 293 | 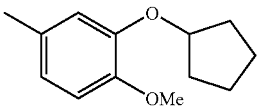 | powder MS(SSI)539 |
| 294 | 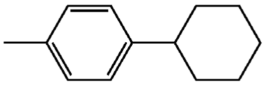 | powder MS(SSI)507 |
Me: methyl group
TABLE 1 (No. 45)
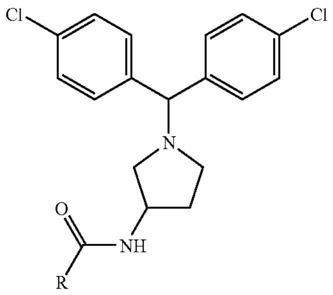
| Ex. Nos. | R | Physicochemical properties etc. |
|---|---|---|
| 295 | 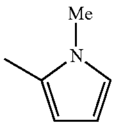 | powder MS(SSI)428 |
| 296 | 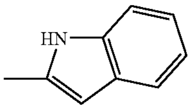 | powder MS(SSI)464 |
| 297 | 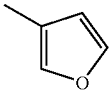 | powder MS(SSI)415 |
| 298 | 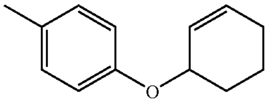 | powder MS(SSI)521 |
| 299 | 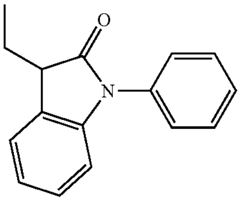 | powder MS(SSI)570 |
| 300 | 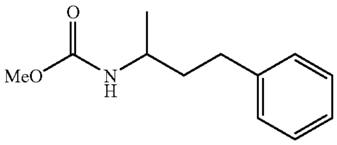 | powder MS(SSI)540 |
Me: methyl group TABLE 1 (No. 46)
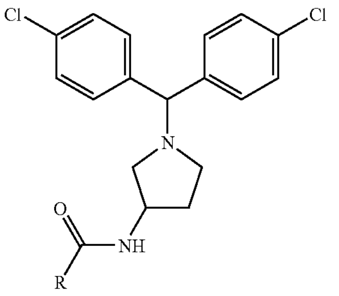
| Ex. Nos. | R | Physicochemical properties etc. |
|---|---|---|
| 301 | 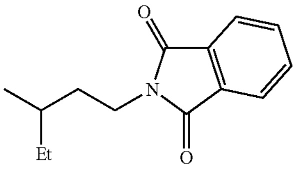 | powder MS(SSI)564 |
| 302 | 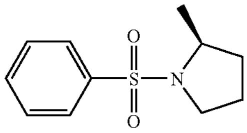 | powder MS(SSI)558 |
| 303 | 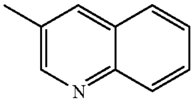 | powder MS(SSI)476 |
| 304 | 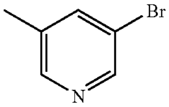 | powder MS(SSI)505 |
| 305 | 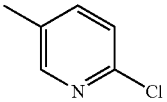 | powder MS(SSI)460 |
| 306 | 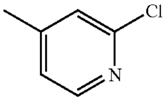 | powder MS(SSI)460 |
| 307 | 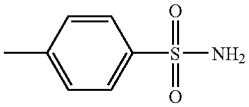 | powder MS(SSI)504 |
Et: ethyl group
TABLE 1 (No. 47)
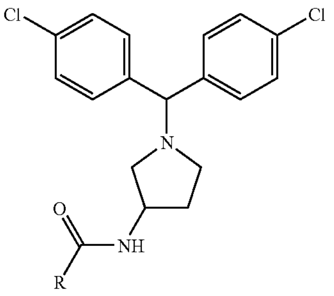
| Ex. Nos. | R | Physicochemical properties etc. |
|---|---|---|
| 308 | 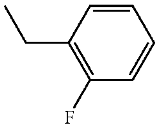 | powder MS(SSI)457 |
| 309 | 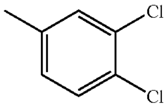 | powder MS(SSI)494 |
| 310 | 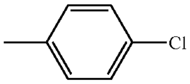 | powder MS(SSI)459 |
| 311 | 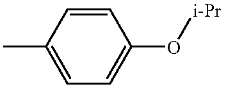 | powder MS(SSI)483 |
| 312 | 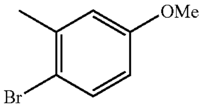 | powder MS(SSI)534 |
| 313 | 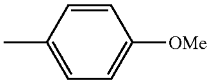 | powder MS(SSI)455 |
| 314 | 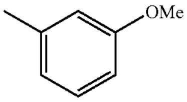 | powder MS(SSI)455 |
Me: methyl group
i-Pr: isopropyl group TABLE 1 (No. 48)
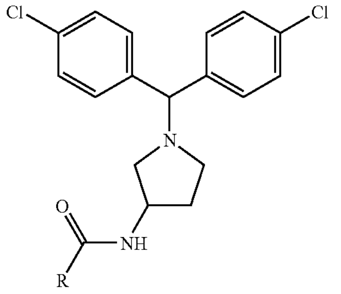
| Ex. Nos. | R | Physicochemical properties etc. |
|---|---|---|
| 315 | 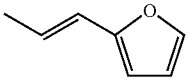 | powder MS(SSI)441 |
| 316 | 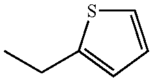 | powder MS(SSI)445 |
| 317 | 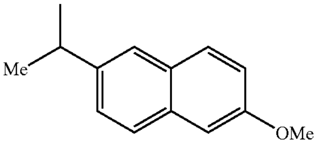 | powder MS(SSI)533 |
| 318 | 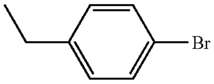 | powder MS(SSI)518 |
| 319 | 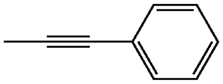 | powder MS(SSI)449 |
| 320 | 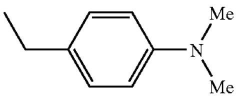 | powder MS(SSI)482 |
| 321 | 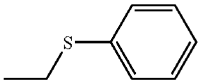 | powder MS(SSI)471 |
| 322 | 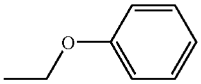 | powder MS(SSI)455 |
Me: methyl group
TABLE 1 (No. 49)
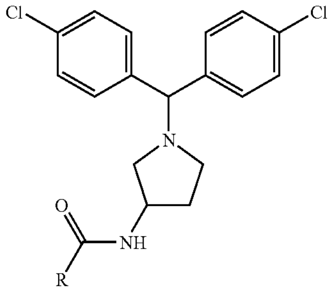
| Ex. Nos. | R | Physicochemical properties etc. |
|---|---|---|
| 323 | 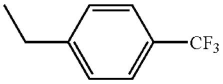 | powder MS(SSI)507 |
| 324 | 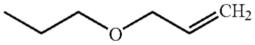 | powder MS(SSI)433 |
| 325 | 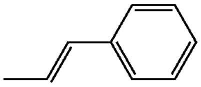 | powder MS(SSI)451 |
| 326 | 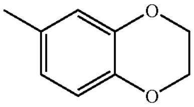 | powder MS(SSI)483 |
| 327 | 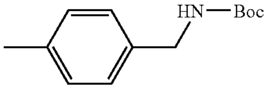 | powder MS(SSI)554 |
| 328 | 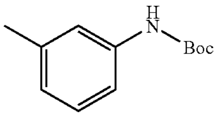 | powder MS(SSI)540 |
| 329 | 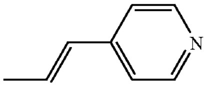 | powder MS(SSI)452 |
| 330 | 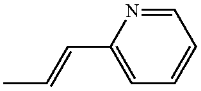 | powder MS(SSI)452 |
Boc: tert-butoxycarbonyl group TABLE 1 (No. 50)
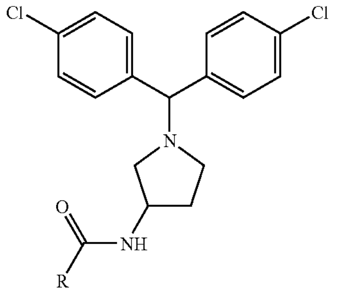
| Ex. Nos. | R | Physicochemical properties etc. |
|---|---|---|
| 331 | 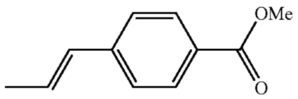 | powder<br>MS(SSI)509 |
| 332 | 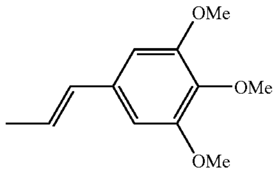 | powder<br>MS(SSI)541 |
Me: methyl group
TABLE 1 (No. 51)
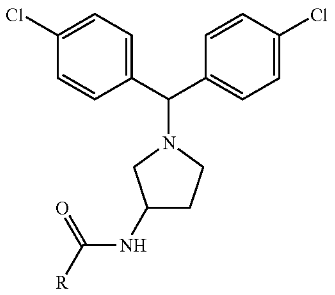
| Ex. Nos. | R | Physicochemical properties etc. |
|---|---|---|
| 333 | 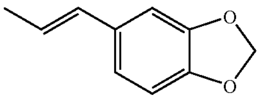 | Powder<br>MS(SSI)495 |
| 334 | 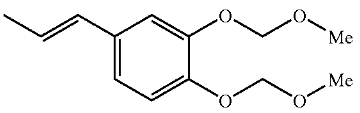 | Powder<br>MS(SSI)571 |
| 335 | 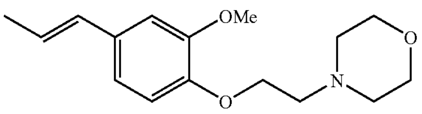 | Powder<br>MS(SSI)610 |
| 336 | 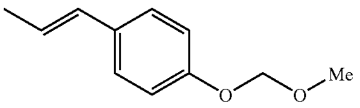 | Powder<br>MS(SSI)511 |

TABLE 1 (No. 51)-continued

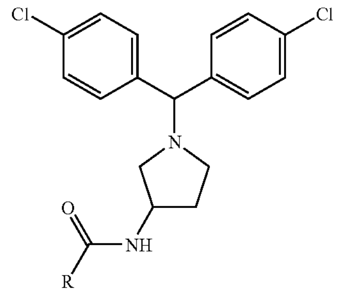

| Ex. Nos. | R | Physicochemical properties etc. |
|---|---|---|
| 337 | 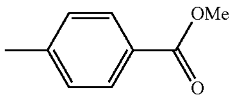 | Powder MS(SSI)483 |
| 338 | 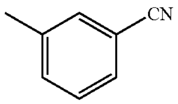 | Powder MS(SSI)450 |
| 339 | 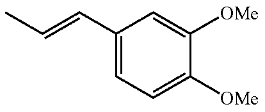 | Powder MS(SSI)511 |

Me: methyl group

TABLE 1 (No. 52)

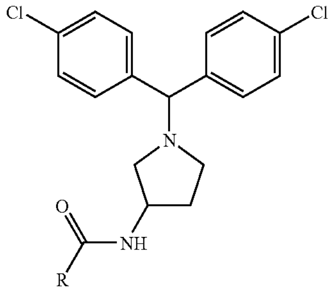

| Ex. Nos. | R | Physicochemical properties etc. |
|---|---|---|
| 340 | 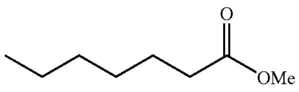 | Powder MS(SSI)477 |
| 341 | 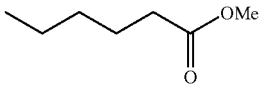 | Powder MS(SSI)463 |
| 342 | 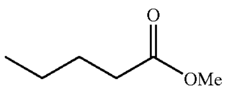 | Powder MS(SSI)449 |
| 343 | 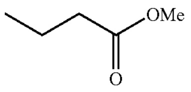 | Powder MS(SSI)435 |

TABLE 1 (No. 52)-continued

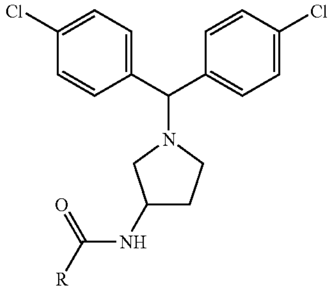

| Ex. Nos. | R | Physicochemical properties etc. |
|---|---|---|
| 344 | 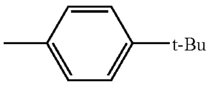 | Powder MS(SSI)481 |
| 345 | 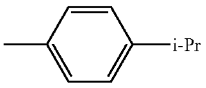 | Powder MS(SSI)467 |
| 346 | 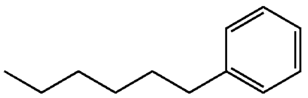 | Powder MS(SSI)495 |

Me: methyl group,
i-Pr: isopropyl group,
t-Bu: tert-butyl group

TABLE 1 (No. 53)
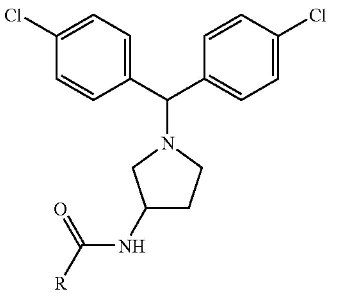
| Ex. Nos. | R | Physicochemical properties etc. |
|---|---|---|
| 347 | 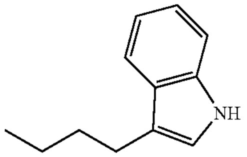 | Powder MS(SSI)506 |
| 348 | 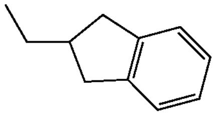 | Powder MS(SSI)479 |
| 349 | 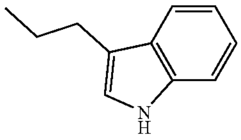 | Powder MS(SSI)492 |
| 350 | 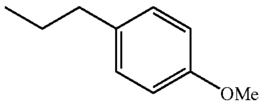 | Powder MS(SSI)483 |
| 351 | 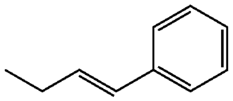 | Powder MS(SSI)465 |
| 352 | 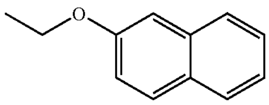 | Powder MS(SSI)505 |
Me: methyl group
TABLE 1 (No. 54)
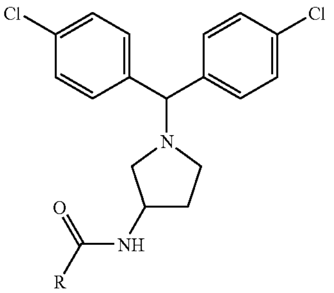
| Ex. Nos. | R | Physicochemical properties etc. |
|---|---|---|
| 353 | 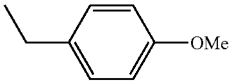 | Powder MS(SSI)469 |
| 354 | 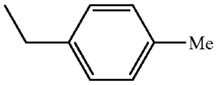 | Powder MS(SSI)453 |
| 355 | 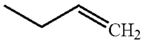 | Powder MS(SSI)389 |
| 356 | 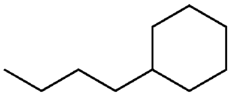 | Powder MS(SSI)473 |
| 357 | 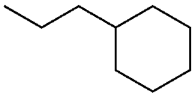 | Powder MS(SSI)459 |
| 358 | 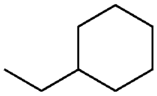 | Powder MS(SSI)445 |
Me: methyl group
TABLE 1 (No. 55)
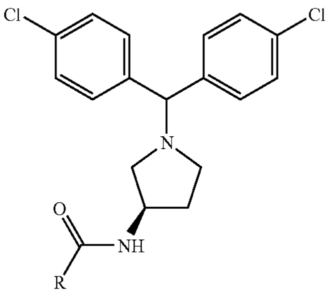
| Ex. Nos. | R | Physicochemical properties etc. |
|---|---|---|
| 359 | 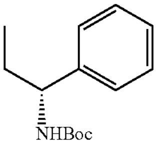 | Powder MS(APCI)568/570[M + H]+ |

TABLE 1 (No. 55)-continued

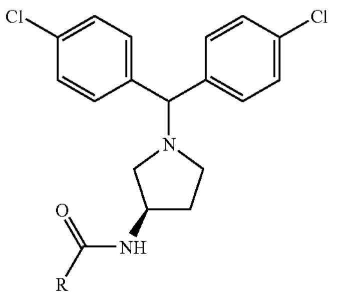

| Ex. Nos. | R | Physicochemical properties etc. |
|---|---|---|
| 360 | 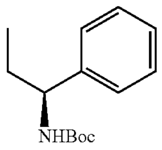 | Powder<br>MS(APCI)568/570[M + H]+ |
| 361 | 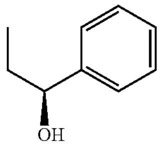 | Powder<br>MS(APCI)469/471[M + H]+ |

TABLE 1 (No. 55)-continued

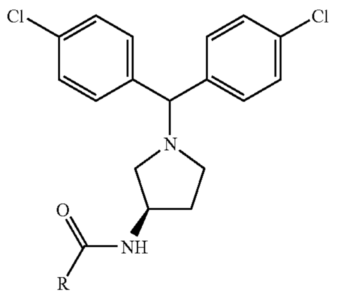

| Ex. Nos. | R | Physicochemical properties etc. |
|---|---|---|
| 362 | 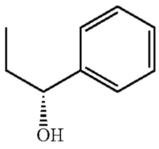 | Powder<br>MS(APCI)469/471[M + H]+ |
| 363 | 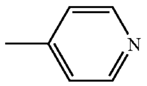 | resin<br>MS(APCI)426/428[M + H]+ |
| 354 | 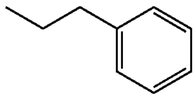 | resin<br>MS(APCI)453/455[M + H]+ |

Boc: tert-butyloxycarbonyl group

TABLE 1 (No. 56)

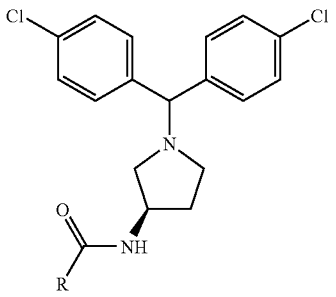

| Ex. Nos. | R | Physicochemical properties etc. |
|---|---|---|
| 365 | 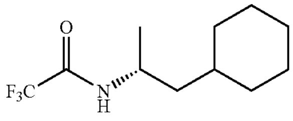 | Powder<br>MS(ESI)570 |
| 366 | 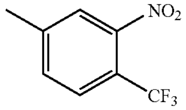 | Powder<br>MS(APCI)538/540[M + H]+ |
| 367 | 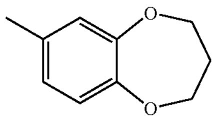 | Powder<br>MS(APCI)497/499[M + H]+ |

TABLE 1 (No. 56)-continued
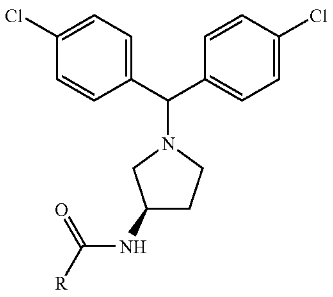
| Ex. Nos. | R | Physicochemical properties etc. |
|---|---|---|
| 368 | 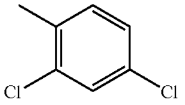 | Powder<br>MS(APCI)493/495[M + H]+ |
| 369 | 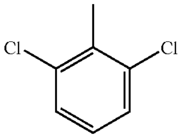 | Powder<br>MS(APCI)493/495[M + H]+ |
| 370 | 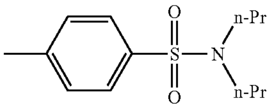 | Powder<br>MS(APCI)588/590[M + H]+ |
| 371 | 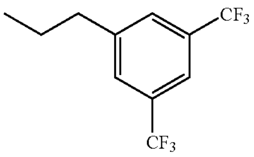 | Powder<br>MS(APCI)589/591[M + H]+ |
n-Pr: n-propyl group
TABLE 1 (No. 57)
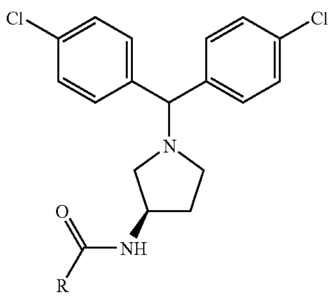
| Ex. Nos. | R | Physicochemical properties etc. |
|---|---|---|
| 372 | 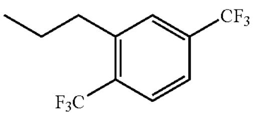 | Powder<br>MS(APCI)589/591[M + H]+ |
TABLE 1 (No. 57)-continued
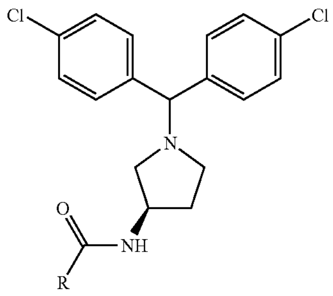
| Ex. Nos. | R | Physicochemical properties etc. |
|---|---|---|
| 373 | 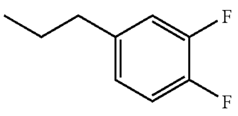 | Powder<br>MS(APCI)489/491[M + H]+ |
| 374 | 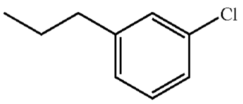 | Powder<br>MS(APCI)487/489[M + H]+ |

TABLE 1 (No. 57)-continued

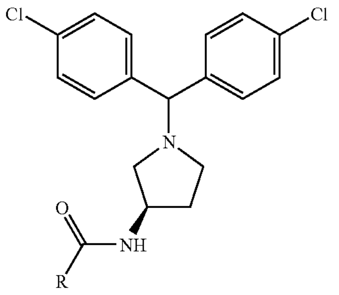

| Ex. Nos. | R | Physicochemical properties etc. |
|---|---|---|
| 375 | 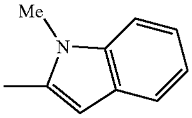 | Powder MS(APCI)478/480[M + H]+ |
| 376 | 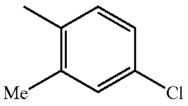 | Powder MS(APCI)473/475[M + H]+ |
| 377 | 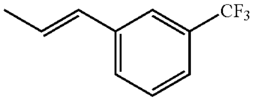 | Powder MS(APCI)519/521[M + H]+ |
| 378 | 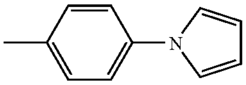 | Powder MS(APCI)490/492[M + H]+ |

Me: methyl group

TABLE 1 (No. 58)

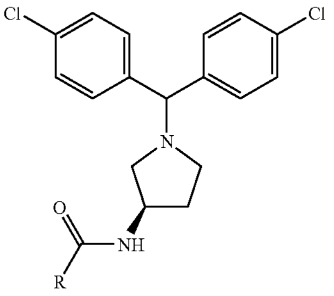

| Ex. Nos. | R | Physicochemical properties etc. |
|---|---|---|
| 379 | 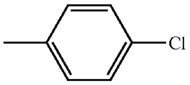 | Powder MS(APCI)459/461[M + H]+ |
| 380 | 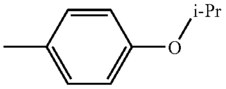 | Powder MS(APCI)483/485[M + H]+ |
| 381 | 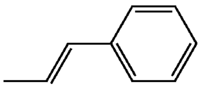 | Powder MS(APCI)451/453[M + H]+ |
| 382 | 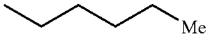 | solid MS(APCI)419/421[M + H]+ |
| 383 | 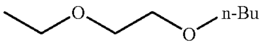 | solid MS(APCI)479/481[M + H]+ |

Me: methyl group,
i-Pr: isopropyl group,
n-Bu: n-butyl group

TABLE 1 (No. 59)

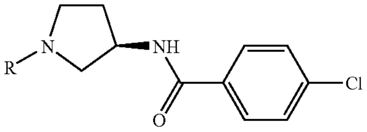

| Ex. Nos. | R | Physicochemical properties etc. |
|---|---|---|
| 384 | 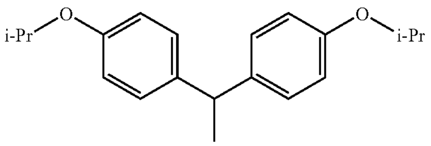 | Powder MS(APCI)507/509[M + H]+ |
| 385 | 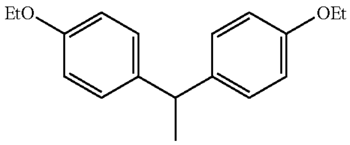 | Powder MS(APCI)479/481[M + H]+ |

TABLE 1 (No. 59)-continued
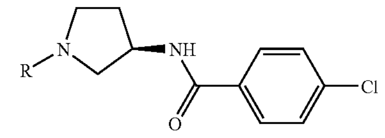
| Ex. Nos. | R | Physicochemical properties etc. |
|---|---|---|
| 386 | 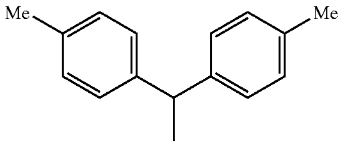 | Powder<br>MS(APCI)419/421[M + H]+ |
Me: methyl group,
Et: ethyl group,
i-Pr: isopropyl group
TABLE 1 (No. 60)
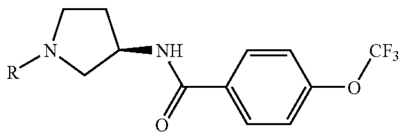
| Ex. Nos. | R | Physicochemical properties etc. |
|---|---|---|
| 387 | 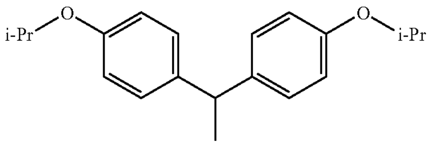 | Powder<br>MS(APCI)557[M + H]+ |
| 388 | 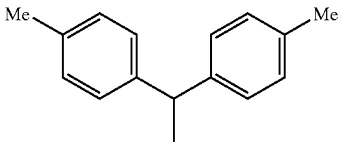 | Powder<br>MS(APCI)469[M + H]+ |
Me: methyl group,
i-Pr: isopropyl group TABLE 1 (No. 61)

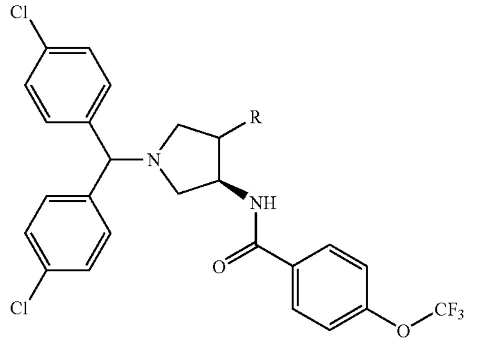

| Ex. Nos. | R | Physicochemical properties etc. |
|---|---|---|
| 389 | 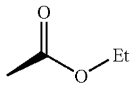 | powder<br>MS(APCI)581/583[M + H]+ |
| 390 |  | powder<br>MS(APCI)525/527[M + H]+ |

Et: ethyl group

TABLE 1 (No. 62)

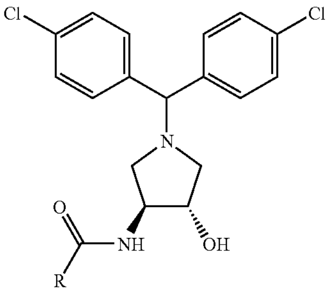

| Ex. Nos. | R | Physicochemical properties etc. |
|---|---|---|
| 391 | $-CF_3$ | powder<br>MS(APCI)433/435[M + H]+ |
| 392 | 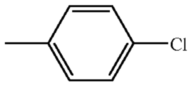 | powder<br>MS(APCI)475/477[M + H]+ |

TABLE 1 (No. 63)

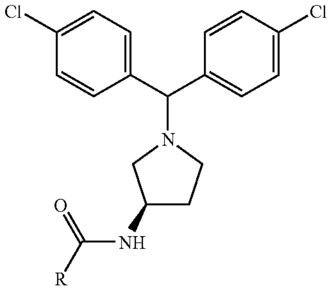

| Ex. Nos. | R | Physicochemical properties etc. |
|---|---|---|
| 393 | 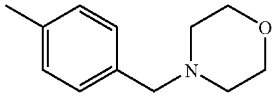 | powder<br>MS(ESI)524[M + H]+ |
| 394 | 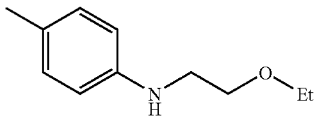 | powder<br>MS(ESI)512[M + H]+ |
| 395 | 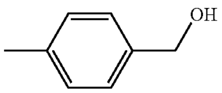 | powder<br>MS(ESI)455[M + H]+ |
| 396 | 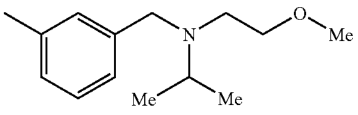 | powder<br>MS(ESI)554[M + H]+ |
| 397 | 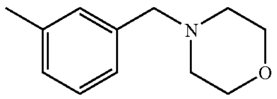 | powder<br>MS(ESI)524[M + H]+ |

TABLE 1 (No. 63)-continued
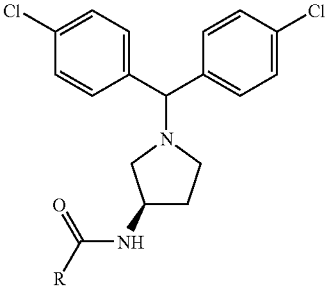
| Ex. Nos. | R | Physicochemical properties etc. |
|---|---|---|
| 398 | 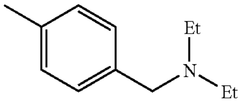 | powder<br>MS(ESI)510[M + H]+ |
| 399 | 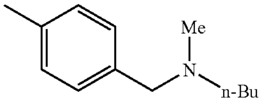 | powder<br>MS(ESI)524[M + H]+ |
Me: methyl group,
Et: ethyl group,
n-Bu: n-butyl group
TABLE 1 (No. 64)
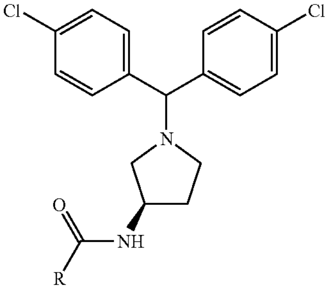
| Ex. Nos. | R | Physicochemical properties etc. |
|---|---|---|
| 400 | 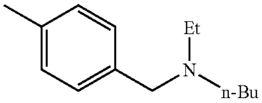 | powder<br>MS(ESI)538[M + H]+ |
| 401 | 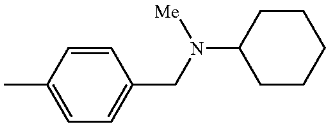 | powder<br>MS(ESI)550[M + H]+ |
| 402 | 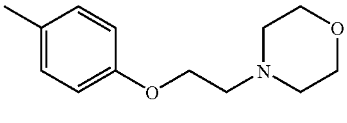 | powder<br>MS(ESI)554[M + H]+ |
| 403 | 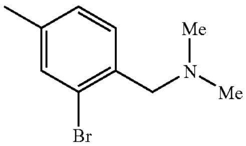 | powder<br>MS(ESI)560[M + H]+ |

TABLE 1 (No. 64)-continued
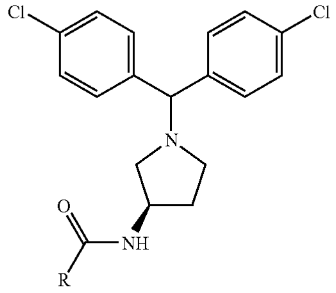
| Ex. Nos. | R | Physicochemical properties etc. |
|---|---|---|
| 404 | 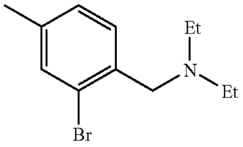 | powder<br>MS(ESI)588[M + H]+ |
| 405 | 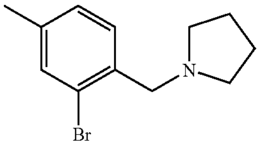 | powder<br>MS(ESI)587[M + H]+ |
Me: methyl group,
Et: ethyl group,
n-Bu: n-butyl group
TABLE 1 (No. 65)
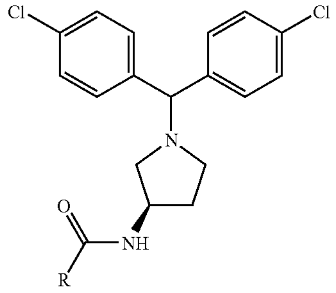
| Ex. Nos. | R | Physicochemical properties etc. |
|---|---|---|
| 406 | 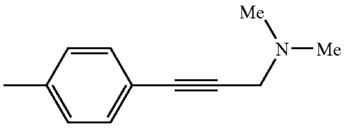 | powder<br>MS(ESI)506[M + H]+ |
| 407 | 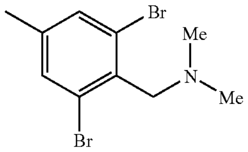 | powder<br>MS(ESI)638[M + H]+ |
| 408 | 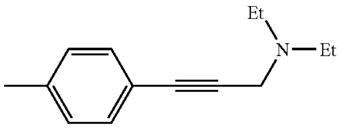 | powder<br>MS(ESI)534[M + H]+ |

TABLE 1 (No. 65)-continued

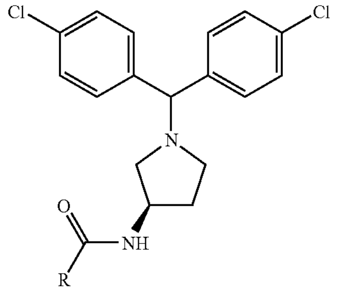

| Ex. Nos. | R | Physicochemical properties etc. |
|---|---|---|
| 409 | 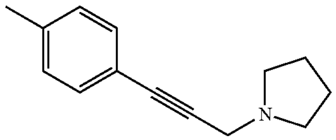 | powder<br>MS(ESI)532[M + H]+ |
| 410 | 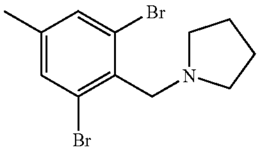 | powder<br>MS(ESI)664[M + H]+ |
| 411 | 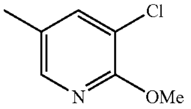 | powder<br>MS(ESI)490[M + H]+ |

Me: methyl group,
Et: ethyl group

TABLE 1 (No. 66)

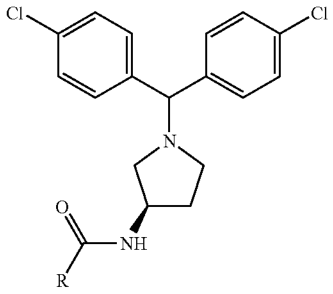

| Ex. Nos. | R | Physicochemical properties etc. |
|---|---|---|
| 412 | 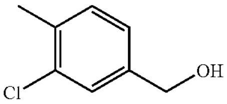 | powder<br>MS(ESI)489[M + H]+ |
| 413 | 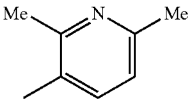 | powder<br>MS(ESI)454[M + H]+ |
| 414 | 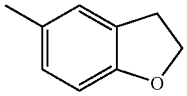 | powder<br>MS(ESI)467[M + H]+ |

TABLE 1 (No. 66)-continued

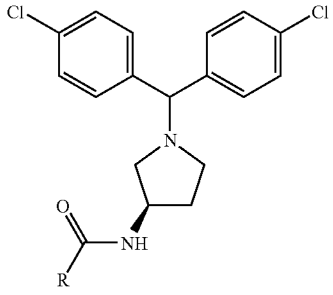

| Ex. Nos. | R | Physicochemical properties etc. |
|---|---|---|
| 415 | 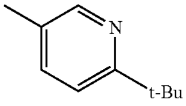 | powder<br>MS(ESI)482[M + H]+ |
| 416 | 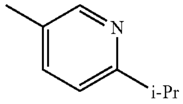 | powder<br>MS(ESI)468[M + H]+ |

TABLE 1 (No. 66)-continued

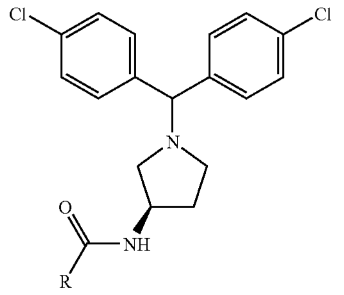

| Ex. Nos. | R | Physicochemical properties etc. |
|---|---|---|
| 417 | 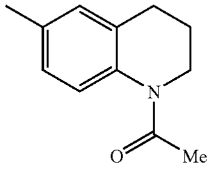 | powder<br>MS(ESI)522[M + H]+ |

Me: methyl group, i-Pr: isopropyl group, t-Bu: tert-butyl group

TABLE 1 (No. 67)

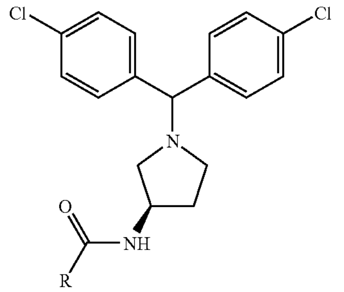

| Ex. Nos. | R | Physicochemical properties etc. |
|---|---|---|
| 418 | 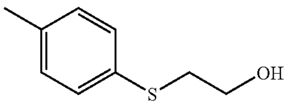 | powder<br>MS(ESI)501[M + H]+ |
| 419 | 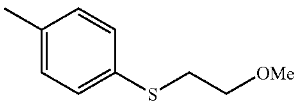 | powder<br>MS(ESI)515[M + H]+ |

TABLE 1 (No. 67)-continued

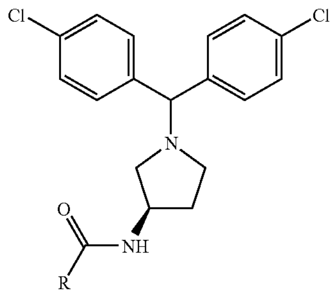

| Ex. Nos. | R | Physicochemical properties etc. |
|---|---|---|
| 420 | 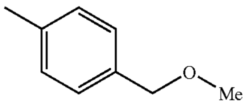 | powder<br>MS(ESI)469[M + H]+ |
| 421 | 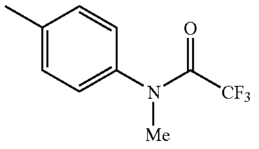 | powder<br>MS(ESI)550[M + H]+ |
| 422 | 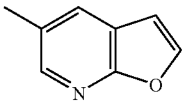 | powder<br>MS(ESI)466[M + H]+ |
| 423 | 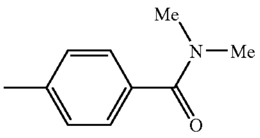 | powder<br>MS(ESI)496[M + H]+ |
| 424 | 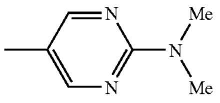 | powder<br>MS(ESI)470[M + H]+ |

Me: methyl group

TABLE 1 (No. 68)

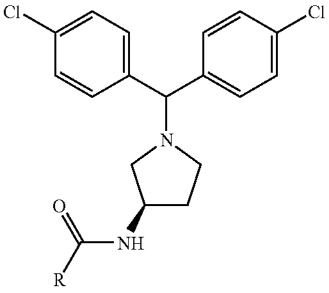

| Ex. Nos. | R | Physicochemical properties etc. |
|---|---|---|
| 425 | 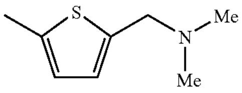 | powder<br>MS(ESI)488[M + H]+ |
| 426 | 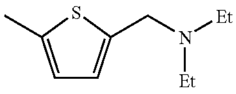 | powder<br>MS(ESI)516[M + H]+ |
| 427 | 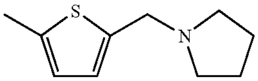 | powder<br>MS(ESI)514[M + H]+ |
| 428 | 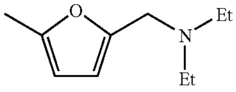 | powder<br>MS(ESI)500[M + H]+ |
| 429 | 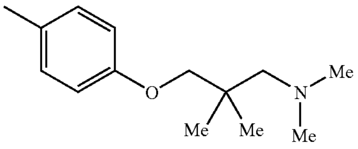 | powder<br>MS(ESI)554[M + H]+ |
| 430 | 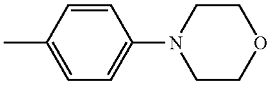 | powder<br>MS(ESI)510[M + H]+ |
| 431 | 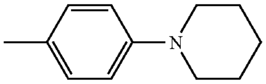 | powder<br>MS(ESI)508[M + H]+ |

Me: methyl group,
Et: ethyl group

Examples 432 to 475

The corresponding materials are treated in the same manner as described in either one of the aforementioned Examples 1 to 5 followed by treating the product in the same manner as described in either one of the Examples 8 to 19 to give the compounds as shown in the following Table 2 (Nos. 1 to 9).

TABLE 2 (No. 1)

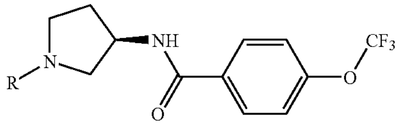

| Ex. Nos. | R | Physicochemical properties etc. |
|---|---|---|
| 432 | 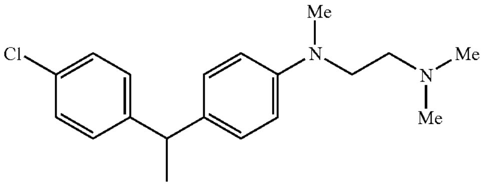 | powder<br>MS(APCI)575/577[M + H]+ |
| 433 | 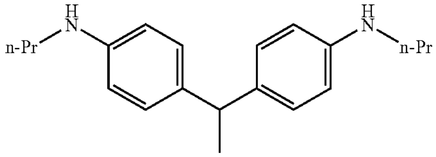 | oil<br>MS(ESI)587[M + H + MeOH]+ |
| 434 | 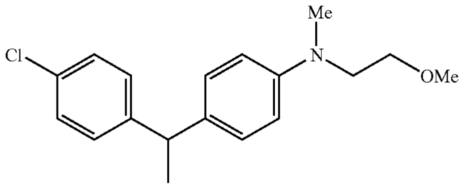 | powder<br>MS(ESI)562/564[M + H]+ |

Me: methyl group,
n-Pr: n-propyl group

TABLE 2 (No. 2)

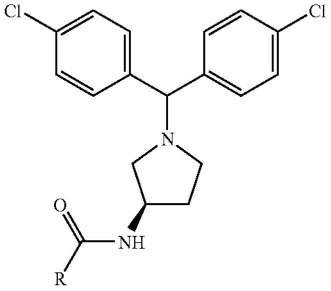

| Ex. Nos. | R | Physicochemical properties etc. |
|---|---|---|
| 435 | 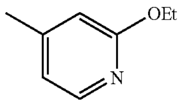 | powder<br>MS(APCI)470/472[M + H]+ |
| 436 | 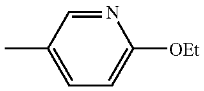 | powder<br>MS(APCI)470/472[M + H]+ |
| 437 | 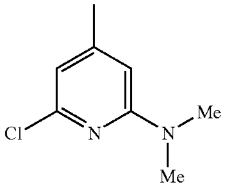 | powder<br>MS(APCI)503/505[M + H]+ |

TABLE 2 (No. 2)-continued

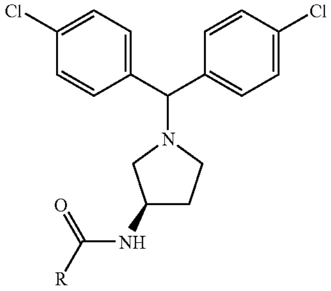

| Ex. Nos. | R | Physicochemical properties etc. |
|---|---|---|
| 438 | 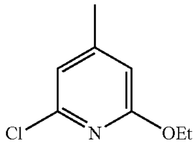 | powder<br>MS(APCI)504/506[M + H]+ |
| 439 | 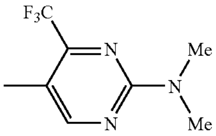 | powder<br>MS(APCI)538/540[M + H]+ |
| 440 | 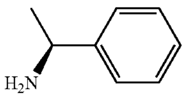 | powder<br>MS(APCI)454/456[M + H]+ |

TABLE 2 (No. 2)-continued
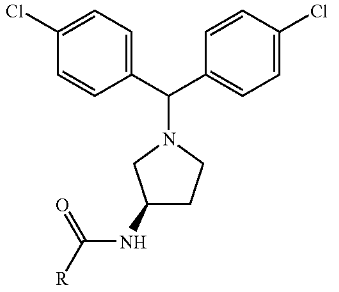
| Ex. Nos. | R | Physicochemical properties etc. |
|---|---|---|
Me: methyl group,
TABLE 2 (No. 2)-continued
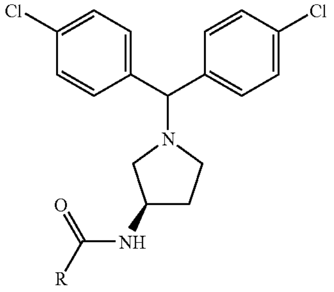
| Ex. Nos. | R | Physicochemical properties etc. |
|---|---|---|
Et: ethyl group
TABLE 2 (No. 3)
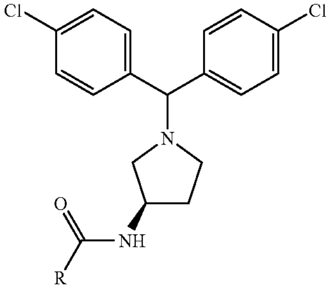
| Ex. Nos. | R | Physicochemical properties etc. |
|---|---|---|
| 441 | 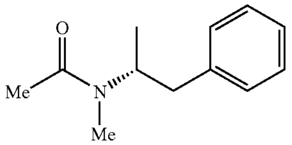 | solid<br>MS(APCI)524/526[M + H]+ |
| 442 | 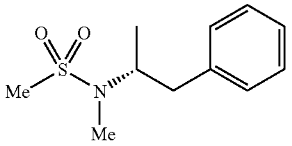 | solid<br>MS(APCI)560/562[M + H]+ |
| 443 | 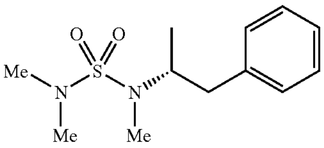 | solid<br>MS(APCI)589/591[M + H]+ |
| 444 | 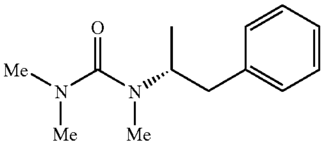 | solid<br>MS(APCI)553/555[M + H]+ |
| 445 | 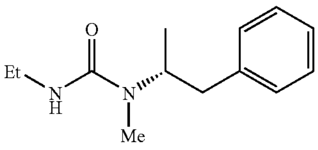 | solid<br>MS(APCI)553/555[M + H]+ |

TABLE 2 (No. 3)-continued
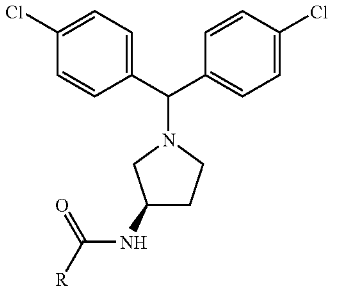
| Ex. Nos. | R | Physicochemical properties etc. |
|---|---|---|
| 446 | 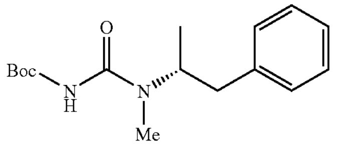 | solid<br>MS(APCI)582/584[M + H]+ |
Me: methyl group,
Et: ethyl group,
Boc: tert-butyloxtcarbonyl group
TABLE 2 (No. 4)
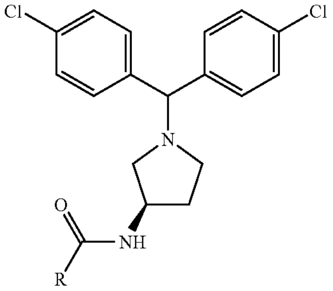
| Ex. Nos. | R | Physicochemical properties etc. |
|---|---|---|
| 447 | 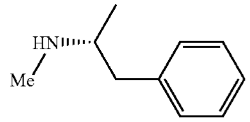 | solid<br>MS(APCI)482/484[M + H]+ |
| 448 | 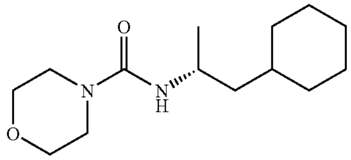 | powder<br>MS(ESI)587 |
| 449 | 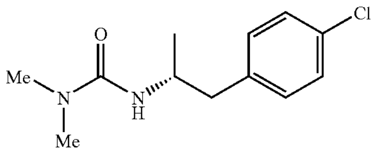 | powder<br>MS(ESI)573 |
| 450 | 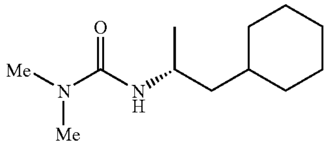 | powder<br>MS(ESI)545 |

TABLE 2 (No. 4)-continued
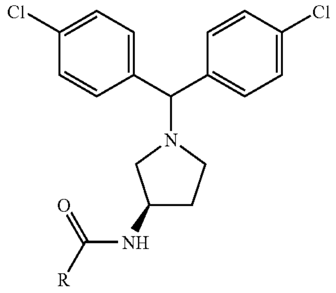
| Ex. Nos. | R | Physicochemical properties etc. |
|---|---|---|
| 451 | 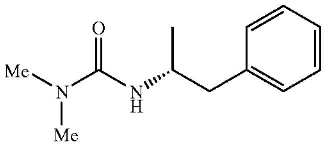 | powder<br>MS(ESI)539 |
| 452 | 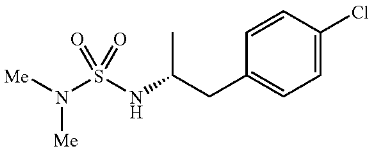 | powder<br>MS(ESI)610 |
Me: methyl group
TABLE 2 (No. 5)
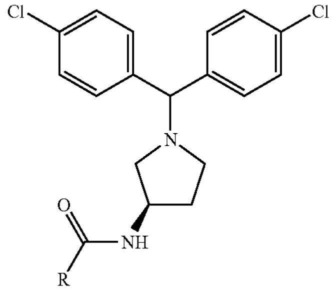
| Ex. Nos. | R | Physicochemical properties etc. |
|---|---|---|
| 453 | 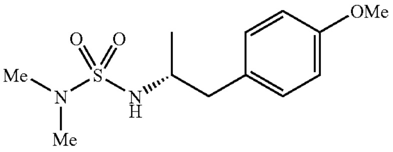 | powder<br>MS(ESI)605 |
| 454 | 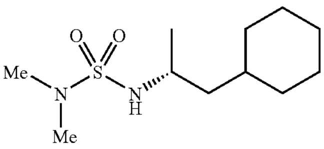 | powder<br>MS(ESI)581 |
| 455 | 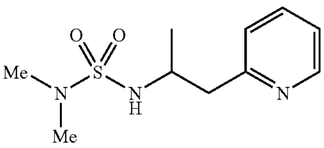 | powder<br>MS(ESI)576 |

TABLE 2 (No. 5)-continued
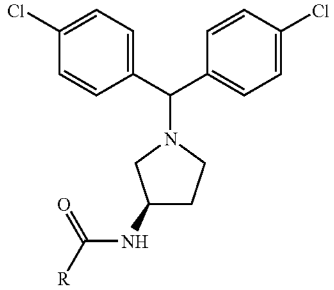
| Ex. Nos. | R | Physicochemical properties etc. |
|---|---|---|
| 456 | 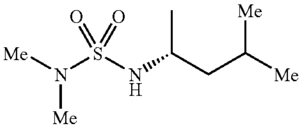 | powder<br>MS(ESI)541 |
| 457 | 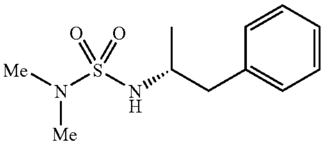 | powder<br>MS(ESI)575 |
| 458 | 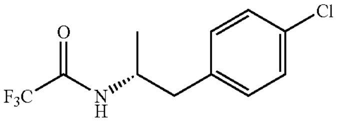 | powder<br>MS(ESI)598 |
Me: methyl group
TABLE 2 (No. 6)
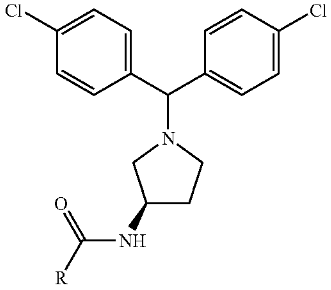
| Ex. Nos. | R | Physicochemical properties etc. |
|---|---|---|
| 459 | 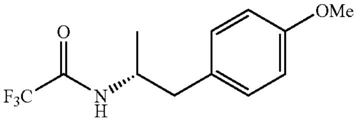 | powder<br>MS(ESI)594 |
| 460 | 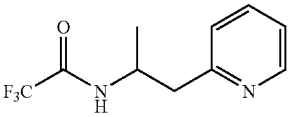 | powder<br>MS(ESI)565 |

TABLE 2 (No. 6)-continued
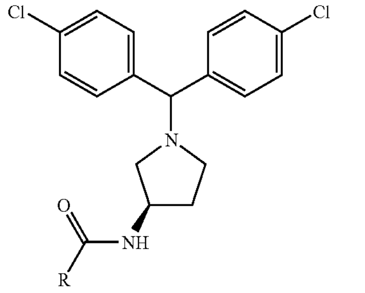
| Ex. Nos. | R | Physicochemical properties etc. |
|---|---|---|
| 461 | 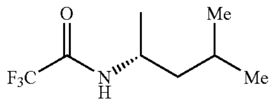 | powder MS(ESI)530 |
| 462 | 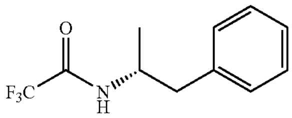 | powder MS(ESI)564 |
| 463 | 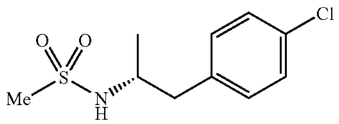 | powder MS(ESI)580 |
| 464 | 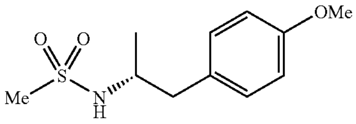 | powder MS(ESI)576 |
| 465 | 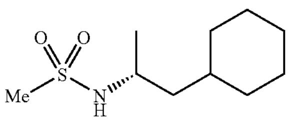 | powder MS(ESI)552 |
Me: methyl group
TABLE 2 (No. 7)
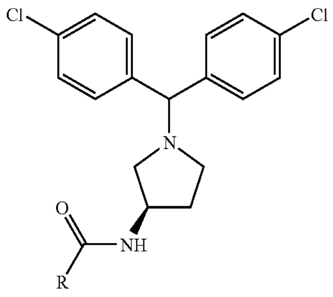
| Ex. Nos. | R | Physicochemical properties etc. |
|---|---|---|
| 466 | 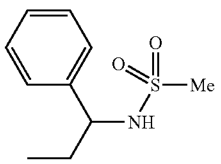 | powder MS(ESI)546 |
TABLE 2 (No. 7)-continued
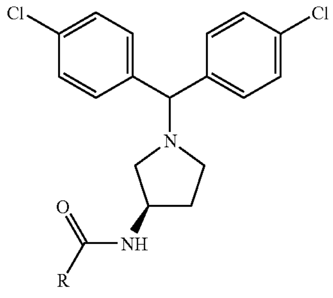
| Ex. Nos. | R | Physicochemical properties etc. |
|---|---|---|
| 467 | 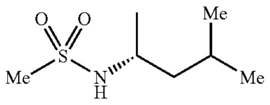 | powder MS(ESI)512 |

TABLE 2 (No. 7)-continued
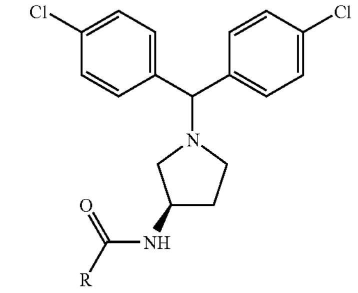
| Ex. Nos. | R | Physicochemical properties etc. |
| --- | --- | --- |
| 468 | 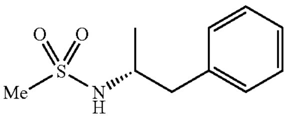 | powder<br>MS(ESI)546 |
Me: methyl group
TABLE 2 (No. 8)
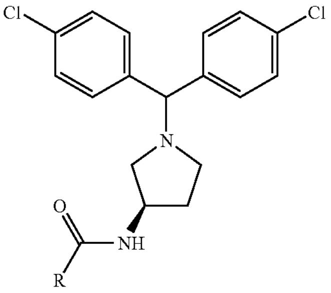
| Ex. Nos. | R | Physicochemical properties etc. |
| --- | --- | --- |
| 469 | 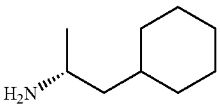 | powder<br>MS(SSI)474 |
| 470 | 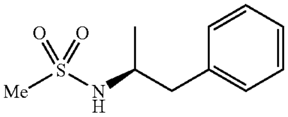 | powder<br>MS(SSI)546 |
| 471 | 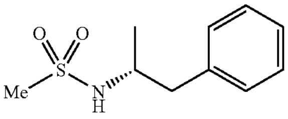 | powder<br>MS(SSI)546 |
| 472 | 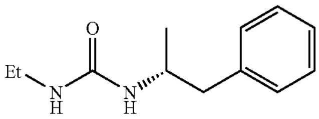 | powder<br>MS(SSI)539 |
| 473 | 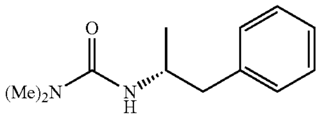 | powder<br>MS(SSI)539 |

TABLE 2 (No. 8)-continued

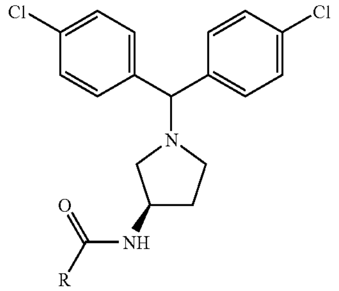

| Ex. Nos. | R | Physicochemical properties etc. |
|---|---|---|
| 474 | 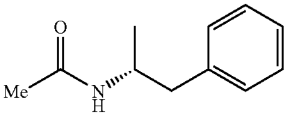 | powder<br>MS(SSI)510 |

Me: methyl group,
Et: ethyl group

TABLE 2 (No. 9)

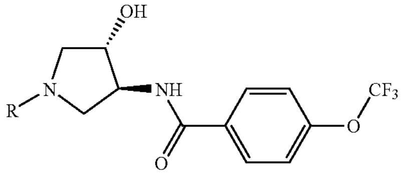

| Ex. Nos. | R | Physicochemical properties etc. |
|---|---|---|
| 475 | 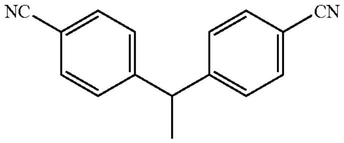 | powder<br>MS(APCI)507[M + H]+ |

Examples 436 to 499

The corresponding materials are treated in the same manner as described in Example 6 or 7 to give the compounds as shown in the following Table 3 (Nos. 1 to 6).

TABLE 3 (No. 1)

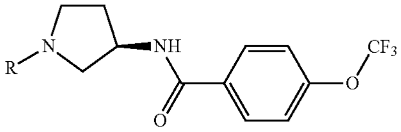

| Ex. Nos. | R | Physicochemical properties etc. |
|---|---|---|
| 476 | 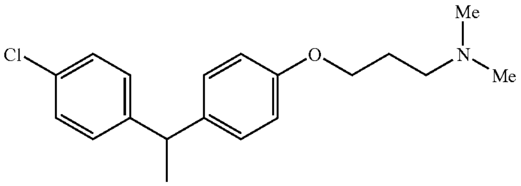 | powder<br>MS(APCI)576/578[M + H]+ |

TABLE 3 (No. 1)-continued
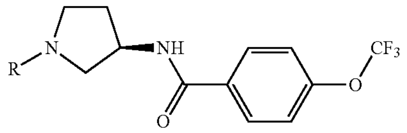
| Ex. Nos. | R | Physicochemical properties etc. |
|---|---|---|
| 477 | 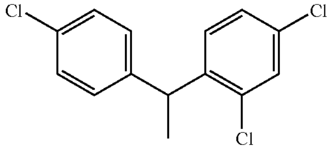 | powder<br>MS(APCI)543/545[M + H]+ |
| 478 | 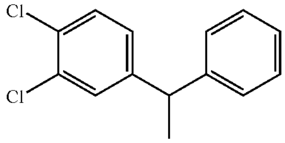 | powder<br>MS(APCI)509/511[M + H]+ |
| 479 | 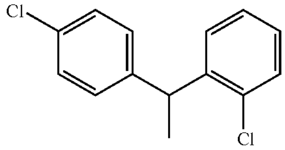 | powder<br>MS(APCI)509/511[M + H]+ |
| 480 | 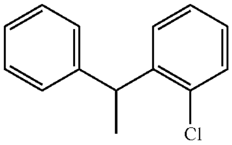 | powder<br>MS(APCI)475/477[M + H]+ |
| 481 | 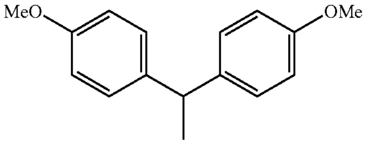 | powder<br>MS(APCI)501[M + H]+ |
Me: methyl group
TABLE 3 (No. 2)
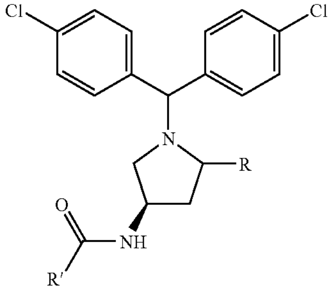
| Ex. Nos. | R | R' | Physicochemical properties etc. |
|---|---|---|---|
| 482 | 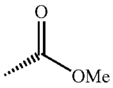 | 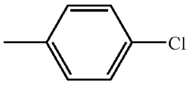 | powder<br>MS(APCI)517/519[M + H]+ |
Me: methyl group TABLE 3 (No. 3)
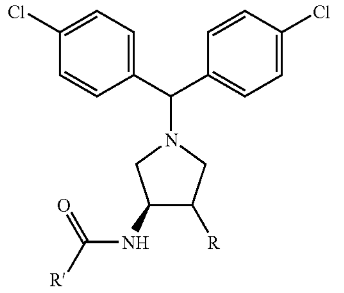
| Ex. Nos. | R | R' | Physicochemical properties etc. |
|---|---|---|---|
| 483 | 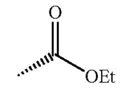 | 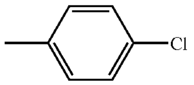 | powder MS(APCI)531/533[M + H]+ |
| 484 | 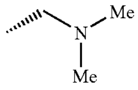 | 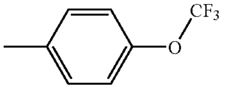 | powder MS(APCI)566/568[M + H]+ |
Me: methyl group,
Et: ethyl group
TABLE 3 (No. 4)
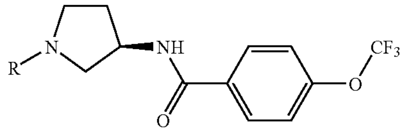
| Ex. Nos. | R | Physicochemical properties etc. |
|---|---|---|
| 485 | 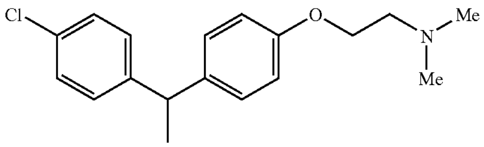 | powder MS(APCI)562/564[M + H]+ |
| 486 | 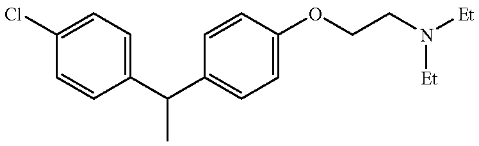 | powder MS(APCI)590/592[M + H]+ |
| 487 | 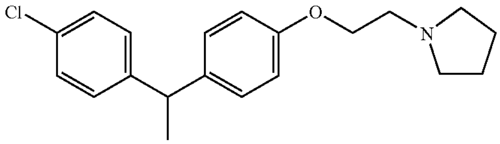 | powder MS(APCI)588/590[M + H]+ |
| 488 | 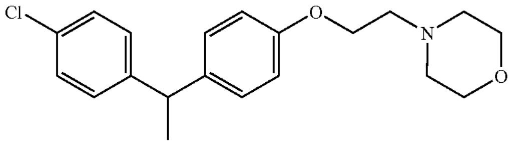 | powder MS(APCI)604/606[M + H]+ |

TABLE 3 (No. 4)-continued
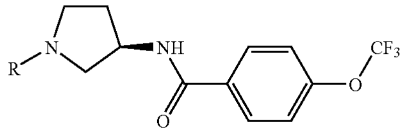
| Ex. Nos. | R | Physicochemical properties etc. |
|---|---|---|
| 489 | 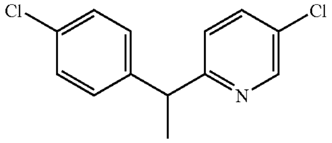 | powder<br>MS(APCI)510/512[M + H]+ |
| 490 | 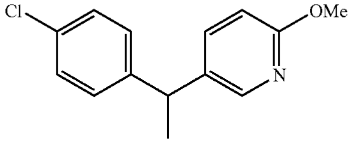 | powder<br>MS(APCI)506/508[M + H]+ |
| 491 | 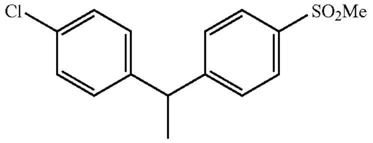 | powder<br>MS(APCI)553/555[M + H]+ |
Me:methyl group,
Et:ethyl group
TABLE 3 (No. 5)
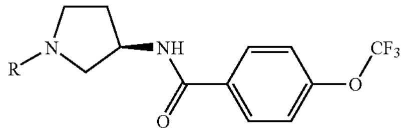
| Ex. Nos. | R | Physicochemical properties etc. |
|---|---|---|
| 492 | 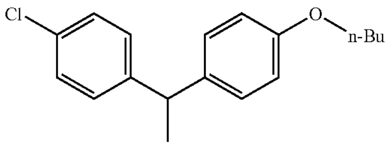 | powder<br>MS(APCI)547/549[M + H]+ |
| 493 | 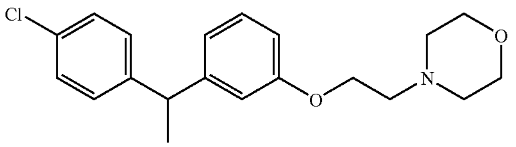 | powder<br>MS(APCI)604/606[M + H]+ |
| 494 | 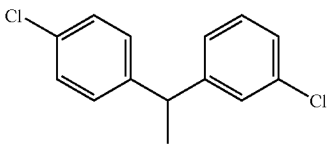 | powder<br>MS(APCI)509/511[M + H]+ |
| 495 | 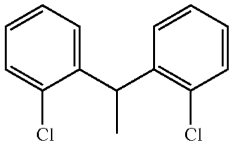 | powder<br>MS(APCI)509/511[M + H]+ |

TABLE 3 (No. 5)-continued

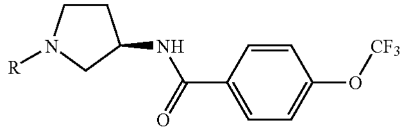

| Ex. Nos. | R | Physicochemical properties etc. |
|---|---|---|
| 496 | 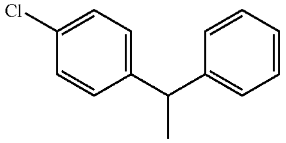 | powder<br>MS(APCI)475/477[M + H]+ |
| 497 | 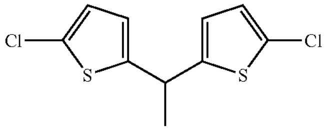 | powder<br>MS(APCI)521/523[M + H]+ |

n-Bu:n-butyl group

TABLE 3 (No. 6)

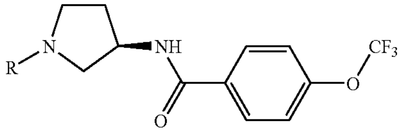

| Ex. Nos. | R | Physicochemical properties etc. |
|---|---|---|
| 498 | 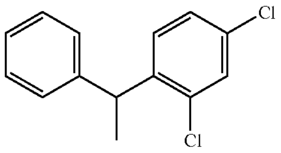 | powder<br>MS(APCI)509/511[M + H]+ |
| 499 | 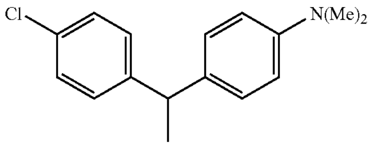 | powder<br>MS(ESI)518/520[M + H]+ |

Me: methyl group

Examples 500 to 507

The corresponding materials are treated in the same manner as described in the Example 6 or 7 followed by treating the product in the same manner as described in either one of the Examples 8 to 19 to give the compounds as shown in the following Table 4 (Nos. 1 to 2).

TABLE 4 (No. 1)

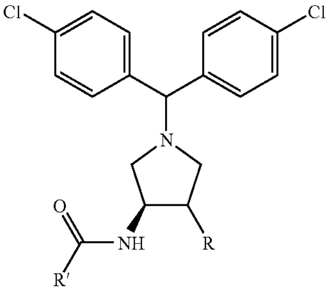

| Ex. Nos. | R | R' | Physicochemical properties etc. |
|---|---|---|---|
| 500 | 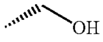 | 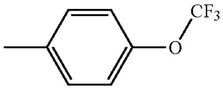 | powder MS(APCI)539/541[M + H]+ |
| 501 | 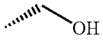 | 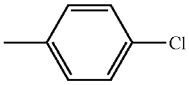 | powder MS(APCI)489/491[M + H]+ |

TABLE 4 (No.2)

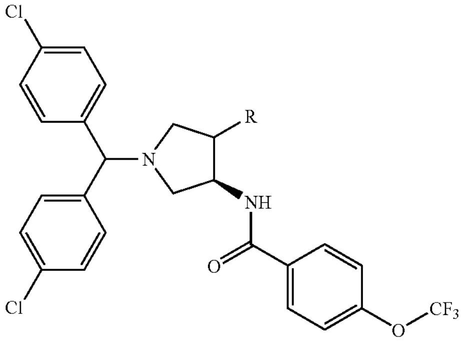

| Ex. Nos. | R | Physicochemical properties etc. |
|---|---|---|
| 502 | 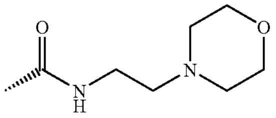 | powder MS(APCI)665/667 [M + H]+ |
| 503 | 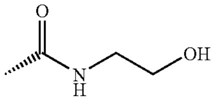 | powder MS(APCI)596/598 [M + H]+ |
| 504 | 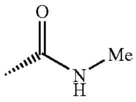 | powder MS(APCI)566/568 [M + H]+ |
| 505 | 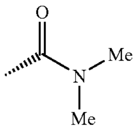 | powder MS(APCI)580/582 [M + H]+ |

TABLE 4 (No.2)-continued

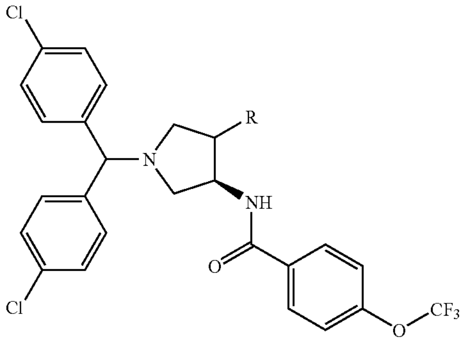

| Ex. Nos. | R | Physicochemical properties etc. |
|---|---|---|
| 506 | 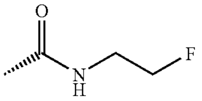 | powder MS(APCI)598/600 [M + H]+ |
| 507 | 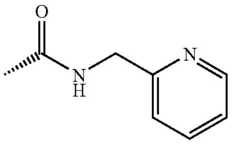 | powder MS(APCI)643/645 [M + H]+ |

Me: methyl group

Examples 508 to 512

The corresponding materials are treated in the same manner as described in the Example 20 to give the compounds as shown in the following Table 5.

TABLE 5

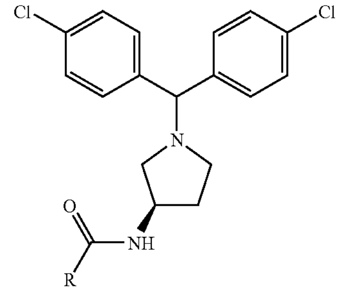

| Ex. Nos. | R | Physicochemical properties etc. |
|---|---|---|
| 508 | 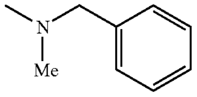 | powder MS(APCI)468/470 [M + H]+ |
| 509 | 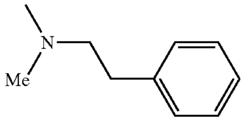 | powder MS(APCI)482/484 [M + H]+ |
| 510 | 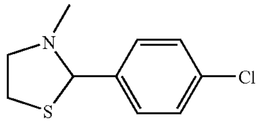 | powder Ms(APCI)546/548 [M + H]+ |
| 511 | 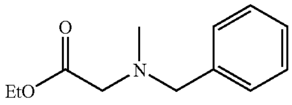 | powder MS(APCI)540/542 [M + H]+ |
| 512 | 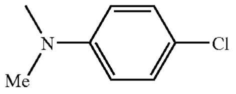 | powder MS(APCI)488/490 [M + H]+ |

Me: methyl group,
Et: ethyl group

Example 513

To a solution of the compound obtained in Example 1 (64 mg) in water/methanol was added 6N HCl (21 μL) and the mixture was concentrated in vacuo to give (3R)-1[bis-(4-chlorophenyl)methyl]-3-[[4-(trifluoromethyloxy)benzoyl]amino]-pyrrolidine hydrochloride (68 mg, yield: 100%) as an amorphous powder.

MS(APCI) m/z; 509/511 $[M+H]^+$

Example 514

(1) The compound obtained in Reference Example 13 (92 mg) was treated in the same manner as described in Example 6 to give (3S,4R)-1-[bis-(4-chlorophenyl)methyl]-3-ethyloxycarbonyl-4-[(4-cyanobenzoyl)amino]pyrrolidine (24 mg, yield: 15%) MS(APCI) m/z; 522/524 $[M+H]^+$ (2) The compound obtained in the above step (1) (200 mg) and sodium borohydride (28.3 mg) were refluxed in tetrahydrofuran under heating. To the reaction mixture was added dropwise methanol (0.5 μL) over a period of 30 minutes and then the mixture was stirred at the same temperature for 1 hour. The reaction mixture was evaporated to remove solvent and thereto was added water and ethyl acetate. The organic layer was washed with water and a saturated brine and dried over magnesium sulfate. After removal of the desiccant, the filtrate was concentrated and the residue was purified by a column chromatography on silica gel (Solvent; n-hexane/ethyl acetate=1:1) to give (3S,4R)-1-[bis-(4-chlorophenyl)methyl]-3-hydroxymethyl-4-[(4-cyanobenzoyl)-amino]pyrrolidine (123.1 mg, yield: 67%).

MS(APCI) m/z; 480/482 $[M+H]^+$ (3) The compound obtained in the above step (2) (60 mg) was dissolved in acentonitrile (7 mL) and thereto was added iodoethane (0.26 mL) and silver oxide (188 mg), and the mixture was stirred at room temperature for 3 days. The insoluble materials were removed by filtration and the filtrate was concentrated, and the residue was purified by a silica gel plate to give (3S,4R)-1-[bis-(4-chlorophenyl)methyl]-3-ethoxy-methyl-4-[(4-cyanobenzoyl)amino]pyrrolidine (13.2 mg, yield: 21%). MS(APCI) m/z; 508/510 $[M+H]^+$

Examples 515 to 594 the corresponding starting materials were treated in the same manner as described in either one of Examples 1 to 5 and 21, and if required, further treated in the same manner as described in either one of Examples 8 to 19, 22 and 513 to give a compound as shown in the following Table 6.

TABLE 6 (No. 1)

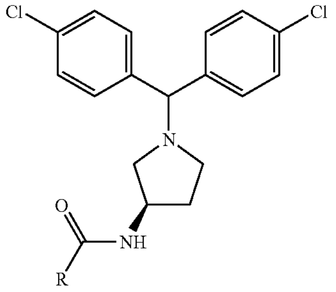

| Ex. Nos. | R | Physicochemical properties etc. |
|---|---|---|
| 515 | 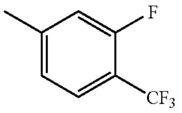 | powder MS(APCI)511/513[M + H]+ |
| 516 | 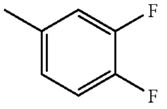 | powder MS(APCI)461/463[M + H]+ |
| 517 | 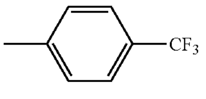 | powder MS(APCI)493/495[M + H]+ |
| 518 | 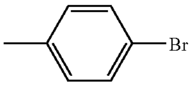 | powder MS(APCI)503/505/507 [M + H]+ |
| 519 | 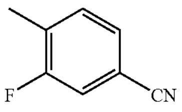 | powder MS(APCI)468/470[M + H]+ |

TABLE 6 (No. 1)-continued

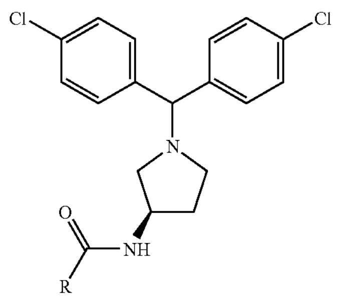

| Ex. Nos. | R | Physicochemical properties etc. |
|---|---|---|
| 520 | 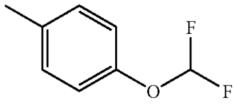 | powder MS(APCI)491/493[M + H]+ |
| 521 | 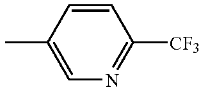 | powder MS(APCI)494/496[M + H]+ |

TABLE 6 (No. 2)

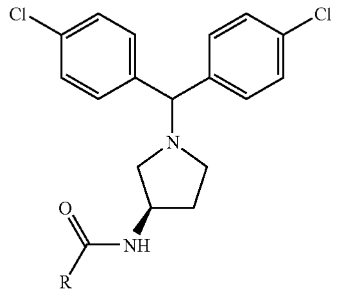

| Ex. Nos. | R | Physicochemical properties etc. |
|---|---|---|
| 522 | 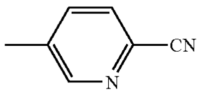 | powder MS(APCI)451/453[M + H]+ |
| 523 | 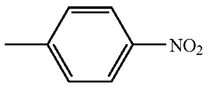 | powder MS(ESI)470[M + H]+ |

TABLE 6 (No. 3)

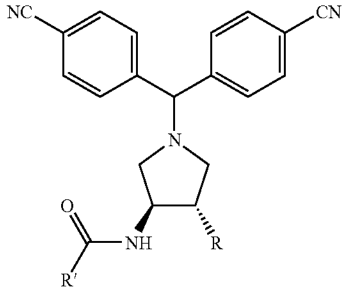

| Ex. Nos. | R | R ' | Physicochemical properties etc. |
|---|---|---|---|
| 524 | OMe | 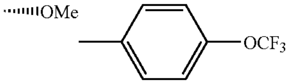 | powder MS(APCI)521 [M + H]+ |
| 525 | OEt | 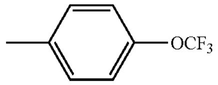 | powder MS(APCI)535 [M + H]+ |
| 526 | H | 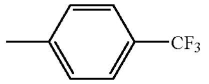 | powder MS(ESI)475 [M + H]+ |
| 527 | H | 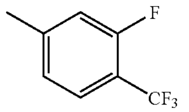 | powder MS(APCI)493 [M + H]+ |
| 528 | OEt | 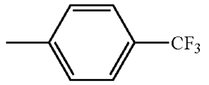 | powder MS(ESI)519 [M + H]+ |
| 529 | OEt | 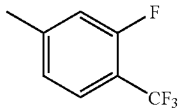 | powder MS(ESI)537 [M + H]+ |

Me: methyl group,
Et: ethyl group

TABLE 6 (No 4)

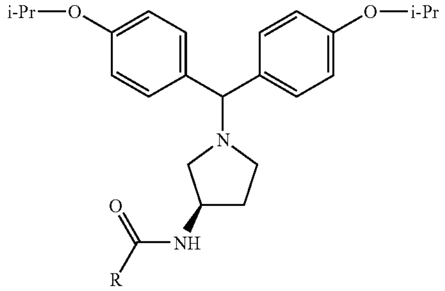

| Ex. Nos. | R | Physicochemical properties etc. |
|---|---|---|
| 530 | 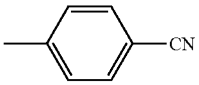 | powder MS(APCI)498[M + H]+ |

TABLE 6 (No 4)-continued
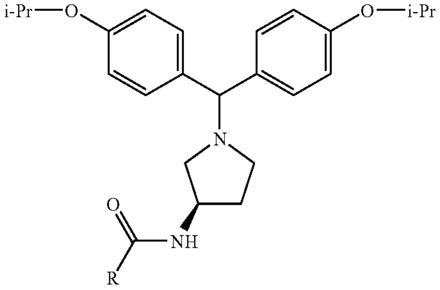
| Ex. Nos. | R | Physicochemical properties etc. |
|---|---|---|
| 531 | 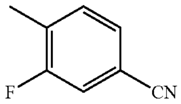 | powder<br>MS(APCI)516[M + H]+ |
i-Pr: isopropyl group
TABLE 6 (No. 5)
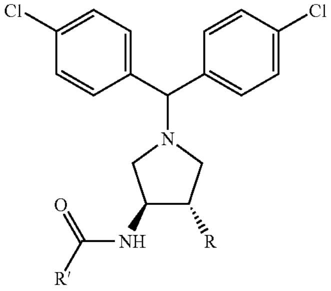
| Ex. Nos. | R | R' | Physicochemical properties etc. |
|---|---|---|---|
| 532 | 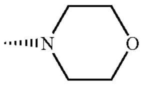 | 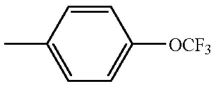 | powder<br>MS(ESI)594[M + H]+ |
| 533 | 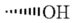 | 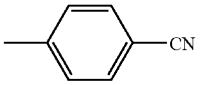 | powder<br>MS(APCI)466/468[M + H]+ |
| 534 | 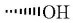 | 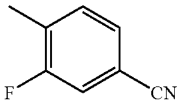 | powder<br>MS(APCI)484/486[M + H]+ |
| 535 | 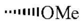 | 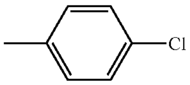 | powder<br>MS(APCI)489/491[M + H]+ |
| 536 |  | 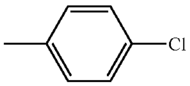 | powder<br>MS(APCI)503/505[M + H]+ |
| 537 |  | 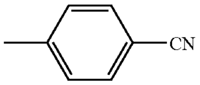 | powder<br>MS(APCI)480/482[M + H]+ |
Me: methyl group,
Et: ethyl group TABLE 6 (No. 6)
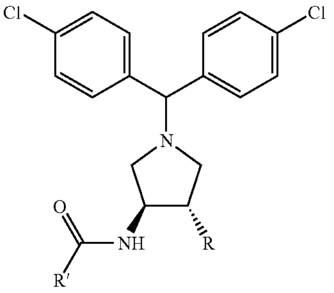
| Ex. Nos. | R | R' | Physicochemical properties etc. |
|---|---|---|---|
| 538 | 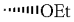 | 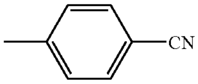 | powder<br>MS(APCI)494/496[M + H]+ |
| 539 |  | 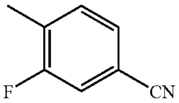 | powder<br>MS(APCI)498/500[M + H]+ |
| 540 |  | 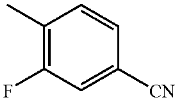 | powder<br>MS(APCI)512/514[M + H]+ |
| 541* | 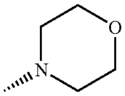 | 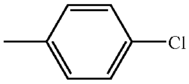 | powder<br>MS(APCI)544/546[M + H]+ |
| 542 | 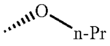 | 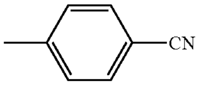 | powder<br>MS(ESI)508[M + H]+ |
| 543* |  | 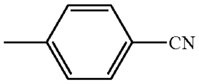 | powder<br>MS(APCI)494/496[M + H]+ |
| 544 | 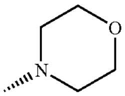 | 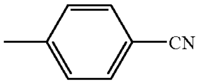 | powder<br>MS(ESI)535[M + H]+ |
*hydrochloride
Me: methyl group,
Et: ethyl group,
n-Pr: n-propyl group TABLE 6 (No. 7)
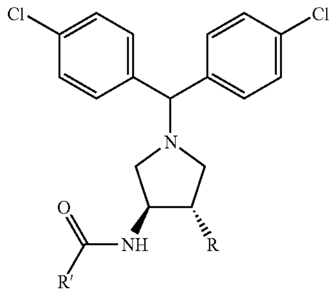
| Ex. Nos. | R | R' | Physicochemical properties etc. |
|---|---|---|---|
| 545 | 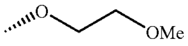 | 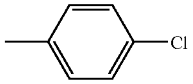 | powder<br>MS(ESI)533[M + H]+ |
| 546 | 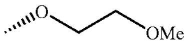 | 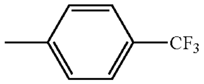 | powder<br>MS(ESI)567[M + H]+ |
| 547 | 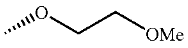 | 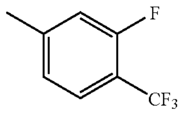 | powder<br>MS(ESI)585[M + H]+ |
| 548 | 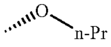 | 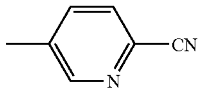 | powder<br>MS(ESI)509[M + H]+ |
| 549 | 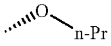 | 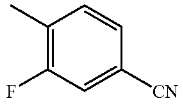 | powder<br>MS(ESI)526[M + H]+ |
| 550 | 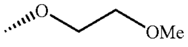 | 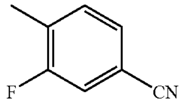 | powder<br>MS(ESI)542[M + H]+ |
| 551 | 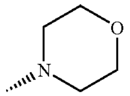 | 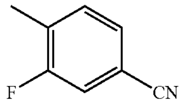 | powder<br>MS(ESI)553[M + H]+ |
Me: methyl group,
n-Pr: n-propyl group TABLE 6 (No. 8)

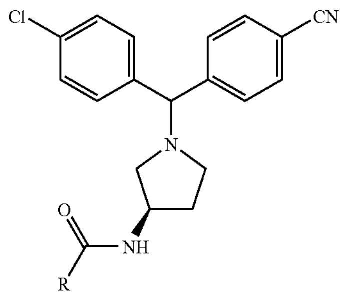

| Ex. Nos. | R | Physicochemical properties etc. |
|---|---|---|
| 552 | 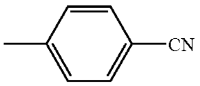 | powder MS(ESI)441[M + H]+ |
| 553 | 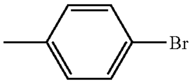 | powder MS(ESI)494[M + H]+ |
| 554 | 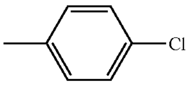 | powder MS(ESI)450[M + H]+ |
| 555 | 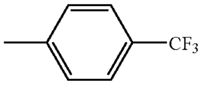 | powder MS(APCI)484/486[M + H]+ |
| 556 | 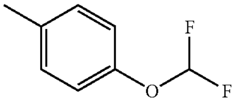 | powder MS(ESI)482[M + H]+ |
| 557 | 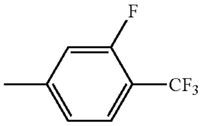 | powder MS(ESI)502[M + H]+ |
| 558 | 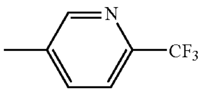 | powder MS(ESI)485[M + H]+ |
| 559 | 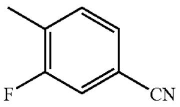 | powder MS(ESI)459[M + H]+ |

TABLE 6 (No. 9)

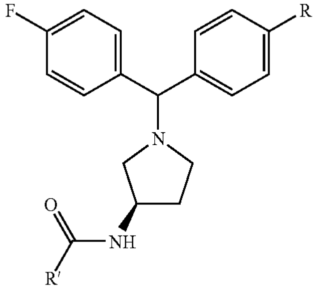

| Ex. Nos. | R | R' | Physicochemical properties etc. |
|---|---|---|---|
| 560 | CN | 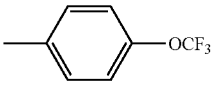 | powder MS(ESI)484[M + H]+ |
| 561 | CN | 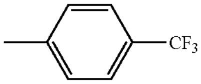 | powder MS(ESI)468[M + H]+ |
| 562 | CN | 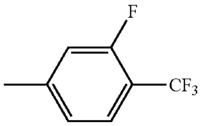 | powder MS(ESI)486[M + H]+ |
| 563 | Cl | 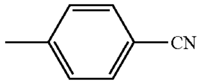 | powder MS(ESI)434[M + H]+ |
| 564 | Cl | 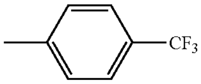 | powder MS(ESI)443[M + H]+ |
| 565 | Cl | 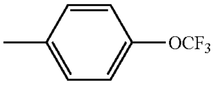 | powder MS(ESI)493[M + H]+ |
| 566 | Cl | 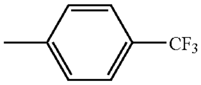 | powder MS(ESI)477[M + H]+ |

TABLE 6 (No. 10)

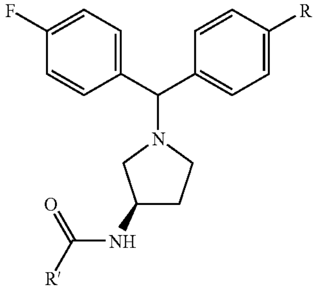

| Ex. Nos. | R | R' | Physicochemical properties etc. |
|---|---|---|---|
| 567 | Cl | 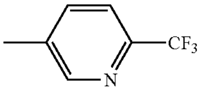 | powder MS(ESI)478[M + H]+ |

TABLE 6 (No. 10)-continued

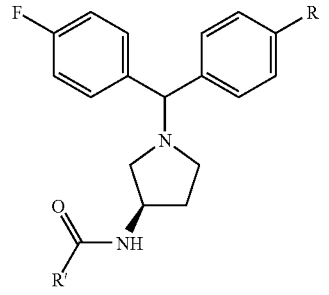

| Ex. Nos. | R | R' | Physicochemical properties etc. |
|---|---|---|---|
| 568 | Cl | 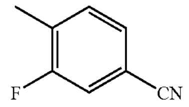 | powder<br>MS(ESI)452[M + H]+ |
| 569 | OMe | 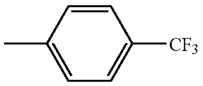 | powder<br>MS(ESI)473[M + H]+ |

Me: methyl group

TABLE 6 (No. 11)

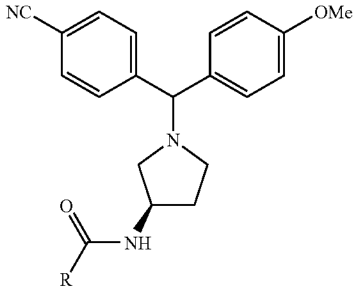

| Ex. Nos. | R | Physicochemical properties etc. |
|---|---|---|
| 570 | 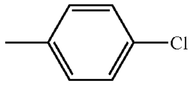 | powder<br>MS(ESI)446[M + H]+ |

TABLE 6 (No. 11)-continued

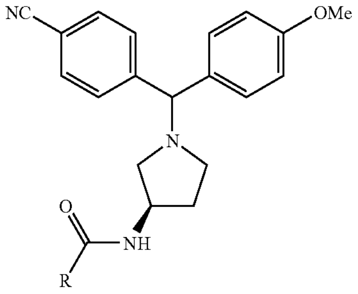

| Ex. Nos. | R | Physicochemical properties etc. |
|---|---|---|
| 571 | 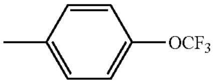 | powder<br>MS(ESI)496[M + H]+ |
| 572 | 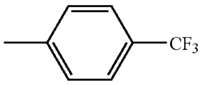 | powder<br>MS(ESI)480[M + H]+ |
| 573 | 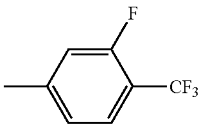 | powder<br>MS(ESI)498[M + H]+ |
| 574 | 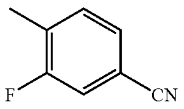 | powder<br>MS(ESI)455[M + H]+ |

Me: methyl group

TABLE 6 (No. 12)

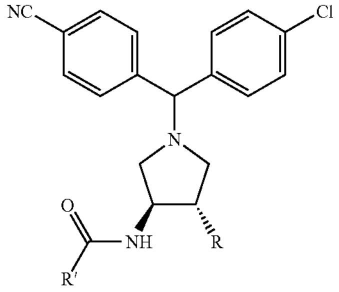

| Ex. Nos. | R | R' | Physicochemical properties etc. |
|---|---|---|---|
| 575 | 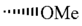 | 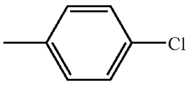 | powder<br>MS(ESI)480[M + H]+ |

TABLE 6 (No. 12)-continued
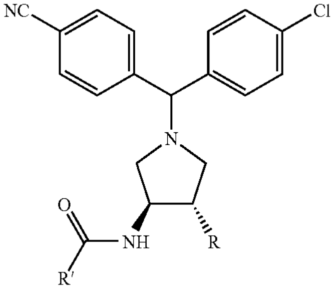
| Ex. Nos. | R | R' | Physicochemical properties etc. |
|---|---|---|---|
| 576 |  | 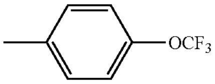 | powder MS(ESI)530[M + H]+ |
| 577 |  | 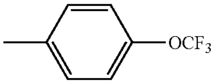 | powder MS(ESI)514[M + H]+ |
| 578 | 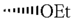 | 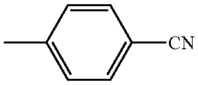 | powder MS(ESI)485[M + H]+ |
| 579 |  | 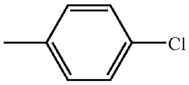 | powder MS(ESI)494[M + H]+ |
| 580 |  | 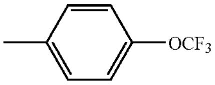 | powder MS(ESI)544[M + H]+ |
| 581 |  | 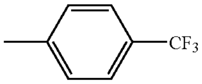 | powder MS(ESI)528[M + H]+ |
Me: methyl group,
Et: ethyl group
TABLE 6 (No. 13)
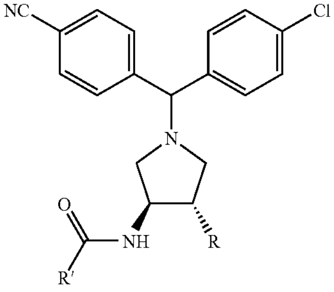
| Ex. Nos. | R | R' | Physicochemical properties etc. |
|---|---|---|---|
| 582 | 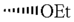 | 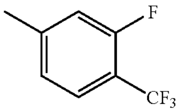 | powder MS(ESI)546[M + H]+ |

TABLE 6 (No. 13)-continued
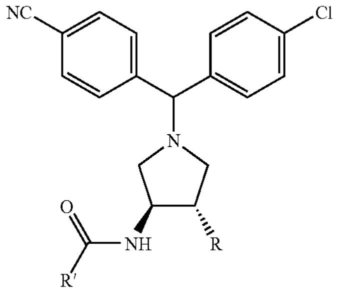
| Ex. Nos. | R | R' | Physicochemical properties etc. |
|---|---|---|---|
| 583 | OEt | 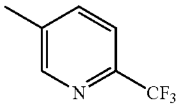 | powder MS(ESI)529[M + H]+ |
| 584 | OEt | 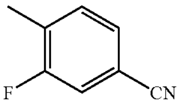 | powder MS(ESI)503[M + H]+ |
| 585 | OMe | 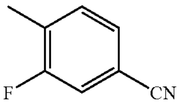 | powder MS(ESI)489[M + H]+ |
| 586 | 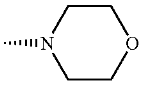 | 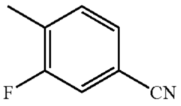 | powder MS(ESI)544[M + H]+ |
Me: methyl group,
Et: ethyl group
TABLE 6 (No. 14)
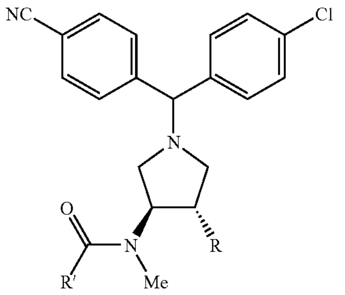
| Ex. Nos. | R | R' | Physico-chemical properties etc. |
|---|---|---|---|
| 587 | OMe | 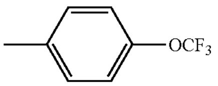 | powder MS(ESI)544[M + H]+ |
Me: methyl group
TABLE 6 (No. 15)
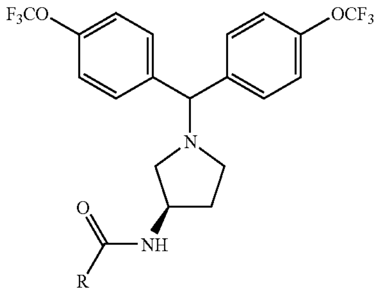
| Ex. Nos. | R | Physicochemical properties etc. |
|---|---|---|
| 588 | 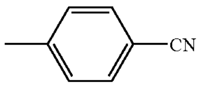 | powder MS(APCI)550[M + H]+ |

TABLE 6 (No. 16)

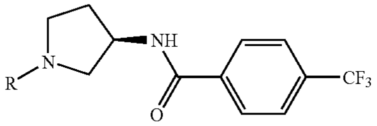

| Ex. Nos. | R | Physicochemical properties etc. |
|---|---|---|
| 598 | 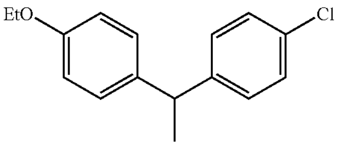 | powder<br>MS(ESI)503[M + H]+ |
| 590 | 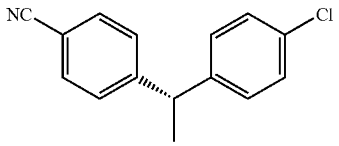 | powder<br>MS(APCI)484/486[M + H]+ |
| 591 | 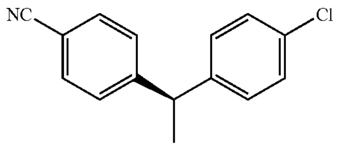 | powder<br>MS(APCI)484/486[M + H]+ |

Et: ethyl group

TABLE 6 (No. 17)

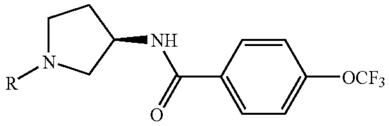

| Ex. Nos. | R | Physicochemical properties etc. |
|---|---|---|
| 592 | 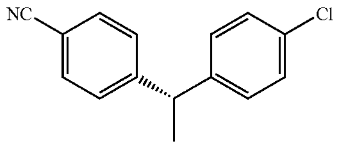 | powder<br>MS(APCI)500/502[M + H]+ |
| 593 | 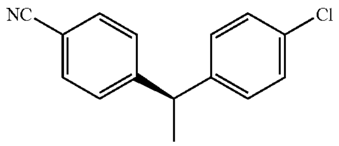 | powder<br>MS(APCI)500/502[M + H]+ |
| 594* | 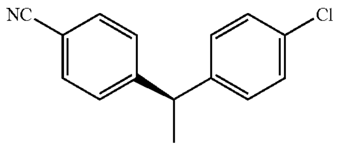 | powder<br>MS(APCI)500/502[M + H]+ |

*hydrochloride

Examples 95 to 619

The corresponding starting materials were treated in the same manner as described in either one of Examples 6 and 7, and if required, further treated in the same manner as described in either one of Examples 8 to 19, 22 and 514 to give a compound as shown in the following Table 7.

TABLE 7 (No. 1)

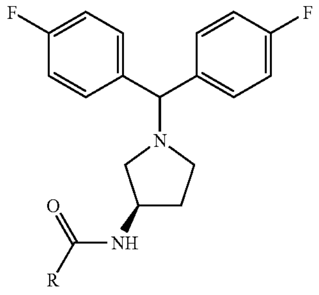

| Ex. Nos. | R | Physicochemical properties etc. |
| --- | --- | --- |
| 595 | 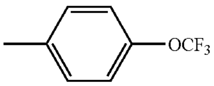 | powder<br>MS(APCI)477[M + H]+ |
| 596 | 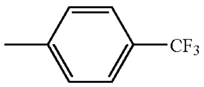 | powder<br>MS(APCI)461[M + H]+ |

TABLE 7 (No. 2)

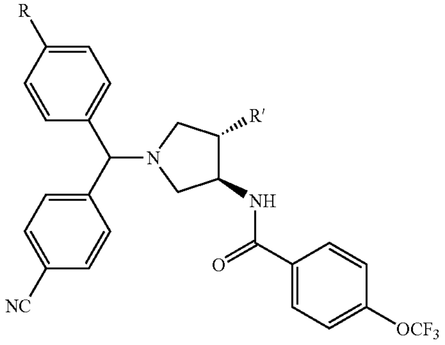

| Ex. Nos. | R | R' | Physicochemical properties etc. |
| --- | --- | --- | --- |
| 597 | Cl | 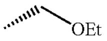 | powder<br>MS(APCI)558/560[M + H]+ |

TABLE 7 (No. 2)-continued

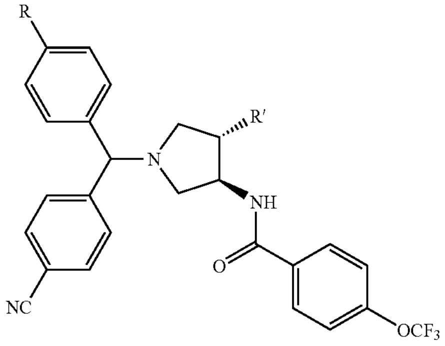

| Ex. Nos. | R | R' | Physicochemical properties etc. |
| --- | --- | --- | --- |
| 598 | CN | 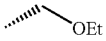 | powder<br>MS(APCI)549[M + H]+ |

Et: ethyl group

TABLE 7 (No. 3)

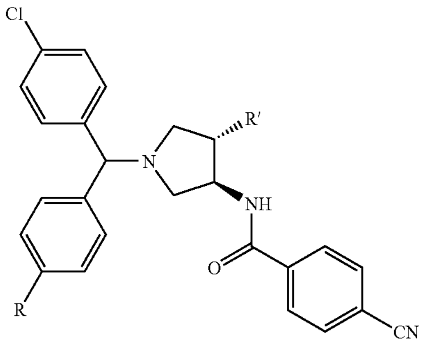

| Ex. Nos. | R | R' | Physicochemical properties etc. |
| --- | --- | --- | --- |
| 599 | —CN | 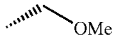 | powder<br>MS(APCI)485/487[M + H]+ |
| 600 | —CN | 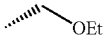 | powder<br>MS(APCI)499/501[M + H]+ |

Me: methyl group,
Et: ethyl group

TABLE 7 (No. 4)

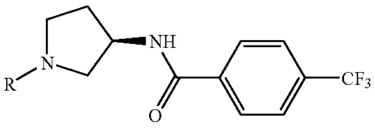

| Ex. Nos. | R | Physicochemical properties etc. |
| --- | --- | --- |
| 601 | 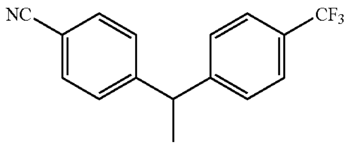 | powder<br>MS(APCI)518[M + H]+ |

TABLE 7 (No. 4)-continued
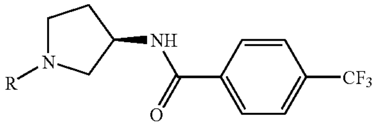
| Ex. Nos. | R | Physicochemical properties etc. |
|---|---|---|
| 602 | 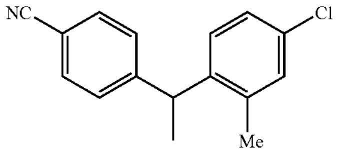 | powder<br>MS(APCI)498/500[M + H]+ |
| 603 | 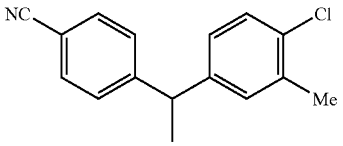 | powder<br>MS(APCI)498/500[M + H]+ |
| 604 | 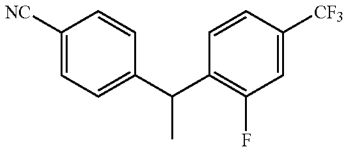 | powder<br>MS(APCI)536[M + H]+ |
| 605 | 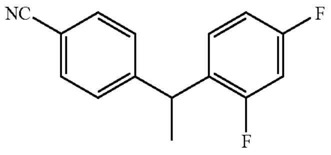 | powder<br>MS(APCI)486[M + H]+ |
| 606 | 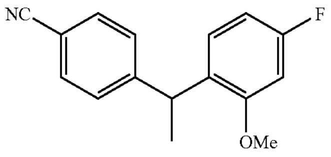 | powder<br>MS(APCI)498[M + H]+ |
Me: methyl group
TABLE 7 (No. 5)
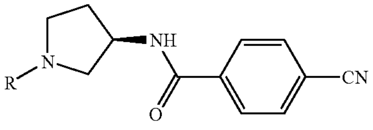
| Ex. Nos. | R | Physicochemical properties etc. |
|---|---|---|
| 607 | 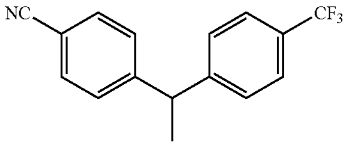 | powder<br>MS(APCI)475[M + H]+ |
| 608 | 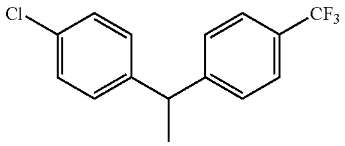 | powder<br>MS(APCI)484/486[M + H]+ |

TABLE 7 (No. 6)
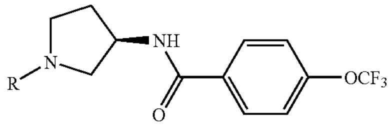
| Ex. Nos. | R | Physicochemical properties etc. |
|---|---|---|
| 609 | 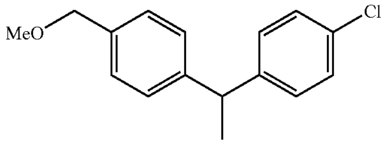 | powder<br>MS(APCI)519/521[M + H]+ |
| 610 | 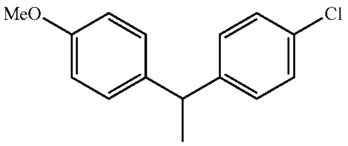 | powder<br>MS(APCI)505/507[M + H]+ |
| 611 | 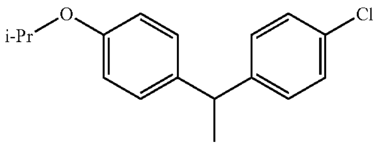 | powder<br>MS(APCI)524[M + H]+ |
| 612 | 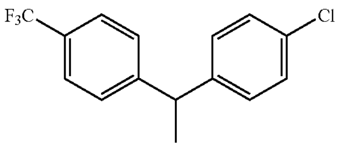 | powder<br>MS(APCI)534[M + H]+ |
| 613 | 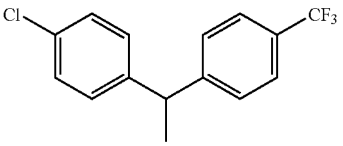 | powder<br>MS(APCI)543/545[M + H]+ |
| 614 | 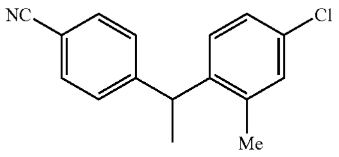 | powder<br>MS(APCI)514/516[M + H]+ |
| 615 | 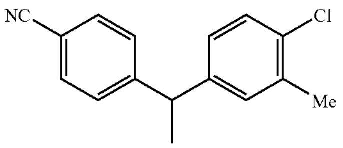 | powder<br>MS(APCI)514/516[M + H]+ |
Me: methyl group,
i-Pr: isopropyl group TABLE 7 (No. 7)

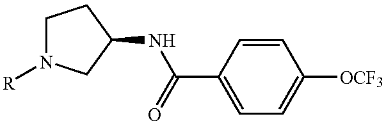

| Ex. Nos. | R | Physicochemical properties etc. |
|---|---|---|
| 616 | 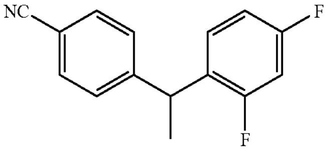 | powder<br>MS(APCI)502[M + H]+ |
| 617 | 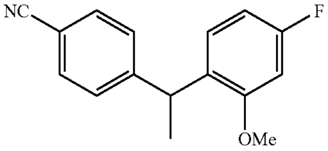 | powder<br>MS(APCI)514[M + H]+ |
| 618 | 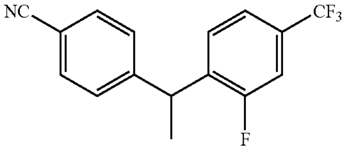 | powder<br>MS(APCI)552[M + H]+ |
| 619 | 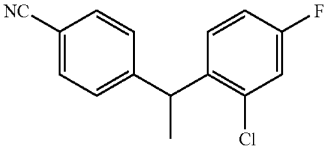 | powder<br>MS(APCI)518/520[M + H]+ |

Me: methyl group

Examples 620 to 631

The corresponding starting materials were treated in the same manner as described in one of Examples 1 to 5 to give a compound as shown in the following Table 8.

TABLE 8 (No. 1)

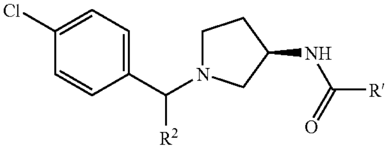

| Ex. Nos. | $R^2$ | R' | Physicochemical properties etc. |
|---|---|---|---|
| 620 | 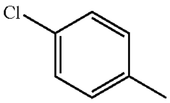 | 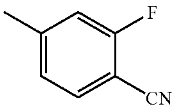 | powder<br>MS(APCI)468/470[M + H]+ |
| 621 | 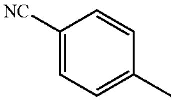 | 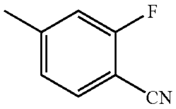 | powder<br>MS(APCI)459/461[M + H]+ |
| 622 | 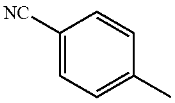 | 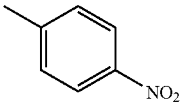 | powder<br>MS(APCI)461/463[M + H]+ |

TABLE 8 (No. 1)-continued

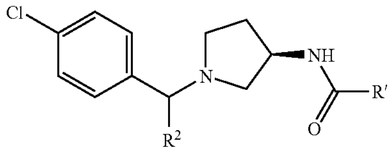

| Ex. Nos. | $R^2$ | R' | Physicochemical properties etc. |
|---|---|---|---|
| 623 | 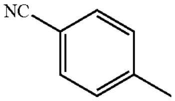 | n-Bu | powder MS(APCI)396/398[M + H]+ |

n-Bu: n-butyl group

TABLE 8 (No. 2)

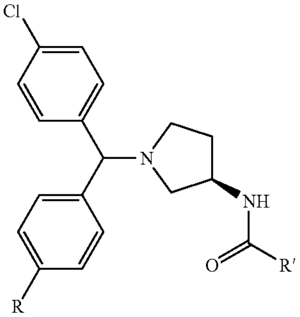

| Ex. Nos. | $R^2$ | R' | Physicochemical properties etc. |
|---|---|---|---|
| 624 | —Cl | 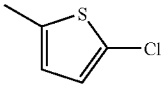 | powder MS(APCI)465/467[M + H]+ |
| 625 | —CN | 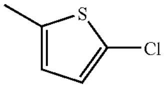 | powder MS(APCI)456/468[M + H]+ |

TABLE 8 (No. 2)-continued

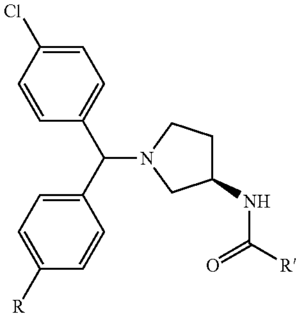

| Ex. Nos. | $R^2$ | R' | Physicochemical properties etc. |
|---|---|---|---|
| 626 | —Cl | 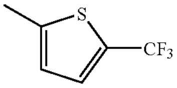 | powder MS(APCI)499/501[M + H]+ |
| 627 | —CN | 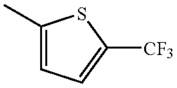 | powder MS(APCI)490/492[M + H]+ |

TABLE 8 (No. 3)

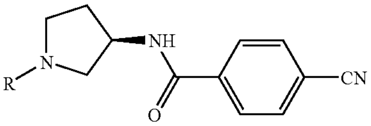

| Ex. Nos. | R | Physicochemical properties etc. |
|---|---|---|
| 628 | 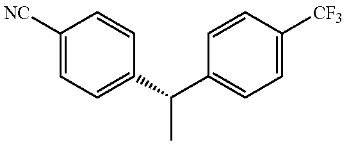 | powder MS(APCI)475[M + H]+ |
| 629 | 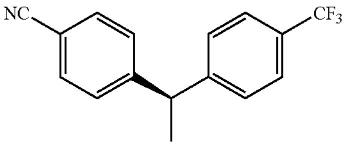 | powder MS(APCI)475[M + H]+ |

TABLE 8 (No. 4)

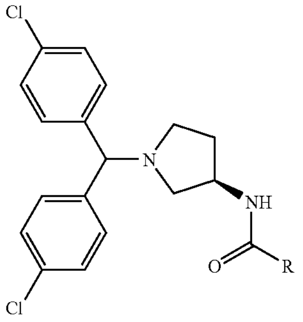

| Ex. Nos. | R | Physicochemical properties etc. |
|---|---|---|
| 630 | 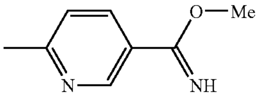 | powder<br>MS(APCI)484/486[M + H]+ |
| 631 | 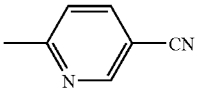 | powder<br>MS(APCI)451/453[M + H]+ |

Me: methyl group

Examples 632 to 708

The corresponding starting materials were treated in the same manner as described in either one of Examples 6 and 7 to give a compound as shown in the following Table 9.

TABLE 9 (No. 1)

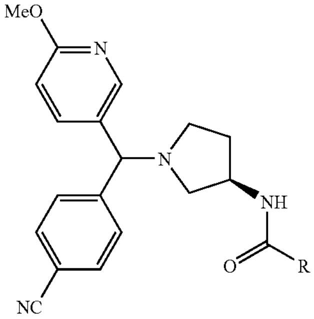

| Ex. Nos. | R | Physicochemical properties etc. |
|---|---|---|
| 632 | 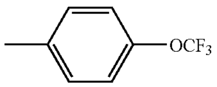 | powder<br>MS(APCI)497[M + H]+ |
| 633 | 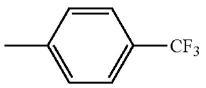 | powder<br>MS(APCI)481[M + H]+ |

TABLE 9 (No. 1)-continued

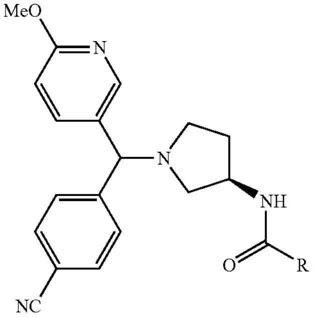

| Ex. Nos. | R | Physicochemical properties etc. |
|---|---|---|
| 634 | 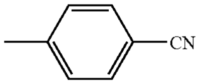 | powder<br>MS(APCI)438[M + H]+ |
| 635 | 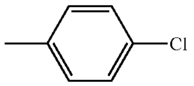 | powder<br>MS(APCI)477/449[M + H]+ |

Me: methyl group

TABLE 9 (No. 2)

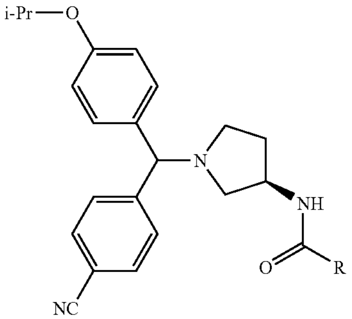

| Ex. Nos. | R | Physicochemical properties etc. |
|---|---|---|
| 636 | 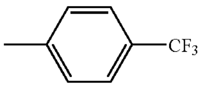 | powder<br>MS(APCI)508[M + H]+ |
| 637 | 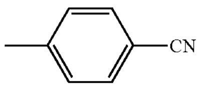 | powder<br>MS(APCI)465[M + H]+ |
| 638 | 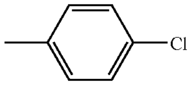 | powder<br>MS(APCI)474/476[M + H]+ |

i-Pr: isopropyl group

TABLE 9 (No. 3)

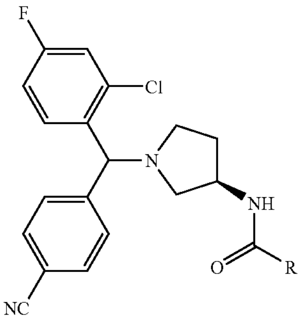

| Ex. Nos. | R | Physicochemical properties etc. |
|---|---|---|
| 639 | 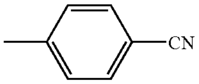 | powder MS(APCI)459/461[M + H]+ |
| 640 | 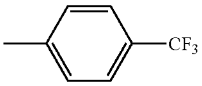 | powder MS(APCI)502/504[M + H]+ |

TABLE 9 (No. 4)

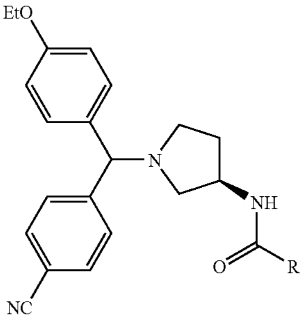

| Ex. Nos. | R | Physicochemical properties etc. |
|---|---|---|
| 641 | 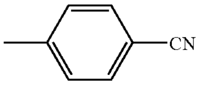 | powder MS(APCI)451[M + H]+ |
| 642 | 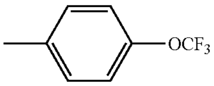 | powder MS(APCI)510[M + H]+ |
| 643 | 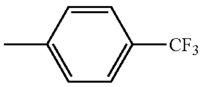 | powder MS(APCI)494[M + H]+ |
| 644 | 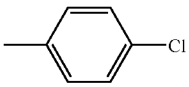 | powder MS(APCI)460/462[M + H]+ |

Et: ethyl group

TABLE 9 (No. 5)

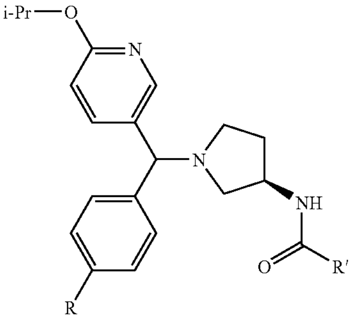

| Ex. Nos. | R | R' | Physico-chemical properties etc. |
|---|---|---|---|
| 645 | —CN | 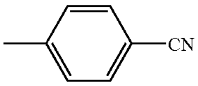 | powder MS(APCI)466[M + H]+ |
| 646 | —CN | 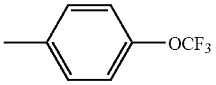 | powder MS(APCI)525[M + H]+ |
| 647 | —CN | 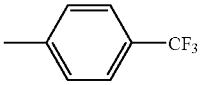 | powder MS(APCI)509[M + H]+ |
| 648 | —CN | 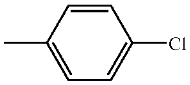 | powder MS(APCI)475/477[M + H]+ |
| 649 | —Cl | 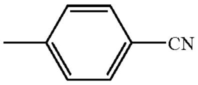 | powder MS(APCI)475/477[M + H]+ |
| 650 | —Cl | 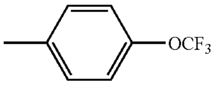 | powder MS(APCI)534/536[M + H]+ |
| 651 | —Cl | 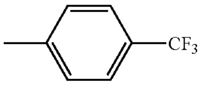 | powder MS(APCI)518/520[M + H]+ |
| 652 | —Cl | 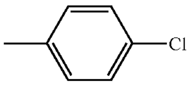 | powder MS(APCI)484/486[M + H]+ |

i-Pr: isopropyl group

TABLE 9 (No. 6)

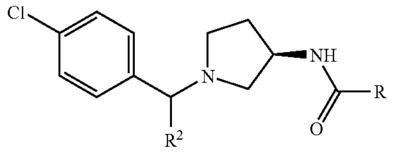

| Ex. Nos. | $R^2$ | R | Physicochemical properties etc. |
|---|---|---|---|
| 653 | 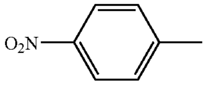 | 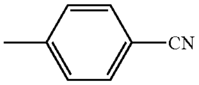 | powder MS(APCI)461/463[M + H]+ |
| 654 | 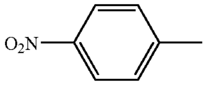 | 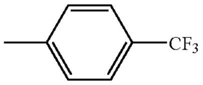 | powder MS(APCI)503/505[M + H]+ |
| 655 | 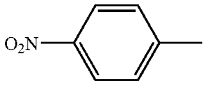 | 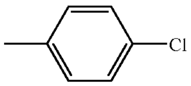 | powder MS(APCI)470/472[M + H]+ |
| 656 | 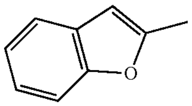 | 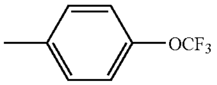 | powder MS(APCI)515/517[M + H]+ |
| 657 | 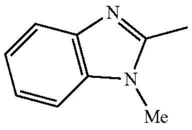 | 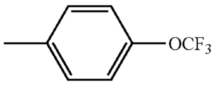 | powder MS(APCI)529/531[M + H]+ |

Me: methyl group

TABLE 9 (No. 7)

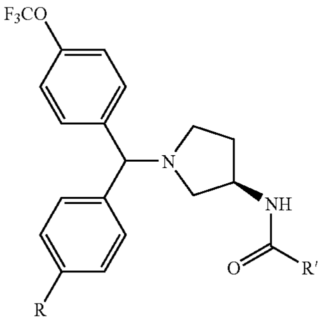

| Ex. Nos. | R | R' | Physicochemical properties etc. |
|---|---|---|---|
| 658 | —CN | 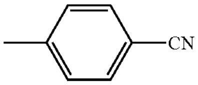 | powder MS(APCI)491 [M + H]+ |
| 659 | —CN | 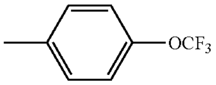 | powder MS(APCI)550 [M + H]+ |
| 660 | —CN | 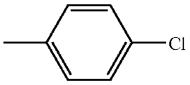 | powder MS(APCI) 500/502[M + H]+ |
| 661 | —Cl | 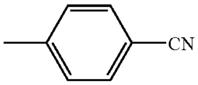 | powder MS(APCI) 500/502[M + H]+ |

TABLE 9 (No. 7)-continued

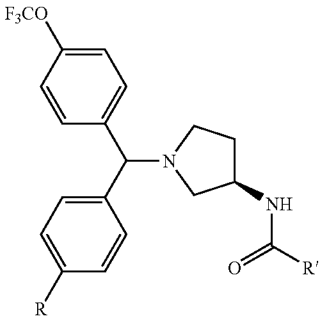

| Ex. Nos. | R | R' | Physicochemical properties etc. |
|---|---|---|---|
| 662 | —Cl | 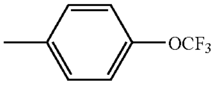 | powder MS(APCI) 559/561[M + H]+ |
| 663 | —Cl | 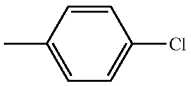 | powder MS(APCI) 509/511[M + H]+ |
| 664 | —CN | 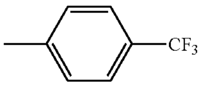 | powder MS(APCI)534 [M + H]+ |

TABLE 9 (No. 7)-continued

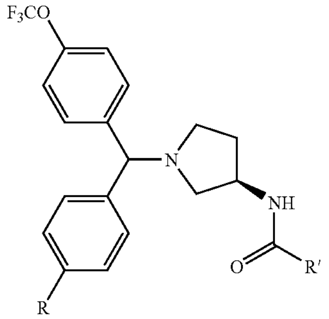

| Ex. Nos. | R | R' | Physicochemical properties etc. |
|---|---|---|---|
| 665 | —Cl | 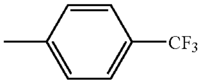 | powder MS(APCI) 543/545[M + H]+ |

TABLE 9 (No. 8)

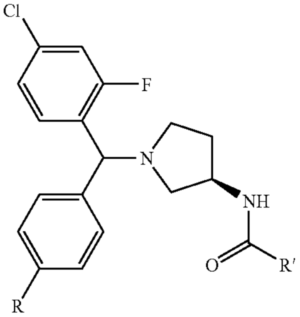

| Ex. Nos. | R | R' | Physicochemical properties etc. |
|---|---|---|---|
| 666 | —CN | 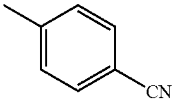 | powder MS(APCI) 459/461[M + H]+ |
| 667 | —CN | 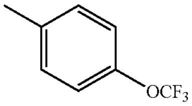 | powder MS(APCI) 518/520[M + H]+ |
| 668 | —CN | 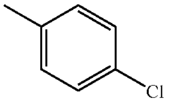 | powder MS(APCI) 468/470[M + H]+ |
| 669 | —Cl | 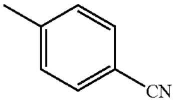 | powder MS(APCI) 468/470[M + H]+ |
| 670 | —Cl | 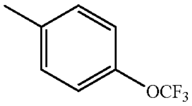 | powder MS(APCI) 527/529[M + H]+ |

TABLE 9 (No. 8)-continued

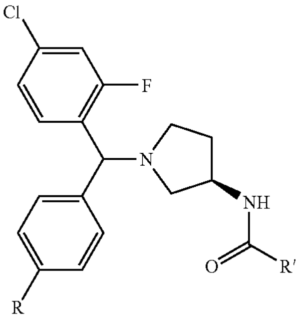

| Ex. Nos. | R | R' | Physicochemical properties etc. |
|---|---|---|---|
| 671 | —CN | 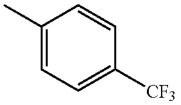 | powder MS(APCI) 502/504[M + H]+ |
| 672 | —Cl | 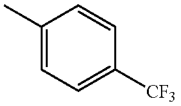 | powder MS(APCI) 511/513[M + H]+ |

TABLE 9 (No. 9)

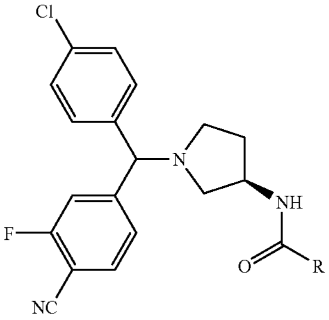

| Ex. Nos. | R | Physicochemical properties etc. |
|---|---|---|
| 673 | 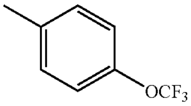 | powder MS(APCI) 518/520[M + H]+ |
| 674 | 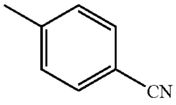 | powder MS(APCI) 459/461[M + H]+ |
| 675 | 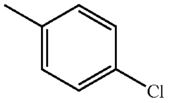 | powder MS(APCI) 468/470[M + H]+ |
| 676 | 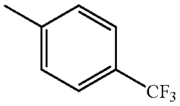 | powder MS(APCI) 502/504[M + H]+ |

TABLE 9 (No. 10)

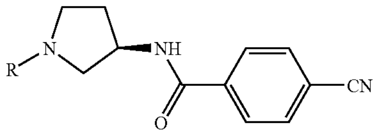

| Ex. Nos. | R | Physicochemical properties etc. |
|---|---|---|
| 677 | 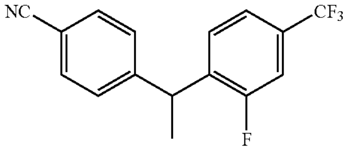 | powder MS(APCI) 493[M + H]+ |
| 678 | 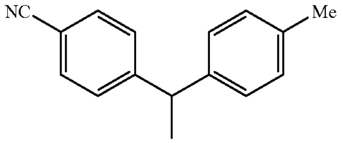 | powder MS(APCI) 421[M + H]+ |
| 679 | 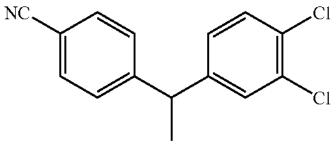 | powder MS(APCI) 475/477[M + H]+ |
| 680 | 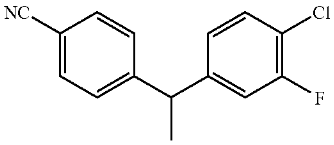 | powder MS(APCI) 459/461[M + H]+ |
| 681 | 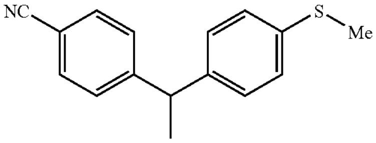 | powder MS(APCI) 453[M + H]+ |
| 682 | 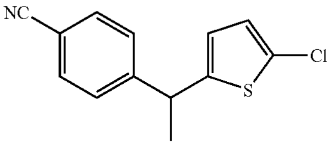 | powder MS(APCI) 447/449[M + H]+ |
| 683 | 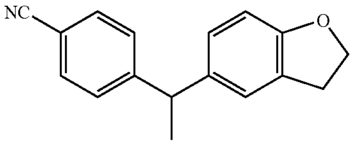 | powder MS(APCI) 449[M + H]+ |
| 684 | 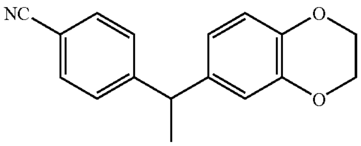 | powder MS(APCI) 465[M + H]+ |

Me: methyl group

TABLE 9 (No. 11)

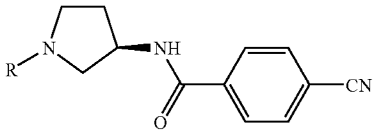

| Ex. Nos. | R | Physicochemical properties etc. |
|---|---|---|
| 685 | 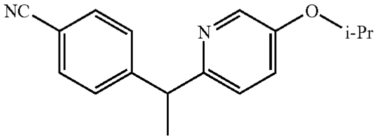 | powder MS(APCI) 466[M + H]+ |
| 686 | 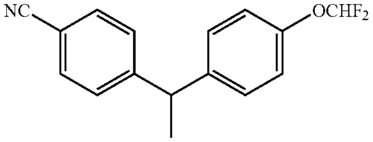 | powder MS(APCI) 473[M + H]+ |
| 687 | 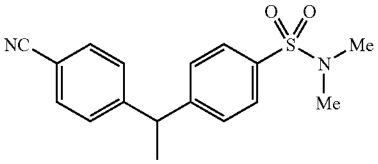 | powder MS(APCI) 514[M + H]+ |
| 688 | 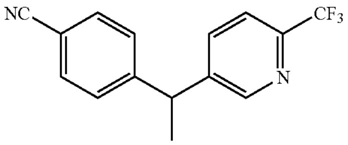 | powder MS(APCI) 476[M + H]+ |
| 689 | 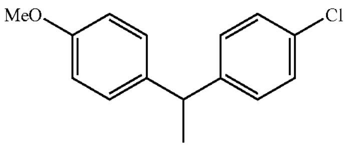 | powder MS(APCI) 446/448[M + H]+ |
| 690 | 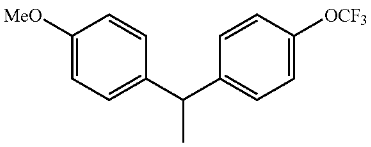 | powder MS(APCI) 496[M + H]+ |
| 691 | 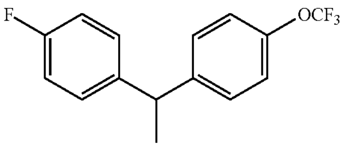 | powder MS(APCI) 484[M + H]+ |

Me: methyl group,
i-Pr: isopropyl group

TABLE 9 (No. 12)

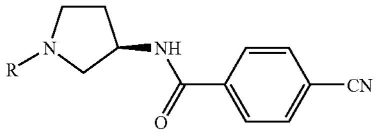

| Ex. Nos. | R | Physicochemical properties etc. |
|---|---|---|
| 692 | 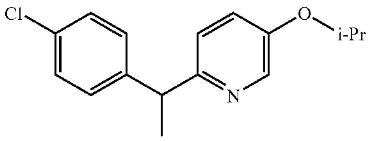 | powder MS(APCI) 475/477[M + H]+ |
| 693 | 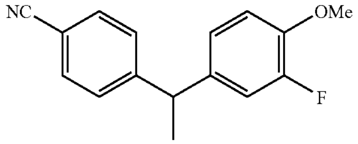 | powder MS(APCI) 455[M + H]+ |
| 694 | 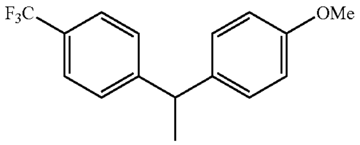 | powder MS(APCI) 480[M + H]+ |
| 695 | 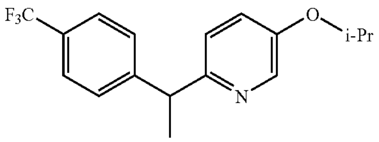 | powder MS(APCI) 509[M + H]+ |
| 696 | 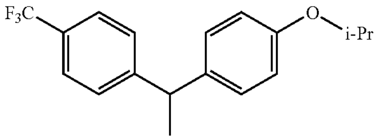 | powder MS(APCI) 508[M + H]+ |

Me: methyl group,
i-Pr: isopropyl group

TABLE 9 (No. 13)

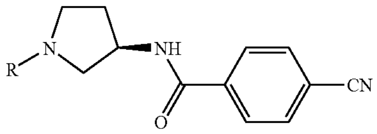

| Ex. Nos. | R | Physicochemical properties etc. |
|---|---|---|
| 697 | 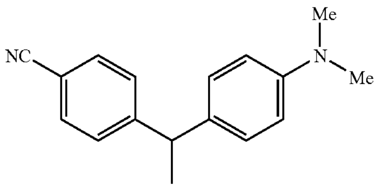 | powder MS(APCI) 450[M + H]+ |

TABLE 9 (No. 13)-continued

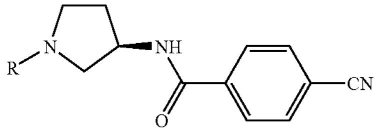

| Ex. Nos. | R | Physicochemical properties etc. |
|---|---|---|
| 698 | 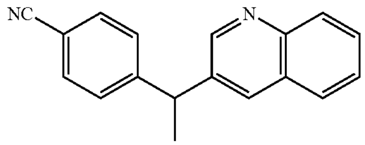 | powder MS(APCI) 458[M + H]+ |
| 699 | 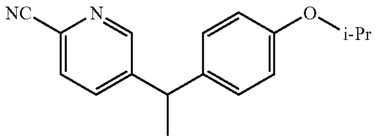 | powder MS(APCI) 466[M + H]+ |
| 700 | 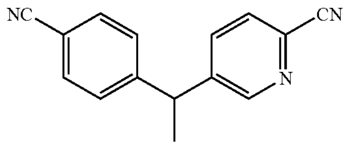 | powder MS(APCI) 433[M + H]+ |
| 701 | 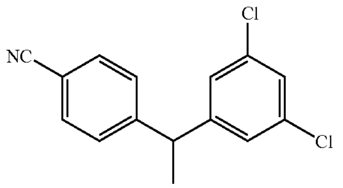 | powder MS(APCI) 475/477[M + H]+ |
| 702 | 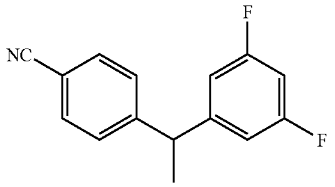 | powder MS(APCI) 443[M + H]+ |
| 703 | 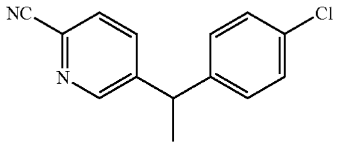 | powder MS(APCI) 442/444 [M + H]+. |

Me: methyl group,
i-Pr: isopropyl group

TABLE 9 (No. 14)

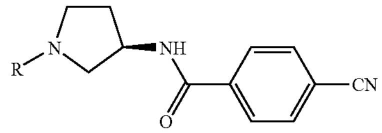

| Ex. Nos. | R | Physicochemical properties etc. |
|---|---|---|
| 704 | 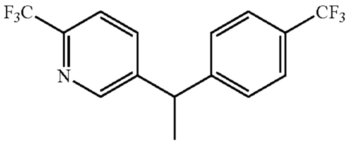 | powder MS(APCI) 519[M + H]+ |
| 705 | 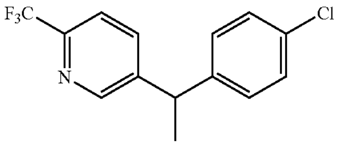 | powder MS(APCI) 485/487[M + H]+ |
| 706 | 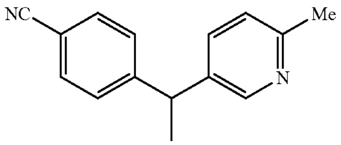 | powder MS(APCI) 422[M + H]+ |
| 707 | 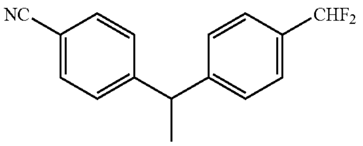 | powder MS(APCI) 457[M + H]+ |
| 708 | 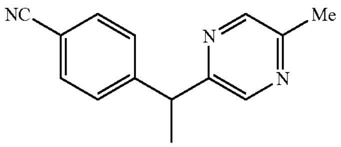 | powder MS(APCI) 423[M + H]+ |

Me: methyl group

Example 709

The corresponding materials were treated in the same manner as described in Example 8 to give (3R)-1-[(4-chlorophenyl)(2-cyanophenyl)methyl]-3-[[4-(trifluoro-methoxy)benzoyl]amino]pyrrolidine as a powder. MS(APCI) m/z: 500/502 $[M+H]^+$ Example 710

The compound obtained in Reference Example 21 (50 mg) and dimethylamine were treated in the same manner as described in Example 19(2) to give (3R)-1-[(4-cyanophenyl)(4-dimethylcarbamoylphenyl)methyl]-3-[[(4-trifluoromethoxy)benzoyl]amino]pyrrolidine as a powder. MS(APCI) m/z: 546/548 $[M+H]^+$ Example 711

To a solution of (3R)-1-[(4-methylthiophenyl)(4-cyanophenyl)methyl]-3-[(4-cyanobenzoyl)amino]pyrrolidine (45.3 mg) in methylene chloride (2 mL) was added trifluoroacetic acid (31 μL) under ice-cooling and the mixture was stirred at room temperature or 30 minutes. Thereto was added m-chloroperbenzoic acid (23 mg) under ice-cooling and the mixture was stirred at the same temperature for 1 hour and then stirred at room temperature for 4 hours. To the reaction mixture was added an aqueous saturated sodium hydrogen carbonate solution and the organic layer was extracted by a diatomaceous earth column (Chem Elut; VARIAN Inc.). The extract was concentrated in vacuo and the resultant crude product was purified by a column chromatography on silica gel (solvent; chloroform/methanol=98:2→90:10). The resultant product was dissolved in t-buthanol and lyophilized to give (3R)-1-[(4-cyanophenyl)-(4-methylsulfinylphenyl)methyl]-3-[(4-cyanobenzoyl)amino]pyrrolidine (42.5 mg, yield: 91%) as a powder. MS(APCI) m/z: 469 $[M+H]^+$ Example 712

To a solution of (3R)-1-[(4-methylthiophenyl)(4-cyanophenyl)methyl]3-[(4-cyanobenzoyl)amino]pyrrolidine (45.3 mg) in methylene chloride (2 mL) was added trifluoroacetic acid (31 μL) under ice-cooling and the mixture was stirred at room temperature for 30 minutes. Thereto was added m-chloroperbenzoic acid (46 mg) under ice-cooling and the mixture was stirred at the same temperature for 1 hour and then stirred at room temperature for 2 hours. To the reaction mixture was added an aqueous saturated sodium hydrogen carbonate solution and the organic layer was extracted by a diatomaceous earth column (Chem Elut). The extract was concentrated in vacuo and the resultant crude product was purified by a column chromatography on silica gel (solvent; hexane/ethyl acetate=40:60→60:40). The resultant product was dissolved in t-buthanol and lyophilized to give (3R)-1-[(4-cyanophenyl)(4-methylsulfonylphenyl)-methyl]-3-[(4-cyanobenzoyl)amino]pyrrolidine (27.4 mg, yield: 57%) as a powder.

MS(APCI) m/z: 485 $[M+H]^+$

Example 713

To a solution of [(4-chlorophenyl)(4-chloro-2-methylphenyl)]methanol (40.1 mg) in methylene chloride (0.65 mL) was added phosphorus tribromide (20 μL) and the mixture was stirred at room temperature overnight. To the reaction mixture was added water and chloroform and the mixture was stirred. The organic layer was extracted by a diatomaceous earth column (Chem Elut) and concentrated in vacuo. To the resultant residue was added diisopropylethylamine (105 μL) and acetonitrile (1 mL) and the mixture was refluxed under heating for 2 days. After cooling to room temperature, to the reaction mixture was added water and ethyl acetate and the organic layer was separated and concentrated in vacuo. The resultant crude product was purified by HPLC (XTerra PrepMS C18 column, solvent; water/methanol=1:1→5:95). The resultant product was dissolved in t-buthanol and lyophilized to give (3R)-1-[(4-chlorophenyl)(4-chloro-2-methylphenyl)methyl]-3-[(4-cyanobenzoyl)amino]pyrrolidine (37.3 mg, yield: 54%) as a powder. MS(APCI) m/z: 464/466 $[M+H]^+$ Examples 714 to 716

The corresponding starting materials were treated in the same manner as described in Example 712 to give the compound as shown in the following Table 10.

TABLE 10

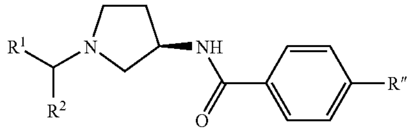

| Ex. Nos. | R[1] | R[2] | R" | Physicochemical properties etc. |
|---|---|---|---|---|
| 714 | 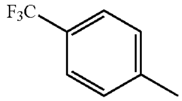 | 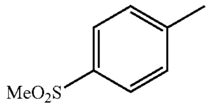 | —CN | powder MS(APCI) 528[M + H]+ |
| 715 | 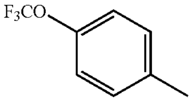 | 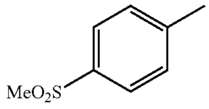 | —CN | powder MS(APCI) 544[M + H]+ |
| 716 | 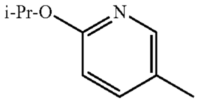 | 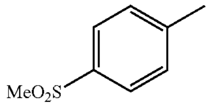 | —CN | powder MS(APCI) 519[M + H]+ |

Me: methyl group,
i-Pr: isopropyl group

Example 717

The corresponding starting materials were treated in the same manner as described in Example 1 to give the compound as shown in the following Table 11.

TABLE 11

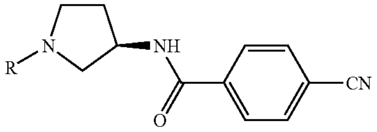

| Ex. Nos. | R | Physicochemical properties etc. |
|---|---|---|
| 717 | 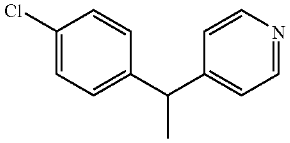 | powder MS(APCI) 417/419[M + H]+ |

Examples 718 to 751

The corresponding starting materials were treated in the same manner as described in either one of Examples 6 and 7 to give the compounds as shown in the following Table 12.

TABLE 12 (No. 1)
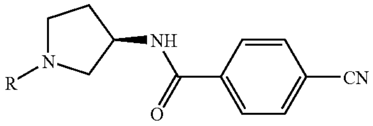
| Ex. Nos. | R | Physicochemical properties etc. |
|---|---|---|
| 718 | 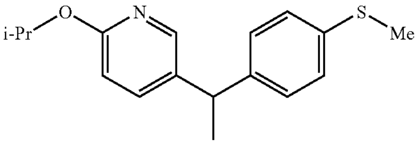 | powder<br>MS(APCI)487[M + H]+ |
| 719 | 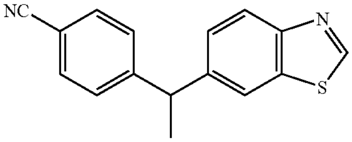 | powder<br>MS(APCI)464[M + H]+ |
| 720 | 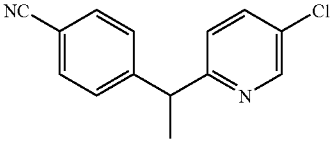 | powder<br>MS(APCI)442/444[M + H]+ |
Me: methyl group,
i-Pr: isopropyl group
TABLE 12 (No. 2)
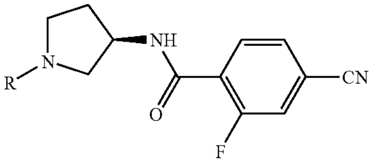
| Ex. Nos. | R | Physicochemical properties etc. |
|---|---|---|
| 721 | 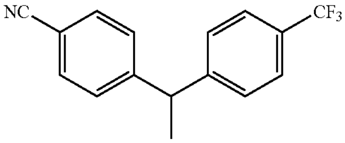 | powder<br>MS(APCI)493[M + H]+ |
| 722 | 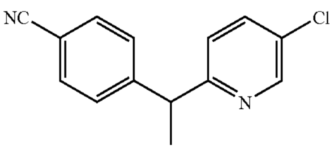 | powder<br>MS(APCI)460/462[M + H]+ |
| 723 | 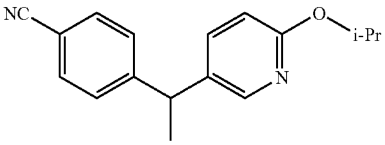 | powder<br>MS(ESI)484[M + H]+ |

TABLE 12 (No. 2)-continued
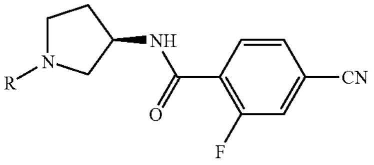
| Ex. Nos. | R | Physicochemical properties etc. |
|---|---|---|
| 724 | 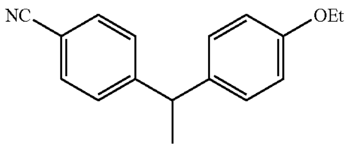 | powder<br>MS(ESI)469[M + H]+ |
| 725 | 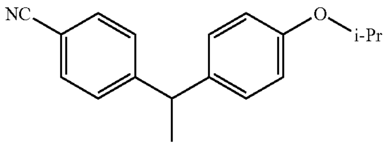 | powder<br>MS(ESI)483[M + H]+ |
| 726 | 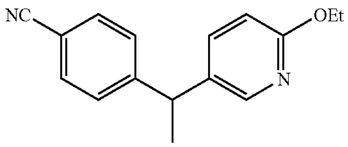 | powder<br>MS(ESI)470[M + H]+ |
| 727 | 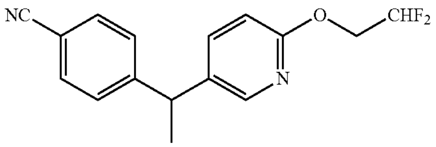 | powder<br>MS(ESI)506[M + H]+ |
Et: ethyl group,
i-Pr: isopropyl group
TABLE 12 (No. 3)
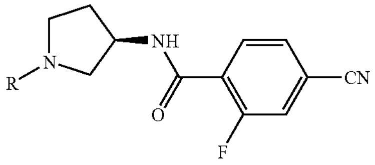
| Ex. Nos. | R | Physicochemical properties etc. |
|---|---|---|
| 728 | 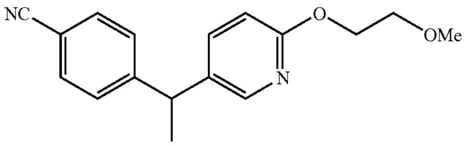 | powder<br>MS(ESI)500[M + H]+ |
| 729 | 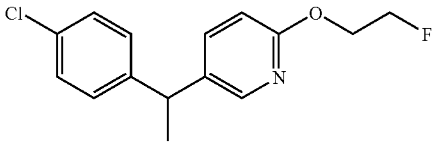 | powder<br>MS(ESI)497[M + H]+ |

TABLE 12 (No. 3)-continued
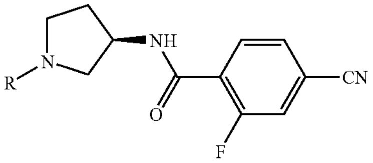
| Ex. Nos. | R | Physicochemical properties etc. |
|---|---|---|
| 730 | 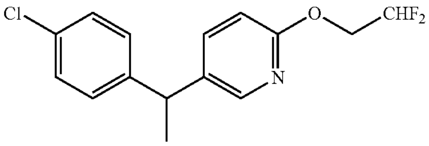 | powder<br>MS(ESI)515[M + H]+ |
| 731 | 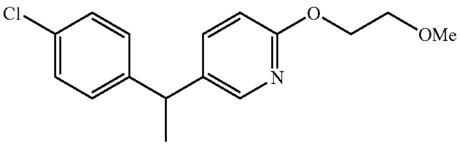 | powder<br>MS(ESI)509[M + H]+ |
| 732 | 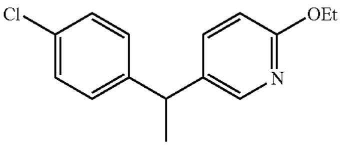 | powder<br>MS(ESI)479[M + H]+ |
| 733 | 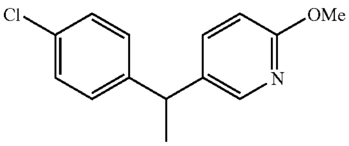 | powder<br>MS(ESI)465[M + H]+ |
| 734 | 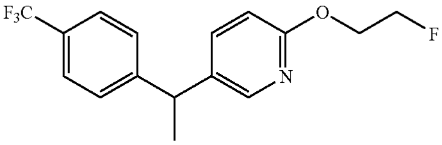 | powder<br>MS(ESI)531[M + H]+ |
Me: methyl group,
Et: ethyl group
TABLE 12 (No. 4)
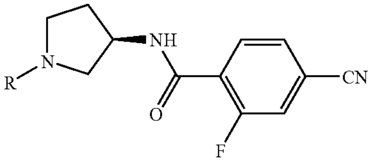
| Ex. Nos. | R | Physicochemical properties etc. |
|---|---|---|
| 735 | 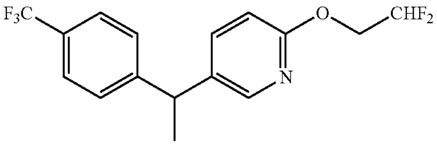 | powder<br>MS(ESI)549[M + H]+ |

TABLE 12 (No. 4)-continued
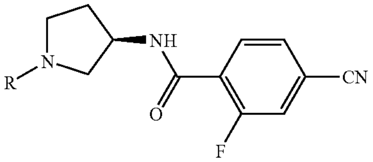
| Ex. Nos. | R | Physicochemical properties etc. |
|---|---|---|
| 736 | 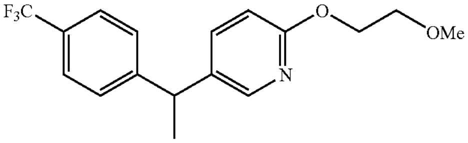 | powder<br>MS(ESI)543[M + H]+ |
| 737 | 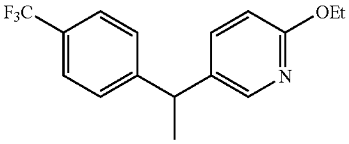 | powder<br>MS(ESI)513[M + H]+ |
| 738 | 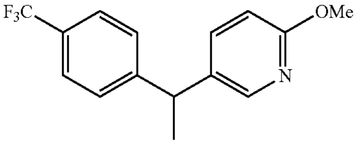 | powder<br>MS(ESI)499[M + H]+ |
Me: methyl group,
Et: ethyl group
TABLE 12 (No. 5)
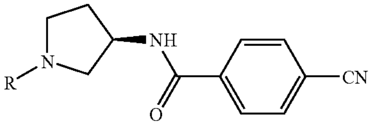
| Ex. Nos. | R | Physicochemical properties etc. |
|---|---|---|
| 739 | 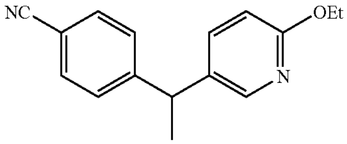 | powder<br>MS(ESI)452[M + H]+ |
| 740 | 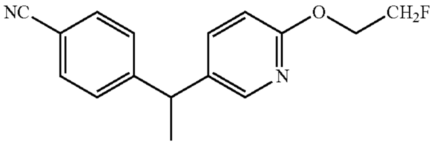 | powder<br>MS(ESI)488[M + H]+ |
| 741 | 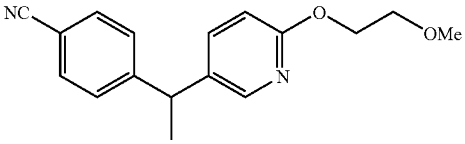 | powder<br>MS(ESI)482[M + H]+ |
| 742 | 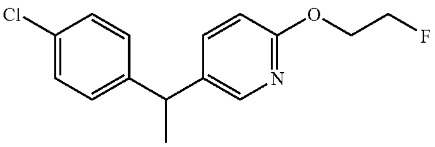 | powder<br>MS(ESI)479[M + H]+ |

TABLE 12 (No. 5)-continued
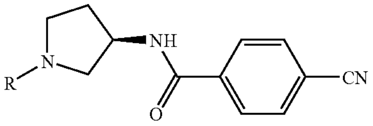
| Ex. Nos. | R | Physicochemical properties etc. |
|---|---|---|
| 743 | 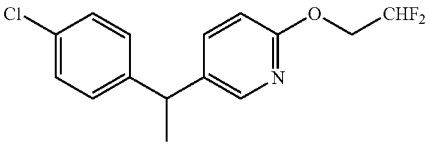 | powder<br>MS(ESI)497[M + H]+ |
| 744 | 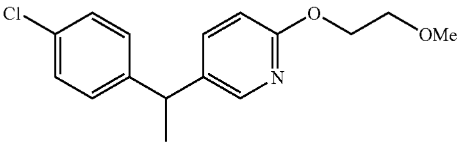 | powder<br>MS(ESI)491[M + H]+ |
| 745 | 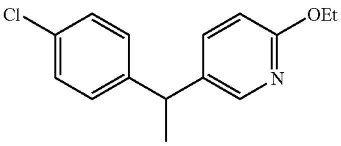 | powder<br>MS(ESI)461[M + H]+ |
Me: methyl group,
Et: ethyl group
TABLE 12 (No. 6)
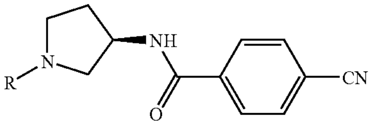
| Ex. Nos. | R | Physicochemical properties etc. |
|---|---|---|
| 746 | 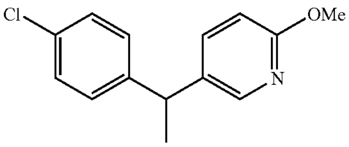 | powder<br>MS(ESI)447[M + H]+ |
| 747 | 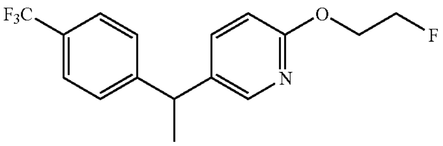 | powder<br>MS(ESI)513[M + H]+ |
| 748 | 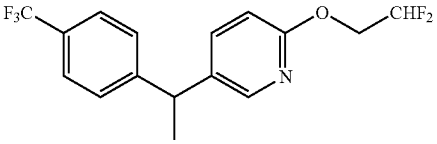 | powder<br>MS(ESI)531[M + H]+ |
| 749 | 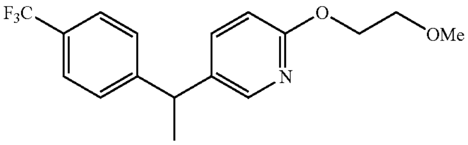 | powder<br>MS(ESI)525[M + H]+ |

TABLE 12 (No. 6)-continued
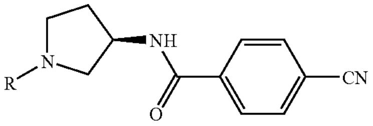
| Ex. Nos. | R | Physicochemical properties etc. |
|---|---|---|
| 750 | 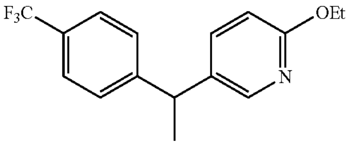 | powder<br>MS(ESI)495[M + H]+ |
| 751 | 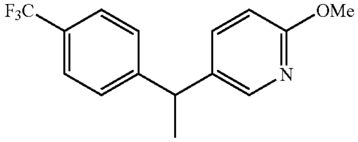 | powder<br>MS(ESI)481[M + H]+ |
Me: methyl group,
Et: ethyl group
TABLE 12 (No. 7)
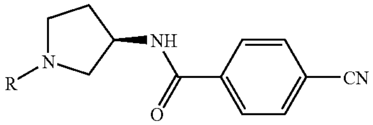
| Ex. Nos. | R | Physicochemical properties etc. |
|---|---|---|
| 752 | 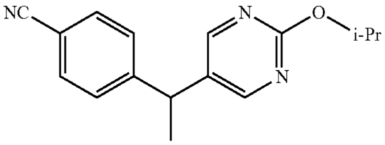 | powder<br>MS(APCI)467[M + H]+ |
| 753 | 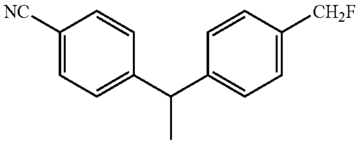 | powder<br>MS(APCI)439[M + H]+ |
| 754 | 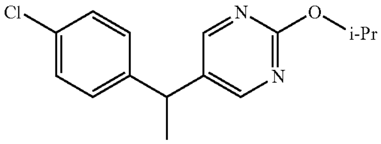 | powder<br>MS(APCI)476/478[M + H]+ |
| 755 | 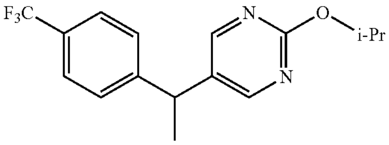 | powder<br>MS(APCI)510[M + H]+ |
| 756 | 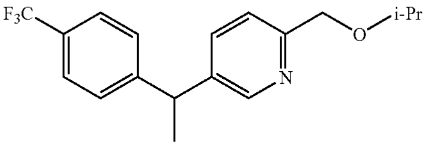 | powder<br>MS(APCI)523[M + H]+ |

TABLE 12 (No. 7)-continued
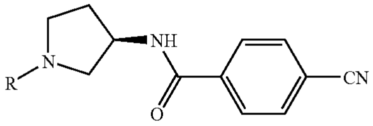
| Ex. Nos. | R | Physicochemical properties etc. |
|---|---|---|
| 757 | 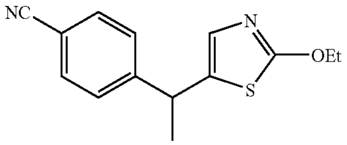 | powder<br>MS(APCI)458[M + H]+ |
| 758 | 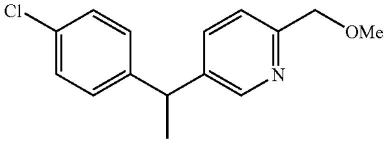 | powder<br>MS(APCI)461/463[M + H]+ |
Me: methyl group,
Et: ethyl group,
i-Pr: isopropyl group
TABLE 12 (No. 8)
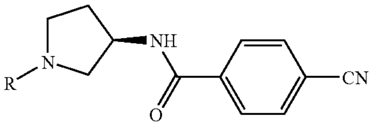
| Ex. Nos. | R | Physicochemical properties etc. |
|---|---|---|
| 759 | 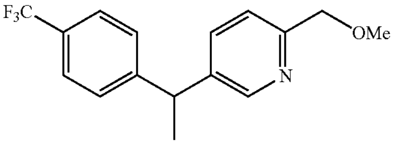 | powder<br>MS(APCI)495[M + H]+ |
| 760 | 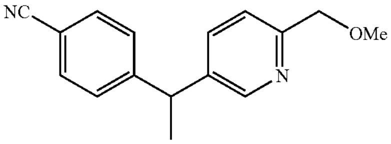 | powder<br>MS(APCI)452[M + H]+ |
| 761 | 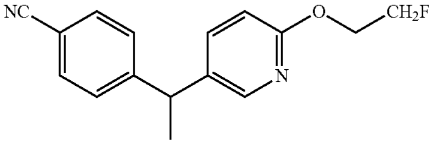 | powder<br>MS(APCI)470[M + H]+ |
Me: methyl group TABLE 12 (No. 9)

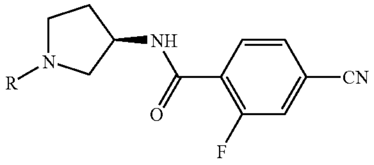

| Ex. Nos. | R | Physicochemical properties etc. |
|---|---|---|
| 762 | 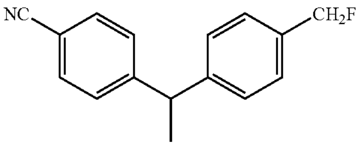 | powder<br>MS(APCI)457[M + H]+ |
| 763 | 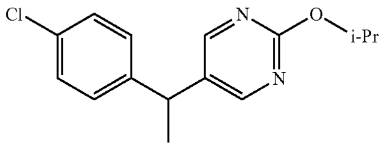 | powder<br>MS(APCI)494/496[M + H]+ |
| 764 | 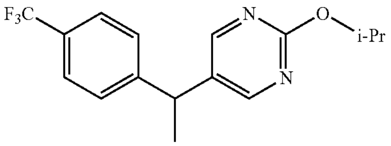 | powder<br>MS(APCI)528[M + H]+ |
| 765 | 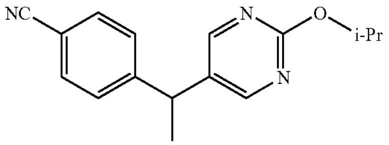 | powder<br>MS(APCI)485[M + H]+ |

i-Pr: isopropyl group

TABLE 12 (No. 10)

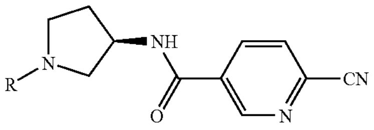

| Ex. Nos. | R | Physicochemical properties etc. |
|---|---|---|
| 766 | 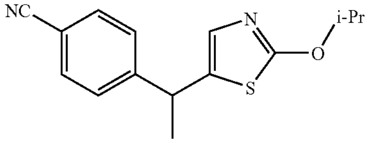 | powder<br>MS(APCI)473[M + H]+ |

i-Pr: isopropyl group

Examples 767 to 769

The corresponding starting materials were treated in the same manner as described in Examples 3 to give a compound as shown in the following Table 13.

TABLE 13

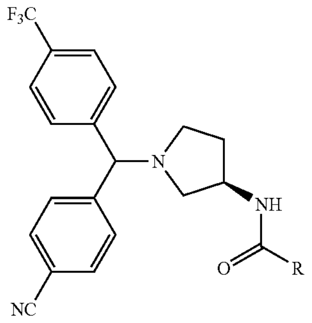

| Ex. Nos. | R | Physicochemical properties etc. |
|---|---|---|
| 767 | 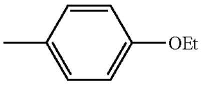 | powder MS(APCI)494[M + H]+ |
| 768 | 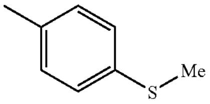 | powder MS(APCI)496[M + H]+ |
| 769 | 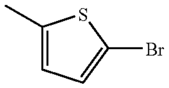 | powder MS(APCI)534/536[M + H]+ |

Me: methyl group,
Et: ethyl group

Examples 770 to 786

The corresponding starting materials were treated in the same manner as described in Example 6 to give the compounds as shown in the following Table 14.

TABLE 14 (No. 1)

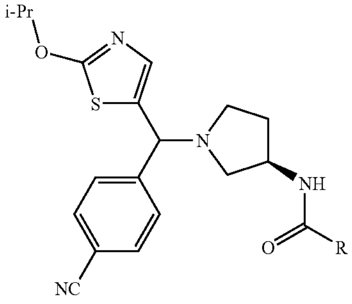

| Ex. Nos. | R | Physicochemical properties etc. |
|---|---|---|
| 770 | 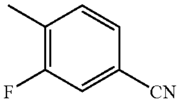 | powder MS(APCI)490[M + H]+ |
| 771 | 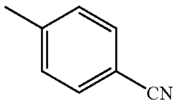 | powder MS(APCI)472[M + H]+ |

i-Pr: isopropyl group

TABLE 14 (No. 2)

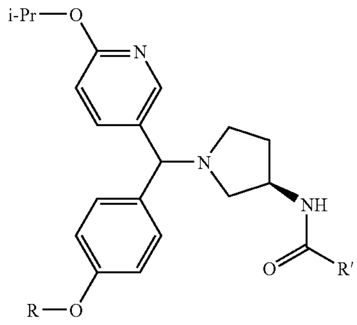

| Ex. Nos. | R | R' | Physicochemical properties etc. |
|---|---|---|---|
| 772 | Me | 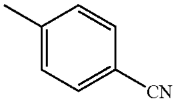 | powder MS(APCI)471[M + H]+ |
| 773 | Me | 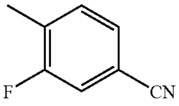 | powder MS(APCI)489[M + H]+ |
| 774 | Me | 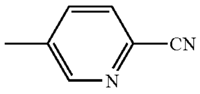 | powder MS(APCI)472[M + H]+ |
| 775 | Et | 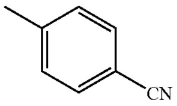 | powder MS(APCI)485[M + H]+ |
| 776 | Et | 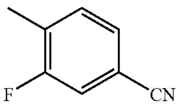 | powder MS(APCI)503[M + H]+ |
| 777 | Et | 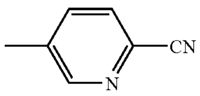 | powder MS(APCI)486[M + H]+ |

Me: methyl group,
Et: ethyl group,
i-Pr: isopropyl group

TABLE 14 (No. 3)
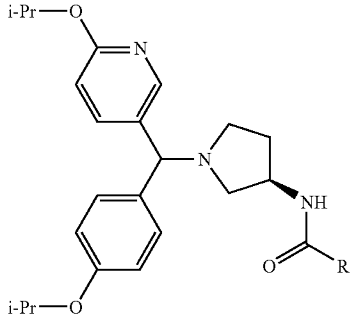
| Ex. Nos. | R | Physicochemical properties etc. |
|---|---|---|
| 778 | 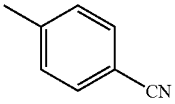 | powder MS(APCI)499[M + H]+ |
| 779 | 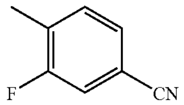 | powder MS(APCI)517[M + H]+ |
TABLE 14 (No. 3)-continued
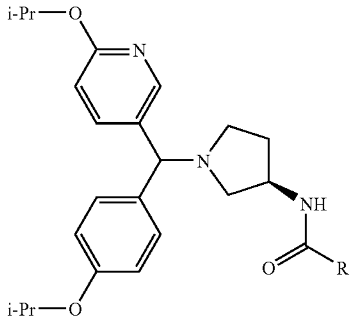
| Ex. Nos. | R | Physicochemical properties etc. |
|---|---|---|
| 780 | 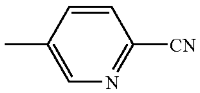 | powder MS(APCI)500[M + H]+ |
i-Pr: isopropyl group
TABLE 14 (No. 4)
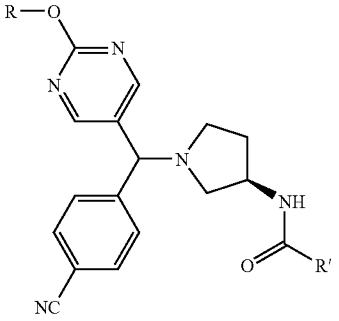
| Ex. Nos. | R | R' | Physicochemical properties etc. |
|---|---|---|---|
| 781 | 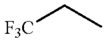 | 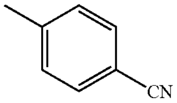 | powder MS(APCI)507[M + H]+ |
| 782 | 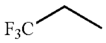 | 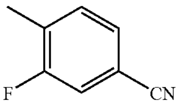 | powder MS(APCI)525[M + H]+ |
| 783 | 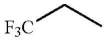 | 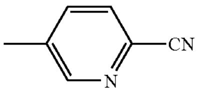 | powder MS(APCI)508[M + H]+ |
| 784 | Et | 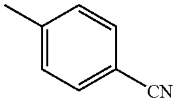 | powder MS(APCI)453[M + H]+ |
| 785 | Et | 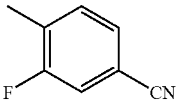 | powder MS(APCI)471[M + H]+ |
Et: ethyl group, TABLE 14 (No. 4)-continued

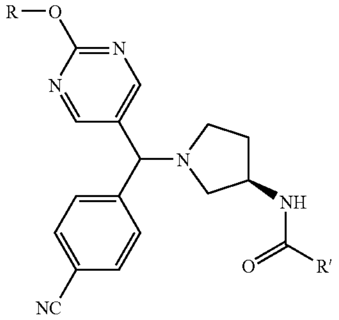

| Ex. Nos. | R | R' | Physicochemical properties etc. |
|---|---|---|---|

i-Pr: isopropyl group

TABLE 14 (No. 5)

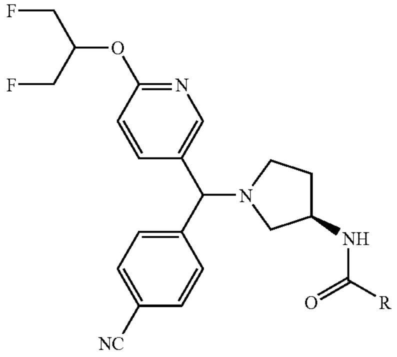

| Ex. Nos. | R | Physicochemical properties etc. |
|---|---|---|
| 786 | 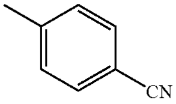 | powder<br>MS(APCI)502[M + H]+ |

Examples 787 to 791

The corresponding starting materials were treated in the same manner as described in Example 1 to give the compounds as shown in the following Table 15.

TABLE 15 (No. 1)

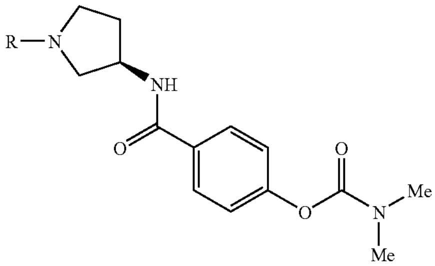

| Ex. Nos. | R | Physicochemical properties etc. |
|---|---|---|
| 787 | 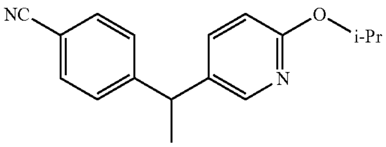 | powder<br>MS(APCI)528[M + H]+ |

TABLE 15 (No. 1)-continued

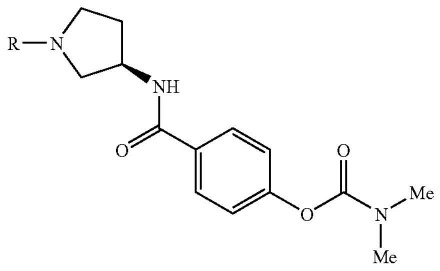

| Ex. Nos. | R | Physicochemical properties etc. |
|---|---|---|
| 788 | 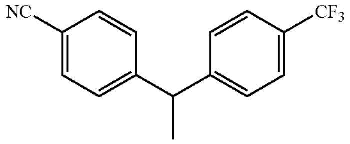 | powder<br>MS(APCI)537[M + H]+ |

Me: methyl group,
i-Pr: isopropyl group

TABLE 15 (No. 2)

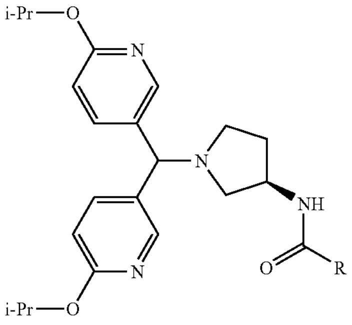

| Ex. Nos. | R | Physicochemical properties etc. |
|---|---|---|
| 789 | 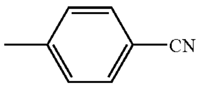 | powder<br>MS(APCI)500[M + H]+ |
| 790 | 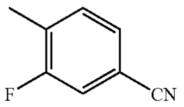 | powder<br>MS(APCI)518[M + H]+ |
| 791 | 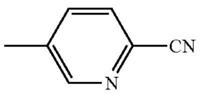 | powder<br>MS(APCI)501[M + H]+ |

i-Pr: isopropyl group

Examples 792 to 829

The corresponding starting materials were treated in the same manner as described in Example 6 to give the compounds as shown in the following Table 16.

TABLE 16 (No. 1)

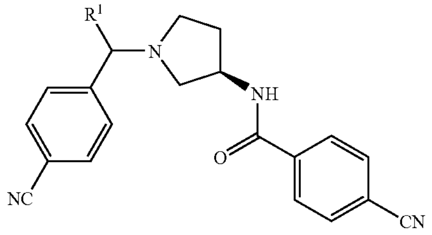

| Ex. Nos. | $R^1$ | Physico-chemical properties etc. |
|---|---|---|
| 792 | 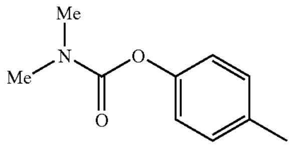 | powder<br>MS(APCI)494[M + H]+ |
| 793 | 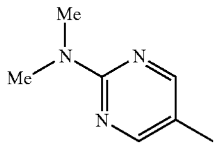 | powder<br>MS(APCI)452[M + H]+ |
| 794 | 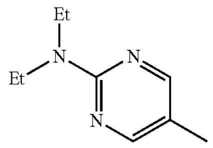 | powder<br>MS(APCI)480[M + H]+ |
| 795 | 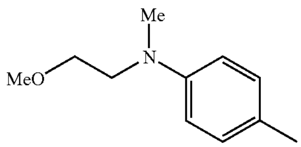 | powder<br>MS(APCI)494[M + H]+ |

TABLE 16 (No. 1)-continued

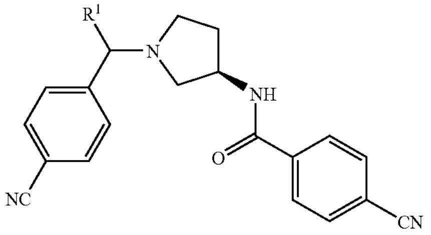

| Ex. Nos. | $R^1$ | Physico-chemical properties etc. |
|---|---|---|
| 796 | 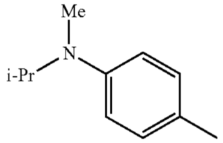 | powder MS(APCI)478[M + H]+ |
| 797 | 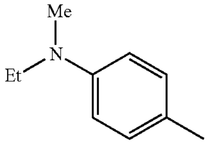 | powder MS(APCI)464[M + H]+ |
| 798 | 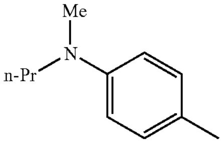 | powder MS(APCI)478[M + H]+ |

Me: methyl group,
Et: ethyl group,
n-Pr: n-propyl group,
i-Pr: isopropyl group

TABLE 16 (No. 2)

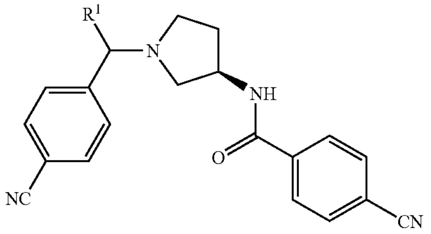

| Ex. Nos. | $R^1$ | Physico-chemical properties etc. |
|---|---|---|
| 799 | 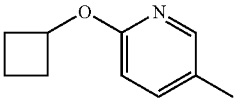 | powder MS(APCI)478[M + H]+ |
| 800 | 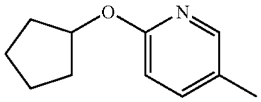 | powder MS(APCI)492[M + H]+ |
| 801 | 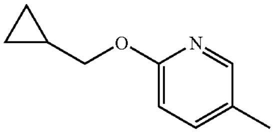 | powder MS(APCI)478[M + H]+ |

TABLE 16 (No. 2)-continued

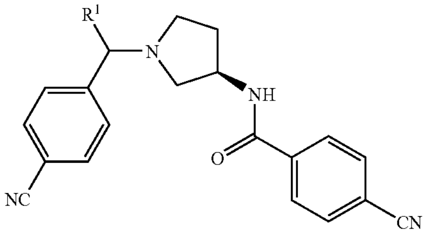

| Ex. Nos. | $R^1$ | Physico-chemical properties etc. |
|---|---|---|
| 802 | 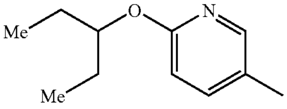 | powder MS(APCI)494[M + H]+ |
| 803 | 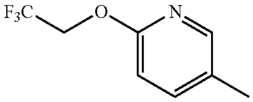 | powder MS(APCI)506[M + H]+ |

Me: methyl group

TABLE 16 (No. 3)

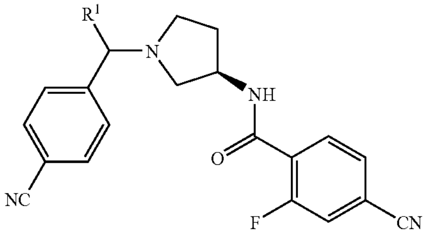

| Ex. Nos. | $R^1$ | Physicochemical properties etc. |
|---|---|---|
| 804 | 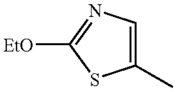 | powder MS(APCI)476[M + H]+ |
| 805 | 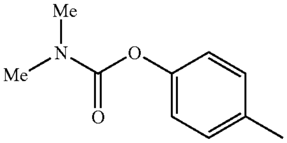 | powder MS(APCI)512[M + H]+ |
| 806 | 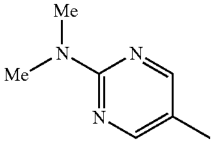 | powder MS(APCI)470[M + H]+ |
| 807 | 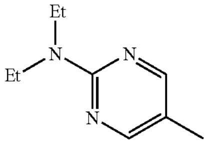 | powder MS(APCI)498[M + H]+ |

TABLE 16 (No. 3)-continued

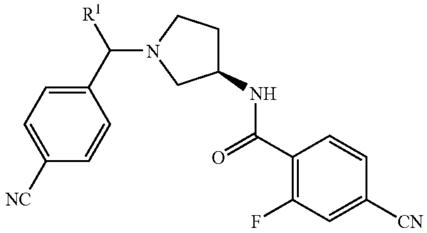

| Ex. Nos. | $R^1$ | Physicochemical properties etc. |
|---|---|---|
| 808 | 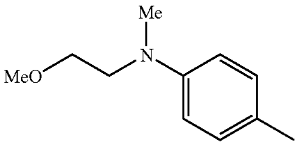 | powder MS(APCI)512[M + H]+ |
| 809 | 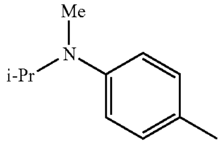 | powder MS(APCI)496[M + H]+ |
| 810 | 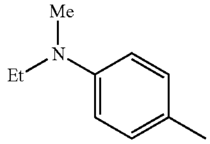 | powder MS(APCI)482[M + H]+ |

Me: methyl group,
Et: ethyl group,
i-Pr: isopropyl group

TABLE 16 (No. 16)

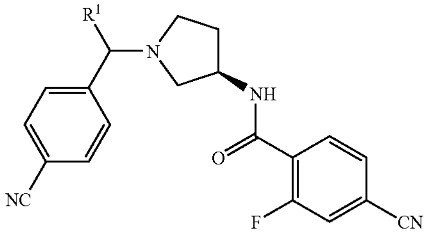

| Ex. Nos. | $R^1$ | Physicochemical properties etc. |
|---|---|---|
| 811 | 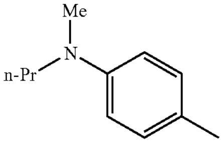 | powder MS(APCI)496[M + H]+ |
| 812 | 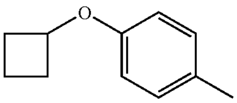 | powder MS(APCI)496[M + H]+ |
| 813 | 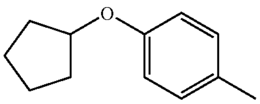 | powder MS(APCI)510[M + H]+ |

TABLE 16 (No. 16)-continued

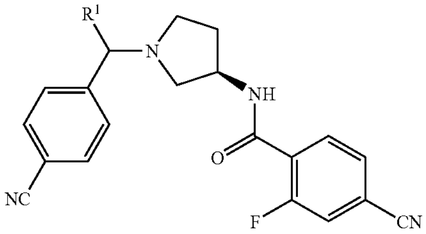

| Ex. Nos. | $R^1$ | Physicochemical properties etc. |
|---|---|---|
| 814 | 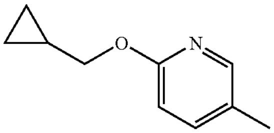 | powder MS(APCI)496[M + H]+ |
| 815 | 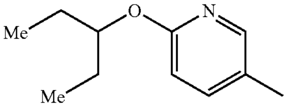 | powder MS(APCI)512[M + H]+ |
| 816 | 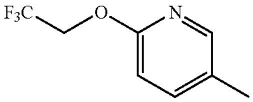 | powder MS(APCI)524[M + H]+ |

Me: methyl group,
n-Pr: n-propyl group

TABLE 16 (No. 5)

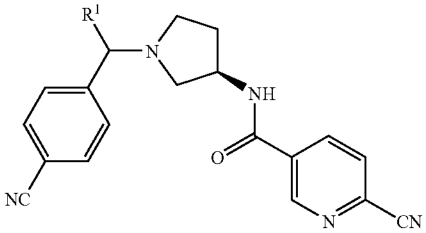

| Ex. Nos. | $R^1$ | Physicochemical properties etc. |
|---|---|---|
| 817 | 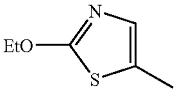 | powder MS(APCI)459[M + H]+ |
| 818 | 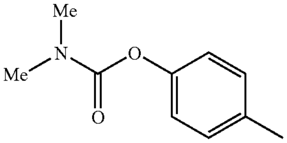 | powder MS(APCI)495[M + H]+ |
| 819 | 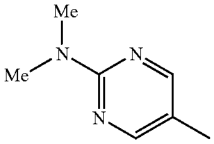 | powder MS(APCI)453[M + H]+ |

TABLE 16 (No. 5)-continued

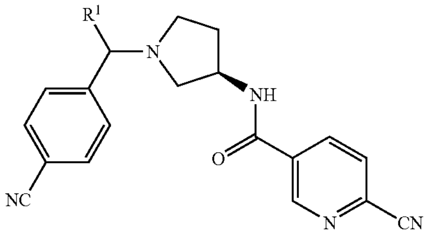

| Ex. Nos. | $R^1$ | Physicochemical properties etc. |
|---|---|---|
| 820 | 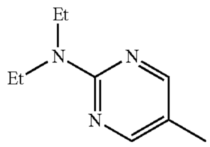 | powder MS(APCI)481[M + H]+ |
| 821 | 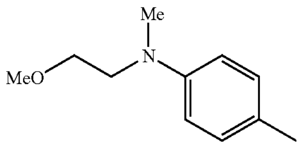 | powder MS(APCI)495[M + H]+ |
| 822 | 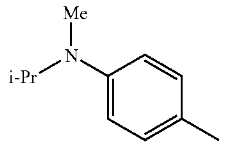 | powder MS(APCI)479[M + H]+ |
| 823 | 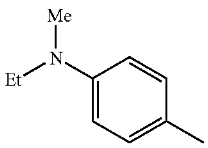 | powder MS(APCI)465[M + H]+ |

Me: methyl group,
Et: ethyl group,
i-Pr: isopropyl group

TABLE 16 (No. 6)

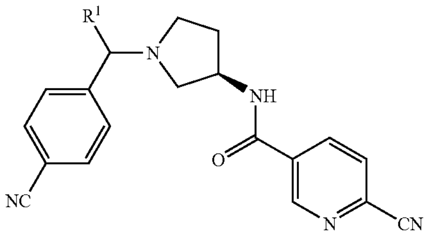

| Ex. Nos. | $R^1$ | Physicochemical properties etc. |
|---|---|---|
| 824 | 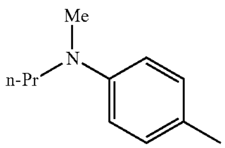 | powder MS(APCI)479[M + H]+ |

TABLE 16 (No. 6)-continued

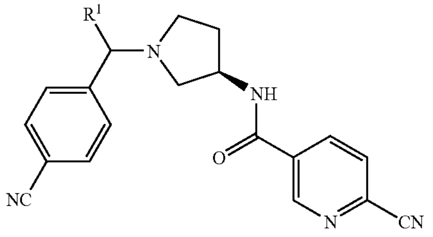

| Ex. Nos. | $R^1$ | Physicochemical properties etc. |
|---|---|---|
| 825 | 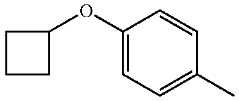 | powder MS(APCI)479[M + H]+ |
| 826 | 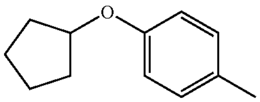 | powder MS(APCI)493[M + H]+ |
| 827 | 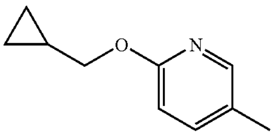 | powder MS(APCI)479[M + H]+ |
| 828 | 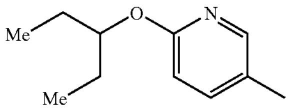 | powder MS(APCI)495[M + H]+ |
| 829 | 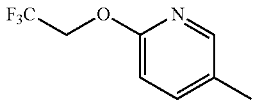 | powder MS(APCI)507[M + H]+ |

Me: methyl group,
n-Pr: n-propyl group

Reference Example 1

(1) To a suspension of 4-hydroxybenzaldehyde (2.0 g), dimethylaminoethyl chloride hydrochloride (2.83 g), dimethylformamide (8 mL) in diisopropylether (1 mL) is added potassium carbonate (5.53 g) and the mixture was stirred at 60° C. overnight. To the reaction mixture was added water and the mixture was extracted with ethyl acetate (×2). The organic layer is concentrated in vacuo and the resultant crude product was purified by a column chromatography on silica gel (solvent; chloroform/methanol=100:0→90:10) to give 4-[2-(dimethylamino)ethoxy]benzaldehyde (674 mg, yield: 21%) as an oil.

MS(APCI) m/z; 194 $[M+H]^+$ (2) To a solution of 1.0M 4-chlorophenylmagnesium bromide in diethylether (2 mL) was added a solution of the compound obtained in the above step (1) (386.5 mg) in tetrahydrofuran (4 mL) under nitrogen gas atmosphere and cooling in dry ice/acetone bath and the mixture is stirred at room temperature overnight. To the reaction mixture was added water and the mixture was extracted with ethyl acetate (×2). The organic layer was concentrated in vacuo and the resultant crude product was purified by a flash column chromatography on NH-silica gel (Chromatorex NH-silica gel, solvent; hexane/ethyl acetate=1:1→0:1) to give (4-chlorophenyl)[4-[2-(dimethylamino)-ethoxy]phenyl]methanol (208 mg, yield: 34%) as an oil.

MS(APCI) m/z; 306/308 $[M+H]^+$

Reference Example 2

(1) To a solution of bis(4-hydroxyphenyl)ketone (1.0 g) in dimethylformamide (10 mL) was added successively potassium carbonate (2.54 g) and isopropyl iodide (1.40 mL) and the mixture was stirred at room temperature for 18 hours. To the reaction mixture was added water and the mixture is extracted with ethyl acetate (×2). The organic layer was concentrated in vacuo and the resultant crude product was purified by a column chromatography on silica gel (solvent; hexane/ethyl acetate=95:5→60:40) to give bis(4-isopropyloxyphenyl)ketone (1.33 g, yield: 96%) as a powder.

MS(APCI) m/z; 299 $[M+H]^+$ (2) To a solution of the compound obtained in the above step (1) (1.33 g) in ethanol (18 μL) and tetrahydrofuran (2 mL) was added sodium borohydride (235 mg) and the mixture was stirred at room temperature for 18 hours. After concentrating the reaction mixture, thereto was added ethyl acetate and water, and the mixture was extracted with ethyl acetate (×2). The organic layer was concentrated in vacuo and the resultant crude product was purified by a column chromatography on silica gel (solvent; hexane/ethyl acetate=95:5→40:60) to give bis(4-isopropyloxyphenyl)methanol (1.30 g, yield: 97%) as an oil.

MS(APCI) m/z; 283 $[M+H]^+$

Reference Example 3

(1) To a solution of 4-bromobenzylalcohol (9.98 g) and triethylamine (11.2 μL) in ethyl acetate (100 mL) was added dropwise methanesulfonyl chloride (7.35 g) under nitrogen gas atmosphere and ice-cooling and the mixture was stirred under ice-cooling for 1 hour. To the reaction mixture was added water and the mixture was extracted with ethyl acetate (×2). After washing successively with water and a saturated brine, the organic layer was dried over anhydrous magnesium sulfate. After evaporation to remove solvent, the resultant crude product was triturated in ethyl acetate/hexane to 4-bromobenzyl methanesulfonate (13.54 g, yield: 91%) as crystals.

MS(EI) m/z; 264/266 $[M+H]^+$ (2) A suspension of the compound obtained in the above step (1) (1.2 g) in methanol was stirred at 85° C. for 4 hours. The reaction mixture was concentrated in vacuo. To the resultant residue was water and the mixture was extracted with ethyl acetate (×2). The organic layer was concentrated in vacuo and the resultant crude product was purified by a column chromatography on silica gel (solvent; hexane/ethyl acetate=80:20→60:40) to give 4-bromobenzylmethylether (0.76 g, yield: 83%) as an oil.

MS(APCI) m/z; 200/202 $[M+H]^+$ (3) To a solution of the compound obtained in the above step (2) (515 mg) in tetrahydrofuran (4 mL) was added dropwise 1.59M butyl lithium-hexane solution (1.61 mL) under nitrogen gas atmosphere and cooling in dry ice/acetone bath and the mixture was stirred for 10 minutes. Thereto was added a solution of 4-chlorobenzaldehyde (360 mg) in tetrahydrofuran (1 mL) and the mixture was stirred at room temperature overnight. To the reaction mixture was added water and the mixture was extracted with ethyl acetate (×2). The organic layer was concentrated in vacuo and the resultant crude product was purified by a column chromatography on silica gel (solvent; hexane/ethyl acetate=80:20→60:40) to give (4-chlorophenyl)[4-(methoxymethyl)phenyl]methanol (459 mg, yield: 68%) as an oil.

MS(APCI) m/z; 247/202 $[M+H-H_2O]^+$

Reference Example 4

(1) To a suspension of bis-(4-carboxyphenyl)ketone (5.0 g) in methylene chloride (100 mL) was added oxalyl chloride (3.4 μL) and dimethylformamide (200 μL) under nitrogen gas atmosphere and cooling in dry ice/acetone bath and the mixture was stirred at room temperature for 4 hours. To the reaction mixture was added tetrahydrofuran (50 mL) and the mixture was stirred at room temperature for 18 hours. The reaction mixture was evaporated to remove solvent and to the residue was added successively tetrahydrofuran (100 mL), triethylamine (7.75 mL) and tert-butylamine (4.86 mL) and the mixture was stirred at room temperature for 1.5 hours. To the reaction mixture was added water and the resultant crystals were collected by filtration to give bis[4-(tert-butylcarbamoyl)phenyl]ketone (6.44 g, yield: 92%) as crystals.

MS(EI) m/z; 381 $[M+H]^+$ (2) To a suspension of the compound obtained in the above step (1) (2.9 g), 2-propanol (15.2 mL) and water (0.9 mL) was added sodium borohydride (232 mg) and the mixture was stirred at 85° C. for 30 minutes. After cooling to room temperature, thereto was added water and the resultant crystals were collected by filtration to give bis[4-(tert-butylcarbamoyl)phenyl]methanol (2.85 g, yield: 97%) as crystals.

MS(APCI) m/z; 383 $[M+H]^+$ (3) A solution of the compound obtained in the above step (2) (4.96 g) in thionyl chloride (40 mL) was refluxed under heating for 5 hours. The reaction mixture was concentrated in vacuo and thereto was added water, and the mixture was extracted with ethyl acetate. The organic layer was washed successively with water and a saturated brine, dried over anhydrous magnesium sulfate and evaporated in vacuo to give chloro[bis-(4-cyanophenyl)]methane (3.59 g, yield: 100%) as an oil.

Reference Example 5

(1) To a solution of 4-cyanobenzaldehyde (3.93 g) in tetrahydrofaran was added dropwise 1.0M 4-chlorophenylmagnesium bromide-diethylether (30 mL) under nitrogen gas atmosphere and cooling in dry ice/methanol bath and the mixture was stirred at the same temperature for 10 minutes. To the reaction mixture was added 10% HCl solution and the aqueous layer was extracted with ethyl acetate (×2). The organic layer was washed with a saturated brine, dried over magnesium sulfate and concentrated in vacuo. To the resultant crude product was added diisopropyl ether and the resultant solid materials were collected by filtration to give (4-chlorophenyl)(4-cyanophenyl)methanol (6.98 g, yield: 96%) as a pale yellow solid.

MS(APCI) m/z; 268, 280 $[M+Cl]^+$ (2) A mixture of the compound obtained in the above step (1) (12.4 g) and thionyl chloride (30 mL) was refluxed under heating for 3 hours and the reaction mixture was concentrated in vacuo. The residue was diluted with ethyl acetate and washed with an aqueous saturated sodium hydrogencarbonate solution, and dried over magnesium sulfate. After evaporation to remove solvent, the residue was purified by a column chromatography on silica gel (solvent; hexane/ethyl acetate=6:1) to give chloro(4-chlorophenyl)(4-cyanophenyl)methane (12.4 g, yield: 93%) as an oil.

Reference Example 6

(1) To a solution of (3R)-3-(tert-butyloxycarbonylamino) pyrrolidine (10.0 g) and triethylamine (5.43 g) in methylene chloride (100 mL) was added dropwise a solution of benzyloxycarbonyl chloride (7.7 mL) in methylene chloride (20 mL) over a period of 15 minutes under nitrogen gas atmosphere and ice-cooling and the mixture was stirred at room temperature for 1 hour. To the reaction mixture was added water (70 mL) and the mixture was extracted with chloroform. The extract was washed successively with water (70 mL), 5% citric acid solution (70 mL) and a saturated brine (70 mL) and the organic layer was dried over anhydrous magnesium sulfate. After concentration in vacuo, the resultant product was triturated in diisopropylether to give (3R)-1-benzyloxycarbonyl-3-(tert-butoxycarbonylamino)pyrrolidine (11.8 g, yield: 70%) as crystals.

MS(APCI) m/z; 321 $[M+H]^+$ (2) To a solution of the compound obtained in the above step (1) (12.1 g) in 1,4-dioxane (100 mL) was added 4N HCl-dioxane (50 mL) and the mixture was stirred at room temperature for 19 hours. The reaction mixture was concentrated in vacuo and the resultant crude product was triturated in diisopropylether to give (3R)-3-amino-1-benzyloxycarbonylpyrrolidine hydrochloride (9.2 g, yield: 94%) as crystals.

MS(APCI) m/z; 283 $[M+H]^+$ (3) To a suspension of the compound obtained in the above step (2) (8.23 g), 4-(trifluoromethyloxy)benzoic acid (6.61 g), triethylamine (6.7 mL) and 1-hydroxybenzotriazole (6.83 g) in methylene chloride (82.3 mL) was added 1-ethyl-3-[3-(dimethylamino)propyl]carbodiimide hydrochloride (7.40 g) and the mixture was stirred at room temperature overnight. To the reaction mixture was added water (58 mL) and the mixture was stirred for 10 minutes. The chloroform layer was separated and washed successively with an aqueous saturated sodium hydrogencarbonate solution (58 mL) and a saturated brine (58 mL). The organic layer was dried over anhydrous magnesium sulfate and concentrated in vacuo. The resultant crude product was purified by a column chromatography on silica gel (solvent; hexane/ethyl acetate=2:1→1:1) to give (3R)-1-benzyloxycarbonyl-3-[[4-(trifluoromethoxy)benzoyl]amino]pyrrolidine (11.29 g, yield: 87%) as an oil.

MS(APCI) m/z; 409 $[M+H]^+$ (4) To a solution of the compound obtained in the above step (3) (11.29 g) in methanol (114 mL) was added 10% palladium-carbon (0.32 g) and the mixture was stirred at room temperature under atmospheric pressure of hydrogen gas for 1.5 hours. After removal of the insoluble materials by filtration, the filtrate was evaporated in vacuo to give (3R)-3-[[4-(trifluoromethoxy)benzoyl]amino]pyrrolidine (7.76 g, yield: 87%) as an oil.

MS(APCI) m/z; 275 $[M+H]^+$

Reference Example 7

(1) To a solution of (3,4-trans)-4-amino-3-ethoxycarbonyl-1-(tert-butoxycarbonyl)pyrrolidine (1.04 g) in methylene chloride (20 mL) was added triethylamine (0.67 mL) and thereto was added dropwise 4-(trifluoromethoxy)benzoyl chloride under ice-cooling. The mixture was stirred at room temperature for 24 hours. To the reaction mixture was added chloroform and the mixture was washed with an aqueous saturated citric acid solution and an aqueous saturated sodium hydrogencarbonate solution and dried over magnesium sulfate. The organic layer was concentrated in vacuo and the crude product was purified by a column chromatography on silica gel (solvent; chloroform/ethyl acetate=10:1) to give (3,4-trans)-3-ethoxycarbonyl-1-(tert-butoxycarbonyl)-4-[[4-(trifluoromethoxy)benzoyl]amino]pyrrolidine (1.34 g, yield: 75%) as an oil.

MS(APCI) m/z; 447 $[M+H]^+$ (2) To a solution of the compound obtained in the above step (1) (1.34 g) in chloroform (15 mL) was added 4N HCl-ethyl acetate (5 mL) and the mixture was stirred at room temperature for 3 hours. The reaction mixture was concentrated in vacuo and the residue was neutralized with 1N sodium hydroxide solution. The organic layer was dried over magnesium sulfate and concentrated in vacuo. The resultant crude product was purified by a column chromatography on silica gel (solvent; chloroform/methanol=49:1) to give (3,4-trans)-3-ethoxycarbonyl-4-[[4-(trifluoromethoxy)benzoyl]amino]-pyrrolidine (943 mg, yield: 91%) as an oil.

MS(APCI) m/z; 347 $[M+H]^+$

Reference Example 8

(1) To a solution of 1-benzyloxycarbonyl-3-pyrroline (5.0 g) in methylene chloride (125 mL) was added 3-chloroperbenzoic acid (12.17 g) and the mixture was stirred at room temperature for 3 days. To the reaction mixture was added a saturated sodium thiosulfate solution (100 mL) and the mixture was stirred for 30 minutes. The reaction mixture was extracted with chloroform (×2) and the extract was washed successively with 2N sodium hydroxide solution (100 mL×2) and a saturated brine. The organic layer was dried over anhydrous magnesium sulfate and evaporated in vacuo to give benzyl 6-oxa-3-azabicyclo[3,1,0]hexan-3-carboxylate (5.58 g, yield: 100%) as an oil.

MS(APCI) m/z; 220 $[M+H]^+$ (2) A mixture of the compound obtained in the above step (1) (5.58 g) and aqueous 28% ammonia was stirred at 40° C. for 2 days. Thereto was added 2N sodium hydroxide solution (50 mL) and the mixture was extracted with chloroform (×3). The organic layer was dried over anhydrous magnesium sulfate and evaporated in vacuo to give (3,4-trans)-4-amino-1-benzyloxycarbonyl-3-hydroxy-pyrrolidine (5.34 g, yield: 92%) as an oil.

MS(APCI) m/z; 237 $[M+H]^+$ (3) To a solution of the compound obtained in the above step (2) (5.34 g) in chloroform (50 mL) was added dropwise a solution of di-tert-butyl dicarbonate (7.40 g) in chloroform (10 mL) under ice-cooling and the mixture was stirred at room temperature for 19 hours. The reaction mixture was washed with water and the organic layer was dried over anhydrous magnesium sulfate and evaporated in vacuo. The resultant crude product was purified by a column chromatography on silica gel (solvent; hexane/ethyl acetate=2:1→1:1) to give (3,4-trans)-1-benzyloxy-carbonyl-3-hydroxy-4-(tert-butoxycarbonylamino)pyrrolidine (5.55 g, yield: 73%) as crystals.

MS(APCI) m/z; 337 $[M+H]^+$ (4) To a solution of the compound obtained in the above step (3) (3.54 g) in methanol (31 mL) and tetrahydrofuran (7 mL) was added palladium hydroxide (20 wt % Pd on carbon, 500 mg) and the mixture was stirred at room temperature under hydrogen gas atmosphere (40 to 45 Parr) overnight. After removal of the insoluble materials by filtration through Cerite, the filtrate was concentrated in vacuo. The residue was triturated in ethyl acetate/diisopropylether to give (3,4-trans)-3-hydroxy-4-(tert-butoxy-carbonylamino)pyrrolidine (2.0 g, yield: 94%) as a powder MS(APCI) m/z; 203 $[M+H]^+$ .

Reference Example 9

(1) A mixture of the compound obtained in Reference Example 8-(1) (26.5 g), (1R,2R)-(−)-N,N'-bis(3,5-di-tert-butylsalicylidene)-1,2-cyclohexanediaminochromium (1.57 g) and trimethylsilylazide (17.7 mL) was stirred at room temperature under nitrogen gas atmosphere for 2 days. After addition of chloroform, the reaction mixture was washed successively with water and a saturated brine. The organic later was dried over anhydrous magnesium sulfate and evaporated in vacuo. The resultant crude product was purified by a column chromatography on silica gel (solvent; hexane/ethyl acetate=10:1→2:1 and then chloroform/methanol=20:1→9:1) to give (3S,4S)-4-azido-1-benzyloxycarbonyl-3-trimethylsilyloxypyrrolidine (Compound a: 20.6 g, yield: 55%) and (3S,4S)-4-azido-1-benzyloxycarbonyl-3-hydroxypyrrolidine (Compound b: 8.16 g, yield: 28%) as an oil, respectively.

Compound a: MS(APCI) m/z; 335 $[M+H]^+$

Compound b: MS(APCI) m/z; 263 $[M+H]^+$ (2) To a solution of the Compound a (20.6 g) or b (8.16 g) obtained in the above step (1) in tetrahydrofuran (740 mL) was added triphenylphosphine (26.67 g) and the mixture was stirred at room temperature overnight. The reaction mixture was concentrated in vacuo and to the residue was added methanol (380 mL) and 0.5N sodium hydroxide solution (380 mL). The mixture was stirred at room temperature overnight. The reaction mixture was concentrated in vacuo and the resultant residue was acidified (pH 3) with 6N HCl and washed with chloroform. The aqueous layer was basified (pH 9) with 5N sodium hydroxide, and the mixture was extracted with chloroform (×3). The organic layer was dried over anhydrous magnesium sulfate and evaporated in vacuo to give (3S,4S)-4-amino-1-benzyloxycarbonyl-3-hydroxy-pyrrolidine (19.6 g, yield: 90%) as an oil.

MS(APCI) m/z; 237 $[M+H]^+$ (3) The compound obtained in the above step (2) (14.61 g) was treated in the same manner as described in Reference Example 8-(3) to give (3S,4S)-1-benzyl-oxycarbonyl-3-hydroxy-4-(tert-butoxycarbonylamino)pyrrolidine (18.59 g, yield: 94%) as crystals.

MS(APCI) m/z; 337 $[M+H]^+$ (4) To a solution of the compound obtained in the above step (3) (18.56 g) in methanol (200 mL) was added 10% palladium-carbon (1.16 g) and the mixture was stirred at room temperature under atmospheric pressure of hydrogen for 3 hours. After removal of the insoluble materials by filtration through Cerite, the filtrate was concentrated in vacuo and then triturated in methanol/diisopropylether to give (3S,4S)-3-hydroxy-4-(tert-butoxycarbonylamino)pyrrolidine (10.8 g, yield: 97%) as crystals.

MS(APCI) m/z; 203 $[M+H]^+$

Reference Example 10

(1) To a solution of (2S,4R)-2-carboxy-4-[(9-fluorenyl)methoxycarbonyl-amino]-1-tert-butoxycarbonylpyrrolidine (122 mg) in dichloromethane was added dimethylaminopyridine (6 mg). Thereto was added dropwise a solution of 1-ethyl-3-(3'-dimethylaminopropyl)carbodiimide (120 mg) in dichloromethane and methanol (0.5 mL) under ice-cooling and the mixture was stirred at the same temperature for 2 hours. After addition of water, the organic layer was extracted by diatomaceous earth column (Chem Elut; VARIAN Inc.). The extract was concentrated in vacuo to give crude (2S,4R)-4-[(9-fluorenyl)methoxycarbonylamino]-2-methoxycarbonyl-1-tert-butoxy-carbonylpyrrolidine. To the crude product was added 20% piperidine/dichloromethane solution (5 mL) and the mixture was stirred at room temperature for 1 hour. After evaporation in vacuo, the residue was purified by a column chromatography on silica gel (solvent; hexane/ethyl acetate=1:1) to give (2S,4R)-4-amino-2-methoxy-carbonyl-1-tert-butoxycarbonyl-pyrrolidine (38 mg, yield: 38%) as an oil.

MS(APCI) m/z; 245 $[M+H]^+$ (2) A solution of the compound obtained in the above step (1) (36 mg), 4-chlorobenzoic acid (30 mg), N-hydroxybenzotriazole (30 mg) and 1-ethyl-3-(3'-dimethylaminopropyl) carbodiimide (43 mg) in dimethylformamide (0.5 mL) was stirred at room temperature for 15 hours. To the reaction mixture was added a saturated brine and the aqueous layer was extracted with ethyl acetate (×2). The organic layer was concentrated in vacuo and the residue was purified by a column chromatography on silica gel (solvent; hexane/ethyl acetate=1:1) to give (2S,4R)-4-[(4-chlorobenzoyl)-amino]-2-methoxycarbonyl-1-tert-butoxycarbonylpyrrolidine (37 mg, yield: 64%) as an oil.

MS(ESI) m/z; 383, 385 $[M+H]^+$ (3) A mixture of the compound obtained in the above step (37 mg) and 4N HCl-dioxane (5 mL) was stirred at room temperature for 15 hours and the reaction mixture was concentrated in vacuo to give (2S,4R)-4-[(4-chlorobenzoyl) amino]-2-methoxycarbonylpyrrolidine.

Reference Example 11

(1) Bis-(4-chlorophenyl)methanol (100 g) was treated in the same manner as described in Reference Example 5-(2) to give chloro[bis(4-chlorophenyl)]methane (100.5 g, yield: 94%).

MS(EI) m/z; 270 $[M+]^+$ (2) The compound obtained in the above step (1) (14.5 g) and (3R)-tert-butyloxycarbonylaminopyrrolidine (10 g) were treated in the same manner as described in Example 5 to give (3R)-1-[bis-(4-chlorophenyl)methyl]-3-tert-butoxy carbonylaminopyrrolidine (18.8 g, yield: 83%) as an oil.

MS(APCI) m/z; 421 $[M+H]^+$ (3) A mixture of the compound obtained in the above step (2) (18 g), trifluoroacetic acid (30 mL) and methylene chloride was stirred at room temperature for 3 hours. The reaction mixture was concentrated in vacuo and to the residue was added an aqueous HCl solution to dissolve precipitates. The solution was washed with diethylether. The aqueous layer was basified with potassium carbonate and extracted with ethyl acetate. The organic layer was washed with water and a saturated brine, dried over sodium sulfate and evaporated in vacuo to give (3R)-3-amino-1-[bis-(4-chlorophenyl)-methyl] pyrrolidine as an oil.

MS(APCI) m/z; 321, 323 $[M+H]^+$

Reference Example 12

The corresponding materials (4-oxo-3-ethoxycarbonyl-1-tert-butoxycarbonyl-pyrrolidine) were treated in the same manner as described in WO03/025577 (page 27) to give (3S,4S)-4-amino-3-ethoxycarbonyl-1-tert-butoxycarbonylpyrrolidine.

Reference Example 13

(1) The compound obtained in Reference Example 12 (1.04 g) and 4-cyano-benzoyl chloride (662 mg) were treated in the same manner as described in Reference Example 7-(1)

to give (3S,4R)-1-(tert-butoxycarbonyl)-3-ethoxycarbonyl-4-[(4-cyano-benzoyl)amino]pyrrolidine (624 mg, yield: 40%) as an oil.

MS(APCI) m/z; 388 [M+H]$^+$ (2) The compound obtained in the above step (1) (624 mg) was treated in the same manner as described in Reference Example 7-(2) to give (3S,4R)-3-ethoxy-carbonyl-4-[(4-cyanobenzoyl)amino]pyrrolidine (94 mg, yield: 20%).

MS(APCI) m/z; 288 [M+H]$^+$

Reference Example 14

(1) The compound obtained in Reference Example 12 (2.07 g) and 4-(trifluoromethoxy)benzoyl chloride (1.51 mL) were treated in the same manner as described in Reference Example 7 to give (3S,4R)-1-(tert-butoxycarbonyl)-3-ethoxy-carbonyl-4-[[4-(trifluoromethoxy)benzoyl]amino] pyrrolidine (3.3 g, yield: 92%).

MS(APCI) m/z; 447 [M+H]$^+$ (2) The compound obtained in the above step (1) (3.3 g) was treated in the same manner as described in Example 514-(2) and (3) to give (3S,4R)-1-(tert-butoxy-carbonyl)-3-ethoxymethyl-4-[[4-(trifluoromethoxy)benzoyl]amino]pyrrolidine (1.14 g, yield: 35%).

MS(APCI) m/z; 433 [M+H]$^+$ (3) The compound obtained in the above step (2) (1.14 g) was treated in the same manner as described in Reference Example 7-(2) to give (3S,4R)-3-ethoxy-methyl-4-[[4-(trifluoromethoxy)benzoyl]amino]pyrrolidine (832.5 mg, yield: 95%).

Reference Example 15

(1) The compound obtained in Reference Example 5 (48.8 g) and (3R)-3-(tert-butoxycarbonylamino)pyrrolidine (28.87 g) were treated in the same manner as described in Example 6 to give (3R)-1-[(4-cyanophenyl)(4-chlorophenyl)-methyl]-3-(tert-butoxycarbonylamino)pyrrolidine (a mixture of diastereomers, 58.1 g, yield: 90.1%).

(2) The mixture obtained in the above step (1) was resolved by a chiral column (CHIRALPACK AD-H; DAICEL CHEMICAL) to give optically active (3R)-1-[(S)-(4-cyanophenyl)(4-chlorophenyl)methyl]-3-(tert-butoxycarbonylamino)-pyrrolidine (22.2 g, yield: 38.2%) and (3R)-1-[(R)-(4-cyanophenyl)(4-chlorophenyl)-methyl]-3-(tert-butoxycarbonylamino)pyrrolidine (22.4 g, yield: 38.6%).

Reference Example 16

(1) To a solution of sodium hydride (0.5 g) in dimethylformamide (15 mL) was added a solution of the compound obtained in Reference Example 9-(1) (compound b, 2.21 g) in dimethylformamide (10 mL) under ice-cooling and the mixture was stirred at room temperature for 1 hour. To the reaction mixture was added 2-methoxyethyl bromide (1.59 mL) and the mixture was stirred at room temperature overnight. After ice-cooling, to the reaction mixture was added sodium hydride (0.5 g) and the mixture was stirred at room temperature for 1 hour. To the reaction mixture was further added 2-methoxyethyl bromide (1.59 mL) and the mixture was stirred at room temperature for 2 hours. The reaction mixture was diluted with diethylether and thereto was added water. The mixture was extracted with ethyl acetate (×2) and the organic layer was concentrated in vacuo. The residue was purified by a column chromatography on silica gel (Solvent; hexane/ethyl acetate=85:15→65:35) to give (3S,4S)-4-azido-1-benzyloxy-carbonyl-3-[2-(methoxy)ethoxy]pyrrolidine (1.78 g, yield: 66%) as an oil. MS(APCI) m/z; 321 [M+H]$^+$ (2) The compound obtained in the above step (1) (2.03 g) was treated in the same manner as described in Reference Example 9-(2) to give (3S,4S)-4-amino-1-benzyloxycarbonyl-3-[2-(methoxy)ethoxy]pyrrolidine (1.82 g, yield: 98%) as an oil. MS(APCI) m/z; 295 [M+H]$^+$ (3) The compound obtained in the above step (2) (1.82 g) was treated in the same manner as described in Reference Example 8-(3) to give (3S,4S)-1-benzyloxy-carbonyl-3-[2-(methoxy)ethoxy]-4-(tert-butoxycarbonylamino)pyrrolidine (2.25 g, yield: 92%) as an oil. MS(APCI) m/z; 395 [M+H]$^+$ (4) To a solution of the compound obtained in the above step (3) (2.25 g) in methanol (40 mL) was added 10% palladium-carbon (200 mg) and the mixture was stirred at room temperature under atmospheric pressure of hydrogen gas for 4 hours. The precipitates were removed by filtration through Cerite and the filtrate was concentrated in vacuo to give (3S,4S)-3-[2-(methoxy)ethoxy]-4-(tert-butoxycarbonyl-amino)pyrrolidine (1.46 g, yield: 98%) as an oil.

MS(APCI) m/z; 261 [M+H]$^+$

Reference Example 17

(1) To 4-bromobenzaldehyde (555 mg) was added [bis(2-methoxyethyl)amino]sulfur trifluoride (555 μL) under ice-cooling and the mixture was stirred at room temperature (under ice cooling, if required) for 30 minutes and then stirred at 60° C. for 2 hours. The resultant crude product was purified by a column chromatography on silica gel (solvent; hexane/ethyl acetate=100:0→95:5) to give 1-bromo-4-(difluoromethyl)-benzene (328 mg, yield: 53%).

G-CMS(EI) m/z: 208/210

(2) To a solution of the compound obtained in the above step (1) (310 mg) in tetrahydrofuran (3 mL) was added dropwise 1.58M n-butyl lithium/hexane (2.37 mL) at −78° C. under nitrogen gas atmosphere and the mixture was stirred at the same temperature 1 hour. To the reaction mixture was added dropwise a solution of 4-cyanobenzaldehyde (197 mg) in tetrahydrofuran (2 mL) and the mixture was stirred at the same temperature for 3 hours. The reaction mixture was concentrated in vacuo and to the residue was added water and ethyl acetate. After stirring, the mixture was extracted with ethyl acetate and the organic layer was filtered through NH-silica gel (Chromatorex NH-silica gel, 2 g). The filtrate was concentrated in vacuo and the crude product was purified by a column chromatography on silica gel (solvent; hexane/ethyl acetate=80:20→65:35) to give (4-cyanophenyl)[4-(difluoromethyl)phenyl]methanol (83.2 mg, yield: 21%).

(3) To the compound obtained in the above step (2) (38.9 mg) was added thionyl chloride (2 mL) and the mixture was stirred at 85° C. for 2 hours. The reaction mixture was concentrated to give chloro(4-cyanophenyl)[4-(difluoromethyl) phenyl]methane.

Reference Example 18

(1) To a solution of 6-methylnicotinic acid (1 g) in tetrahydrofuran (10 mL) was added lithium aluminum hydride (277 mg) and the mixture was stirred at room temperature for 1 hour. To the reaction mixture was added an aqueous solution of sodium hydroxide and water. After stirring, the mixture was filtered and the organic layer was separated and concentrated in vacuo. The resultant crude product was purified by a column chromatography on silica gel (solvent; chloroform/ methanol=98:2→90:10) to give 6-methylpyridin-3-ylmethyl alcohol (434 mg, yield: 49%).

MS(APCI) m/z: 124 $[M+H]^+$ (2) To a solution of the compound obtained in the above step (1) (430 mg) in methylene chloride (10 mL) was added 1,1,1-tris(acetyloxy)-1,1-dihydro-1,2-benziodoxol-3-(1H)-one (1.48 g) and the mixture was stirred at room temperature for 30 minutes. To the reaction mixture was added an aqueous saturated sodium hydrogencarbonate solution. After stirring, the mixture was extracted with chloroform and the extract was concentrated in vacuo. The resultant crude product was purified by a column chromatography on silica gel (solvent; hexane/ethyl acetate=70:30→50:50) to give 6-methylpyridin-3-carbaldehyde (224 mg, yield: 53%).

MS(APCI) m/z: 122 $[M+H]^+$ (3) To a solution of 4-iodobenzonitrile (460 mg) in tetrahydrofuran (5 mL) was added dropwise 1.58M n-butyl lithium/hexane (1.25 mL) at −78° C. under nitrogen gas atmosphere and the mixture was stirred at the same temperature for 30 minutes. Thereto was added the compound obtained in the above step (2) (220 mg) and the mixture was stirred at the same temperature for 1 hour. After warming to room temperature, to the reaction mixture was added water and ethyl acetate. After stirring, the organic layer was separated and concentrated in vacuo. The resultant crude product was purified by a column chromatography on silica gel (solvent; hexane/ethyl acetate=50:50→0:100) to give (4-cyanophenyl)(6-methylpyridin-3-yl)methanol (111 mg, yield: 27%).

MS(APCI) m/z: 225 $[M+H]^+$

Reference Example 19

(1) A mixture of 4-dimethylsulfamoylbenzoic acid (688 mg) and thionyl chloride (5 mL) was stirred at 90° C. overnight. The reaction mixture was concentrated to give 4-dimethylsulfamoylbenzoyl chloride (495 mg) as a white solid.

(2) To a solution of 4-cyanophenylboronic acid (353 mg), [bis-(triphenyl-phosphino)-dichloro]palladium (28 mg) and potassium phosphate trihydrate (692 mg) in toluene (5 mL) was added the compound obtained in the above step (1) (495 mg) and the mixture was stirred at 110° C. for 1.5 hours. After cooling to room temperature, the reaction mixture was filtered through silica gel (5 g) and the filtrate was concentrated in vacuo. The resultant crude product was purified by a column chromatography on silica gel (solvent; hexane/ethyl acetate=33:67→65:35) to give (4-cyanophenyl)(4-dimethylsulfamoylphenyl)ketone (234 mg) as a white solid.

(3) To a solution of the compound obtained in the above step (2) (234 mg) in tetrahydrofuran (5 mL) and methanol (1 mL) was added sodium borohydride (56 mg) at 0° C. and the mixture was stirred at the same temperature for 10 minutes and then stirred at room temperature for 2 hours. The reaction mixture was concentrated in vacuo and thereto was added water and ethyl acetate. After stirring, the organic layer was extracted by a diatomaceous earth column (Chem Elut). The extract was concentrated in vacuo and the resultant crude product was purified by a column chromatography on silica gel (solvent; hexane/ethyl acetate=70:30→50:50) to give (4-cyanophenyl)(4-dimethyl-sulfamoylphenyl)methanol as a viscous liquid.

Reference Example 20

(1) To a solution of 5-bromo-1H-pyridin-2-one (2 g) and silver carbonate (4.3 g) in chloroform (40 mL) was added isopropyl iodide (11.5 mL) and the mixture was stirred at room temperature for 2 hours. The reaction mixture was filtered through silica gel (20 g) and the filtrate was concentrated in vacuo. The resultant crude product was purified by a column chromatography on silica gel (solvent; hexane/ethyl acetate=98:2→90:10) to give 5-bromo-2-isopropyloxypyridine (2.41 g, yield: 97%).

MS(APCI) m/z: 216/218 $[M+H]^+$ (2) The compound obtained in the above step (1) (2.4 g) was treated in the same manner as described in Reference Example 17(2) to give (4-cyanophenyl)(6-isopropyl-oxypyridin-3-yl)methanol (1.88 g; yield: 63%).

MS(APCI) m/z: 269 $[M+H]^+$

Reference Example 21

(1) The corresponding starting materials were treated in the same manner as described in Reference Example 1(2) to give (4-cyanophenyl)(4-methoxycarbonyl-phenyl)methanol. Subsequently, the product was reacted with phosphorus tribromide to give bromo(4-cyanophenyl)(4-methoxycarbonylphenyl)methane.

MS(APCI) m/z: 259/261 $[M+H]^+$ (2) The compound obtained in the above step (1) and the compound obtained in Reference Example 6 were treated in the same manner as described in Example 6 to give (3R)-1-[(4-cyanophenyl)(4-methoxycarbonylphenyl)methyl]-3-[[4-(trifluoromethyl)-benzoyl]amino]pyrrolidine (427 mg).

MS(APCI) m/z: 533/535 $[M+H]^+$ (3) The compound obtained in the above step (2) was treated in the same manner as described in Example 19(1) to give (3R)-1-[(4-carboxyphenyl)(4-cyanophenyl)-methyl]-3-[[4-(trifluoromethyl)benzoyl]amino]pyrrolidine (344 mg).

MS(APCI) m/z: 519/521 $[M+H]^+$

Reference Example 22

(1) To a solution of 5-methyl-2-pyrazinecarboxylic acid (1.0 g) in tetrahydrofuran (10 mL) was added triethylamine (1.1 mL) and isobutyl chloroformate (1.0 mL), and the mixture was stirred at 0° C. for 30 minutes. To the reaction mixture was added sodium borohydride (603 mg) and methanol (5 mL) at −78° C. After stirring, to the mixture was added aqueous ammonium chloride and the mixture was extracted with ethyl acetate. The organic layer was separated and concentrated in vacuo. The resultant crude product was purified by a column chromatography on silica gel (solvent; chloroform/methanol=90:10) to give 5-methylpyrazin-2-ylmethyl alcohol (592 mg, yield: 66%).

MS(APCI) m/z: 125 $[M+H]^+$ (2) The compound obtained in the above step (1) was treated in the same manner as described in Reference Example 18(2) and (3) to give (4-cyanophenyl)(5-methylpyrazin-2-yl)methanol (44 mg, yield: 8.1%).

MS(APCI) m/z: 226 $[M+H]^+$

Reference Example 23

(1) To a solution of sodium isopropyloxide (984 mg) in isopropanol (10 mL) was added 2-chloro-5-bromopyrimidine (1.934 g) and the mixture was stirred at room temperature for 2 hours under nitrogen gas atmosphere. To the reaction mixture was added water and ethyl acetate. After stirring, the mixture was extracted with ethyl acetate. The extract was dried over magnesium sulfate and filtered. The filtrate was concentrated in vacuo and the resultant crude product was purified by a column chromatography on silica gel (solvent; hexane/ethyl acetate=100:0→90:10) to give 2-isopropyloxy-5-bromopyrimidine (1.7 g, yield: 78%)

MS(APCI) m/z: 217/219 $[M+H]^+$ .

(2) To a solution of the compound obtained in the above step (1) (434 mg) in tetrahydrofuran (20 mL) and diethylether (20 mL) was added dropwise 1.58 M butyl lithium (1.27 mL) at a temperature below −100° C. over a period of 5 minutes and the mixture was stirred at the same temperature for 30 minutes. Thereto was added dropwise 4-cyanobenzaldehyde (262 mg) in tetrahydrofuran (5 mL) at the same temperature for 3 hours. After warming to room temperature, to the reaction mixture was added water and ethyl acetate. After stirring, the mixture was extracted with ethyl acetate. The extracts was dried over sodium sulfate and filtered. The filtrate was concentrated in vacuo and the resultant crude product was purified by a column chromatography on silica gel (solvent; hexane/ethyl acetate=60:40→30:70) to give (4-cyanophenyl)(2-isopropyloxy-pyrimidin-5-yl)methanol (174 mg, yield: 32%).

MS(APCI) m/z: 270 [M+H]$^+$

Reference Example 24

(1) To a solution of 4-bromobenzylalcohol (561 mg) in methylene chloride (3 mL) was added [bis-(2-methoxyethyl)amino]sulfur trifluoride (590 µL) over a period of 5 minutes under ice-cooling and the mixture was stirred at the same temperature for 1 hours and then stirred at room temperature for 1 hour. The reaction mixture was concentrated in vacuo and the resultant crude product was purified by a column chromatography on silica gel (solvent; hexane/ethyl acetate=100:0→95:5) to give 1-bromo-4-fluoromethyl-benzene (340 mg, yield: 60%).

GCMS(EI) m/z: 188/190

(2) The compound obtained in the above step (1) (300 mg) was treated in the same manner as described in Reference Example 17(2) to give (4-cyanophenyl)(4-fluoro-methylphenyl)methanol (227 mg, yield: 59%).

Reference Example 25

(1) To a solution of 5-bromo-2-methylpyridine (5.0 g) in carbon tetrachloride (50 mL) was added N-bromosuccinimide (6.2 g) and 2,2'-azobis(2-methylpropionitrile) (239 mg) and the mixture was stirred at 85° C. for 1 hour. After cooling, the reaction mixture was filtered to remove the insoluble materials and the filtrate was concentrated in vacuo. The resultant crude product was purified by a column chromatography on silica gel (solvent; hexane/ethyl acetate=100:0→92:8) to give 5-bromo-2-bromomethyl-pyridine (3.7 g, yield: 51%).

MS(APCI) m/z: 250/252 [M+H]$^+$ (2) To a solution of sodium isopropyloxide (1.82 g) in isopropanol (24 mL) was added the compound obtained in the above step (1) (1.85 g) in 2-propanol (10 mL) at 85° C. and the mixture was stirred for 30 minutes. After cooling, the reaction mixture was concentrated in vacuo and thereto was added water and ethyl acetate. The mixture was extracted with chloroform and the extract was concentrated in vacuo. The resultant crude product was purified by a column chromatography on silica gel (solvent; hexane/ethyl acetate=99:1→90:10) to give 5-bromo-2-isopropyloxymethyl-pyridine (1.47 g, yield: 87%).

MS(APCI) m/z: 230/232 [M+H]$^+$ (3) The compound obtained in the above step (2) (400 mg) and 4-trifluoro-methylbenzaldehyde were treated in the same manner as described in Reference Example 17(2) to give (6-isopropyloxymethylpyridin-3-yl)(4-trifluoromethylphenyl)methanol (333 mg, yield: 57%).

MS(APCI) m/z: 326 [M+H]$^+$

Reference Example 26

(1) To a solution of sodium isopropyloxide (10.0 g) in 2-propanol (100 mL) was added 2-bromothiazol (10.0 g) at 85° C. and the mixture was stirred for 15 hours. After cooling, the reaction mixture was concentrated in vacuo and thereto was added water. The mixture was extracted with diethylether and the extract was washed with water and a saturated brine, dried over magnesium sulfate and concentrated in vacuo to give 2-isopropyloxythiazol (6.39 g, yield: 73%). MS(APCI) m/z: 144 [M+H]$^+$ (2) The compound obtained in the above step (1) (1.0 g) was treated in the same manner as described in Reference Example 17(2) to give (4-cyanophenyl)(2-isopropyloxythiazol-5-yl)methanol (1.62 g, yield: 85%).

MS(APCI) m/z: 275 [M+H]$^+$

Reference Example 27

To a solution of 2,2,2-trifluoroethanol (3.1 g) in dioxane (20 mL) was added sodium hydride (1.4 g) at 0° C. and the mixture was stirred at room temperature under nitrogen gas atmosphere for 30 minutes. Thereto was added 5-bromo-2-chloro-pyrimidine (3.0 g) and the mixture was stirred at room temperature overnight. Thereto was added water and ethyl acetate and the mixture was stirred and filtered. The filtrate was concentrated in vacuo and the resultant crude product was purified by a column chromatography on silica gel (solvent; hexane/ethyl acetate=95:5→90:10) to give 5-bromo-2-(2,2-trifluoroethoxy)-pyrimidine (3.0 g, yield: 38%).

MS(APCI) m/z; 257/259 [M+H]$^+$

Reference Example 28

(1) To a solution of the compound obtained in Reference Example 20-(1) (1.0 g) in tetrahydrofuran (10 mL) was added dropwise 1.58 M n-butyl lithium (3.0 mL) at −78° C. under nitrogen gas atmosphere and the mixture was stirred at the same temperature for 1 hours. Thereto was added a solution of 6-chloro-3-formylpyridine (660 mg) in tetrahydrofuran (2 mL) and the mixture was stirred at the same temperature for 1 hour. After warming to room temperature, thereto was added water and the mixture was extracted with ethyl acetate. The extract was concentrated in vacuo and the resultant crude product was purified by a column chromatography on silica gel (solvent; hexane/ethyl acetate=80:20→60:40) to give (6-chloropyridin-3-yl)(6-isopropyloxy-pyridin-3-yl)methanol (733 mg, yield: 57%).

MS(APCI) m/z; 279/281 [M+H]$^+$ (2) To a solution of the compound obtained in the above step (1) (733 mg) and triethylamine (735 µL) in methylene chloride (12 mL) was added dropwise methanesulfonyl chloride (245 µL) under ice cooling and the mixture was stirred at the same temperature for 1 hour. Thereto was added (3R)-(+)-(tert-butoxycarbonylamino)pyrrolidine (637 mg) and acetonitrile (25 mL) and the mixture was stirred at 85° C. for 18 hours. Thereto was added water and the mixture was extracted with ethyl acetate. The extract was washed with water, dried over magnesium sulfate and concentrated in vacuo. The resultant crude product was purified by a column chromatography on silica gel (solvent; hexane/ethyl acetate=90:10→67:33) to give (3R)-1-[(6-chloro-pyridin-3-yl)(6-isopropyloxypyridin-3-yl)methyl]-3-(tert-butoxycarbonylamino)-pyrrolidine (635 mg, yield: 54%).

MS(APCI) m/z; 447/449 [M+H]$^+$ (3) To a solution of the compound obtained in the above step (2) (506 mg) in 2-propanol (15 mL) was added sodium isopropoxide (411 mg) and the mixture was stirred by using a microwave synthesizer (Biotage LTD.) at 155° C. for 2 hours. Thereto was added an aqueous saturated sodium hydrogen-carbonate solution and the mixture was extracted with chloroform. The extract was dried over magnesium sulfate and concentrated in vacuo to give (3R)-3-amino-1-[(6-chloropyridin-3-yl)(6-isopropyl-oxypyridin-3-yl)methyl]pyrrolidine (476 mg) as a brown oil.

Reference Example 29

To a solution of 4-fluorobenzaldehyde (1.5 g) and methylethylamine (1.56 mL) in dimethylsulfoxide (9 mL) was added potassium carbonate (2.17 g) and the mixture was stirred by using a microwave synthesizer (Biotage LTD.) at 120° C. for 2 hours. Thereto was added water and the mixture was extracted with ethyl acetate. The extract was dried over magnesium sulfate and concentrated in vacuo. The resultant crude product was purified by a column chromatography on silica gel (solvent; hexane/ethyl acetate=95:5→80:20) to give 4-(N-ethyl-N-methylamino)benzaldehyde (1.89 g, yield: 89%).

MS(APCI) m/z; 164 $[M+H]^+$

Reference Example 30

To a solution of 4-hydroxybenzaldehyde (1.22 g) in pyridine (5 mL) was added dimethylcarbamyl chloride (1.0 mL) and the mixture was stirred at 60° C. overnight. Thereto was added diluted HCl and ethyl acetate and stirred. The organic layer was extracted by diatomaceous earth column. The organic layer was concentrated and the resultant crude product was purified by a column chromatography on silica gel (solvent; hexane/ethyl acetate=80:20→60:40) to give 4-formylphenyl dimethylcarbamate (1.67 g, yield: 86%).

MS(APCI) m/z; 194 $[M+H]^+$

INDUSTRIAL APPLICABILITY

A compound [I] of the present invention may be useful as: (i) an agent for prevention and/or treatment of a CB1 receptor-mediated diseases exemplified as above; (ii) an agent for withdrawal from a chronic treatment, alcohol dependence, smoking dependence, nicotine dependence, or drug abuse (e.g., an opioid, barbiturate, marijuana, cocaine, amphetamine, phencyclidine, a hallucinogenic agent, a benzodiazepine compound and the like); or (iii) an agent for enhancing analgesic activity of analgesic or narcotic drugs and the like.

The invention claimed is:

1. A compound of the formula [I]:

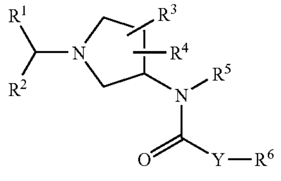

[I]

wherein each of $R^1$ and $R^2$ is (A) independently (a) a phenyl group optionally substituted by the same or different one to two group(s) selected from the group consisting of (i) a halogen atom, (ii) cyano group, (iii) an alkyloxy group optionally substituted by a morpholino group, (iv) an amino group optionally substituted by a group selected from the group consisting of an alkyl group, an alkyloxyalkyl group and a cycloalkyl group, (v) an alkylthio group and (vi) an alkylenedioxy group, (b) a thienyl group optionally substituted by a halogen atom, (c) a quinolyl group, (d) a thiazolyl group optionally substituted by an alkyloxy group, (e) a morpholinyl group, (f) a pyrimidinyl group optionally substituted by a di(alkyl) amino group, (g) a benzimidazolyl group optionally substituted by an alkyl group or (h) a pyridyl group optionally substituted by a group selected from the group consisting of a cycloalkyloxy group or an alkyloxy group optionally substituted by one to three halogen atom(s), or (B) both of the groups combine each other together with an adjacent CH group to form a group of the formula:

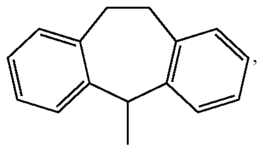, either one of $R^3$ and $R^4$ is a hydrogen atom and another is a hydrogen atom, a hydroxyl group, a hydroxyalkyl group, an alkyloxy group, an alkyloxyalkyl group, an alkyloxyalkyloxy group, a carboxyl group, an alkyloxycarbonyl group, a saturated or unsaturated, 4- to 10-membered, nitrogen- or oxygen-containing heterocyclic group, a carbamoyl group or a mono- or dialkylcarbamoyl group (the alkyl moiety of said group being optionally substituted by a group selected from a halogen atom, a hydroxyl group, a mono- or di-alkylamino group and a saturated or unsaturated, 4- to 10-membered, nitrogen- or oxygen-containing heterocyclic group) or both of $R^3$ and $R^4$ combine each other to form an oxo group, $R^5$ is a hydrogen atom or an alkyl group, Y is a single bond, an oxygen atom or a group of the formula: —N—($R^7$)—, $R^6$ is: a cyclic group selected from (i.) a monocyclo-, bicyclo or tri-cyclo-$C_{3-10}$ alkyl group (said cycloalkyl group being fused to a benzene ring) and (ii.) a saturated or unsaturated, 3- to 14-membered, sulfur-, nitrogen- or oxygen-containing heterocyclic group optionally forming a spiro-ring with a cycloalkyl ring, wherein said cyclic group may be optionally substituted by the same or different one to four groups selected from (1) a halogen atom, (2) an oxo group, (3) a nitro group, (4) a cyano group, (5) an alkyl group optionally substituted by the same or different one to three groups selected from a halogen atom, a 5- to 10-membered aryl-carbonyl group, a mono-, di- or tri-halogeno-arylcarbonyl group, a 5- to 10-membered aryl group, a hydroxyl group, a saturated or unsaturated, 4- to 10-membered, nitrogen- or oxygen-containing heterocyclic group optionally substituted by an oxo group, an alkyloxy group and an imino group, (6) an aminoalkyl group (the amino moiety of said group being optionally substituted by the same or different one to two groups selected from an alkyloxy-carbonyl group, a 5- to 10-membered aryl-carbonyl group, a 5- to 10-membered aryl-alkyloxy-carbonyl group, an alkyl group, an alkyloxyalkyl group and a cycloalkyl group), (7) a cycloalkyl group, (8) an alkenyl group optionally substituted by an alkyloxycarbonyl group, (9) an amino group optionally substituted by one to two groups selected from an alkyl group, an alkyloxy-carbonyl group, a 5- to 10-membered aryl-alkyloxycarbonyl group, an alkyloxyalkyl group and a halogenoalkylcarbonyl group, (10) a 5- to 10-membered aryl group optionally substituted by the same or different one to three groups selected from a halogen atom and a saturated or unsaturated, 4- to 10-membered, nitrogen- or oxygen-containing heterocyclic group, (11) a saturated or unsaturated, 4- to 10-membered, nitrogen- or oxygen-containing heterocyclic group optionally substituted by the same or different one to three groups selected from a halogen atom, an oxo group and a saturated or unsaturated, 4- to 10-membered, nitrogen- or oxygen-containing heterocyclic group, (12) an alkyloxy group optionally substituted by the same or different one to three groups selected from a halogen atom, an alkyloxy group, a 5- to 10-membered aryl group, a saturated or unsaturated, 4- to 10-membered, nitrogen- or oxygen-containing heterocyclic group and a mono- or di-alkylamino group, (13) a cycloalkyloxy group, (14) a cycloalkenyloxy group, (15) a 5- to 10-membered aryloxy group, (16) a 5- to 10-membered aryl-carbonyl group optionally substituted by the same or different one to three halogen atoms, (17) an alkylcarbonyl group, (18) an alkyloxycarbonyl group, (19) a 5- to 10-membered aryl-alkyloxycarbonyl group, (20) a group of the formula: —$SO_2R_b$ in which $R_b$ is an alkyl group, an aryl group optionally substituted by one to three halogen atoms, an amino group optionally substituted by one to two alkyl groups or a saturated or unsaturated, 4- to 10-membered, nitrogen- or oxygen-containing heterocyclic group optionally substituted by the same or different one to three alkyl groups, (21) an alkynyl group optionally substituted by a group selected from a mono- or di-alkylamino group and a saturated or unsaturated, 4- to 10-membered, nitrogen- or oxygen-containing heterocyclic group, (22) an alkylthio group (the alkyl moiety of said group being optionally substituted by a group selected from a hydroxyl group and an alkyloxy group), (23) a carbamoyl group (the amino moiety of said group being optionally substituted by an alkyl group) and (24) a carbamoyloxy group optionally substituted by one or two alkyl groups; and $R^7$ is an alkyl group or an alkyloxycarbonyl-alkyl group, or a pharmaceutically acceptable salt thereof.

2. The compound according to claim 1 or a pharmaceutically acceptable salt thereof in which $R^1$ and $R^2$ are the same or different and a phenyl group optionally substituted by one or two halogen atoms, either one of $R^3$ and $R^4$ is a hydrogen atom, another is a hydrogen atom or a $C_{1-6}$ alkyloxy group, $R^5$ is a hydrogen atom, Y is a single bond and $R^6$ is a $C_{3-10}$ mono-bi- or tri-cycloalkyl group (said cycloalkyl group being optionally fused to a benzene ring) optionally substituted by one to four groups selected from the group consisting of the following (i) to (vi):

(i) an oxo group; (ii) a $C_{1-6}$ alkyl group optionally substituted by a halogenophenyl-carbonyl group; (iii) an amino-a $C_{1-6}$ alkyl group (amino moiety of said group being optionally substituted by a $C_{1-6}$ alkyloxy-carbonyl group; (iv) an amino group optionally substituted by a $C_{1-6}$ alkyloxy-carbonyl group; (v) a phenyl group optionally substituted by one to three halogen atoms; and (vi) a benzoyl group optionally substituted by one to three halogen atoms.

3. The compound according to claim 1 or a pharmaceutically acceptable salt thereof in which $R^1$ and $R^2$ are the same or different and a (a) phenyl group optionally substituted by one to three groups selected from a halogen atom, a cyano group, a $C_{1-6}$ alkyloxy group, a trifluoro-$C_{1-6}$ alkyl group, an amino group substituted by one or two groups selected from a $C_{1-6}$ alkyl group and a $C_{1-6}$ alkyloxy-$C_{1-6}$ alkyl group and a di($C_{1-6}$ alkyl)carbamoyloxy group, or (b) a sulfur-, oxygen- or nitrogen-containing 5- to 10-membered heterocyclic group optionally substituted by one to three groups selected from a $C_{1-6}$ alkyloxy group, a di($C_{1-6}$ alkyl)amino group, a $C_{3-8}$ cycloalkyloxy group, a $C_{3-8}$ cycloalkyl-$C_{1-6}$ alkyloxy group and a trihalogeno-$C_{1-6}$ alkyloxy group, one of $R^3$ and $R^4$ is a hydrogen atom, another is a hydrogen atom or a $C_{1-6}$ alkyloxy group, $R^5$ is a hydrogen atom, Y is a single bond and $R^6$ is a saturated or unsaturated 3- to 14-membered, monocyclic-bicyclic- or tricyclic-heterocyclic group (said heterocyclic group optionally constituting a spiro-ring with a $C_{3-8}$ cycloalkyl group) optionally substituted by one to three groups selected from the group consisting of the following (i) to (xiv):

(i) an oxo group; (ii) a halogen atom; (iii) a cyano group; (iv) a $C_{1-6}$ alkyl group (said group being optionally substituted by one to three groups selected from a halogen atom, a $C_{1-6}$ alkyloxy group, an imino group, a phenyl group and a pyrrolidinyl group); (v) an amino-$C_{1-6}$ alkyl group (amino moiety of said group being optionally substituted by one or two $C_{1-6}$ alkyl groups); (vi) an amino group optionally substituted by one or two $C_{1-6}$ alkyl groups; (vii) a phenyl group optionally substituted by one to three halogen atoms; (viii) a heterocyclic group selected from a furyl group, a pyridyl group and a pyrimidinyl group; (ix) a $C_{1-6}$ alkyloxy group optionally substituted by one to three groups selected from halogen atoms and a phenyl group; (x) a $C_{1-6}$ alkyl-carbonyl group; (xi) a $C_{1-6}$ alkyloxy-carbonyl group; (xii) a $C_{1-6}$ alkylsulfonyl group; (xiii) an aminosulfonyl group; (xiv) a benzenesulfonyl group optionally substituted by one to three halogen atoms; and (xv) a morpholinosulfonyl group.

4. The compound according to claim 1 or a pharmaceutically acceptable salt thereof in which $R^6$ is a mono-, bi- or tri-cycloalkyl group (said cycloalkyl group being optionally fused by a benzene ring) substituted by the same or different one to four groups selected from an oxo group, a $C_{1-6}$ alkyl group, a halogenobenzoyl-$C_{1-6}$ alkyl group, a $C_{1-6}$ alkyloxy-carbonylamino group, a $C_{1-6}$ alkyloxy-carbonylamino-$C_{1-6}$ alkyl group, a halogenobenzoyl group, a phenyl group and a halogenophenyl group.

5. The compound according to claim 1 or a pharmaceutically acceptable salt thereof in which $R^6$ is a heterocyclic group substituted by the same or different one to three groups selected from an oxo group, a chlorine atom, a bromine atom, a cyano group, a $C_{1-6}$ alkyl group, a $C_{1-6}$ alkyloxy group, a diphenyl-$C_{1-6}$ alkyl group, a $C_{1-6}$ alkyl-carbonyl group, a trifluoro-$C_{1-6}$ alkyl group, a trifluoro-$C_{1-6}$ alkyloxy group, a $C_{1-6}$ alkyloxy-carbonyl group, a di($C_{1-6}$ alkylamino-$C_{1-6}$ alkyl group, a di($C_{1-6}$ alkylamino group, a phenyl group, a chlorophenyl group, a pyrrolidinyl-$C_{1-6}$ alkyl group, a pyridyl group, a pyrimidinyl group, a furyl group, a $C_{1-6}$ alkylsulfonyl group, an aminosulfonyl group, a morpholinosulfonyl group, a benzene-sulfonyl group, a $C_{1-6}$ alkyloxy-imino-$C_{1-6}$ alkyl group, a chlorobenzenesulfonyl group, a benzyl group and a benzyloxy group.

6. The compound according to claim 5 or a pharmaceutically acceptable salt thereof in which one of $R^3$ and $R^4$ is a hydrogen atom and the other is a hydrogen atom, a hydroxyl group, a $C_{1-6}$ alkyloxy group or a morpholino group.

7. A compound selected from the group consisting of:

(3R)-1-[(4-cyanophenyl)(4-chlorophenyl)methyl]-3-[[5-(trifluoromethyl)-2-thenoyl]amino]pyrrolidine;

(3R)-1-[(4-cyanophenyl)(2-isopropyloxythiazol-5-yl)methyl]-3-[(6-cyanonicotinoyl)amino]pyrrolidine, (3R)-1-[(4-methoxyphenyl)(6-isopropyloxypyridin-3-yl)methyl]-3-[[(6-cyanopyridin-3-yl)carbonyl]amino]pyrrolidine; (3R)-1-[(4-ethoxyphenyl)(6-isopropyloxypyridin-3-yl)methyl]-3-[[(6-cyanopyridin-3-yl)carbonyl]amino]pyrrolidine;

(3R)-1-[(4-isopropyloxyphenyl)(6-isopropyloxypyridin-3-yl)methyl]-3-[[(6-cyanopyridin-3-yl)carbonyl]amino]pyrrolidine;

(3R)-1-[(4-cyanophenyl)(2-ethoxythiazol-5-yl)methyl]-3-[[(6-cyanopyridin-3-yl)carbonyl]amino]pyrrolidine; (3R)-1-[bis-(6-isopropyloxypyridin-3-yl)methyl]-3-[[(6-cyanopyridin-3-yl)carbonyl]amino]pyrrolidine; (3R)-1-[(4-cyanophenyl)(2-dimethylaminopyrimidin-5-yl)methyl]-3-[[(6-cyanopyridin-3-yl)carbonyl]amino]pyrrolidine;

(3R)-1-[(4-cyanophenyl)(2-diethylaminopyrimidin-5-yl)methyl]-3-[[(6-cyanopyridin-3-yl)carbonyl]amino]pyrrolidine;

(3R)-1-[(4-cyanophenyl)[4-[N-(2-methoxyethyl)-N-methylaminophenyl]]-methyl]-3-[[(6-cyanopyridin-3-yl)carbonyl]amino]pyrrolidine;

(3R)-1-[(4-cyanophenyl)[4-[N-(2-methoxyethyl)-N-methylaminophenyl]]methyl]-3-[[(6-cyanopyridin-3-yl)carbonyl]amino]pyrrolidine;

(3R)-1-[(4-cyanophenyl)[4-(N-isopropyl-N-methylamino)phenyl]methyl]-3-[[(6-cyanopyridin-3-yl)carbonyl]amino]pyrrolidine;

(3R)-1-[(4-cyanophenyl) [4-(N-ethyl-N-methylamino)phenyl]methyl]-3-[[(6-cyanopyridin-3-yl)carbonyl]amino]pyrrolidine;

(3R)-1-[(4-cyanophenyl) [4-(N-methyl-N-n-propylamino)phenyl]methyl]-3-[[(6-cyanopyridin-3-yl)carbonyl]amino]pyrrolidine;

(3R)-1-[(4-cyanophenyl)(6-cyclobutyloxypyridin-3-yl)methyl]-3-[[(6-cyanopyridin-3-yl)carbonyl]amino]pyrrolidine;

(3R)-1-[(4-cyanophenyl)(6-cyclopentyloxypyridin-3-yl)methyl]-3-[[(6-cyanopyridin-3-yl)carbonyl]amino]pyrrolidine; (3R)-1-[(4-cyanophenyl)[6-(3-pentyloxy)pyridin-3-yl]methyl]-3-[[(6-cyanopyridin-3-yl)carbonyl]amino]pyrrolidine; and (3R)-1-[(4-cyanophenyl)[6-(2,2,2-trifluoroethoxy)pyridin-3-yl]methyl]-3-[[(6-cyanopyridin-3-yl)carbonyl]amino]pyrrolidine or a pharmaceutically acceptable salt thereof.

* * * * *